(12) United States Patent
Boudreault et al.

(10) Patent No.: US 10,199,581 B2
(45) Date of Patent: *Feb. 5, 2019

(54) ORGANIC ELECTROLUMINESCENT MATERIALS AND DEVICES

(71) Applicant: Universal Display Corporation, Ewing, NJ (US)

(72) Inventors: Pierre-Luc T. Boudreault, Pennington, NJ (US); Alexey Dyatkin, Ambler, PA (US); David Zenan Li, Princeton, NJ (US); Scott Joseph, Ewing, NJ (US); Chuanjun Xia, Lawrenceville, NJ (US); Hitoshi Yamamoto, Pennington, NJ (US); Michael S. Weaver, Princeton, NJ (US); Bert Alleyne, Newtown, PA (US); James Fiordeliso, Yardley, PA (US)

(73) Assignee: UNIVERSAL DISPLAY CORPORATION, Ewing ( * ) Notice: Subject to any disclaimer, the term of this patent is extended or adjusted under 35 U.S.C. 154(b) by 934 days.

This patent is subject to a terminal disclaimer.

(21) Appl. No.: 13/932,508

(22) Filed: Jul. 1, 2013

(65) Prior Publication Data

US 2015/0001472 A1 Jan. 1, 2015

(51) Int. Cl.
*H01L 51/50* (2006.01)
*H01L 51/00* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
USPC ..................................................... 556/40, 41
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

European Patent Office, European Search Report from European Application No. EP 14174024, dated Dec. 3, 2014, pp. 1-6.
(Continued)

*Primary Examiner* — Andrew K Bohaty
*Assistant Examiner* — Dylan C Kershner
(74) *Attorney, Agent, or Firm* — Duane Morris LLP

(57) ABSTRACT

A compound having an ancillary ligand $L^1$ having the formula:

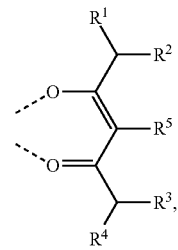

Formula I is disclosed. The ligand $L^1$ is coordinated to a metal M having an atomic number greater than 40, and two adjacent substituents are optionally joined to form into a
(Continued)

Formula I ring. Such compound is suitable for use as emitters in organic light emitting devices.

22 Claims, 3 Drawing Sheets

(51) Int. Cl.
 *C07F 15/00* (2006.01)
 *C09K 11/06* (2006.01)
(52) U.S. Cl.
 CPC ............... *C09K 2211/1007* (2013.01); *C09K 2211/1029* (2013.01); *C09K 2211/185* (2013.01); *H01L 51/5016* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,316,064 B1 | 11/2001 | Onozawa et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,740,957 B2 | 6/2010 | Kim et al. |
| 9,163,174 B2 * | 10/2015 | Alleyne ............... C07F 15/0033 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0072964 A1 * | 4/2003 | Kwong ............... C07D 215/04 |
| | | 428/690 |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0104979 A1 | 5/2007 | Kim et al. |
| 2007/0104980 A1 | 5/2007 | Kim et al. |
| 2007/0190359 A1 | 8/2007 | Knowles et al. |
| 2007/0224450 A1 | 9/2007 | Kim et al. |
| 2007/0247061 A1 * | 10/2007 | Adamovich ......... H01L 51/5016 |
| | | 313/504 |
| 2007/0278936 A1 | 12/2007 | Herron et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0074033 A1 | 3/2008 | Ionkin et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0261076 A1 * | 10/2008 | Kwong ............... C07F 15/0033 |
| | | 428/690 |
| 2008/0286604 A1 * | 11/2008 | Inoue ............... C07F 15/0033 |
| | | 428/690 |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0085476 A1 | 4/2009 | Park et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0119190 A1 | 5/2012 | Alleyne et al. |
| 2012/0181511 A1 * | 7/2012 | Ma ............... C07F 15/0033 |
| | | 257/40 |
| 2012/0217868 A1 | 8/2012 | Ma et al. |
| 2013/0137866 A1 * | 5/2013 | Inoue ............... C07F 15/0033 |
| | | 544/225 |
| 2013/0146848 A1 * | 6/2013 | Ma ............... C07F 15/0033 |
| | | 257/40 |
| 2013/0299795 A1 * | 11/2013 | Xia ............... H01L 51/0085 |
| | | 257/40 |
| 2014/0246656 A1 * | 9/2014 | Inoue ............... H01L 51/0085 |
| | | 257/40 |
| 2015/0188061 A1 * | 7/2015 | Xia ............... H01L 51/0085 |
| | | 257/40 |
| 2015/0236277 A1 * | 8/2015 | Boudreault ......... H01L 51/0085 |
| | | 257/40 |
| 2015/0236279 A1 * | 8/2015 | Szigethy ............. H01L 51/0085 |
| | | 257/40 |
| 2015/0295187 A1 * | 10/2015 | Boudreault ......... H01L 51/0085 |
| | | 257/40 |
| 2015/0315222 A1 * | 11/2015 | Boudreault ......... H01L 51/0085 |
| | | 257/40 |

FOREIGN PATENT DOCUMENTS

| | | |
|---|---|---|
| EP | 2034538 | 3/2009 |
| EP | 2602302 A2 | 6/2013 |
| JP | 2000-212744 | 8/2000 |
| JP | 200511610 | 1/2005 |
| JP | 2007123392 | 5/2007 |
| JP | 2007254297 | 10/2007 |
| JP | 2008074939 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |

(56) References Cited

FOREIGN PATENT DOCUMENTS

| WO | 20050124889 | | 12/2005 | | |
|---|---|---|---|---|---|
| WO | 2006009024 | | 1/2006 | | |
| WO | 2006056418 | | 6/2006 | | |
| WO | 2006072002 | | 7/2006 | | |
| WO | 2006082742 | | 8/2006 | | |
| WO | 2006098120 | | 9/2006 | | |
| WO | 2006100298 | | 9/2006 | | |
| WO | 2006103874 | | 10/2006 | | |
| WO | 2006114966 | | 11/2006 | | |
| WO | 2006132173 | | 12/2006 | | |
| WO | 2007002683 | | 1/2007 | | |
| WO | 2007004380 | | 1/2007 | | |
| WO | 2007063754 | | 6/2007 | | |
| WO | 2007063796 | | 6/2007 | | |
| WO | 2008056746 | | 5/2008 | | |
| WO | 2008101842 | | 8/2008 | | |
| WO | 2008132085 | | 11/2008 | | |
| WO | 2009000673 | | 12/2008 | | |
| WO | 2009003898 | | 1/2009 | | |
| WO | 2009008311 | | 1/2009 | | |
| WO | 2009018009 | | 2/2009 | | |
| WO | WO 2009021126 | A2 * | 2/2009 | ............ | C07C 15/38 |
| WO | 2009050290 | | 4/2009 | | |
| WO | 2009021126 | | 5/2009 | | |
| WO | 2009062578 | | 5/2009 | | |
| WO | 2009063833 | | 5/2009 | | |
| WO | 2009066778 | | 5/2009 | | |
| WO | 2009066779 | | 5/2009 | | |
| WO | 2009086028 | | 7/2009 | | |
| WO | 2009100991 | | 8/2009 | | |
| WO | 2010033550 | | 3/2010 | | |
| WO | 2012148511 | | 1/2012 | | |

OTHER PUBLICATIONS

Brittain, Harry G., "Solvent Dependence of the Optical Activity associated with Tris (DD-dicampholylmethanato) europium(III)," J. Chem Soc. Dalton Trans., No. 6, (1983), pp. 1165-1170.
Ficker, Robert et al., "Nickel (II) Bis(d-campholyl-l-campholyl-methanate)," Acta Crystallographica Section C Crystal Structure Communications, vol. 52, No. 3, (1996), pp. 543-545.
Hayashi, Tamio et al., "Chirality Transfer from Optically Active Allylsilanes to ?-Allylpalladium Complexes," J. Chem. Soc., Chem. Commun., No. 13, (1983), pp. 736-737.
Kandybin et al., "Volatile complexes of Nb(IV) with new sterically hindered ?-diketones," Russian Journal of General Chemistry, vol. 69, No. 6, (1999), pp. 866-875.
Nandurkar, Nitin S. et al., "Synthesis of Sterically Hindered 1,3-Diketones", Synthetic Communications 2007, 37, pp. 4111-4115.
Man, Eugene H. Man et al., "The Claisen Acylation of Methyl Ketones with Branched Chain Aliphatic Esters", JACS 1951, vol. 73, pp. 901-903.
Kim, Do Han et al., "Highly Efficient Red Phosphorescent Dopants in Organic Light-Emitting Devices", Adv. Mater. 2011, vol. 23, pp. 2721-2726.
Tsujimoto, Hidetaka et al., "Pure Red Electrophosphorescence from polymer light-emitting diodes doped with highly emissive bis-cyclometalated iridium (III) complexes", J. Organomet. Chem. 2010, vol. 695, pp. 1972-1978.
Noine, Keiji et al., "Red Phosphorescent Iridium Complexes Having a Bulky Ancillary Ligand for Solution-Processed Organic Light-Emitting Diodes", J. of Photopolymer Sci. Tech. 2008, 21 (2), pp. 323-325.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).

(56) References Cited

OTHER PUBLICATIONS

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5''-Bis(dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic LIght-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Notice of Reasons for Rejection dated Oct. 31, 2017 for corresponding Japanese Patent Application No. 2014-133449.

Seebach, Dieter, et al., "Synthesis of the Lithlum Enolate of (S)-(+)-sec-Butyl Methyl Ketone and Formation of Chiral 1,3-Diketones by Acylation" Angew. Chem. Int. Ed. Engl., vol. 11, Issue 2, Feb. 1972, pp. 127-128.

* cited by examiner

Formula I

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same. More particularly, the compounds disclosed herein are novel ancillary ligands for metal complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

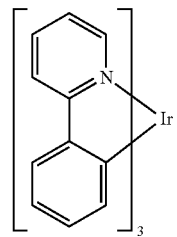

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound is provided that comprises a first ligand $L^1$ having the formula:

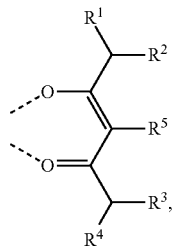

Formula I; wherein $R^1$, $R^2$, $R^3$, and $R^4$ are independently selected from group consisting of alkyl, cycloalkyl, aryl, and heteroaryl; wherein at least one of $R^1$, $R^2$, $R^3$, and $R^4$ has at least two C; wherein $R^5$ is selected from group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein the first ligand $L^1$ is coordinated to a metal M having an atomic number greater than 40; and wherein two adjacent substituents are optionally joined to form into a ring.

According to another aspect of the present disclosure, a first device comprising a first organic light emitting device is provided. The first organic light emitting device can comprise an anode, a cathode, and an organic layer, disposed between the anode and the cathode. The organic layer can include a compound comprising the first ligand $L^1$ having Formula I. The first device can be a consumer product, an organic light-emitting device, and/or a lighting panel.

The compounds disclosed herein are novel ancillary ligands for metal complexes. The incorporation of these ligands can narrow the emission spectrum, decrease evaporation temperature, and improve device efficiency. The inventors have discovered that incorporating these novel ancillary ligands in iridium complexes improved sublimation of the resulting iridium complexes, color spectrum of phosphorescence by these iridium complexes, and their EQE.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
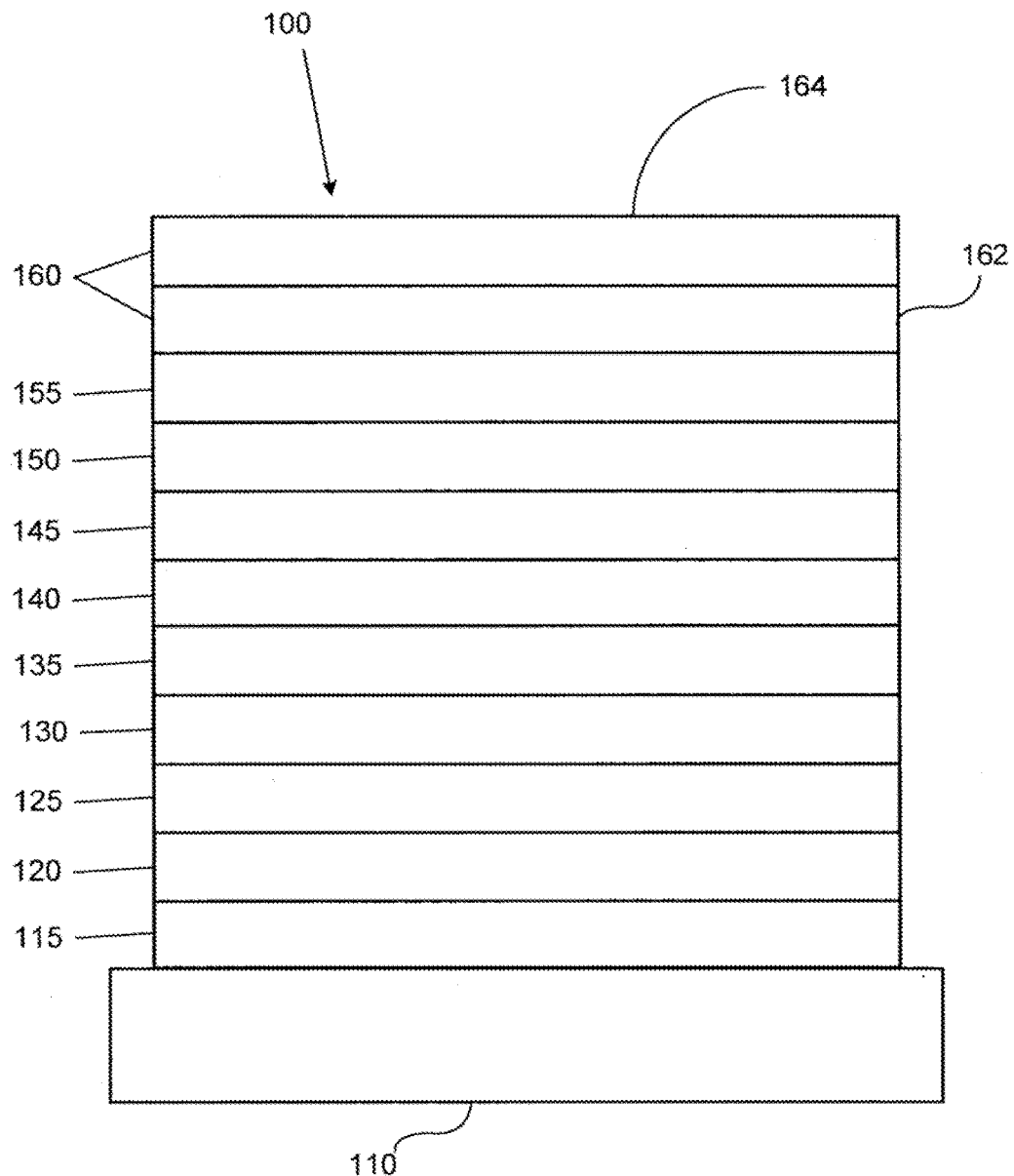
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
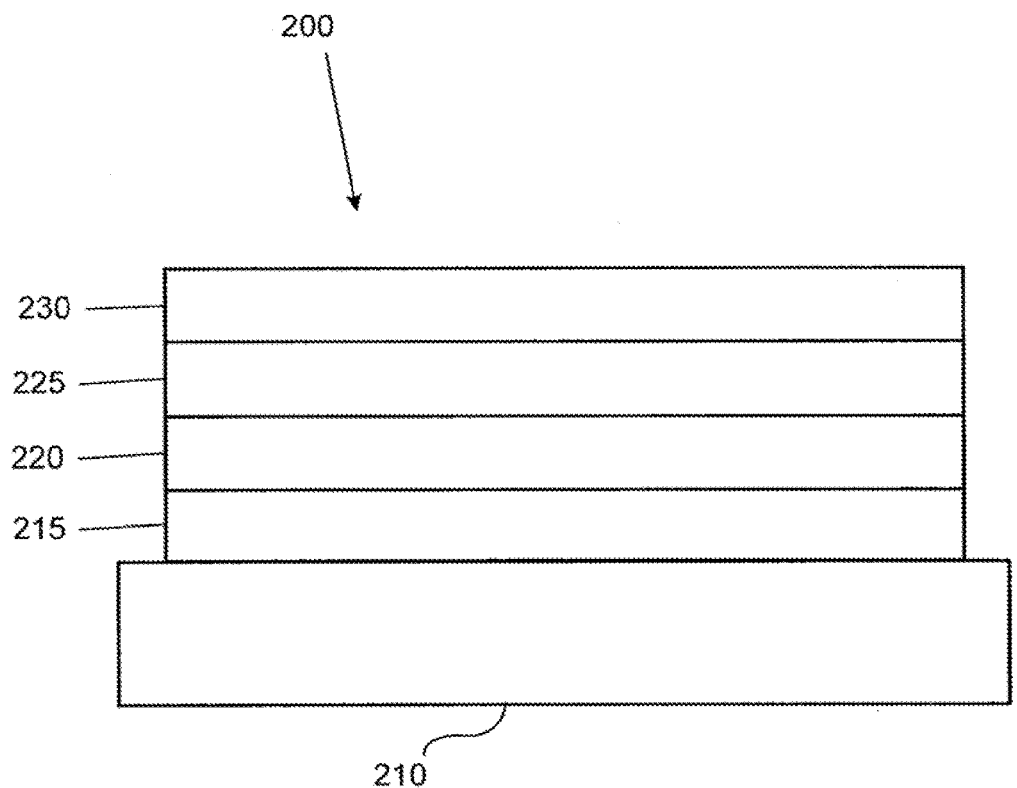
FIG. 2 shows an inverted organic light emitting device that does not have a separate electron transport layer.
Figure 3:
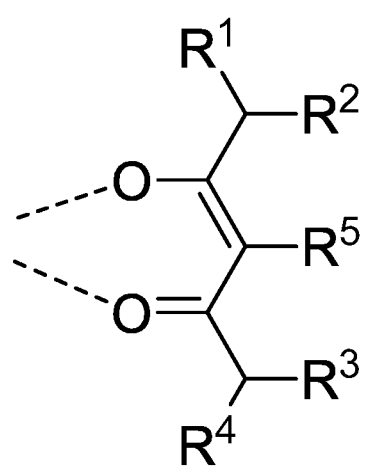
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aralkyl, heterocyclic group, aryl, aromatic group, and heteroaryl are known to the art, and are defined in U.S. Pat. No. 7,279,704 at cols. 31-32, which are incorporated herein by reference.

As used herein, "substituted" indicates that a substituent other than H is bonded to the relevant carbon. Thus, where $R^2$ is monosubstituted, then one $R^2$ must be other than H. Similarly, where $R^3$ is disubstituted, then two of $R^3$ must be other than H. Similarly, where $R^2$ is unsubstituted $R^2$ is hydrogen for all available positions.

According to an embodiment, novel ancillary ligands for metal complexes are disclosed. The inventors have discovered that incorporation of these ligands unexpectedly narrow the emission spectrum, decrease evaporation temperature, and improve device efficiency.

According to an embodiment, a compound is provided that comprises a first ligand $L^1$ having the formula:

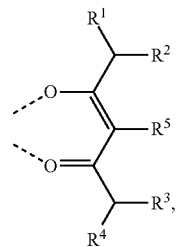

Formula I; wherein $R^1$, $R^2$, $R^3$, and $R^4$ are independently selected from group consisting of alkyl, cycloalkyl, aryl, and heteroaryl; wherein at least one of $R^1$, $R^2$, $R^3$, and $R^4$ has at least two C; wherein $R^5$ is selected from group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein the first ligand $L^1$ is coordinated to a metal M having an atomic number greater than 40; and wherein two adjacent substituents are optionally joined to form into a ring. The dash lines in Formula I show the connection points to the metal.

In one embodiment the metal M is Ir. In one embodiment $R^5$ is selected from group consisting of hydrogen, deuterium, alkyl, cycloalkyl, and combinations thereof. In one embodiment, $R^5$ is hydrogen.

In another embodiment, $R^1$, $R^2$, $R^3$, and $R^4$ are alkyl or cycloalkyl. In one embodiment, $R^1$, $R^2$, $R^3$, and $R^4$ are selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof.

In one embodiment, the compound has the formula of $M(L^1)_x(L^2)_y(L^3)_z$; wherein $L^2$ is a second ligand and $L^3$ is a third ligand and $L^2$ and $L^3$ can be the same or different; x is 1, 2, or 3; y is 0, 1, or 2; z is 0, 1, or 2; and x+y+z is the oxidation state of the metal M.

In one embodiment, $L^2$ and $L^3$ are independently selected from the group consisting of:

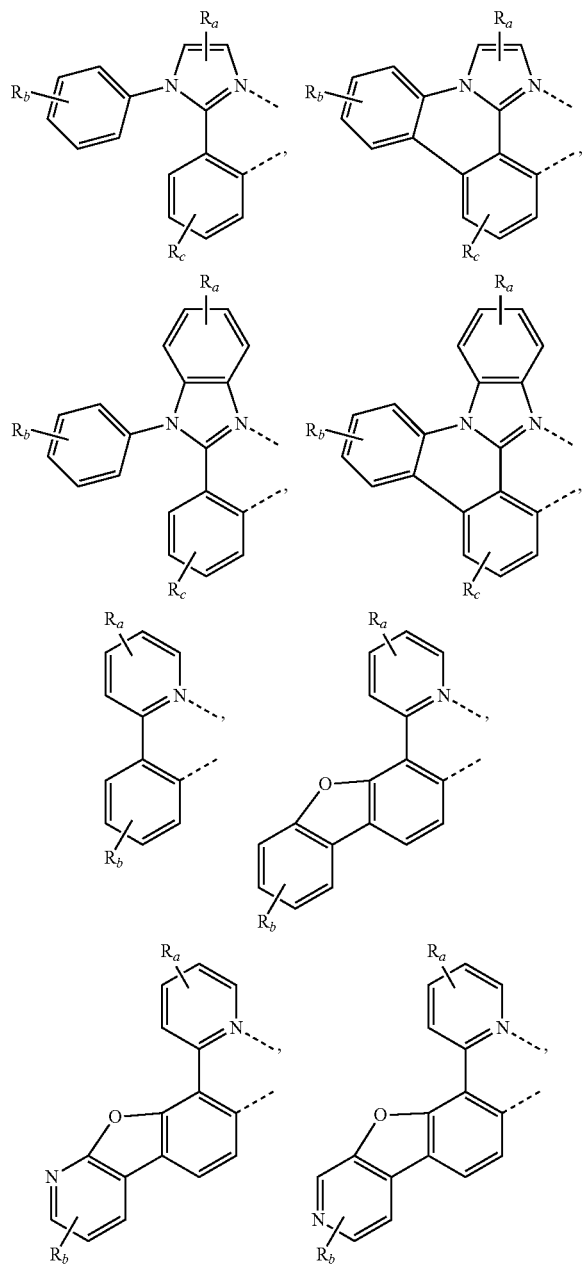

-continued

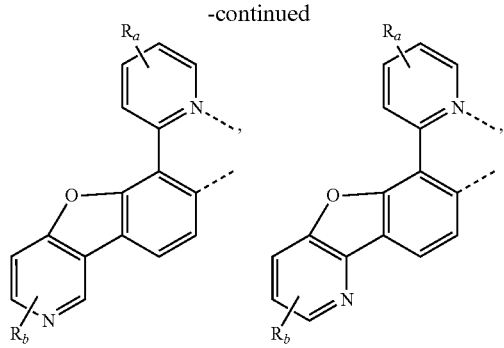

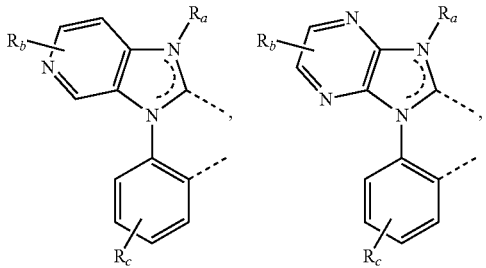

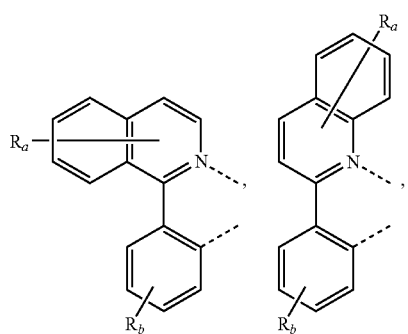

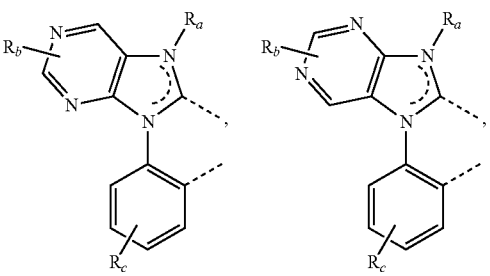

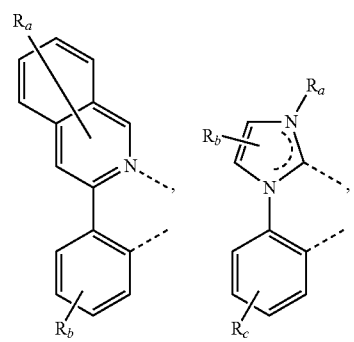

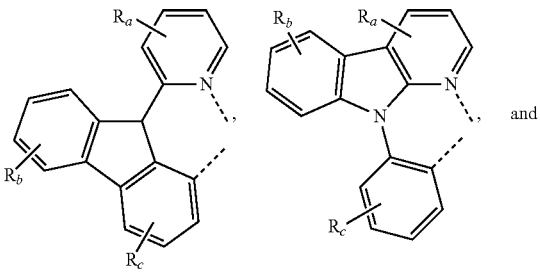

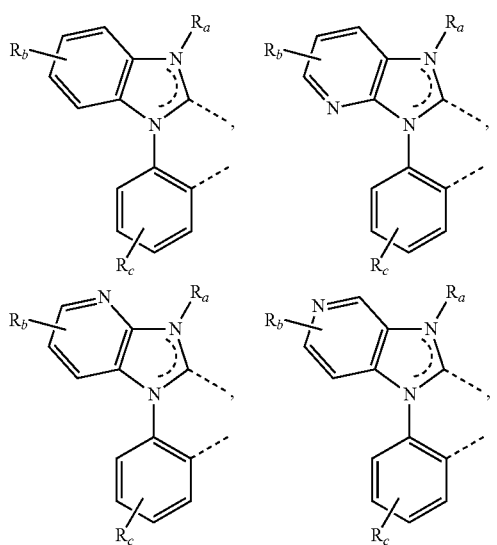

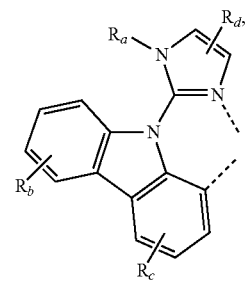

and wherein $R_a$, $R_b$, $R_c$, and $R_d$ can represent mono, di, tri, or tetra substitution, or no substitution; and $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand. In another embodiment, $L^3$ is same as $L^2$ and the compound has the formula of $M(L^1)(L^2)_2$.

In another embodiment where the compound has the formula of $M(L^1)_x(L^2)_y(L^3)_z$, the first ligand $L^1$ is selected from group consisting of:

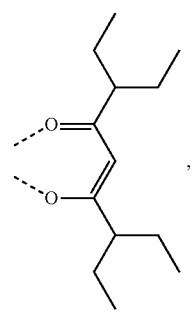 $L_{A1}$
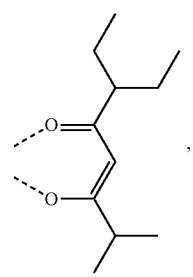 $L_{A2}$
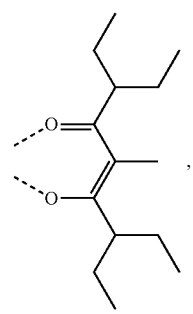 $L_{A3}$
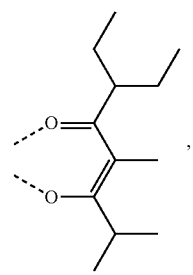 $L_{A4}$
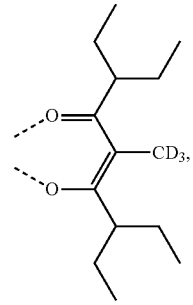 $L_{A5}$
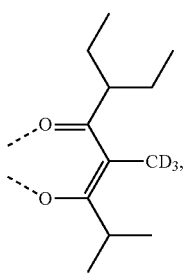 $L_{A6}$
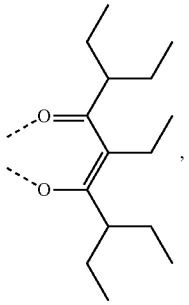 $L_{A7}$
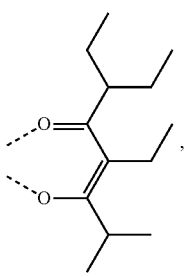 $L_{A8}$
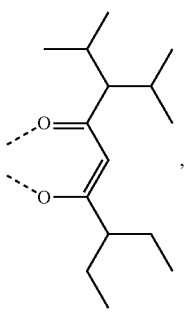 $L_{A9}$
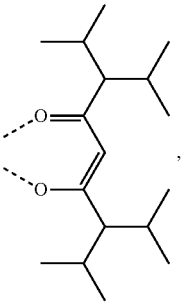 $L_{A10}$

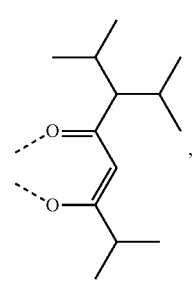 L<sub>A11</sub>
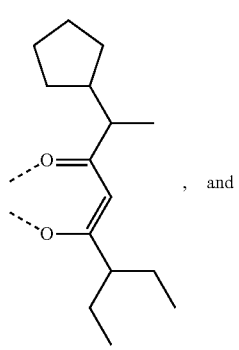 L<sub>A12</sub> , and
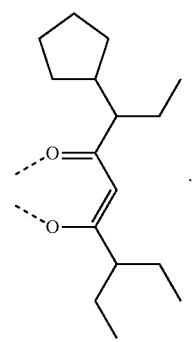 L<sub>A13</sub> .
In one embodiment, the second ligand L² is selected from group consisting of:
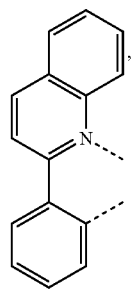 L<sub>Q1</sub>
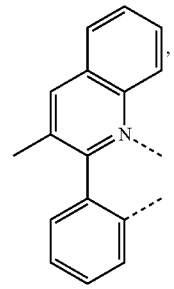 L<sub>Q2</sub>
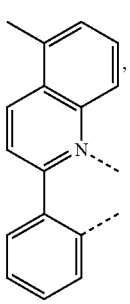 L<sub>Q3</sub>
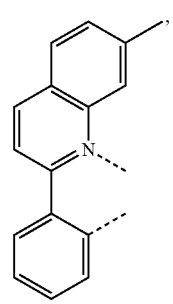 L<sub>Q4</sub>
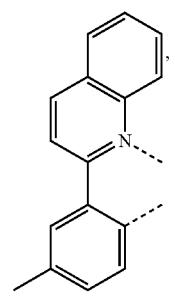 L<sub>Q5</sub>
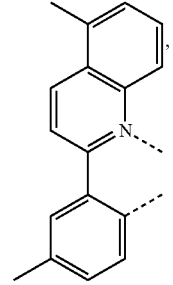 L<sub>Q6</sub>

-continued
$L_{Q7}$
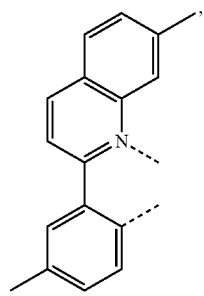
$L_{Q8}$
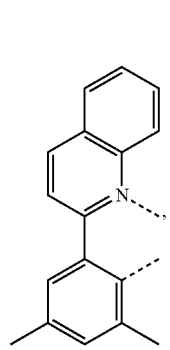
$L_{Q9}$
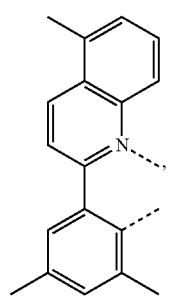
$L_{Q10}$
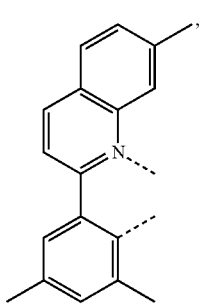
$L_{Q11}$
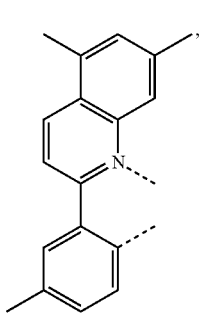
-continued
$L_{Q12}$
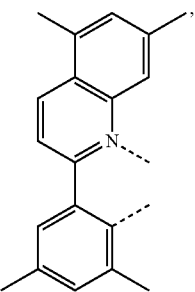
$L_{Q13}$
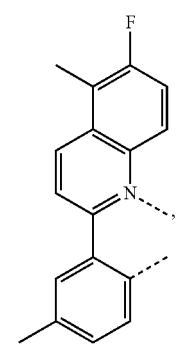
$L_{Q14}$
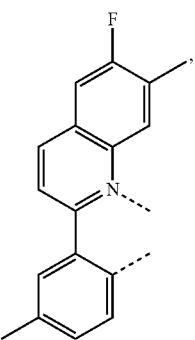
$L_{Q15}$
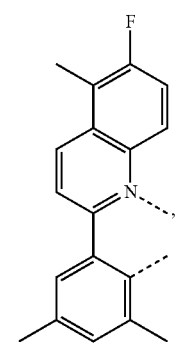

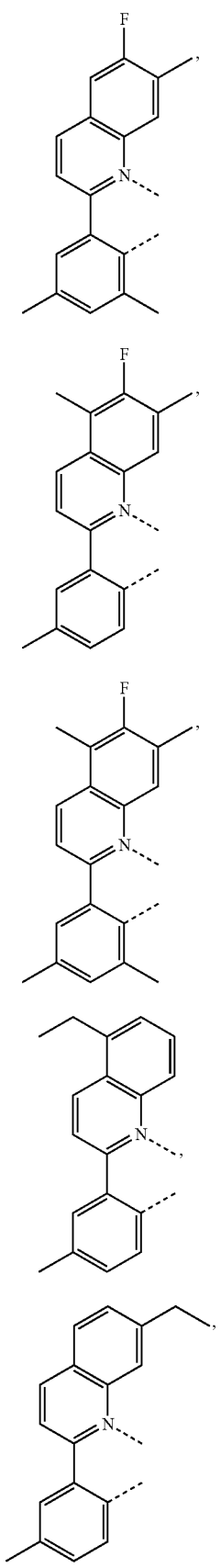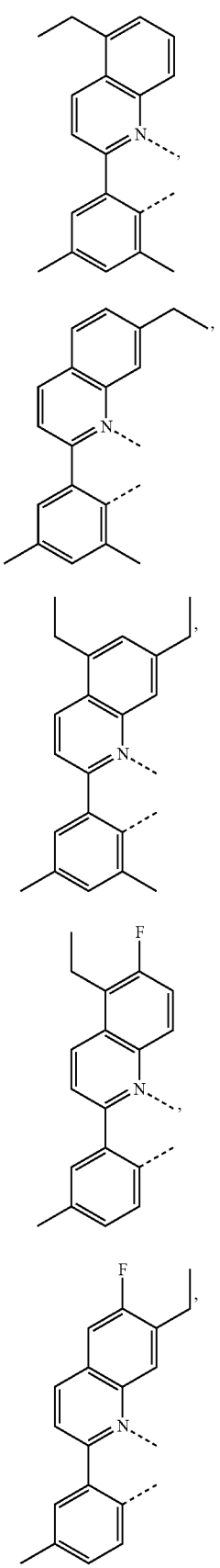

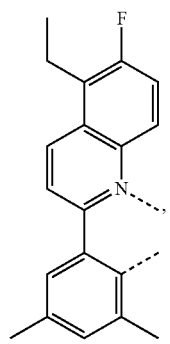 L_Q26
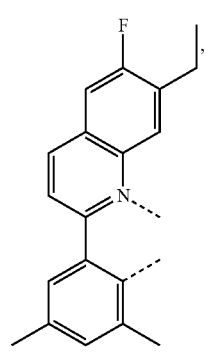 L_Q27
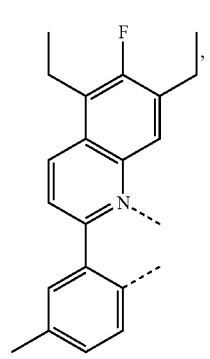 L_Q28
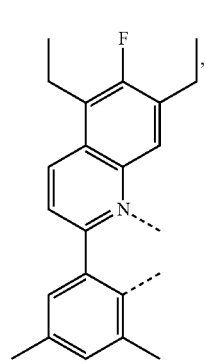 L_Q29
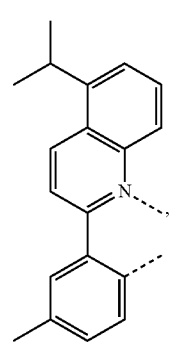 L_Q30
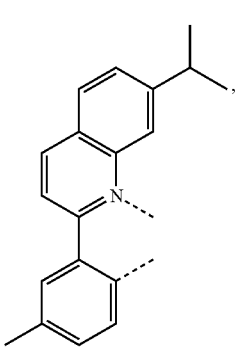 L_Q31
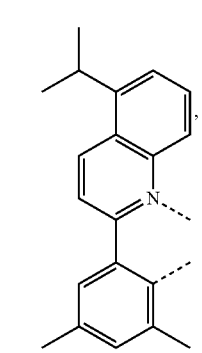 L_Q32
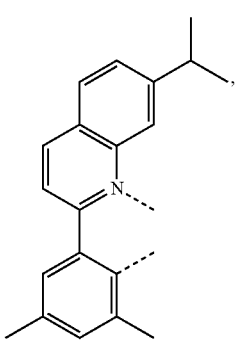 L_Q33

-continued
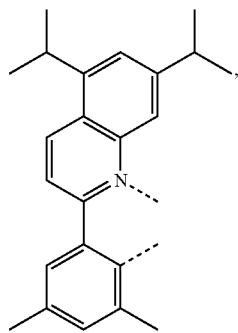  L_Q34
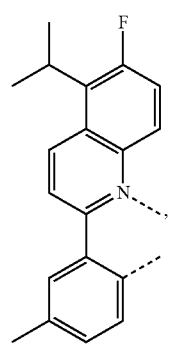  L_Q35
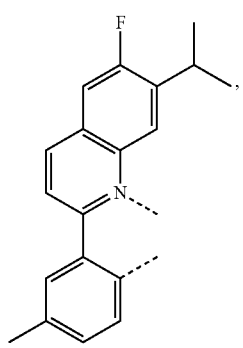  L_Q36
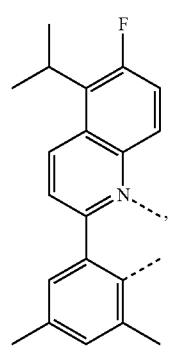  L_Q37
-continued
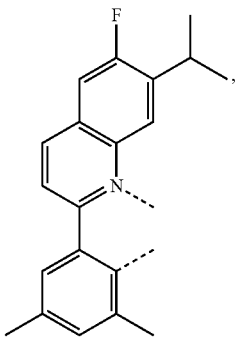  L_Q38
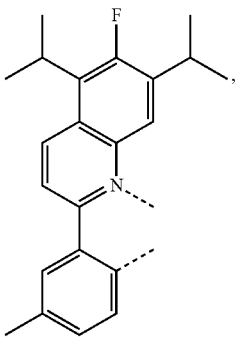  L_Q39
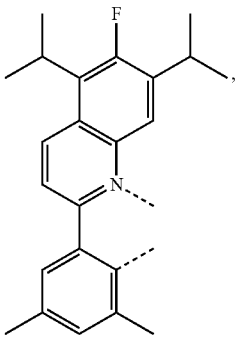  L_Q40
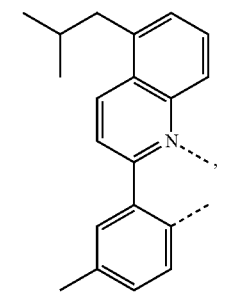  L_Q41
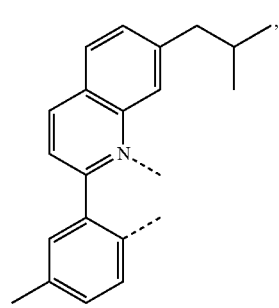  L_Q42

L_{Q43}
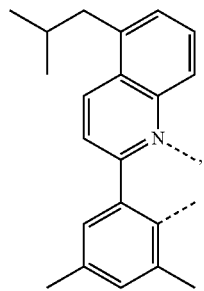
L_{Q44}
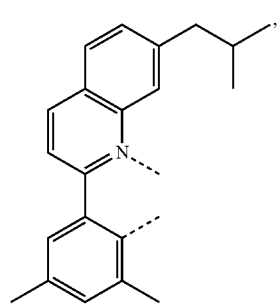
L_{Q45}
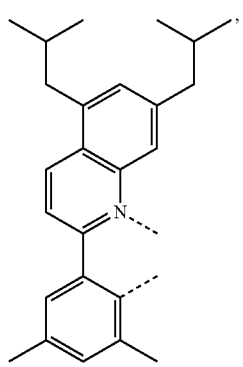
L_{Q46}
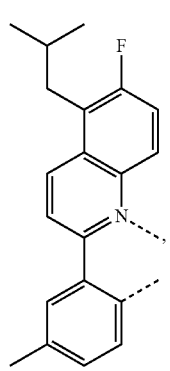
L_{Q47}
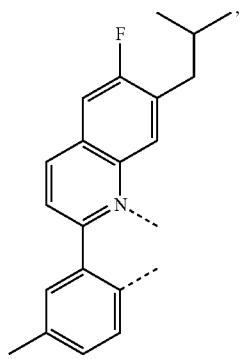
L_{Q48}
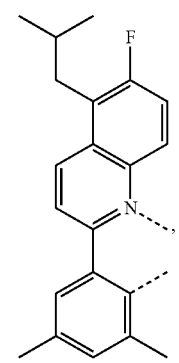
L_{Q49}
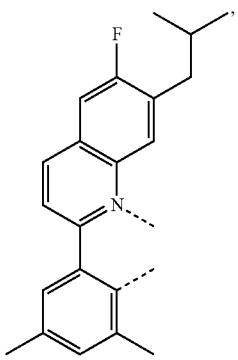
L_{Q50}
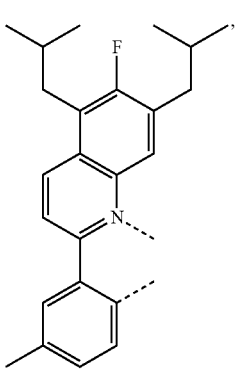

-continued
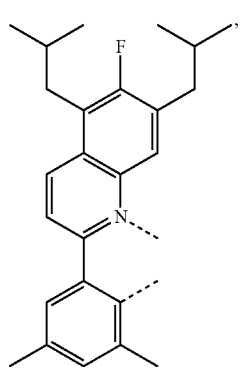
L<sub>Q51</sub>
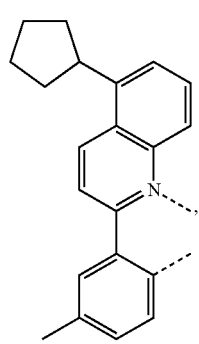
L<sub>Q52</sub>
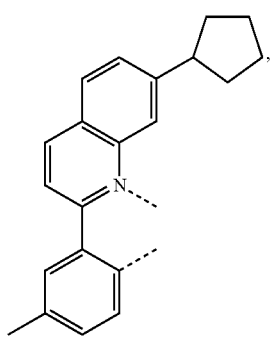
L<sub>Q53</sub>
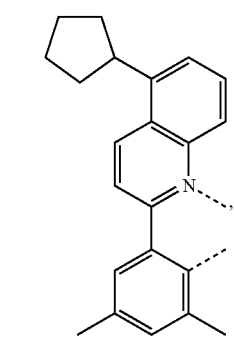
L<sub>Q54</sub>
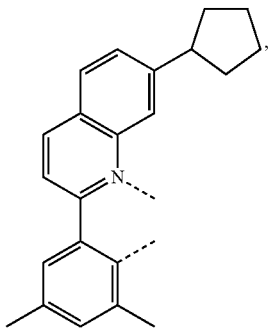
L<sub>Q55</sub>
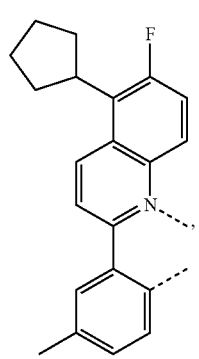
L<sub>Q56</sub>
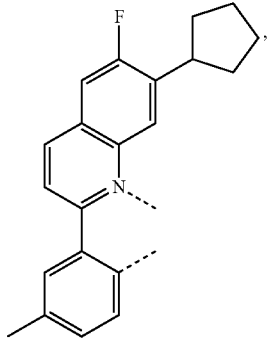
L<sub>Q57</sub>
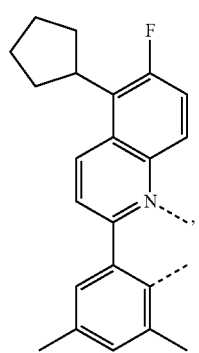
L<sub>Q58</sub>

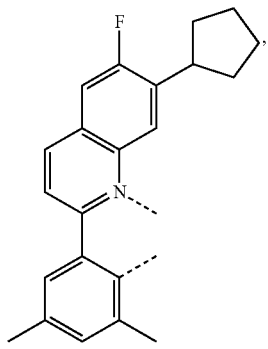  L<sub>Q59</sub>
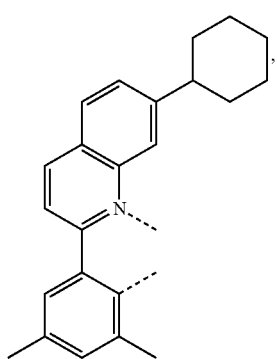  L<sub>Q63</sub>
L<sub>Q60</sub>
L<sub>Q64</sub>
L<sub>Q61</sub>
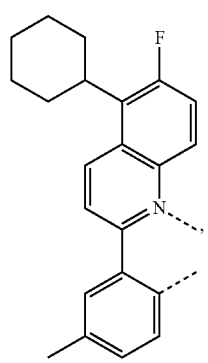  L<sub>Q65</sub>
L<sub>Q62</sub>
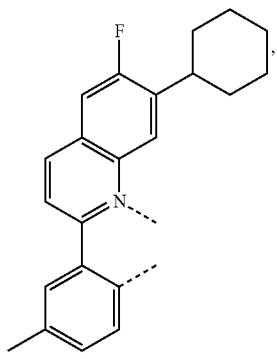
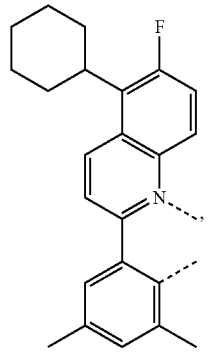  L<sub>Q66</sub>

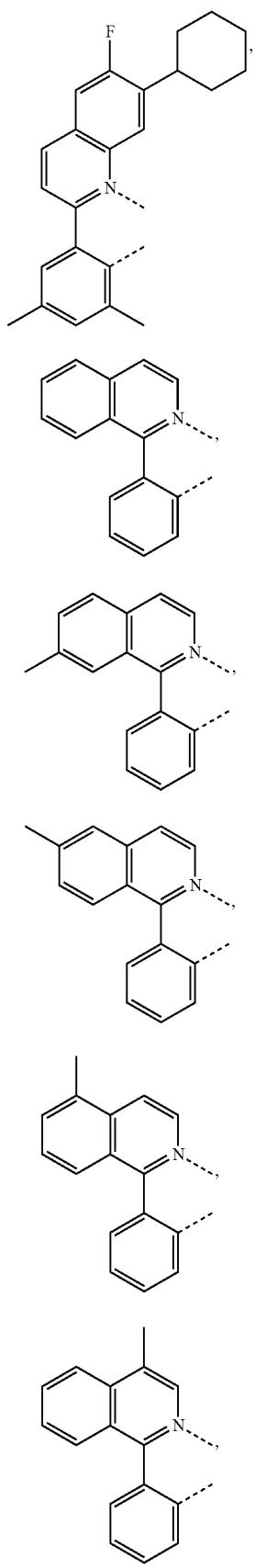

L_{Q67}
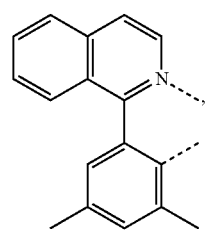
L_{Q73}
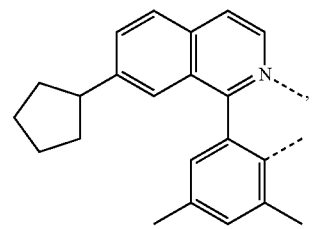
L_{Q74}
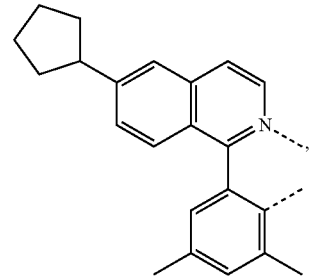
L_{Q75}
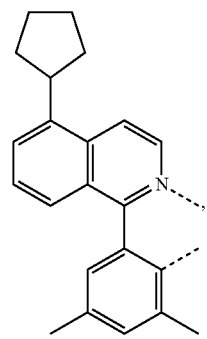
L_{Q76}

L_Q78 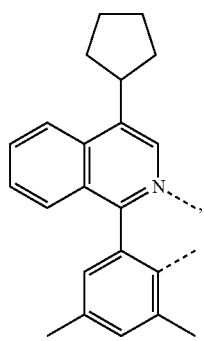
L_Q79 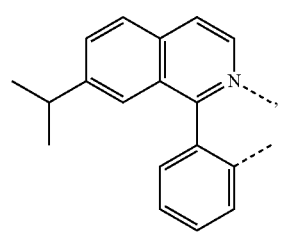
L_Q80 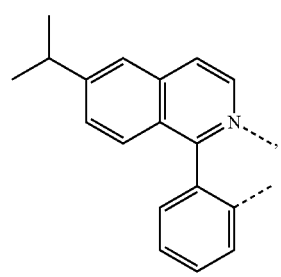
L_Q81 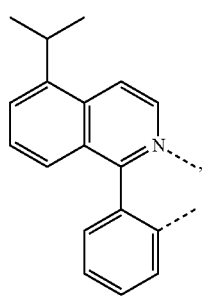
L_Q82 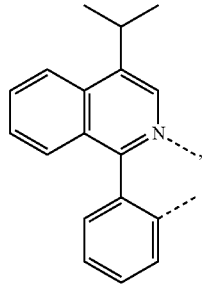
L_Q83 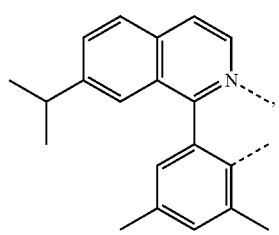
L_Q84 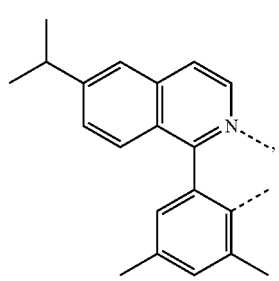
L_Q85 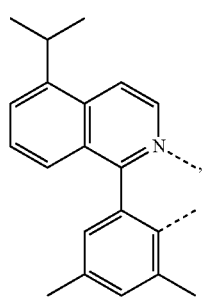
L_Q86 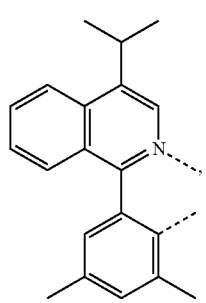
L_Q87 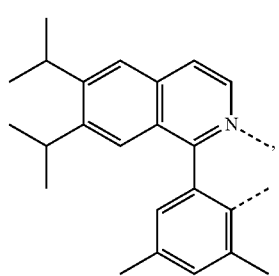

-continued
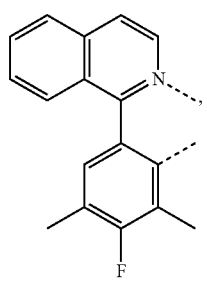 L<sub>Q88</sub>
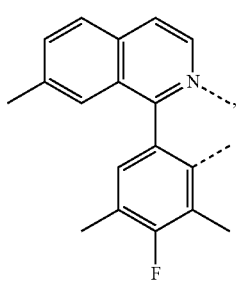 L<sub>Q89</sub>
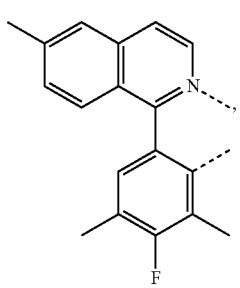 L<sub>Q90</sub>
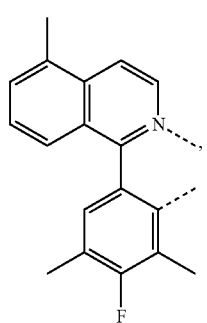 L<sub>Q91</sub>
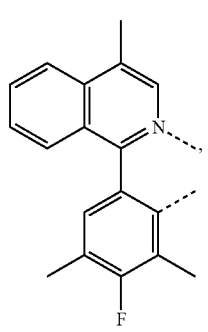 L<sub>Q92</sub>
-continued
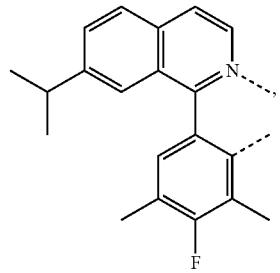 L<sub>Q93</sub>
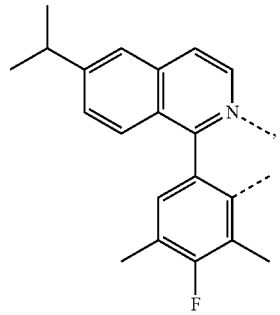 L<sub>Q94</sub>
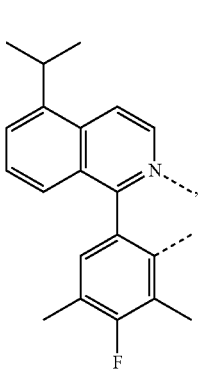 L<sub>Q95</sub>
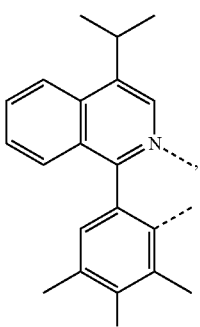 L<sub>Q96</sub>
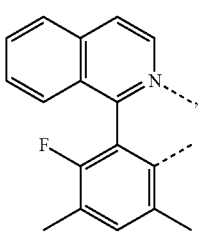 L<sub>Q97</sub>

L<sub>Q98</sub>
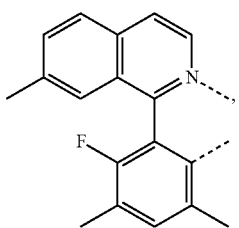
L<sub>Q99</sub>
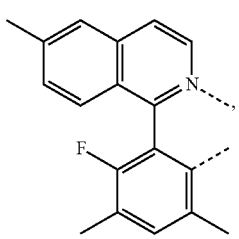
L<sub>Q100</sub>
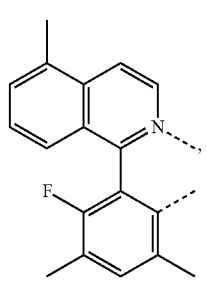
L<sub>Q101</sub>
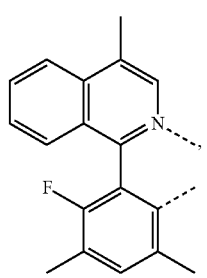
L<sub>Q102</sub>
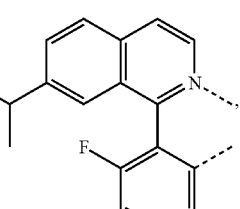
L<sub>Q103</sub>
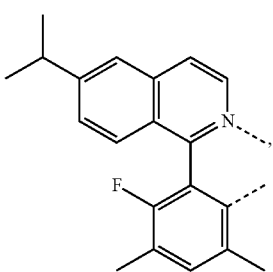
L<sub>Q104</sub>
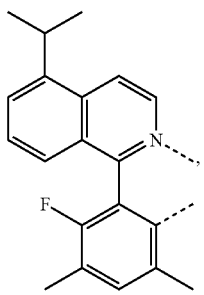
L<sub>Q105</sub>
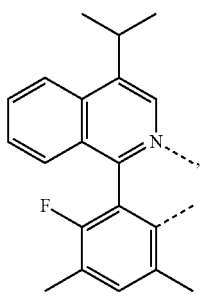
L<sub>Q106</sub>
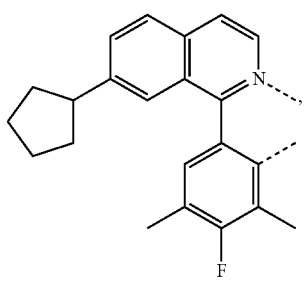
L<sub>Q107</sub>
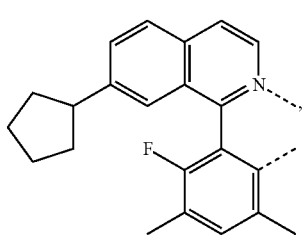
L<sub>Q108</sub>
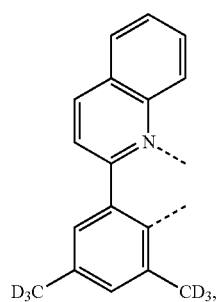

L_{Q109}
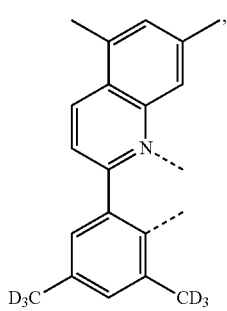
L_{Q110}
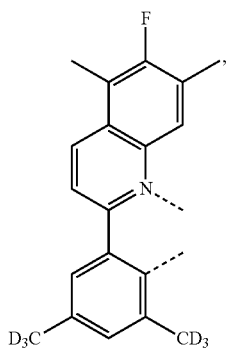
L_{Q111}
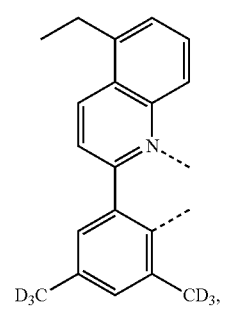
L_{Q112}
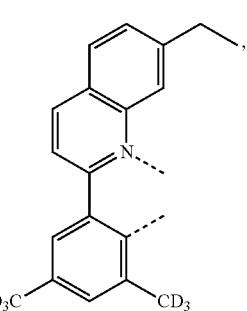
L_{Q113}
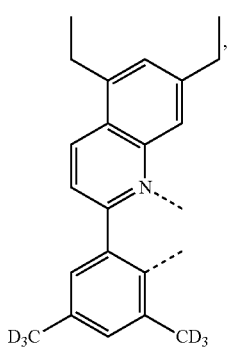
L_{Q114}
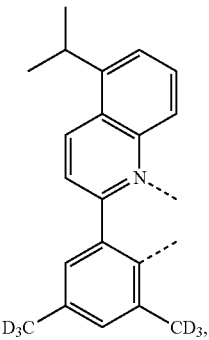
L_{Q115}
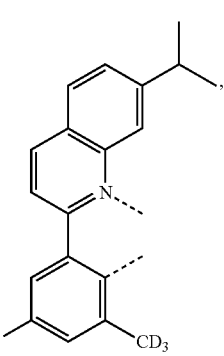
L_{Q116}
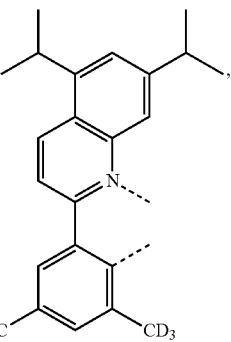
L_{Q117}
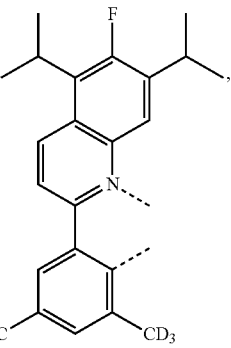

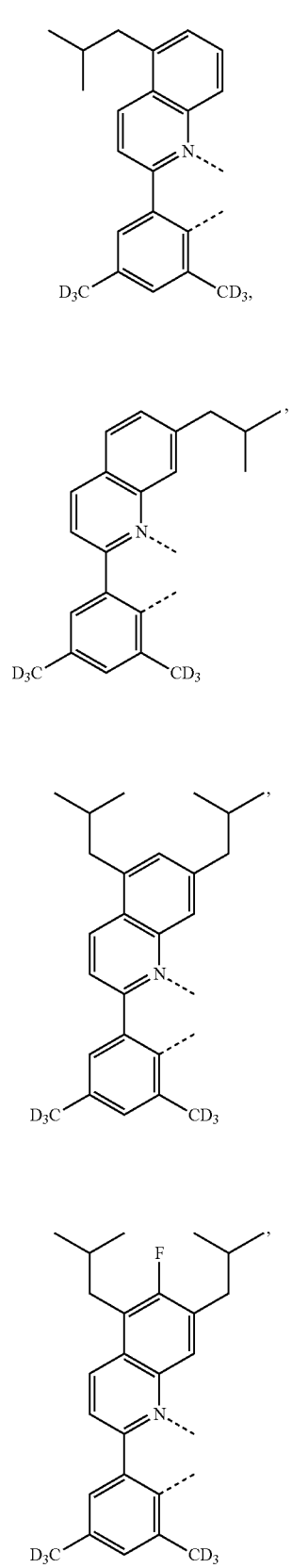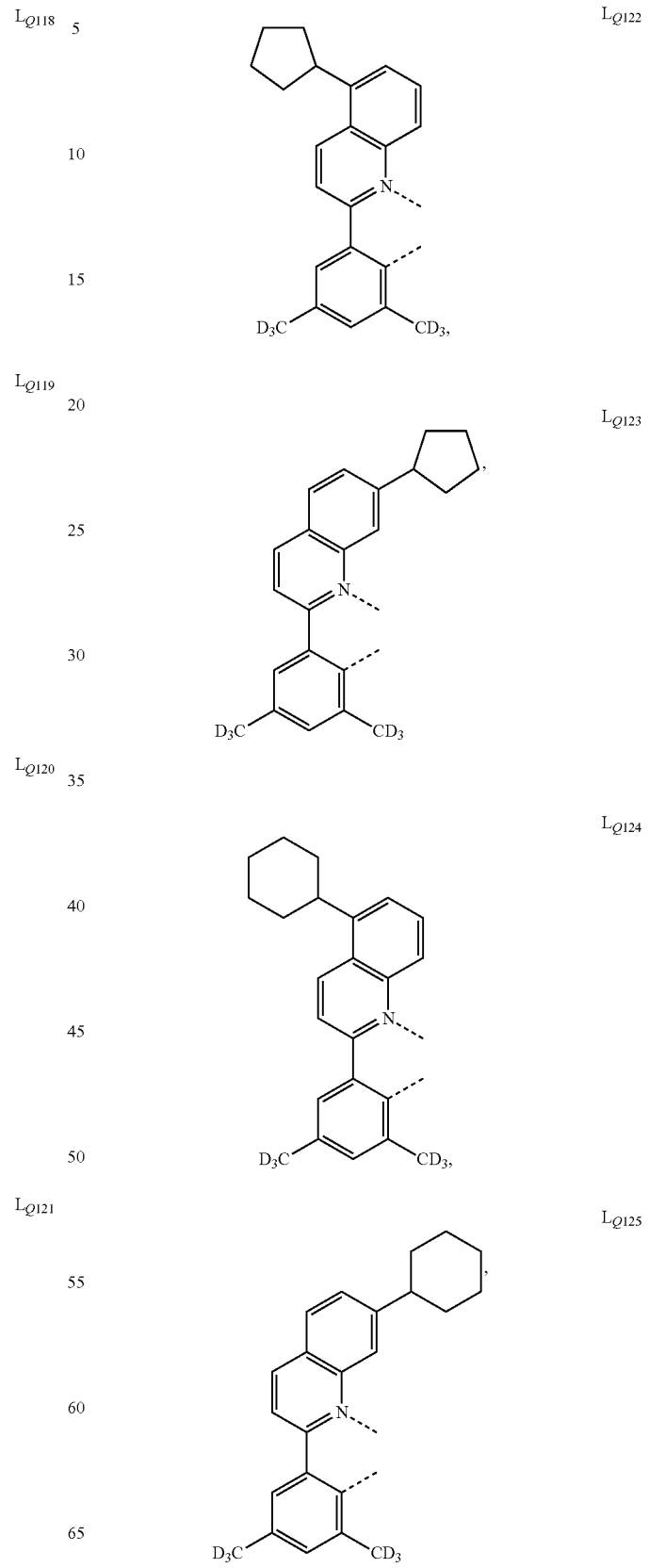

L_{Q126}
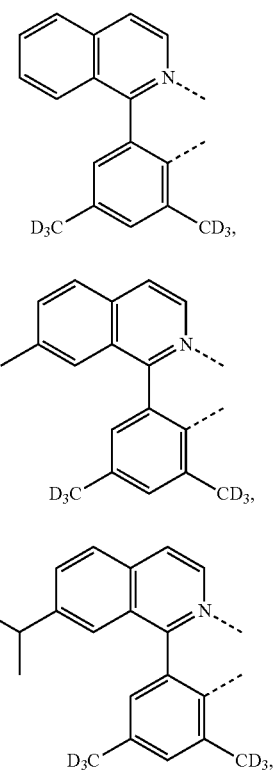
L_{Q127}
L_{Q128}
L_{Q129}
L_{Q130}
L_{Q131}
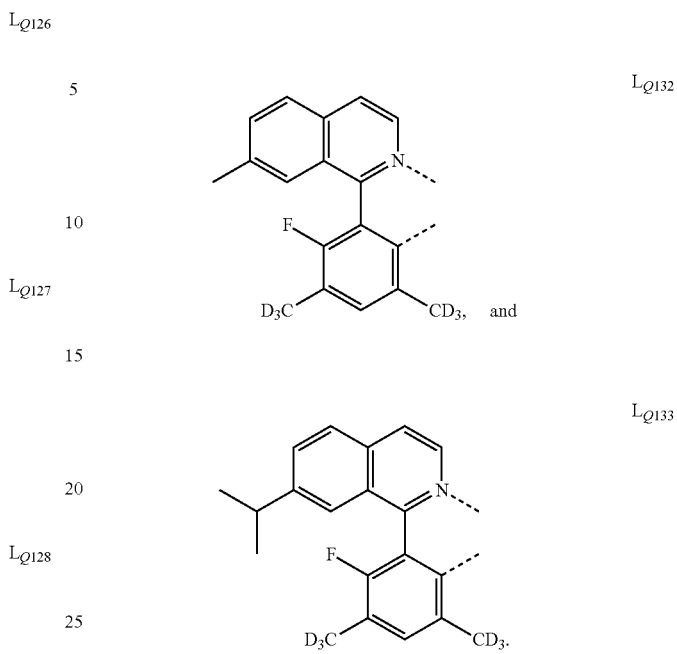
L_{Q132}
L_{Q133}
In one embodiment, the compound having the formula of $M(L^1)(L^2)_2$ can be selected from the group consisting of Compound 1 to Compound 1729 defined in Table 1 below:
Compound 8
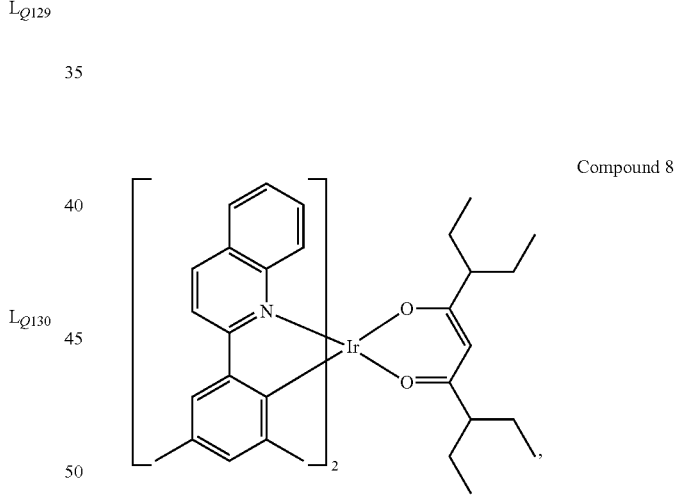
Compound 9
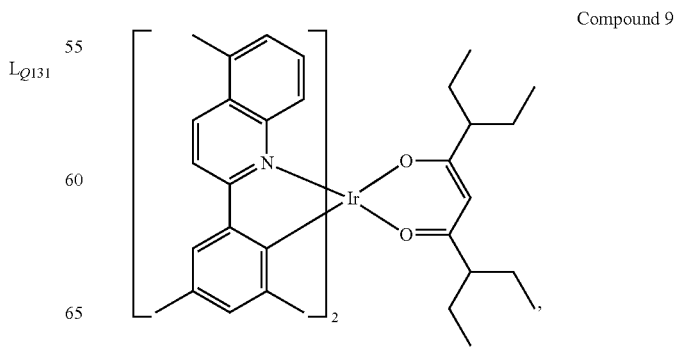

Compound 12
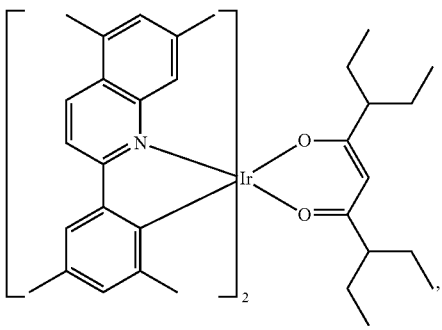
Compound 55
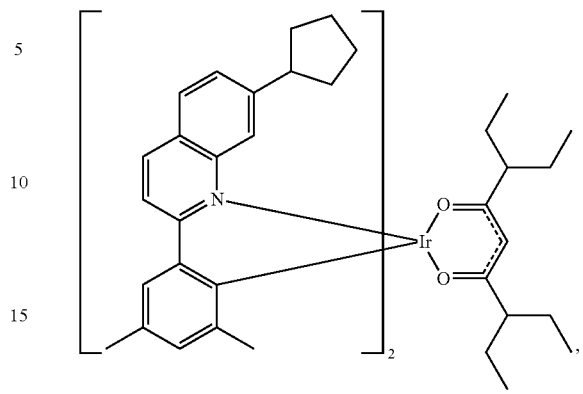
Compound 32
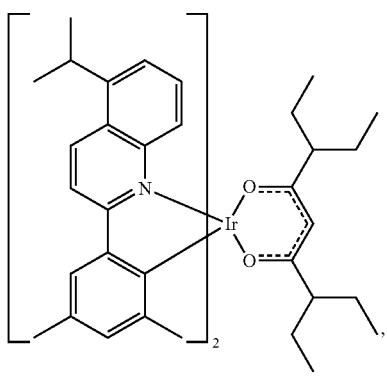
Compound 62
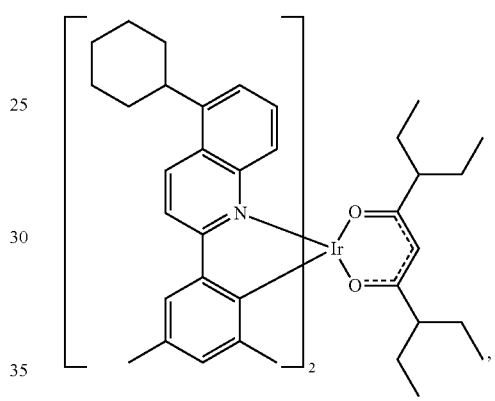
Compound 43
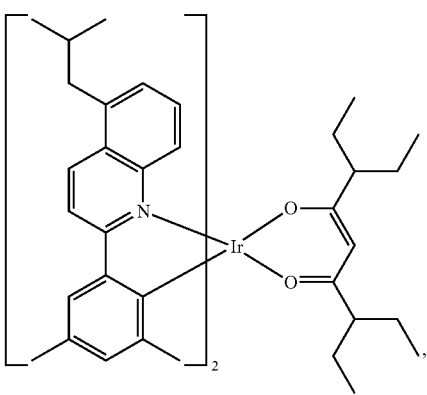
Compound 83
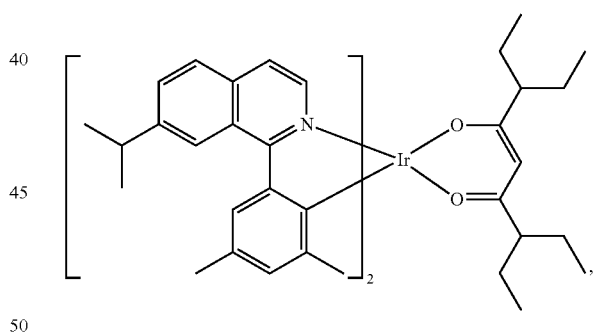
Compound 54
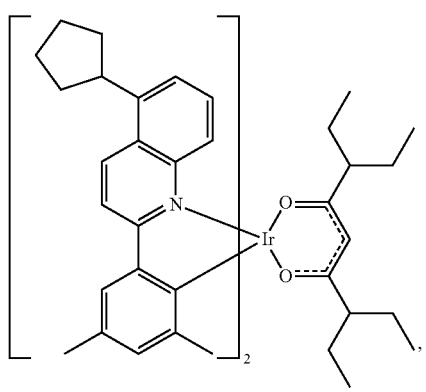
Compound 93
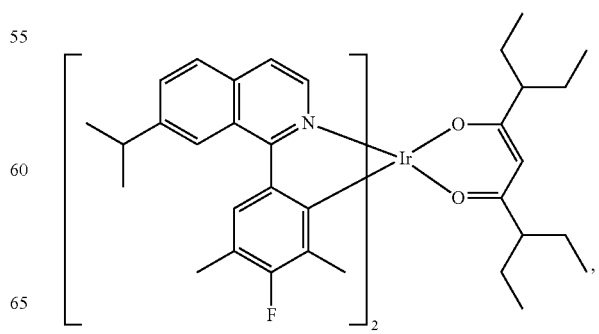

Compound 118

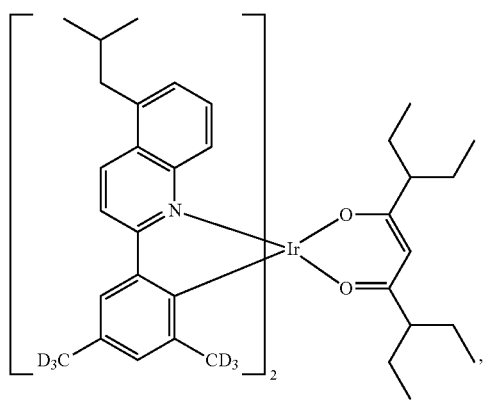

Compound 141

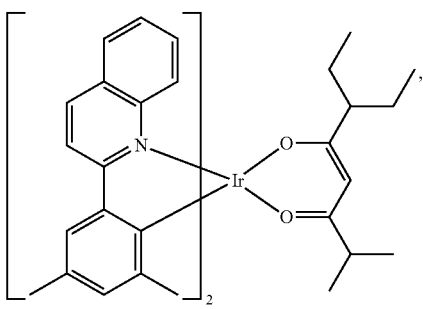

Compound 142

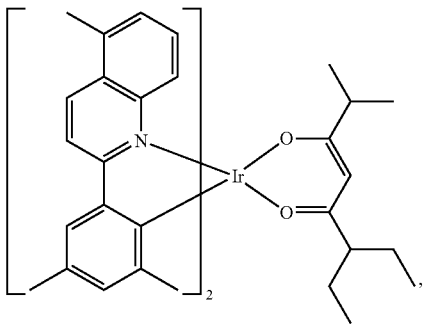

Compound 176

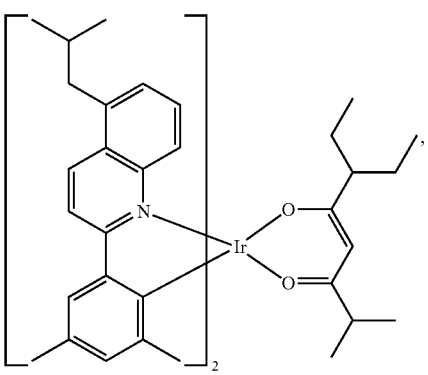

Compound 278

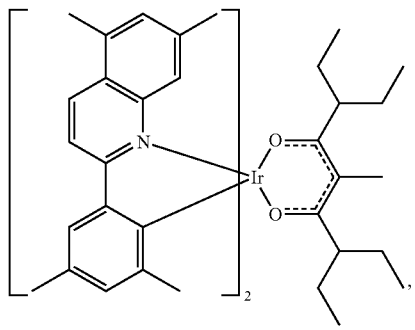

, and

Compound 320

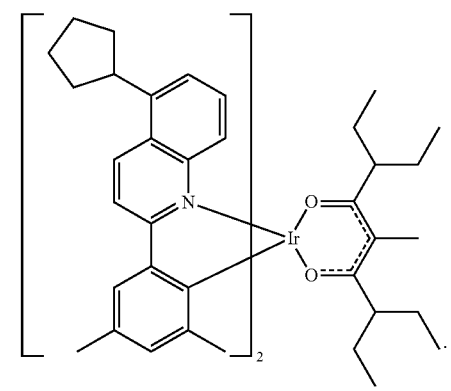

.

In one embodiment, the compound comprising the first ligand $L^1$ having Formula I as defined herein can be selected from the group consisting of:

TABLE 1

| Compound number | $L^1$ | $L^2$ |
|---|---|---|
| 1. | $L_{A1}$ | $L_{Q1}$ |
| 2. | $L_{A1}$ | $L_{Q2}$ |
| 3. | $L_{A1}$ | $L_{Q3}$ |
| 4. | $L_{A1}$ | $L_{Q4}$ |
| 5. | $L_{A1}$ | $L_{Q5}$ |
| 6. | $L_{A1}$ | $L_{Q6}$ |
| 7. | $L_{A1}$ | $L_{Q7}$ |
| 8. | $L_{A1}$ | $L_{Q8}$ |
| 9. | $L_{A1}$ | $L_{Q9}$ |
| 10. | $L_{A1}$ | $L_{Q10}$ |
| 11. | $L_{A1}$ | $L_{Q11}$ |
| 12. | $L_{A1}$ | $L_{Q12}$ |
| 13. | $L_{A1}$ | $L_{Q13}$ |
| 14. | $L_{A1}$ | $L_{Q14}$ |
| 15. | $L_{A1}$ | $L_{Q15}$ |
| 16. | $L_{A1}$ | $L_{Q16}$ |
| 17. | $L_{A1}$ | $L_{Q17}$ |
| 18. | $L_{A1}$ | $L_{Q18}$ |
| 19. | $L_{A1}$ | $L_{Q19}$ |
| 20. | $L_{A1}$ | $L_{Q20}$ |
| 21. | $L_{A1}$ | $L_{Q21}$ |
| 22. | $L_{A1}$ | $L_{Q22}$ |
| 23. | $L_{A1}$ | $L_{Q23}$ |
| 24. | $L_{A1}$ | $L_{Q24}$ |
| 25. | $L_{A1}$ | $L_{Q25}$ |
| 26. | $L_{A1}$ | $L_{Q26}$ |
| 27. | $L_{A1}$ | $L_{Q27}$ |
| 28. | $L_{A1}$ | $L_{Q28}$ |
| 29. | $L_{A1}$ | $L_{Q29}$ |
| 30. | $L_{A1}$ | $L_{Q30}$ |
| 31. | $L_{A1}$ | $L_{Q31}$ |
| 32. | $L_{A1}$ | $L_{Q32}$ |

TABLE 1-continued

| Compound number | $L^1$ | $L^2$ |
|---|---|---|
| 33. | $L_{A1}$ | $L_{Q33}$ |
| 34. | $L_{A1}$ | $L_{Q34}$ |
| 35. | $L_{A1}$ | $L_{Q35}$ |
| 36. | $L_{A1}$ | $L_{Q36}$ |
| 37. | $L_{A1}$ | $L_{Q37}$ |
| 38. | $L_{A1}$ | $L_{Q38}$ |
| 39. | $L_{A1}$ | $L_{Q39}$ |
| 40. | $L_{A1}$ | $L_{Q40}$ |
| 41. | $L_{A1}$ | $L_{Q41}$ |
| 42. | $L_{A1}$ | $L_{Q42}$ |
| 43. | $L_{A1}$ | $L_{Q43}$ |
| 44. | $L_{A1}$ | $L_{Q44}$ |
| 45. | $L_{A1}$ | $L_{Q45}$ |
| 46. | $L_{A1}$ | $L_{Q46}$ |
| 47. | $L_{A1}$ | $L_{Q47}$ |
| 48. | $L_{A1}$ | $L_{Q48}$ |
| 49. | $L_{A1}$ | $L_{Q49}$ |
| 50. | $L_{A1}$ | $L_{Q50}$ |
| 51. | $L_{A1}$ | $L_{Q51}$ |
| 52. | $L_{A1}$ | $L_{Q52}$ |
| 53. | $L_{A1}$ | $L_{Q53}$ |
| 54. | $L_{A1}$ | $L_{Q54}$ |
| 55. | $L_{A1}$ | $L_{Q55}$ |
| 56. | $L_{A1}$ | $L_{Q56}$ |
| 57. | $L_{A1}$ | $L_{Q57}$ |
| 58. | $L_{A1}$ | $L_{Q58}$ |
| 59. | $L_{A1}$ | $L_{Q59}$ |
| 60. | $L_{A1}$ | $L_{Q60}$ |
| 61. | $L_{A1}$ | $L_{Q61}$ |
| 62. | $L_{A1}$ | $L_{Q62}$ |
| 63. | $L_{A1}$ | $L_{Q63}$ |
| 64. | $L_{A1}$ | $L_{Q64}$ |
| 65. | $L_{A1}$ | $L_{Q65}$ |
| 66. | $L_{A1}$ | $L_{Q66}$ |
| 67. | $L_{A1}$ | $L_{Q67}$ |
| 68. | $L_{A1}$ | $L_{Q68}$ |
| 69. | $L_{A1}$ | $L_{Q69}$ |
| 70. | $L_{A1}$ | $L_{Q70}$ |
| 71. | $L_{A1}$ | $L_{Q71}$ |
| 72. | $L_{A1}$ | $L_{Q72}$ |
| 73. | $L_{A1}$ | $L_{Q73}$ |
| 74. | $L_{A1}$ | $L_{Q74}$ |
| 75. | $L_{A1}$ | $L_{Q75}$ |
| 76. | $L_{A1}$ | $L_{Q76}$ |
| 77. | $L_{A1}$ | $L_{Q77}$ |
| 78. | $L_{A1}$ | $L_{Q78}$ |
| 79. | $L_{A1}$ | $L_{Q79}$ |
| 80. | $L_{A1}$ | $L_{Q80}$ |
| 81. | $L_{A1}$ | $L_{Q81}$ |
| 82. | $L_{A1}$ | $L_{Q82}$ |
| 83. | $L_{A1}$ | $L_{Q83}$ |
| 84. | $L_{A1}$ | $L_{Q84}$ |
| 85. | $L_{A1}$ | $L_{Q85}$ |
| 86. | $L_{A1}$ | $L_{Q86}$ |
| 87. | $L_{A1}$ | $L_{Q87}$ |
| 88. | $L_{A1}$ | $L_{Q88}$ |
| 89. | $L_{A1}$ | $L_{Q89}$ |
| 90. | $L_{A1}$ | $L_{Q90}$ |
| 91. | $L_{A1}$ | $L_{Q91}$ |
| 92. | $L_{A1}$ | $L_{Q92}$ |
| 93. | $L_{A1}$ | $L_{Q93}$ |
| 94. | $L_{A1}$ | $L_{Q94}$ |
| 95. | $L_{A1}$ | $L_{Q95}$ |
| 96. | $L_{A1}$ | $L_{Q96}$ |
| 97. | $L_{A1}$ | $L_{Q97}$ |
| 98. | $L_{A1}$ | $L_{Q98}$ |
| 99. | $L_{A1}$ | $L_{Q99}$ |
| 100. | $L_{A1}$ | $L_{Q100}$ |
| 101. | $L_{A1}$ | $L_{Q101}$ |
| 102. | $L_{A1}$ | $L_{Q102}$ |
| 103. | $L_{A1}$ | $L_{Q103}$ |
| 104. | $L_{A1}$ | $L_{Q104}$ |
| 105. | $L_{A1}$ | $L_{Q105}$ |
| 106. | $L_{A1}$ | $L_{Q106}$ |
| 107. | $L_{A1}$ | $L_{Q107}$ |
| 108. | $L_{A1}$ | $L_{Q108}$ |
| 109. | $L_{A1}$ | $L_{Q109}$ |
| 110. | $L_{A1}$ | $L_{Q110}$ |
| 111. | $L_{A1}$ | $L_{Q111}$ |
| 112. | $L_{A1}$ | $L_{Q112}$ |
| 113. | $L_{A1}$ | $L_{Q113}$ |
| 114. | $L_{A1}$ | $L_{Q114}$ |
| 115. | $L_{A1}$ | $L_{Q115}$ |
| 116. | $L_{A1}$ | $L_{Q116}$ |
| 117. | $L_{A1}$ | $L_{Q117}$ |
| 118. | $L_{A1}$ | $L_{Q118}$ |
| 119. | $L_{A1}$ | $L_{Q119}$ |
| 120. | $L_{A1}$ | $L_{Q120}$ |
| 121. | $L_{A1}$ | $L_{Q121}$ |
| 122. | $L_{A1}$ | $L_{Q122}$ |
| 123. | $L_{A1}$ | $L_{Q123}$ |
| 124. | $L_{A1}$ | $L_{Q124}$ |
| 125. | $L_{A1}$ | $L_{Q125}$ |
| 126. | $L_{A1}$ | $L_{Q126}$ |
| 127. | $L_{A1}$ | $L_{Q127}$ |
| 128. | $L_{A1}$ | $L_{Q128}$ |
| 129. | $L_{A1}$ | $L_{Q129}$ |
| 130. | $L_{A1}$ | $L_{Q130}$ |
| 131. | $L_{A1}$ | $L_{Q131}$ |
| 132. | $L_{A1}$ | $L_{Q132}$ |
| 133. | $L_{A1}$ | $L_{Q133}$ |
| 134. | $L_{A2}$ | $L_{Q1}$ |
| 135. | $L_{A2}$ | $L_{Q2}$ |
| 136. | $L_{A2}$ | $L_{Q3}$ |
| 137. | $L_{A2}$ | $L_{Q4}$ |
| 138. | $L_{A2}$ | $L_{Q5}$ |
| 139. | $L_{A2}$ | $L_{Q6}$ |
| 140. | $L_{A2}$ | $L_{Q7}$ |
| 141. | $L_{A2}$ | $L_{Q8}$ |
| 142. | $L_{A2}$ | $L_{Q9}$ |
| 143. | $L_{A2}$ | $L_{Q10}$ |
| 144. | $L_{A2}$ | $L_{Q11}$ |
| 145. | $L_{A2}$ | $L_{Q12}$ |
| 146. | $L_{A2}$ | $L_{Q13}$ |
| 147. | $L_{A2}$ | $L_{Q14}$ |
| 148. | $L_{A2}$ | $L_{Q15}$ |
| 149. | $L_{A2}$ | $L_{Q16}$ |
| 150. | $L_{A2}$ | $L_{Q17}$ |
| 151. | $L_{A2}$ | $L_{Q18}$ |
| 152. | $L_{A2}$ | $L_{Q19}$ |
| 153. | $L_{A2}$ | $L_{Q20}$ |
| 154. | $L_{A2}$ | $L_{Q21}$ |
| 155. | $L_{A2}$ | $L_{Q22}$ |
| 156. | $L_{A2}$ | $L_{Q23}$ |
| 157. | $L_{A2}$ | $L_{Q24}$ |
| 158. | $L_{A2}$ | $L_{Q25}$ |
| 159. | $L_{A2}$ | $L_{Q26}$ |
| 160. | $L_{A2}$ | $L_{Q27}$ |
| 161. | $L_{A2}$ | $L_{Q28}$ |
| 162. | $L_{A2}$ | $L_{Q29}$ |
| 163. | $L_{A2}$ | $L_{Q30}$ |
| 164. | $L_{A2}$ | $L_{Q31}$ |
| 165. | $L_{A2}$ | $L_{Q32}$ |
| 166. | $L_{A2}$ | $L_{Q33}$ |
| 167. | $L_{A2}$ | $L_{Q34}$ |
| 168. | $L_{A2}$ | $L_{Q35}$ |
| 169. | $L_{A2}$ | $L_{Q36}$ |
| 170. | $L_{A2}$ | $L_{Q37}$ |
| 171. | $L_{A2}$ | $L_{Q38}$ |
| 172. | $L_{A2}$ | $L_{Q39}$ |
| 173. | $L_{A2}$ | $L_{Q40}$ |
| 174. | $L_{A2}$ | $L_{Q41}$ |
| 175. | $L_{A2}$ | $L_{Q42}$ |
| 176. | $L_{A2}$ | $L_{Q43}$ |
| 177. | $L_{A2}$ | $L_{Q44}$ |
| 178. | $L_{A2}$ | $L_{Q45}$ |
| 179. | $L_{A2}$ | $L_{Q46}$ |
| 180. | $L_{A2}$ | $L_{Q47}$ |
| 181. | $L_{A2}$ | $L_{Q48}$ |
| 182. | $L_{A2}$ | $L_{Q49}$ |
| 183. | $L_{A2}$ | $L_{Q50}$ |
| 184. | $L_{A2}$ | $L_{Q51}$ |
| 185. | $L_{A2}$ | $L_{Q52}$ |
| 186. | $L_{A2}$ | $L_{Q53}$ |

TABLE 1-continued

| Compound number | $L^1$ | $L^2$ |
|---|---|---|
| 187. | $L_{A2}$ | $L_{Q54}$ |
| 188. | $L_{A2}$ | $L_{Q55}$ |
| 189. | $L_{A2}$ | $L_{Q56}$ |
| 190. | $L_{A2}$ | $L_{Q57}$ |
| 191. | $L_{A2}$ | $L_{Q58}$ |
| 192. | $L_{A2}$ | $L_{Q59}$ |
| 193. | $L_{A2}$ | $L_{Q60}$ |
| 194. | $L_{A2}$ | $L_{Q61}$ |
| 195. | $L_{A2}$ | $L_{Q62}$ |
| 196. | $L_{A2}$ | $L_{Q63}$ |
| 197. | $L_{A2}$ | $L_{Q64}$ |
| 198. | $L_{A2}$ | $L_{Q65}$ |
| 199. | $L_{A2}$ | $L_{Q66}$ |
| 200. | $L_{A2}$ | $L_{Q67}$ |
| 201. | $L_{A2}$ | $L_{Q68}$ |
| 202. | $L_{A2}$ | $L_{Q69}$ |
| 203. | $L_{A2}$ | $L_{Q70}$ |
| 204. | $L_{A2}$ | $L_{Q71}$ |
| 205. | $L_{A2}$ | $L_{Q72}$ |
| 206. | $L_{A2}$ | $L_{Q73}$ |
| 207. | $L_{A2}$ | $L_{Q74}$ |
| 208. | $L_{A2}$ | $L_{Q75}$ |
| 209. | $L_{A2}$ | $L_{Q76}$ |
| 210. | $L_{A2}$ | $L_{Q77}$ |
| 211. | $L_{A2}$ | $L_{Q78}$ |
| 212. | $L_{A2}$ | $L_{Q79}$ |
| 213. | $L_{A2}$ | $L_{Q80}$ |
| 214. | $L_{A2}$ | $L_{Q81}$ |
| 215. | $L_{A2}$ | $L_{Q82}$ |
| 216. | $L_{A2}$ | $L_{Q83}$ |
| 217. | $L_{A2}$ | $L_{Q84}$ |
| 218. | $L_{A2}$ | $L_{Q85}$ |
| 219. | $L_{A2}$ | $L_{Q86}$ |
| 220. | $L_{A2}$ | $L_{Q87}$ |
| 221. | $L_{A2}$ | $L_{Q88}$ |
| 222. | $L_{A2}$ | $L_{Q89}$ |
| 223. | $L_{A2}$ | $L_{Q90}$ |
| 224. | $L_{A2}$ | $L_{Q91}$ |
| 225. | $L_{A2}$ | $L_{Q92}$ |
| 226. | $L_{A2}$ | $L_{Q93}$ |
| 227. | $L_{A2}$ | $L_{Q94}$ |
| 228. | $L_{A2}$ | $L_{Q95}$ |
| 229. | $L_{A2}$ | $L_{Q96}$ |
| 230. | $L_{A2}$ | $L_{Q97}$ |
| 231. | $L_{A2}$ | $L_{Q98}$ |
| 232. | $L_{A2}$ | $L_{Q99}$ |
| 233. | $L_{A2}$ | $L_{Q100}$ |
| 234. | $L_{A2}$ | $L_{Q101}$ |
| 235. | $L_{A2}$ | $L_{Q102}$ |
| 236. | $L_{A2}$ | $L_{Q103}$ |
| 237. | $L_{A2}$ | $L_{Q104}$ |
| 238. | $L_{A2}$ | $L_{Q105}$ |
| 239. | $L_{A2}$ | $L_{Q106}$ |
| 240. | $L_{A2}$ | $L_{Q107}$ |
| 241. | $L_{A2}$ | $L_{Q108}$ |
| 242. | $L_{A2}$ | $L_{Q109}$ |
| 243. | $L_{A2}$ | $L_{Q110}$ |
| 244. | $L_{A2}$ | $L_{Q111}$ |
| 245. | $L_{A2}$ | $L_{Q112}$ |
| 246. | $L_{A2}$ | $L_{Q113}$ |
| 247. | $L_{A2}$ | $L_{Q114}$ |
| 248. | $L_{A2}$ | $L_{Q115}$ |
| 249. | $L_{A2}$ | $L_{Q116}$ |
| 250. | $L_{A2}$ | $L_{Q117}$ |
| 251. | $L_{A2}$ | $L_{Q118}$ |
| 252. | $L_{A2}$ | $L_{Q119}$ |
| 253. | $L_{A2}$ | $L_{Q120}$ |
| 254. | $L_{A2}$ | $L_{Q121}$ |
| 255. | $L_{A2}$ | $L_{Q122}$ |
| 256. | $L_{A2}$ | $L_{Q123}$ |
| 257. | $L_{A2}$ | $L_{Q124}$ |
| 258. | $L_{A2}$ | $L_{Q125}$ |
| 259. | $L_{A2}$ | $L_{Q126}$ |
| 260. | $L_{A2}$ | $L_{Q127}$ |
| 261. | $L_{A2}$ | $L_{Q128}$ |
| 262. | $L_{A2}$ | $L_{Q129}$ |
| 263. | $L_{A2}$ | $L_{Q130}$ |
| 264. | $L_{A2}$ | $L_{Q131}$ |
| 265. | $L_{A2}$ | $L_{Q132}$ |
| 266. | $L_{A2}$ | $L_{Q133}$ |
| 267. | $L_{A3}$ | $L_{Q1}$ |
| 268. | $L_{A3}$ | $L_{Q2}$ |
| 269. | $L_{A3}$ | $L_{Q3}$ |
| 270. | $L_{A3}$ | $L_{Q4}$ |
| 271. | $L_{A3}$ | $L_{Q5}$ |
| 272. | $L_{A3}$ | $L_{Q6}$ |
| 273. | $L_{A3}$ | $L_{Q7}$ |
| 274. | $L_{A3}$ | $L_{Q8}$ |
| 275. | $L_{A3}$ | $L_{Q9}$ |
| 276. | $L_{A3}$ | $L_{Q10}$ |
| 277. | $L_{A3}$ | $L_{Q11}$ |
| 278. | $L_{A3}$ | $L_{Q12}$ |
| 279. | $L_{A3}$ | $L_{Q13}$ |
| 280. | $L_{A3}$ | $L_{Q14}$ |
| 281. | $L_{A3}$ | $L_{Q15}$ |
| 282. | $L_{A3}$ | $L_{Q16}$ |
| 283. | $L_{A3}$ | $L_{Q17}$ |
| 284. | $L_{A3}$ | $L_{Q18}$ |
| 285. | $L_{A3}$ | $L_{Q19}$ |
| 286. | $L_{A3}$ | $L_{Q20}$ |
| 287. | $L_{A3}$ | $L_{Q21}$ |
| 288. | $L_{A3}$ | $L_{Q22}$ |
| 289. | $L_{A3}$ | $L_{Q23}$ |
| 290. | $L_{A3}$ | $L_{Q24}$ |
| 291. | $L_{A3}$ | $L_{Q25}$ |
| 292. | $L_{A3}$ | $L_{Q26}$ |
| 293. | $L_{A3}$ | $L_{Q27}$ |
| 294. | $L_{A3}$ | $L_{Q28}$ |
| 295. | $L_{A3}$ | $L_{Q29}$ |
| 296. | $L_{A3}$ | $L_{Q30}$ |
| 297. | $L_{A3}$ | $L_{Q31}$ |
| 298. | $L_{A3}$ | $L_{Q32}$ |
| 299. | $L_{A3}$ | $L_{Q33}$ |
| 300. | $L_{A3}$ | $L_{Q34}$ |
| 301. | $L_{A3}$ | $L_{Q35}$ |
| 302. | $L_{A3}$ | $L_{Q36}$ |
| 303. | $L_{A3}$ | $L_{Q37}$ |
| 304. | $L_{A3}$ | $L_{Q38}$ |
| 305. | $L_{A3}$ | $L_{Q39}$ |
| 306. | $L_{A3}$ | $L_{Q40}$ |
| 307. | $L_{A3}$ | $L_{Q41}$ |
| 308. | $L_{A3}$ | $L_{Q42}$ |
| 309. | $L_{A3}$ | $L_{Q43}$ |
| 310. | $L_{A3}$ | $L_{Q44}$ |
| 311. | $L_{A3}$ | $L_{Q45}$ |
| 312. | $L_{A3}$ | $L_{Q46}$ |
| 313. | $L_{A3}$ | $L_{Q47}$ |
| 314. | $L_{A3}$ | $L_{Q48}$ |
| 315. | $L_{A3}$ | $L_{Q49}$ |
| 316. | $L_{A3}$ | $L_{Q50}$ |
| 317. | $L_{A3}$ | $L_{Q51}$ |
| 318. | $L_{A3}$ | $L_{Q52}$ |
| 319. | $L_{A3}$ | $L_{Q53}$ |
| 320. | $L_{A3}$ | $L_{Q54}$ |
| 321. | $L_{A3}$ | $L_{Q55}$ |
| 322. | $L_{A3}$ | $L_{Q56}$ |
| 323. | $L_{A3}$ | $L_{Q57}$ |
| 324. | $L_{A3}$ | $L_{Q58}$ |
| 325. | $L_{A3}$ | $L_{Q59}$ |
| 326. | $L_{A3}$ | $L_{Q60}$ |
| 327. | $L_{A3}$ | $L_{Q61}$ |
| 328. | $L_{A3}$ | $L_{Q62}$ |
| 329. | $L_{A3}$ | $L_{Q63}$ |
| 330. | $L_{A3}$ | $L_{Q64}$ |
| 331. | $L_{A3}$ | $L_{Q65}$ |
| 332. | $L_{A3}$ | $L_{Q66}$ |
| 333. | $L_{A3}$ | $L_{Q67}$ |
| 334. | $L_{A3}$ | $L_{Q68}$ |
| 335. | $L_{A3}$ | $L_{Q69}$ |
| 336. | $L_{A3}$ | $L_{Q70}$ |
| 337. | $L_{A3}$ | $L_{Q71}$ |
| 338. | $L_{A3}$ | $L_{Q72}$ |
| 339. | $L_{A3}$ | $L_{Q73}$ |
| 340. | $L_{A3}$ | $L_{Q74}$ |

TABLE 1-continued

| Compound number | L¹ | L² |
|---|---|---|
| 341. | $L_{43}$ | $L_{Q75}$ |
| 342. | $L_{43}$ | $L_{Q76}$ |
| 343. | $L_{43}$ | $L_{Q77}$ |
| 344. | $L_{43}$ | $L_{Q78}$ |
| 345. | $L_{43}$ | $L_{Q79}$ |
| 346. | $L_{43}$ | $L_{Q80}$ |
| 347. | $L_{43}$ | $L_{Q81}$ |
| 348. | $L_{43}$ | $L_{Q82}$ |
| 349. | $L_{43}$ | $L_{Q83}$ |
| 350. | $L_{43}$ | $L_{Q84}$ |
| 351. | $L_{43}$ | $L_{Q85}$ |
| 352. | $L_{43}$ | $L_{Q86}$ |
| 353. | $L_{43}$ | $L_{Q87}$ |
| 354. | $L_{43}$ | $L_{Q88}$ |
| 355. | $L_{43}$ | $L_{Q89}$ |
| 356. | $L_{43}$ | $L_{Q90}$ |
| 357. | $L_{43}$ | $L_{Q91}$ |
| 358. | $L_{43}$ | $L_{Q92}$ |
| 359. | $L_{43}$ | $L_{Q93}$ |
| 360. | $L_{43}$ | $L_{Q94}$ |
| 361. | $L_{43}$ | $L_{Q95}$ |
| 362. | $L_{43}$ | $L_{Q96}$ |
| 363. | $L_{43}$ | $L_{Q97}$ |
| 364. | $L_{43}$ | $L_{Q98}$ |
| 365. | $L_{43}$ | $L_{Q99}$ |
| 366. | $L_{43}$ | $L_{Q100}$ |
| 367. | $L_{43}$ | $L_{Q101}$ |
| 368. | $L_{43}$ | $L_{Q102}$ |
| 369. | $L_{43}$ | $L_{Q103}$ |
| 370. | $L_{43}$ | $L_{Q104}$ |
| 371. | $L_{43}$ | $L_{Q105}$ |
| 372. | $L_{43}$ | $L_{Q106}$ |
| 373. | $L_{43}$ | $L_{Q107}$ |
| 374. | $L_{43}$ | $L_{Q108}$ |
| 375. | $L_{43}$ | $L_{Q109}$ |
| 376. | $L_{43}$ | $L_{Q110}$ |
| 377. | $L_{43}$ | $L_{Q111}$ |
| 378. | $L_{43}$ | $L_{Q112}$ |
| 379. | $L_{43}$ | $L_{Q113}$ |
| 380. | $L_{43}$ | $L_{Q114}$ |
| 381. | $L_{43}$ | $L_{Q115}$ |
| 382. | $L_{43}$ | $L_{Q116}$ |
| 383. | $L_{43}$ | $L_{Q117}$ |
| 384. | $L_{43}$ | $L_{Q118}$ |
| 385. | $L_{43}$ | $L_{Q119}$ |
| 386. | $L_{43}$ | $L_{Q120}$ |
| 387. | $L_{43}$ | $L_{Q121}$ |
| 388. | $L_{43}$ | $L_{Q122}$ |
| 389. | $L_{43}$ | $L_{Q123}$ |
| 390. | $L_{43}$ | $L_{Q124}$ |
| 391. | $L_{43}$ | $L_{Q125}$ |
| 392. | $L_{43}$ | $L_{Q126}$ |
| 393. | $L_{43}$ | $L_{Q127}$ |
| 394. | $L_{43}$ | $L_{Q128}$ |
| 395. | $L_{43}$ | $L_{Q129}$ |
| 396. | $L_{43}$ | $L_{Q130}$ |
| 397. | $L_{43}$ | $L_{Q131}$ |
| 398. | $L_{43}$ | $L_{Q132}$ |
| 399. | $L_{43}$ | $L_{Q133}$ |
| 400. | $L_{44}$ | $L_{Q1}$ |
| 401. | $L_{44}$ | $L_{Q2}$ |
| 402. | $L_{44}$ | $L_{Q3}$ |
| 403. | $L_{44}$ | $L_{Q4}$ |
| 404. | $L_{44}$ | $L_{Q5}$ |
| 405. | $L_{44}$ | $L_{Q6}$ |
| 406. | $L_{44}$ | $L_{Q7}$ |
| 407. | $L_{44}$ | $L_{Q8}$ |
| 408. | $L_{44}$ | $L_{Q9}$ |
| 409. | $L_{44}$ | $L_{Q10}$ |
| 410. | $L_{44}$ | $L_{Q11}$ |
| 411. | $L_{44}$ | $L_{Q12}$ |
| 412. | $L_{44}$ | $L_{Q13}$ |
| 413. | $L_{44}$ | $L_{Q14}$ |
| 414. | $L_{44}$ | $L_{Q15}$ |
| 415. | $L_{44}$ | $L_{Q16}$ |
| 416. | $L_{44}$ | $L_{Q17}$ |
| 417. | $L_{44}$ | $L_{Q18}$ |
| 418. | $L_{44}$ | $L_{Q19}$ |
| 419. | $L_{44}$ | $L_{Q20}$ |
| 420. | $L_{44}$ | $L_{Q21}$ |
| 421. | $L_{44}$ | $L_{Q22}$ |
| 422. | $L_{44}$ | $L_{Q23}$ |
| 423. | $L_{44}$ | $L_{Q24}$ |
| 424. | $L_{44}$ | $L_{Q25}$ |
| 425. | $L_{44}$ | $L_{Q26}$ |
| 426. | $L_{44}$ | $L_{Q27}$ |
| 427. | $L_{44}$ | $L_{Q28}$ |
| 428. | $L_{44}$ | $L_{Q29}$ |
| 429. | $L_{44}$ | $L_{Q30}$ |
| 430. | $L_{44}$ | $L_{Q31}$ |
| 431. | $L_{44}$ | $L_{Q32}$ |
| 432. | $L_{44}$ | $L_{Q33}$ |
| 433. | $L_{44}$ | $L_{Q34}$ |
| 434. | $L_{44}$ | $L_{Q35}$ |
| 435. | $L_{44}$ | $L_{Q36}$ |
| 436. | $L_{44}$ | $L_{Q37}$ |
| 437. | $L_{44}$ | $L_{Q38}$ |
| 438. | $L_{44}$ | $L_{Q39}$ |
| 439. | $L_{44}$ | $L_{Q40}$ |
| 440. | $L_{44}$ | $L_{Q41}$ |
| 441. | $L_{44}$ | $L_{Q42}$ |
| 442. | $L_{44}$ | $L_{Q43}$ |
| 443. | $L_{44}$ | $L_{Q44}$ |
| 444. | $L_{44}$ | $L_{Q45}$ |
| 445. | $L_{44}$ | $L_{Q46}$ |
| 446. | $L_{44}$ | $L_{Q47}$ |
| 447. | $L_{44}$ | $L_{Q48}$ |
| 448. | $L_{44}$ | $L_{Q49}$ |
| 449. | $L_{44}$ | $L_{Q50}$ |
| 450. | $L_{44}$ | $L_{Q51}$ |
| 451. | $L_{44}$ | $L_{Q52}$ |
| 452. | $L_{44}$ | $L_{Q53}$ |
| 453. | $L_{44}$ | $L_{Q54}$ |
| 454. | $L_{44}$ | $L_{Q55}$ |
| 455. | $L_{44}$ | $L_{Q56}$ |
| 456. | $L_{44}$ | $L_{Q57}$ |
| 457. | $L_{44}$ | $L_{Q58}$ |
| 458. | $L_{44}$ | $L_{Q59}$ |
| 459. | $L_{44}$ | $L_{Q60}$ |
| 460. | $L_{44}$ | $L_{Q61}$ |
| 461. | $L_{44}$ | $L_{Q62}$ |
| 462. | $L_{44}$ | $L_{Q63}$ |
| 463. | $L_{44}$ | $L_{Q64}$ |
| 464. | $L_{44}$ | $L_{Q65}$ |
| 465. | $L_{44}$ | $L_{Q66}$ |
| 466. | $L_{44}$ | $L_{Q67}$ |
| 467. | $L_{44}$ | $L_{Q68}$ |
| 468. | $L_{44}$ | $L_{Q69}$ |
| 469. | $L_{44}$ | $L_{Q70}$ |
| 470. | $L_{44}$ | $L_{Q71}$ |
| 471. | $L_{44}$ | $L_{Q72}$ |
| 472. | $L_{44}$ | $L_{Q73}$ |
| 473. | $L_{44}$ | $L_{Q74}$ |
| 474. | $L_{44}$ | $L_{Q75}$ |
| 475. | $L_{44}$ | $L_{Q76}$ |
| 476. | $L_{44}$ | $L_{Q77}$ |
| 477. | $L_{44}$ | $L_{Q78}$ |
| 478. | $L_{44}$ | $L_{Q79}$ |
| 479. | $L_{44}$ | $L_{Q80}$ |
| 480. | $L_{44}$ | $L_{Q81}$ |
| 481. | $L_{44}$ | $L_{Q82}$ |
| 482. | $L_{44}$ | $L_{Q83}$ |
| 483. | $L_{44}$ | $L_{Q84}$ |
| 484. | $L_{44}$ | $L_{Q85}$ |
| 485. | $L_{44}$ | $L_{Q86}$ |
| 486. | $L_{44}$ | $L_{Q87}$ |
| 487. | $L_{44}$ | $L_{Q88}$ |
| 488. | $L_{44}$ | $L_{Q89}$ |
| 489. | $L_{44}$ | $L_{Q90}$ |
| 490. | $L_{44}$ | $L_{Q91}$ |
| 491. | $L_{44}$ | $L_{Q92}$ |
| 492. | $L_{44}$ | $L_{Q93}$ |
| 493. | $L_{44}$ | $L_{Q94}$ |
| 494. | $L_{44}$ | $L_{Q95}$ |

TABLE 1-continued

| Compound number | $L^1$ | $L^2$ |
|---|---|---|
| 495. | $L_{44}$ | $L_{Q96}$ |
| 496. | $L_{44}$ | $L_{Q97}$ |
| 497. | $L_{44}$ | $L_{Q98}$ |
| 498. | $L_{44}$ | $L_{Q99}$ |
| 499. | $L_{44}$ | $L_{Q100}$ |
| 500. | $L_{44}$ | $L_{Q101}$ |
| 501. | $L_{44}$ | $L_{Q102}$ |
| 502. | $L_{44}$ | $L_{Q103}$ |
| 503. | $L_{44}$ | $L_{Q104}$ |
| 504. | $L_{44}$ | $L_{Q105}$ |
| 505. | $L_{44}$ | $L_{Q106}$ |
| 506. | $L_{44}$ | $L_{Q107}$ |
| 507. | $L_{44}$ | $L_{Q108}$ |
| 508. | $L_{44}$ | $L_{Q109}$ |
| 509. | $L_{44}$ | $L_{Q110}$ |
| 510. | $L_{44}$ | $L_{Q111}$ |
| 511. | $L_{44}$ | $L_{Q112}$ |
| 512. | $L_{44}$ | $L_{Q113}$ |
| 513. | $L_{44}$ | $L_{Q114}$ |
| 514. | $L_{44}$ | $L_{Q115}$ |
| 515. | $L_{44}$ | $L_{Q116}$ |
| 516. | $L_{44}$ | $L_{Q117}$ |
| 517. | $L_{44}$ | $L_{Q118}$ |
| 518. | $L_{44}$ | $L_{Q119}$ |
| 519. | $L_{44}$ | $L_{Q120}$ |
| 520. | $L_{44}$ | $L_{Q121}$ |
| 521. | $L_{44}$ | $L_{Q122}$ |
| 522. | $L_{44}$ | $L_{Q123}$ |
| 523. | $L_{44}$ | $L_{Q124}$ |
| 524. | $L_{44}$ | $L_{Q125}$ |
| 525. | $L_{44}$ | $L_{Q126}$ |
| 526. | $L_{44}$ | $L_{Q127}$ |
| 527. | $L_{44}$ | $L_{Q128}$ |
| 528. | $L_{44}$ | $L_{Q129}$ |
| 529. | $L_{44}$ | $L_{Q130}$ |
| 530. | $L_{44}$ | $L_{Q131}$ |
| 531. | $L_{44}$ | $L_{Q132}$ |
| 532. | $L_{44}$ | $L_{Q133}$ |
| 533. | $L_{45}$ | $L_{Q1}$ |
| 534. | $L_{45}$ | $L_{Q2}$ |
| 535. | $L_{45}$ | $L_{Q3}$ |
| 536. | $L_{45}$ | $L_{Q4}$ |
| 537. | $L_{45}$ | $L_{Q5}$ |
| 538. | $L_{45}$ | $L_{Q6}$ |
| 539. | $L_{45}$ | $L_{Q7}$ |
| 540. | $L_{45}$ | $L_{Q8}$ |
| 541. | $L_{45}$ | $L_{Q9}$ |
| 542. | $L_{45}$ | $L_{Q10}$ |
| 543. | $L_{45}$ | $L_{Q11}$ |
| 544. | $L_{45}$ | $L_{Q12}$ |
| 545. | $L_{45}$ | $L_{Q13}$ |
| 546. | $L_{45}$ | $L_{Q14}$ |
| 547. | $L_{45}$ | $L_{Q15}$ |
| 548. | $L_{45}$ | $L_{Q16}$ |
| 549. | $L_{45}$ | $L_{Q17}$ |
| 550. | $L_{45}$ | $L_{Q18}$ |
| 551. | $L_{45}$ | $L_{Q19}$ |
| 552. | $L_{45}$ | $L_{Q20}$ |
| 553. | $L_{45}$ | $L_{Q21}$ |
| 554. | $L_{45}$ | $L_{Q22}$ |
| 555. | $L_{45}$ | $L_{Q23}$ |
| 556. | $L_{45}$ | $L_{Q24}$ |
| 557. | $L_{45}$ | $L_{Q25}$ |
| 558. | $L_{45}$ | $L_{Q26}$ |
| 559. | $L_{45}$ | $L_{Q27}$ |
| 560. | $L_{45}$ | $L_{Q28}$ |
| 561. | $L_{45}$ | $L_{Q29}$ |
| 562. | $L_{45}$ | $L_{Q30}$ |
| 563. | $L_{45}$ | $L_{Q31}$ |
| 564. | $L_{45}$ | $L_{Q32}$ |
| 565. | $L_{45}$ | $L_{Q33}$ |
| 566. | $L_{45}$ | $L_{Q34}$ |
| 567. | $L_{45}$ | $L_{Q35}$ |
| 568. | $L_{45}$ | $L_{Q36}$ |
| 569. | $L_{45}$ | $L_{Q37}$ |
| 570. | $L_{45}$ | $L_{Q38}$ |
| 571. | $L_{45}$ | $L_{Q39}$ |
| 572. | $L_{45}$ | $L_{Q40}$ |
| 573. | $L_{45}$ | $L_{Q41}$ |
| 574. | $L_{45}$ | $L_{Q42}$ |
| 575. | $L_{45}$ | $L_{Q43}$ |
| 576. | $L_{45}$ | $L_{Q44}$ |
| 577. | $L_{45}$ | $L_{Q45}$ |
| 578. | $L_{45}$ | $L_{Q46}$ |
| 579. | $L_{45}$ | $L_{Q47}$ |
| 580. | $L_{45}$ | $L_{Q48}$ |
| 581. | $L_{45}$ | $L_{Q49}$ |
| 582. | $L_{45}$ | $L_{Q50}$ |
| 583. | $L_{45}$ | $L_{Q51}$ |
| 584. | $L_{45}$ | $L_{Q52}$ |
| 585. | $L_{45}$ | $L_{Q53}$ |
| 586. | $L_{45}$ | $L_{Q54}$ |
| 587. | $L_{45}$ | $L_{Q55}$ |
| 588. | $L_{45}$ | $L_{Q56}$ |
| 589. | $L_{45}$ | $L_{Q57}$ |
| 590. | $L_{45}$ | $L_{Q58}$ |
| 591. | $L_{45}$ | $L_{Q59}$ |
| 592. | $L_{45}$ | $L_{Q60}$ |
| 593. | $L_{45}$ | $L_{Q61}$ |
| 594. | $L_{45}$ | $L_{Q62}$ |
| 595. | $L_{45}$ | $L_{Q63}$ |
| 596. | $L_{45}$ | $L_{Q64}$ |
| 597. | $L_{45}$ | $L_{Q65}$ |
| 598. | $L_{45}$ | $L_{Q66}$ |
| 599. | $L_{45}$ | $L_{Q67}$ |
| 600. | $L_{45}$ | $L_{Q68}$ |
| 601. | $L_{45}$ | $L_{Q69}$ |
| 602. | $L_{45}$ | $L_{Q70}$ |
| 603. | $L_{45}$ | $L_{Q71}$ |
| 604. | $L_{45}$ | $L_{Q72}$ |
| 605. | $L_{45}$ | $L_{Q73}$ |
| 606. | $L_{45}$ | $L_{Q74}$ |
| 607. | $L_{45}$ | $L_{Q75}$ |
| 608. | $L_{45}$ | $L_{Q76}$ |
| 609. | $L_{45}$ | $L_{Q77}$ |
| 610. | $L_{45}$ | $L_{Q78}$ |
| 611. | $L_{45}$ | $L_{Q79}$ |
| 612. | $L_{45}$ | $L_{Q80}$ |
| 613. | $L_{45}$ | $L_{Q81}$ |
| 614. | $L_{45}$ | $L_{Q82}$ |
| 615. | $L_{45}$ | $L_{Q83}$ |
| 616. | $L_{45}$ | $L_{Q84}$ |
| 617. | $L_{45}$ | $L_{Q85}$ |
| 618. | $L_{45}$ | $L_{Q86}$ |
| 619. | $L_{45}$ | $L_{Q87}$ |
| 620. | $L_{45}$ | $L_{Q88}$ |
| 621. | $L_{45}$ | $L_{Q89}$ |
| 622. | $L_{45}$ | $L_{Q90}$ |
| 623. | $L_{45}$ | $L_{Q91}$ |
| 624. | $L_{45}$ | $L_{Q92}$ |
| 625. | $L_{45}$ | $L_{Q93}$ |
| 626. | $L_{45}$ | $L_{Q94}$ |
| 627. | $L_{45}$ | $L_{Q95}$ |
| 628. | $L_{45}$ | $L_{Q96}$ |
| 629. | $L_{45}$ | $L_{Q97}$ |
| 630. | $L_{45}$ | $L_{Q98}$ |
| 631. | $L_{45}$ | $L_{Q99}$ |
| 632. | $L_{45}$ | $L_{Q100}$ |
| 633. | $L_{45}$ | $L_{Q101}$ |
| 634. | $L_{45}$ | $L_{Q102}$ |
| 635. | $L_{45}$ | $L_{Q103}$ |
| 636. | $L_{45}$ | $L_{Q104}$ |
| 637. | $L_{45}$ | $L_{Q105}$ |
| 638. | $L_{45}$ | $L_{Q106}$ |
| 639. | $L_{45}$ | $L_{Q107}$ |
| 640. | $L_{45}$ | $L_{Q108}$ |
| 641. | $L_{45}$ | $L_{Q109}$ |
| 642. | $L_{45}$ | $L_{Q110}$ |
| 643. | $L_{45}$ | $L_{Q111}$ |
| 644. | $L_{45}$ | $L_{Q112}$ |
| 645. | $L_{45}$ | $L_{Q113}$ |
| 646. | $L_{45}$ | $L_{Q114}$ |
| 647. | $L_{45}$ | $L_{Q115}$ |
| 648. | $L_{45}$ | $L_{Q116}$ |

TABLE 1-continued

| Compound number | $L^1$ | $L^2$ |
|---|---|---|
| 649. | $L_{A5}$ | $L_{Q117}$ |
| 650. | $L_{A5}$ | $L_{Q118}$ |
| 651. | $L_{A5}$ | $L_{Q119}$ |
| 652. | $L_{A5}$ | $L_{Q120}$ |
| 653. | $L_{A5}$ | $L_{Q121}$ |
| 654. | $L_{A5}$ | $L_{Q122}$ |
| 655. | $L_{A5}$ | $L_{Q123}$ |
| 656. | $L_{A5}$ | $L_{Q124}$ |
| 657. | $L_{A5}$ | $L_{Q125}$ |
| 658. | $L_{A5}$ | $L_{Q126}$ |
| 659. | $L_{A5}$ | $L_{Q127}$ |
| 660. | $L_{A5}$ | $L_{Q128}$ |
| 661. | $L_{A5}$ | $L_{Q129}$ |
| 662. | $L_{A5}$ | $L_{Q130}$ |
| 663. | $L_{A5}$ | $L_{Q131}$ |
| 664. | $L_{A5}$ | $L_{Q132}$ |
| 665. | $L_{A5}$ | $L_{Q133}$ |
| 666. | $L_{A6}$ | $L_{Q1}$ |
| 667. | $L_{A6}$ | $L_{Q2}$ |
| 668. | $L_{A6}$ | $L_{Q3}$ |
| 669. | $L_{A6}$ | $L_{Q4}$ |
| 670. | $L_{A6}$ | $L_{Q5}$ |
| 671. | $L_{A6}$ | $L_{Q6}$ |
| 672. | $L_{A6}$ | $L_{Q7}$ |
| 673. | $L_{A6}$ | $L_{Q8}$ |
| 674. | $L_{A6}$ | $L_{Q9}$ |
| 675. | $L_{A6}$ | $L_{Q10}$ |
| 676. | $L_{A6}$ | $L_{Q11}$ |
| 677. | $L_{A6}$ | $L_{Q12}$ |
| 678. | $L_{A6}$ | $L_{Q13}$ |
| 679. | $L_{A6}$ | $L_{Q14}$ |
| 680. | $L_{A6}$ | $L_{Q15}$ |
| 681. | $L_{A6}$ | $L_{Q16}$ |
| 682. | $L_{A6}$ | $L_{Q17}$ |
| 683. | $L_{A6}$ | $L_{Q18}$ |
| 684. | $L_{A6}$ | $L_{Q19}$ |
| 685. | $L_{A6}$ | $L_{Q20}$ |
| 686. | $L_{A6}$ | $L_{Q21}$ |
| 687. | $L_{A6}$ | $L_{Q22}$ |
| 688. | $L_{A6}$ | $L_{Q23}$ |
| 689. | $L_{A6}$ | $L_{Q24}$ |
| 690. | $L_{A6}$ | $L_{Q25}$ |
| 691. | $L_{A6}$ | $L_{Q26}$ |
| 692. | $L_{A6}$ | $L_{Q27}$ |
| 693. | $L_{A6}$ | $L_{Q28}$ |
| 694. | $L_{A6}$ | $L_{Q29}$ |
| 695. | $L_{A6}$ | $L_{Q30}$ |
| 696. | $L_{A6}$ | $L_{Q31}$ |
| 697. | $L_{A6}$ | $L_{Q32}$ |
| 698. | $L_{A6}$ | $L_{Q33}$ |
| 699. | $L_{A6}$ | $L_{Q34}$ |
| 700. | $L_{A6}$ | $L_{Q35}$ |
| 701. | $L_{A6}$ | $L_{Q36}$ |
| 702. | $L_{A6}$ | $L_{Q37}$ |
| 703. | $L_{A6}$ | $L_{Q38}$ |
| 704. | $L_{A6}$ | $L_{Q39}$ |
| 705. | $L_{A6}$ | $L_{Q40}$ |
| 706. | $L_{A6}$ | $L_{Q41}$ |
| 707. | $L_{A6}$ | $L_{Q42}$ |
| 708. | $L_{A6}$ | $L_{Q43}$ |
| 709. | $L_{A6}$ | $L_{Q44}$ |
| 710. | $L_{A6}$ | $L_{Q45}$ |
| 711. | $L_{A6}$ | $L_{Q46}$ |
| 712. | $L_{A6}$ | $L_{Q47}$ |
| 713. | $L_{A6}$ | $L_{Q48}$ |
| 714. | $L_{A6}$ | $L_{Q49}$ |
| 715. | $L_{A6}$ | $L_{Q50}$ |
| 716. | $L_{A6}$ | $L_{Q51}$ |
| 717. | $L_{A6}$ | $L_{Q52}$ |
| 718. | $L_{A6}$ | $L_{Q53}$ |
| 719. | $L_{A6}$ | $L_{Q54}$ |
| 720. | $L_{A6}$ | $L_{Q55}$ |
| 721. | $L_{A6}$ | $L_{Q56}$ |
| 722. | $L_{A6}$ | $L_{Q57}$ |
| 723. | $L_{A6}$ | $L_{Q58}$ |
| 724. | $L_{A6}$ | $L_{Q59}$ |
| 725. | $L_{A6}$ | $L_{Q60}$ |
| 726. | $L_{A6}$ | $L_{Q61}$ |
| 727. | $L_{A6}$ | $L_{Q62}$ |
| 728. | $L_{A6}$ | $L_{Q63}$ |
| 729. | $L_{A6}$ | $L_{Q64}$ |
| 730. | $L_{A6}$ | $L_{Q65}$ |
| 731. | $L_{A6}$ | $L_{Q66}$ |
| 732. | $L_{A6}$ | $L_{Q67}$ |
| 733. | $L_{A6}$ | $L_{Q68}$ |
| 734. | $L_{A6}$ | $L_{Q69}$ |
| 735. | $L_{A6}$ | $L_{Q70}$ |
| 736. | $L_{A6}$ | $L_{Q71}$ |
| 737. | $L_{A6}$ | $L_{Q72}$ |
| 738. | $L_{A6}$ | $L_{Q73}$ |
| 739. | $L_{A6}$ | $L_{Q74}$ |
| 740. | $L_{A6}$ | $L_{Q75}$ |
| 741. | $L_{A6}$ | $L_{Q76}$ |
| 742. | $L_{A6}$ | $L_{Q77}$ |
| 743. | $L_{A6}$ | $L_{Q78}$ |
| 744. | $L_{A6}$ | $L_{Q79}$ |
| 745. | $L_{A6}$ | $L_{Q80}$ |
| 746. | $L_{A6}$ | $L_{Q81}$ |
| 747. | $L_{A6}$ | $L_{Q82}$ |
| 748. | $L_{A6}$ | $L_{Q83}$ |
| 749. | $L_{A6}$ | $L_{Q84}$ |
| 750. | $L_{A6}$ | $L_{Q85}$ |
| 751. | $L_{A6}$ | $L_{Q86}$ |
| 752. | $L_{A6}$ | $L_{Q87}$ |
| 753. | $L_{A6}$ | $L_{Q88}$ |
| 754. | $L_{A6}$ | $L_{Q89}$ |
| 755. | $L_{A6}$ | $L_{Q90}$ |
| 756. | $L_{A6}$ | $L_{Q91}$ |
| 757. | $L_{A6}$ | $L_{Q92}$ |
| 758. | $L_{A6}$ | $L_{Q93}$ |
| 759. | $L_{A6}$ | $L_{Q94}$ |
| 760. | $L_{A6}$ | $L_{Q95}$ |
| 761. | $L_{A6}$ | $L_{Q96}$ |
| 762. | $L_{A6}$ | $L_{Q97}$ |
| 763. | $L_{A6}$ | $L_{Q98}$ |
| 764. | $L_{A6}$ | $L_{Q99}$ |
| 765. | $L_{A6}$ | $L_{Q100}$ |
| 766. | $L_{A6}$ | $L_{Q101}$ |
| 767. | $L_{A6}$ | $L_{Q102}$ |
| 768. | $L_{A6}$ | $L_{Q103}$ |
| 769. | $L_{A6}$ | $L_{Q104}$ |
| 770. | $L_{A6}$ | $L_{Q105}$ |
| 771. | $L_{A6}$ | $L_{Q106}$ |
| 772. | $L_{A6}$ | $L_{Q107}$ |
| 773. | $L_{A6}$ | $L_{Q108}$ |
| 774. | $L_{A6}$ | $L_{Q109}$ |
| 775. | $L_{A6}$ | $L_{Q110}$ |
| 776. | $L_{A6}$ | $L_{Q111}$ |
| 777. | $L_{A6}$ | $L_{Q112}$ |
| 778. | $L_{A6}$ | $L_{Q113}$ |
| 779. | $L_{A6}$ | $L_{Q114}$ |
| 780. | $L_{A6}$ | $L_{Q115}$ |
| 781. | $L_{A6}$ | $L_{Q116}$ |
| 782. | $L_{A6}$ | $L_{Q117}$ |
| 783. | $L_{A6}$ | $L_{Q118}$ |
| 784. | $L_{A6}$ | $L_{Q119}$ |
| 785. | $L_{A6}$ | $L_{Q120}$ |
| 786. | $L_{A6}$ | $L_{Q121}$ |
| 787. | $L_{A6}$ | $L_{Q122}$ |
| 788. | $L_{A6}$ | $L_{Q123}$ |
| 789. | $L_{A6}$ | $L_{Q124}$ |
| 790. | $L_{A6}$ | $L_{Q125}$ |
| 791. | $L_{A6}$ | $L_{Q126}$ |
| 792. | $L_{A6}$ | $L_{Q127}$ |
| 793. | $L_{A6}$ | $L_{Q128}$ |
| 794. | $L_{A6}$ | $L_{Q129}$ |
| 795. | $L_{A6}$ | $L_{Q130}$ |
| 796. | $L_{A6}$ | $L_{Q131}$ |
| 797. | $L_{A6}$ | $L_{Q132}$ |
| 798. | $L_{A6}$ | $L_{Q133}$ |
| 799. | $L_{A7}$ | $L_{Q1}$ |
| 800. | $L_{A7}$ | $L_{Q2}$ |
| 801. | $L_{A7}$ | $L_{Q3}$ |
| 802. | $L_{A7}$ | $L_{Q4}$ |

TABLE 1-continued

| Compound number | $L^1$ | $L^2$ |
|---|---|---|
| 803. | $L_{A7}$ | $L_{Q5}$ |
| 804. | $L_{A7}$ | $L_{Q6}$ |
| 805. | $L_{A7}$ | $L_{Q7}$ |
| 806. | $L_{A7}$ | $L_{Q8}$ |
| 807. | $L_{A7}$ | $L_{Q9}$ |
| 808. | $L_{A7}$ | $L_{Q10}$ |
| 809. | $L_{A7}$ | $L_{Q11}$ |
| 810. | $L_{A7}$ | $L_{Q12}$ |
| 811. | $L_{A7}$ | $L_{Q13}$ |
| 812. | $L_{A7}$ | $L_{Q14}$ |
| 813. | $L_{A7}$ | $L_{Q15}$ |
| 814. | $L_{A7}$ | $L_{Q16}$ |
| 815. | $L_{A7}$ | $L_{Q17}$ |
| 816. | $L_{A7}$ | $L_{Q18}$ |
| 817. | $L_{A7}$ | $L_{Q19}$ |
| 818. | $L_{A7}$ | $L_{Q20}$ |
| 819. | $L_{A7}$ | $L_{Q21}$ |
| 820. | $L_{A7}$ | $L_{Q22}$ |
| 821. | $L_{A7}$ | $L_{Q23}$ |
| 822. | $L_{A7}$ | $L_{Q24}$ |
| 823. | $L_{A7}$ | $L_{Q25}$ |
| 824. | $L_{A7}$ | $L_{Q26}$ |
| 825. | $L_{A7}$ | $L_{Q27}$ |
| 826. | $L_{A7}$ | $L_{Q28}$ |
| 827. | $L_{A7}$ | $L_{Q29}$ |
| 828. | $L_{A7}$ | $L_{Q30}$ |
| 829. | $L_{A7}$ | $L_{Q31}$ |
| 830. | $L_{A7}$ | $L_{Q32}$ |
| 831. | $L_{A7}$ | $L_{Q33}$ |
| 832. | $L_{A7}$ | $L_{Q34}$ |
| 833. | $L_{A7}$ | $L_{Q35}$ |
| 834. | $L_{A7}$ | $L_{Q36}$ |
| 835. | $L_{A7}$ | $L_{Q37}$ |
| 836. | $L_{A7}$ | $L_{Q38}$ |
| 837. | $L_{A7}$ | $L_{Q39}$ |
| 838. | $L_{A7}$ | $L_{Q40}$ |
| 839. | $L_{A7}$ | $L_{Q41}$ |
| 840. | $L_{A7}$ | $L_{Q42}$ |
| 841. | $L_{A7}$ | $L_{Q43}$ |
| 842. | $L_{A7}$ | $L_{Q44}$ |
| 843. | $L_{A7}$ | $L_{Q45}$ |
| 844. | $L_{A7}$ | $L_{Q46}$ |
| 845. | $L_{A7}$ | $L_{Q47}$ |
| 846. | $L_{A7}$ | $L_{Q48}$ |
| 847. | $L_{A7}$ | $L_{Q49}$ |
| 848. | $L_{A7}$ | $L_{Q50}$ |
| 849. | $L_{A7}$ | $L_{Q51}$ |
| 850. | $L_{A7}$ | $L_{Q52}$ |
| 851. | $L_{A7}$ | $L_{Q53}$ |
| 852. | $L_{A7}$ | $L_{Q54}$ |
| 853. | $L_{A7}$ | $L_{Q55}$ |
| 854. | $L_{A7}$ | $L_{Q56}$ |
| 855. | $L_{A7}$ | $L_{Q57}$ |
| 856. | $L_{A7}$ | $L_{Q58}$ |
| 857. | $L_{A7}$ | $L_{Q59}$ |
| 858. | $L_{A7}$ | $L_{Q60}$ |
| 859. | $L_{A7}$ | $L_{Q61}$ |
| 860. | $L_{A7}$ | $L_{Q62}$ |
| 861. | $L_{A7}$ | $L_{Q63}$ |
| 862. | $L_{A7}$ | $L_{Q64}$ |
| 863. | $L_{A7}$ | $L_{Q65}$ |
| 864. | $L_{A7}$ | $L_{Q66}$ |
| 865. | $L_{A7}$ | $L_{Q67}$ |
| 866. | $L_{A7}$ | $L_{Q68}$ |
| 867. | $L_{A7}$ | $L_{Q69}$ |
| 868. | $L_{A7}$ | $L_{Q70}$ |
| 869. | $L_{A7}$ | $L_{Q71}$ |
| 870. | $L_{A7}$ | $L_{Q72}$ |
| 871. | $L_{A7}$ | $L_{Q73}$ |
| 872. | $L_{A7}$ | $L_{Q74}$ |
| 873. | $L_{A7}$ | $L_{Q75}$ |
| 874. | $L_{A7}$ | $L_{Q76}$ |
| 875. | $L_{A7}$ | $L_{Q77}$ |
| 876. | $L_{A7}$ | $L_{Q78}$ |
| 877. | $L_{A7}$ | $L_{Q79}$ |
| 878. | $L_{A7}$ | $L_{Q80}$ |
| 879. | $L_{A7}$ | $L_{Q81}$ |
| 880. | $L_{A7}$ | $L_{Q82}$ |
| 881. | $L_{A7}$ | $L_{Q83}$ |
| 882. | $L_{A7}$ | $L_{Q84}$ |
| 883. | $L_{A7}$ | $L_{Q85}$ |
| 884. | $L_{A7}$ | $L_{Q86}$ |
| 885. | $L_{A7}$ | $L_{Q87}$ |
| 886. | $L_{A7}$ | $L_{Q88}$ |
| 887. | $L_{A7}$ | $L_{Q89}$ |
| 888. | $L_{A7}$ | $L_{Q90}$ |
| 889. | $L_{A7}$ | $L_{Q91}$ |
| 890. | $L_{A7}$ | $L_{Q92}$ |
| 891. | $L_{A7}$ | $L_{Q93}$ |
| 892. | $L_{A7}$ | $L_{Q94}$ |
| 893. | $L_{A7}$ | $L_{Q95}$ |
| 894. | $L_{A7}$ | $L_{Q96}$ |
| 895. | $L_{A7}$ | $L_{Q97}$ |
| 896. | $L_{A7}$ | $L_{Q98}$ |
| 897. | $L_{A7}$ | $L_{Q99}$ |
| 898. | $L_{A7}$ | $L_{Q100}$ |
| 899. | $L_{A7}$ | $L_{Q101}$ |
| 900. | $L_{A7}$ | $L_{Q102}$ |
| 901. | $L_{A7}$ | $L_{Q103}$ |
| 902. | $L_{A7}$ | $L_{Q104}$ |
| 903. | $L_{A7}$ | $L_{Q105}$ |
| 904. | $L_{A7}$ | $L_{Q106}$ |
| 905. | $L_{A7}$ | $L_{Q107}$ |
| 906. | $L_{A7}$ | $L_{Q108}$ |
| 907. | $L_{A7}$ | $L_{Q109}$ |
| 908. | $L_{A7}$ | $L_{Q110}$ |
| 909. | $L_{A7}$ | $L_{Q111}$ |
| 910. | $L_{A7}$ | $L_{Q112}$ |
| 911. | $L_{A7}$ | $L_{Q113}$ |
| 912. | $L_{A7}$ | $L_{Q114}$ |
| 913. | $L_{A7}$ | $L_{Q115}$ |
| 914. | $L_{A7}$ | $L_{Q116}$ |
| 915. | $L_{A7}$ | $L_{Q117}$ |
| 916. | $L_{A7}$ | $L_{Q118}$ |
| 917. | $L_{A7}$ | $L_{Q119}$ |
| 918. | $L_{A7}$ | $L_{Q120}$ |
| 919. | $L_{A7}$ | $L_{Q121}$ |
| 920. | $L_{A7}$ | $L_{Q122}$ |
| 921. | $L_{A7}$ | $L_{Q123}$ |
| 922. | $L_{A7}$ | $L_{Q124}$ |
| 923. | $L_{A7}$ | $L_{Q125}$ |
| 924. | $L_{A7}$ | $L_{Q126}$ |
| 925. | $L_{A7}$ | $L_{Q127}$ |
| 926. | $L_{A7}$ | $L_{Q128}$ |
| 927. | $L_{A7}$ | $L_{Q129}$ |
| 928. | $L_{A7}$ | $L_{Q130}$ |
| 929. | $L_{A7}$ | $L_{Q131}$ |
| 930. | $L_{A7}$ | $L_{Q132}$ |
| 931. | $L_{A7}$ | $L_{Q133}$ |
| 932. | $L_{A8}$ | $L_{Q1}$ |
| 933. | $L_{A8}$ | $L_{Q2}$ |
| 934. | $L_{A8}$ | $L_{Q3}$ |
| 935. | $L_{A8}$ | $L_{Q4}$ |
| 936. | $L_{A8}$ | $L_{Q5}$ |
| 937. | $L_{A8}$ | $L_{Q6}$ |
| 938. | $L_{A8}$ | $L_{Q7}$ |
| 939. | $L_{A8}$ | $L_{Q8}$ |
| 940. | $L_{A8}$ | $L_{Q9}$ |
| 941. | $L_{A8}$ | $L_{Q10}$ |
| 942. | $L_{A8}$ | $L_{Q11}$ |
| 943. | $L_{A8}$ | $L_{Q12}$ |
| 944. | $L_{A8}$ | $L_{Q13}$ |
| 945. | $L_{A8}$ | $L_{Q14}$ |
| 946. | $L_{A8}$ | $L_{Q15}$ |
| 947. | $L_{A8}$ | $L_{Q16}$ |
| 948. | $L_{A8}$ | $L_{Q17}$ |
| 949. | $L_{A8}$ | $L_{Q18}$ |
| 950. | $L_{A8}$ | $L_{Q19}$ |
| 951. | $L_{A8}$ | $L_{Q20}$ |
| 952. | $L_{A8}$ | $L_{Q21}$ |
| 953. | $L_{A8}$ | $L_{Q22}$ |
| 954. | $L_{A8}$ | $L_{Q23}$ |
| 955. | $L_{A8}$ | $L_{Q24}$ |
| 956. | $L_{A8}$ | $L_{Q25}$ |

TABLE 1-continued

| Compound number | $L^1$ | $L^2$ |
|---|---|---|
| 957. | $L_{48}$ | $L_{Q26}$ |
| 958. | $L_{48}$ | $L_{Q27}$ |
| 959. | $L_{48}$ | $L_{Q28}$ |
| 960. | $L_{48}$ | $L_{Q29}$ |
| 961. | $L_{48}$ | $L_{Q30}$ |
| 962. | $L_{48}$ | $L_{Q31}$ |
| 963. | $L_{48}$ | $L_{Q32}$ |
| 964. | $L_{48}$ | $L_{Q33}$ |
| 965. | $L_{48}$ | $L_{Q34}$ |
| 966. | $L_{48}$ | $L_{Q35}$ |
| 967. | $L_{48}$ | $L_{Q36}$ |
| 968. | $L_{48}$ | $L_{Q37}$ |
| 969. | $L_{48}$ | $L_{Q38}$ |
| 970. | $L_{48}$ | $L_{Q39}$ |
| 971. | $L_{48}$ | $L_{Q40}$ |
| 972. | $L_{48}$ | $L_{Q41}$ |
| 973. | $L_{48}$ | $L_{Q42}$ |
| 974. | $L_{48}$ | $L_{Q43}$ |
| 975. | $L_{48}$ | $L_{Q44}$ |
| 976. | $L_{48}$ | $L_{Q45}$ |
| 977. | $L_{48}$ | $L_{Q46}$ |
| 978. | $L_{48}$ | $L_{Q47}$ |
| 979. | $L_{48}$ | $L_{Q48}$ |
| 980. | $L_{48}$ | $L_{Q49}$ |
| 981. | $L_{48}$ | $L_{Q50}$ |
| 982. | $L_{48}$ | $L_{Q51}$ |
| 983. | $L_{48}$ | $L_{Q52}$ |
| 984. | $L_{48}$ | $L_{Q53}$ |
| 985. | $L_{48}$ | $L_{Q54}$ |
| 986. | $L_{48}$ | $L_{Q55}$ |
| 987. | $L_{48}$ | $L_{Q56}$ |
| 988. | $L_{48}$ | $L_{Q57}$ |
| 989. | $L_{48}$ | $L_{Q58}$ |
| 990. | $L_{48}$ | $L_{Q59}$ |
| 991. | $L_{48}$ | $L_{Q60}$ |
| 992. | $L_{48}$ | $L_{Q61}$ |
| 993. | $L_{48}$ | $L_{Q62}$ |
| 994. | $L_{48}$ | $L_{Q63}$ |
| 995. | $L_{48}$ | $L_{Q64}$ |
| 996. | $L_{48}$ | $L_{Q65}$ |
| 997. | $L_{48}$ | $L_{Q66}$ |
| 998. | $L_{48}$ | $L_{Q67}$ |
| 999. | $L_{48}$ | $L_{Q68}$ |
| 1000. | $L_{48}$ | $L_{Q69}$ |
| 1001. | $L_{48}$ | $L_{Q70}$ |
| 1002. | $L_{48}$ | $L_{Q71}$ |
| 1003. | $L_{48}$ | $L_{Q72}$ |
| 1004. | $L_{48}$ | $L_{Q73}$ |
| 1005. | $L_{48}$ | $L_{Q74}$ |
| 1006. | $L_{48}$ | $L_{Q75}$ |
| 1007. | $L_{48}$ | $L_{Q76}$ |
| 1008. | $L_{48}$ | $L_{Q77}$ |
| 1009. | $L_{48}$ | $L_{Q78}$ |
| 1010. | $L_{48}$ | $L_{Q79}$ |
| 1011. | $L_{48}$ | $L_{Q80}$ |
| 1012. | $L_{48}$ | $L_{Q81}$ |
| 1013. | $L_{48}$ | $L_{Q82}$ |
| 1014. | $L_{48}$ | $L_{Q83}$ |
| 1015. | $L_{48}$ | $L_{Q84}$ |
| 1016. | $L_{48}$ | $L_{Q85}$ |
| 1017. | $L_{48}$ | $L_{Q86}$ |
| 1018. | $L_{48}$ | $L_{Q87}$ |
| 1019. | $L_{48}$ | $L_{Q88}$ |
| 1020. | $L_{48}$ | $L_{Q89}$ |
| 1021. | $L_{48}$ | $L_{Q90}$ |
| 1022. | $L_{48}$ | $L_{Q91}$ |
| 1023. | $L_{48}$ | $L_{Q92}$ |
| 1024. | $L_{48}$ | $L_{Q93}$ |
| 1025. | $L_{48}$ | $L_{Q94}$ |
| 1026. | $L_{48}$ | $L_{Q95}$ |
| 1027. | $L_{48}$ | $L_{Q96}$ |
| 1028. | $L_{48}$ | $L_{Q97}$ |
| 1029. | $L_{48}$ | $L_{Q98}$ |
| 1030. | $L_{48}$ | $L_{Q99}$ |
| 1031. | $L_{48}$ | $L_{Q100}$ |
| 1032. | $L_{48}$ | $L_{Q101}$ |
| 1033. | $L_{48}$ | $L_{Q102}$ |
| 1034. | $L_{48}$ | $L_{Q103}$ |
| 1035. | $L_{48}$ | $L_{Q104}$ |
| 1036. | $L_{48}$ | $L_{Q105}$ |
| 1037. | $L_{48}$ | $L_{Q106}$ |
| 1038. | $L_{48}$ | $L_{Q107}$ |
| 1039. | $L_{48}$ | $L_{Q108}$ |
| 1040. | $L_{48}$ | $L_{Q109}$ |
| 1041. | $L_{48}$ | $L_{Q110}$ |
| 1042. | $L_{48}$ | $L_{Q111}$ |
| 1043. | $L_{48}$ | $L_{Q112}$ |
| 1044. | $L_{48}$ | $L_{Q113}$ |
| 1045. | $L_{48}$ | $L_{Q114}$ |
| 1046. | $L_{48}$ | $L_{Q115}$ |
| 1047. | $L_{48}$ | $L_{Q116}$ |
| 1048. | $L_{48}$ | $L_{Q117}$ |
| 1049. | $L_{48}$ | $L_{Q118}$ |
| 1050. | $L_{48}$ | $L_{Q119}$ |
| 1051. | $L_{48}$ | $L_{Q120}$ |
| 1052. | $L_{48}$ | $L_{Q121}$ |
| 1053. | $L_{48}$ | $L_{Q122}$ |
| 1054. | $L_{48}$ | $L_{Q123}$ |
| 1055. | $L_{48}$ | $L_{Q124}$ |
| 1056. | $L_{48}$ | $L_{Q125}$ |
| 1057. | $L_{48}$ | $L_{Q126}$ |
| 1058. | $L_{48}$ | $L_{Q127}$ |
| 1059. | $L_{48}$ | $L_{Q128}$ |
| 1060. | $L_{48}$ | $L_{Q129}$ |
| 1061. | $L_{48}$ | $L_{Q130}$ |
| 1062. | $L_{48}$ | $L_{Q131}$ |
| 1063. | $L_{48}$ | $L_{Q132}$ |
| 1064. | $L_{48}$ | $L_{Q133}$ |
| 1065. | $L_{49}$ | $L_{Q1}$ |
| 1066. | $L_{49}$ | $L_{Q2}$ |
| 1067. | $L_{49}$ | $L_{Q3}$ |
| 1068. | $L_{49}$ | $L_{Q4}$ |
| 1069. | $L_{49}$ | $L_{Q5}$ |
| 1070. | $L_{49}$ | $L_{Q6}$ |
| 1071. | $L_{49}$ | $L_{Q7}$ |
| 1072. | $L_{49}$ | $L_{Q8}$ |
| 1073. | $L_{49}$ | $L_{Q9}$ |
| 1074. | $L_{49}$ | $L_{Q10}$ |
| 1075. | $L_{49}$ | $L_{Q11}$ |
| 1076. | $L_{49}$ | $L_{Q12}$ |
| 1077. | $L_{49}$ | $L_{Q13}$ |
| 1078. | $L_{49}$ | $L_{Q14}$ |
| 1079. | $L_{49}$ | $L_{Q15}$ |
| 1080. | $L_{49}$ | $L_{Q16}$ |
| 1081. | $L_{49}$ | $L_{Q17}$ |
| 1082. | $L_{49}$ | $L_{Q18}$ |
| 1083. | $L_{49}$ | $L_{Q19}$ |
| 1084. | $L_{49}$ | $L_{Q20}$ |
| 1085. | $L_{49}$ | $L_{Q21}$ |
| 1086. | $L_{49}$ | $L_{Q22}$ |
| 1087. | $L_{49}$ | $L_{Q23}$ |
| 1088. | $L_{49}$ | $L_{Q24}$ |
| 1089. | $L_{49}$ | $L_{Q25}$ |
| 1090. | $L_{49}$ | $L_{Q26}$ |
| 1091. | $L_{49}$ | $L_{Q27}$ |
| 1092. | $L_{49}$ | $L_{Q28}$ |
| 1093. | $L_{49}$ | $L_{Q29}$ |
| 1094. | $L_{49}$ | $L_{Q30}$ |
| 1095. | $L_{49}$ | $L_{Q31}$ |
| 1096. | $L_{49}$ | $L_{Q32}$ |
| 1097. | $L_{49}$ | $L_{Q33}$ |
| 1098. | $L_{49}$ | $L_{Q34}$ |
| 1099. | $L_{49}$ | $L_{Q35}$ |
| 1100. | $L_{49}$ | $L_{Q36}$ |
| 1101. | $L_{49}$ | $L_{Q37}$ |
| 1102. | $L_{49}$ | $L_{Q38}$ |
| 1103. | $L_{49}$ | $L_{Q39}$ |
| 1104. | $L_{49}$ | $L_{Q40}$ |
| 1105. | $L_{49}$ | $L_{Q41}$ |
| 1106. | $L_{49}$ | $L_{Q42}$ |
| 1107. | $L_{49}$ | $L_{Q43}$ |
| 1108. | $L_{49}$ | $L_{Q44}$ |
| 1109. | $L_{49}$ | $L_{Q45}$ |
| 1110. | $L_{49}$ | $L_{Q46}$ |

TABLE 1-continued

| Compound number | $L^1$ | $L^2$ |
|---|---|---|
| 1111. | $L_{49}$ | $L_{Q47}$ |
| 1112. | $L_{49}$ | $L_{Q48}$ |
| 1113. | $L_{49}$ | $L_{Q49}$ |
| 1114. | $L_{49}$ | $L_{Q50}$ |
| 1115. | $L_{49}$ | $L_{Q51}$ |
| 1116. | $L_{49}$ | $L_{Q52}$ |
| 1117. | $L_{49}$ | $L_{Q53}$ |
| 1118. | $L_{49}$ | $L_{Q54}$ |
| 1119. | $L_{49}$ | $L_{Q55}$ |
| 1120. | $L_{49}$ | $L_{Q56}$ |
| 1121. | $L_{49}$ | $L_{Q57}$ |
| 1122. | $L_{49}$ | $L_{Q58}$ |
| 1123. | $L_{49}$ | $L_{Q59}$ |
| 1124. | $L_{49}$ | $L_{Q60}$ |
| 1125. | $L_{49}$ | $L_{Q61}$ |
| 1126. | $L_{49}$ | $L_{Q62}$ |
| 1127. | $L_{49}$ | $L_{Q63}$ |
| 1128. | $L_{49}$ | $L_{Q64}$ |
| 1129. | $L_{49}$ | $L_{Q65}$ |
| 1130. | $L_{49}$ | $L_{Q66}$ |
| 1131. | $L_{49}$ | $L_{Q67}$ |
| 1132. | $L_{49}$ | $L_{Q68}$ |
| 1133. | $L_{49}$ | $L_{Q69}$ |
| 1134. | $L_{49}$ | $L_{Q70}$ |
| 1135. | $L_{49}$ | $L_{Q71}$ |
| 1136. | $L_{49}$ | $L_{Q72}$ |
| 1137. | $L_{49}$ | $L_{Q73}$ |
| 1138. | $L_{49}$ | $L_{Q74}$ |
| 1139. | $L_{49}$ | $L_{Q75}$ |
| 1140. | $L_{49}$ | $L_{Q76}$ |
| 1141. | $L_{49}$ | $L_{Q77}$ |
| 1142. | $L_{49}$ | $L_{Q78}$ |
| 1143. | $L_{49}$ | $L_{Q79}$ |
| 1144. | $L_{49}$ | $L_{Q80}$ |
| 1145. | $L_{49}$ | $L_{Q81}$ |
| 1146. | $L_{49}$ | $L_{Q82}$ |
| 1147. | $L_{49}$ | $L_{Q83}$ |
| 1148. | $L_{49}$ | $L_{Q84}$ |
| 1149. | $L_{49}$ | $L_{Q85}$ |
| 1150. | $L_{49}$ | $L_{Q86}$ |
| 1151. | $L_{49}$ | $L_{Q87}$ |
| 1152. | $L_{49}$ | $L_{Q88}$ |
| 1153. | $L_{49}$ | $L_{Q89}$ |
| 1154. | $L_{49}$ | $L_{Q90}$ |
| 1155. | $L_{49}$ | $L_{Q91}$ |
| 1156. | $L_{49}$ | $L_{Q92}$ |
| 1157. | $L_{49}$ | $L_{Q93}$ |
| 1158. | $L_{49}$ | $L_{Q94}$ |
| 1159. | $L_{49}$ | $L_{Q95}$ |
| 1160. | $L_{49}$ | $L_{Q96}$ |
| 1161. | $L_{49}$ | $L_{Q97}$ |
| 1162. | $L_{49}$ | $L_{Q98}$ |
| 1163. | $L_{49}$ | $L_{Q99}$ |
| 1164. | $L_{49}$ | $L_{Q100}$ |
| 1165. | $L_{49}$ | $L_{Q101}$ |
| 1166. | $L_{49}$ | $L_{Q102}$ |
| 1167. | $L_{49}$ | $L_{Q103}$ |
| 1168. | $L_{49}$ | $L_{Q104}$ |
| 1169. | $L_{49}$ | $L_{Q105}$ |
| 1170. | $L_{49}$ | $L_{Q106}$ |
| 1171. | $L_{49}$ | $L_{Q107}$ |
| 1172. | $L_{49}$ | $L_{Q108}$ |
| 1173. | $L_{49}$ | $L_{Q109}$ |
| 1174. | $L_{49}$ | $L_{Q110}$ |
| 1175. | $L_{49}$ | $L_{Q111}$ |
| 1176. | $L_{49}$ | $L_{Q112}$ |
| 1177. | $L_{49}$ | $L_{Q113}$ |
| 1178. | $L_{49}$ | $L_{Q114}$ |
| 1179. | $L_{49}$ | $L_{Q115}$ |
| 1180. | $L_{49}$ | $L_{Q116}$ |
| 1181. | $L_{49}$ | $L_{Q117}$ |
| 1182. | $L_{49}$ | $L_{Q118}$ |
| 1183. | $L_{49}$ | $L_{Q119}$ |
| 1184. | $L_{49}$ | $L_{Q120}$ |
| 1185. | $L_{49}$ | $L_{Q121}$ |
| 1186. | $L_{49}$ | $L_{Q122}$ |
| 1187. | $L_{49}$ | $L_{Q123}$ |
| 1188. | $L_{49}$ | $L_{Q124}$ |
| 1189. | $L_{49}$ | $L_{Q125}$ |
| 1190. | $L_{49}$ | $L_{Q126}$ |
| 1191. | $L_{49}$ | $L_{Q127}$ |
| 1192. | $L_{49}$ | $L_{Q128}$ |
| 1193. | $L_{49}$ | $L_{Q129}$ |
| 1194. | $L_{49}$ | $L_{Q130}$ |
| 1195. | $L_{49}$ | $L_{Q131}$ |
| 1196. | $L_{49}$ | $L_{Q132}$ |
| 1197. | $L_{49}$ | $L_{Q133}$ |
| 1198. | $L_{410}$ | $L_{Q1}$ |
| 1199. | $L_{410}$ | $L_{Q2}$ |
| 1200. | $L_{410}$ | $L_{Q3}$ |
| 1201. | $L_{410}$ | $L_{Q4}$ |
| 1202. | $L_{410}$ | $L_{Q5}$ |
| 1203. | $L_{410}$ | $L_{Q6}$ |
| 1204. | $L_{410}$ | $L_{Q7}$ |
| 1205. | $L_{410}$ | $L_{Q8}$ |
| 1206. | $L_{410}$ | $L_{Q9}$ |
| 1207. | $L_{410}$ | $L_{Q10}$ |
| 1208. | $L_{410}$ | $L_{Q11}$ |
| 1209. | $L_{410}$ | $L_{Q12}$ |
| 1210. | $L_{410}$ | $L_{Q13}$ |
| 1211. | $L_{410}$ | $L_{Q14}$ |
| 1212. | $L_{410}$ | $L_{Q15}$ |
| 1213. | $L_{410}$ | $L_{Q16}$ |
| 1214. | $L_{410}$ | $L_{Q17}$ |
| 1215. | $L_{410}$ | $L_{Q18}$ |
| 1216. | $L_{410}$ | $L_{Q19}$ |
| 1217. | $L_{410}$ | $L_{Q20}$ |
| 1218. | $L_{410}$ | $L_{Q21}$ |
| 1219. | $L_{410}$ | $L_{Q22}$ |
| 1220. | $L_{410}$ | $L_{Q23}$ |
| 1221. | $L_{410}$ | $L_{Q24}$ |
| 1222. | $L_{410}$ | $L_{Q25}$ |
| 1223. | $L_{410}$ | $L_{Q26}$ |
| 1224. | $L_{410}$ | $L_{Q27}$ |
| 1225. | $L_{410}$ | $L_{Q28}$ |
| 1226. | $L_{410}$ | $L_{Q29}$ |
| 1227. | $L_{410}$ | $L_{Q30}$ |
| 1228. | $L_{410}$ | $L_{Q31}$ |
| 1229. | $L_{410}$ | $L_{Q32}$ |
| 1230. | $L_{410}$ | $L_{Q33}$ |
| 1231. | $L_{410}$ | $L_{Q34}$ |
| 1232. | $L_{410}$ | $L_{Q35}$ |
| 1233. | $L_{410}$ | $L_{Q36}$ |
| 1234. | $L_{410}$ | $L_{Q37}$ |
| 1235. | $L_{410}$ | $L_{Q38}$ |
| 1236. | $L_{410}$ | $L_{Q39}$ |
| 1237. | $L_{410}$ | $L_{Q40}$ |
| 1238. | $L_{410}$ | $L_{Q41}$ |
| 1239. | $L_{410}$ | $L_{Q42}$ |
| 1240. | $L_{410}$ | $L_{Q43}$ |
| 1241. | $L_{410}$ | $L_{Q44}$ |
| 1242. | $L_{410}$ | $L_{Q45}$ |
| 1243. | $L_{410}$ | $L_{Q46}$ |
| 1244. | $L_{410}$ | $L_{Q47}$ |
| 1245. | $L_{410}$ | $L_{Q48}$ |
| 1246. | $L_{410}$ | $L_{Q49}$ |
| 1247. | $L_{410}$ | $L_{Q50}$ |
| 1248. | $L_{410}$ | $L_{Q51}$ |
| 1249. | $L_{410}$ | $L_{Q52}$ |
| 1250. | $L_{410}$ | $L_{Q53}$ |
| 1251. | $L_{410}$ | $L_{Q54}$ |
| 1252. | $L_{410}$ | $L_{Q55}$ |
| 1253. | $L_{410}$ | $L_{Q56}$ |
| 1254. | $L_{410}$ | $L_{Q57}$ |
| 1255. | $L_{410}$ | $L_{Q58}$ |
| 1256. | $L_{410}$ | $L_{Q59}$ |
| 1257. | $L_{410}$ | $L_{Q60}$ |
| 1258. | $L_{410}$ | $L_{Q61}$ |
| 1259. | $L_{410}$ | $L_{Q62}$ |
| 1260. | $L_{410}$ | $L_{Q63}$ |
| 1261. | $L_{410}$ | $L_{Q64}$ |
| 1262. | $L_{410}$ | $L_{Q65}$ |
| 1263. | $L_{410}$ | $L_{Q66}$ |
| 1264. | $L_{410}$ | $L_{Q67}$ |

TABLE 1-continued

| Compound number | $L^1$ | $L^2$ |
|---|---|---|
| 1265. | $L_{A10}$ | $L_{Q68}$ |
| 1266. | $L_{A10}$ | $L_{Q69}$ |
| 1267. | $L_{A10}$ | $L_{Q70}$ |
| 1268. | $L_{A10}$ | $L_{Q71}$ |
| 1269. | $L_{A10}$ | $L_{Q72}$ |
| 1270. | $L_{A10}$ | $L_{Q73}$ |
| 1271. | $L_{A10}$ | $L_{Q74}$ |
| 1272. | $L_{A10}$ | $L_{Q75}$ |
| 1273. | $L_{A10}$ | $L_{Q76}$ |
| 1274. | $L_{A10}$ | $L_{Q77}$ |
| 1275. | $L_{A10}$ | $L_{Q78}$ |
| 1276. | $L_{A10}$ | $L_{Q79}$ |
| 1277. | $L_{A10}$ | $L_{Q80}$ |
| 1278. | $L_{A10}$ | $L_{Q81}$ |
| 1279. | $L_{A10}$ | $L_{Q82}$ |
| 1280. | $L_{A10}$ | $L_{Q83}$ |
| 1281. | $L_{A10}$ | $L_{Q84}$ |
| 1282. | $L_{A10}$ | $L_{Q85}$ |
| 1283. | $L_{A10}$ | $L_{Q86}$ |
| 1284. | $L_{A10}$ | $L_{Q87}$ |
| 1285. | $L_{A10}$ | $L_{Q88}$ |
| 1286. | $L_{A10}$ | $L_{Q89}$ |
| 1287. | $L_{A10}$ | $L_{Q90}$ |
| 1288. | $L_{A10}$ | $L_{Q91}$ |
| 1289. | $L_{A10}$ | $L_{Q92}$ |
| 1290. | $L_{A10}$ | $L_{Q93}$ |
| 1291. | $L_{A10}$ | $L_{Q94}$ |
| 1292. | $L_{A10}$ | $L_{Q95}$ |
| 1293. | $L_{A10}$ | $L_{Q96}$ |
| 1294. | $L_{A10}$ | $L_{Q97}$ |
| 1295. | $L_{A10}$ | $L_{Q98}$ |
| 1296. | $L_{A10}$ | $L_{Q99}$ |
| 1297. | $L_{A10}$ | $L_{Q100}$ |
| 1298. | $L_{A10}$ | $L_{Q101}$ |
| 1299. | $L_{A10}$ | $L_{Q102}$ |
| 1300. | $L_{A10}$ | $L_{Q103}$ |
| 1301. | $L_{A10}$ | $L_{Q104}$ |
| 1302. | $L_{A10}$ | $L_{Q105}$ |
| 1303. | $L_{A10}$ | $L_{Q106}$ |
| 1304. | $L_{A10}$ | $L_{Q107}$ |
| 1305. | $L_{A10}$ | $L_{Q108}$ |
| 1306. | $L_{A10}$ | $L_{Q109}$ |
| 1307. | $L_{A10}$ | $L_{Q110}$ |
| 1308. | $L_{A10}$ | $L_{Q111}$ |
| 1309. | $L_{A10}$ | $L_{Q112}$ |
| 1310. | $L_{A10}$ | $L_{Q113}$ |
| 1311. | $L_{A10}$ | $L_{Q114}$ |
| 1312. | $L_{A10}$ | $L_{Q115}$ |
| 1313. | $L_{A10}$ | $L_{Q116}$ |
| 1314. | $L_{A10}$ | $L_{Q117}$ |
| 1315. | $L_{A10}$ | $L_{Q118}$ |
| 1316. | $L_{A10}$ | $L_{Q119}$ |
| 1317. | $L_{A10}$ | $L_{Q120}$ |
| 1318. | $L_{A10}$ | $L_{Q121}$ |
| 1319. | $L_{A10}$ | $L_{Q122}$ |
| 1320. | $L_{A10}$ | $L_{Q123}$ |
| 1321. | $L_{A10}$ | $L_{Q124}$ |
| 1322. | $L_{A10}$ | $L_{Q125}$ |
| 1323. | $L_{A10}$ | $L_{Q126}$ |
| 1324. | $L_{A10}$ | $L_{Q127}$ |
| 1325. | $L_{A10}$ | $L_{Q128}$ |
| 1326. | $L_{A10}$ | $L_{Q129}$ |
| 1327. | $L_{A10}$ | $L_{Q130}$ |
| 1328. | $L_{A10}$ | $L_{Q131}$ |
| 1329. | $L_{A10}$ | $L_{Q132}$ |
| 1330. | $L_{A10}$ | $L_{Q133}$ |
| 1331. | $L_{A11}$ | $L_{Q1}$ |
| 1332. | $L_{A11}$ | $L_{Q2}$ |
| 1333. | $L_{A11}$ | $L_{Q3}$ |
| 1334. | $L_{A11}$ | $L_{Q4}$ |
| 1335. | $L_{A11}$ | $L_{Q5}$ |
| 1336. | $L_{A11}$ | $L_{Q6}$ |
| 1337. | $L_{A11}$ | $L_{Q7}$ |
| 1338. | $L_{A11}$ | $L_{Q8}$ |
| 1339. | $L_{A11}$ | $L_{Q9}$ |
| 1340. | $L_{A11}$ | $L_{Q10}$ |
| 1341. | $L_{A11}$ | $L_{Q11}$ |
| 1342. | $L_{A11}$ | $L_{Q12}$ |
| 1343. | $L_{A11}$ | $L_{Q13}$ |
| 1344. | $L_{A11}$ | $L_{Q14}$ |
| 1345. | $L_{A11}$ | $L_{Q15}$ |
| 1346. | $L_{A11}$ | $L_{Q16}$ |
| 1347. | $L_{A11}$ | $L_{Q17}$ |
| 1348. | $L_{A11}$ | $L_{Q18}$ |
| 1349. | $L_{A11}$ | $L_{Q19}$ |
| 1350. | $L_{A11}$ | $L_{Q20}$ |
| 1351. | $L_{A11}$ | $L_{Q21}$ |
| 1352. | $L_{A11}$ | $L_{Q22}$ |
| 1353. | $L_{A11}$ | $L_{Q23}$ |
| 1354. | $L_{A11}$ | $L_{Q24}$ |
| 1355. | $L_{A11}$ | $L_{Q25}$ |
| 1356. | $L_{A11}$ | $L_{Q26}$ |
| 1357. | $L_{A11}$ | $L_{Q27}$ |
| 1358. | $L_{A11}$ | $L_{Q28}$ |
| 1359. | $L_{A11}$ | $L_{Q29}$ |
| 1360. | $L_{A11}$ | $L_{Q30}$ |
| 1361. | $L_{A11}$ | $L_{Q31}$ |
| 1362. | $L_{A11}$ | $L_{Q32}$ |
| 1363. | $L_{A11}$ | $L_{Q33}$ |
| 1364. | $L_{A11}$ | $L_{Q34}$ |
| 1365. | $L_{A11}$ | $L_{Q35}$ |
| 1366. | $L_{A11}$ | $L_{Q36}$ |
| 1367. | $L_{A11}$ | $L_{Q37}$ |
| 1368. | $L_{A11}$ | $L_{Q38}$ |
| 1369. | $L_{A11}$ | $L_{Q39}$ |
| 1370. | $L_{A11}$ | $L_{Q40}$ |
| 1371. | $L_{A11}$ | $L_{Q41}$ |
| 1372. | $L_{A11}$ | $L_{Q42}$ |
| 1373. | $L_{A11}$ | $L_{Q43}$ |
| 1374. | $L_{A11}$ | $L_{Q44}$ |
| 1375. | $L_{A11}$ | $L_{Q45}$ |
| 1376. | $L_{A11}$ | $L_{Q46}$ |
| 1377. | $L_{A11}$ | $L_{Q47}$ |
| 1378. | $L_{A11}$ | $L_{Q48}$ |
| 1379. | $L_{A11}$ | $L_{Q49}$ |
| 1380. | $L_{A11}$ | $L_{Q50}$ |
| 1381. | $L_{A11}$ | $L_{Q51}$ |
| 1382. | $L_{A11}$ | $L_{Q52}$ |
| 1383. | $L_{A11}$ | $L_{Q53}$ |
| 1384. | $L_{A11}$ | $L_{Q54}$ |
| 1385. | $L_{A11}$ | $L_{Q55}$ |
| 1386. | $L_{A11}$ | $L_{Q56}$ |
| 1387. | $L_{A11}$ | $L_{Q57}$ |
| 1388. | $L_{A11}$ | $L_{Q58}$ |
| 1389. | $L_{A11}$ | $L_{Q59}$ |
| 1390. | $L_{A11}$ | $L_{Q60}$ |
| 1391. | $L_{A11}$ | $L_{Q61}$ |
| 1392. | $L_{A11}$ | $L_{Q62}$ |
| 1393. | $L_{A11}$ | $L_{Q63}$ |
| 1394. | $L_{A11}$ | $L_{Q64}$ |
| 1395. | $L_{A11}$ | $L_{Q65}$ |
| 1396. | $L_{A11}$ | $L_{Q66}$ |
| 1397. | $L_{A11}$ | $L_{Q67}$ |
| 1398. | $L_{A11}$ | $L_{Q68}$ |
| 1399. | $L_{A11}$ | $L_{Q69}$ |
| 1400. | $L_{A11}$ | $L_{Q70}$ |
| 1401. | $L_{A11}$ | $L_{Q71}$ |
| 1402. | $L_{A11}$ | $L_{Q72}$ |
| 1403. | $L_{A11}$ | $L_{Q73}$ |
| 1404. | $L_{A11}$ | $L_{Q74}$ |
| 1405. | $L_{A11}$ | $L_{Q75}$ |
| 1406. | $L_{A11}$ | $L_{Q76}$ |
| 1407. | $L_{A11}$ | $L_{Q77}$ |
| 1408. | $L_{A11}$ | $L_{Q78}$ |
| 1409. | $L_{A11}$ | $L_{Q79}$ |
| 1410. | $L_{A11}$ | $L_{Q80}$ |
| 1411. | $L_{A11}$ | $L_{Q81}$ |
| 1412. | $L_{A11}$ | $L_{Q82}$ |
| 1413. | $L_{A11}$ | $L_{Q83}$ |
| 1414. | $L_{A11}$ | $L_{Q84}$ |
| 1415. | $L_{A11}$ | $L_{Q85}$ |
| 1416. | $L_{A11}$ | $L_{Q86}$ |
| 1417. | $L_{A11}$ | $L_{Q87}$ |
| 1418. | $L_{A11}$ | $L_{Q88}$ |

TABLE 1-continued

| Compound number | L¹ | L² |
|---|---|---|
| 1419. | $L_{A11}$ | $L_{Q89}$ |
| 1420. | $L_{A11}$ | $L_{Q90}$ |
| 1421. | $L_{A11}$ | $L_{Q91}$ |
| 1422. | $L_{A11}$ | $L_{Q92}$ |
| 1423. | $L_{A11}$ | $L_{Q93}$ |
| 1424. | $L_{A11}$ | $L_{Q94}$ |
| 1425. | $L_{A11}$ | $L_{Q95}$ |
| 1426. | $L_{A11}$ | $L_{Q96}$ |
| 1427. | $L_{A11}$ | $L_{Q97}$ |
| 1428. | $L_{A11}$ | $L_{Q98}$ |
| 1429. | $L_{A11}$ | $L_{Q99}$ |
| 1430. | $L_{A11}$ | $L_{Q100}$ |
| 1431. | $L_{A11}$ | $L_{Q101}$ |
| 1432. | $L_{A11}$ | $L_{Q102}$ |
| 1433. | $L_{A11}$ | $L_{Q103}$ |
| 1434. | $L_{A11}$ | $L_{Q104}$ |
| 1435. | $L_{A11}$ | $L_{Q105}$ |
| 1436. | $L_{A11}$ | $L_{Q106}$ |
| 1437. | $L_{A11}$ | $L_{Q107}$ |
| 1438. | $L_{A11}$ | $L_{Q108}$ |
| 1439. | $L_{A11}$ | $L_{Q109}$ |
| 1440. | $L_{A11}$ | $L_{Q110}$ |
| 1441. | $L_{A11}$ | $L_{Q111}$ |
| 1442. | $L_{A11}$ | $L_{Q112}$ |
| 1443. | $L_{A11}$ | $L_{Q113}$ |
| 1444. | $L_{A11}$ | $L_{Q114}$ |
| 1445. | $L_{A11}$ | $L_{Q115}$ |
| 1446. | $L_{A11}$ | $L_{Q116}$ |
| 1447. | $L_{A11}$ | $L_{Q117}$ |
| 1448. | $L_{A11}$ | $L_{Q118}$ |
| 1449. | $L_{A11}$ | $L_{Q119}$ |
| 1450. | $L_{A11}$ | $L_{Q120}$ |
| 1451. | $L_{A11}$ | $L_{Q121}$ |
| 1452. | $L_{A11}$ | $L_{Q122}$ |
| 1453. | $L_{A11}$ | $L_{Q123}$ |
| 1454. | $L_{A11}$ | $L_{Q124}$ |
| 1455. | $L_{A11}$ | $L_{Q125}$ |
| 1456. | $L_{A11}$ | $L_{Q126}$ |
| 1457. | $L_{A11}$ | $L_{Q127}$ |
| 1458. | $L_{A11}$ | $L_{Q128}$ |
| 1459. | $L_{A11}$ | $L_{Q129}$ |
| 1460. | $L_{A11}$ | $L_{Q130}$ |
| 1461. | $L_{A11}$ | $L_{Q131}$ |
| 1462. | $L_{A11}$ | $L_{Q132}$ |
| 1463. | $L_{A11}$ | $L_{Q133}$ |
| 1464. | $L_{A12}$ | $L_{Q1}$ |
| 1465. | $L_{A12}$ | $L_{Q2}$ |
| 1466. | $L_{A12}$ | $L_{Q3}$ |
| 1467. | $L_{A12}$ | $L_{Q4}$ |
| 1468. | $L_{A12}$ | $L_{Q5}$ |
| 1469. | $L_{A12}$ | $L_{Q6}$ |
| 1470. | $L_{A12}$ | $L_{Q7}$ |
| 1471. | $L_{A12}$ | $L_{Q8}$ |
| 1472. | $L_{A12}$ | $L_{Q9}$ |
| 1473. | $L_{A12}$ | $L_{Q10}$ |
| 1474. | $L_{A12}$ | $L_{Q11}$ |
| 1475. | $L_{A12}$ | $L_{Q12}$ |
| 1476. | $L_{A12}$ | $L_{Q13}$ |
| 1477. | $L_{A12}$ | $L_{Q14}$ |
| 1478. | $L_{A12}$ | $L_{Q15}$ |
| 1479. | $L_{A12}$ | $L_{Q16}$ |
| 1480. | $L_{A12}$ | $L_{Q17}$ |
| 1481. | $L_{A12}$ | $L_{Q18}$ |
| 1482. | $L_{A12}$ | $L_{Q19}$ |
| 1483. | $L_{A12}$ | $L_{Q20}$ |
| 1484. | $L_{A12}$ | $L_{Q21}$ |
| 1485. | $L_{A12}$ | $L_{Q22}$ |
| 1486. | $L_{A12}$ | $L_{Q23}$ |
| 1487. | $L_{A12}$ | $L_{Q24}$ |
| 1488. | $L_{A12}$ | $L_{Q25}$ |
| 1489. | $L_{A12}$ | $L_{Q26}$ |
| 1490. | $L_{A12}$ | $L_{Q27}$ |
| 1491. | $L_{A12}$ | $L_{Q28}$ |
| 1492. | $L_{A12}$ | $L_{Q29}$ |
| 1493. | $L_{A12}$ | $L_{Q30}$ |
| 1494. | $L_{A12}$ | $L_{Q31}$ |
| 1495. | $L_{A12}$ | $L_{Q32}$ |
| 1496. | $L_{A12}$ | $L_{Q33}$ |
| 1497. | $L_{A12}$ | $L_{Q34}$ |
| 1498. | $L_{A12}$ | $L_{Q35}$ |
| 1499. | $L_{A12}$ | $L_{Q36}$ |
| 1500. | $L_{A12}$ | $L_{Q37}$ |
| 1501. | $L_{A12}$ | $L_{Q38}$ |
| 1502. | $L_{A12}$ | $L_{Q39}$ |
| 1503. | $L_{A12}$ | $L_{Q40}$ |
| 1504. | $L_{A12}$ | $L_{Q41}$ |
| 1505. | $L_{A12}$ | $L_{Q42}$ |
| 1506. | $L_{A12}$ | $L_{Q43}$ |
| 1507. | $L_{A12}$ | $L_{Q44}$ |
| 1508. | $L_{A12}$ | $L_{Q45}$ |
| 1509. | $L_{A12}$ | $L_{Q46}$ |
| 1510. | $L_{A12}$ | $L_{Q47}$ |
| 1511. | $L_{A12}$ | $L_{Q48}$ |
| 1512. | $L_{A12}$ | $L_{Q49}$ |
| 1513. | $L_{A12}$ | $L_{Q50}$ |
| 1514. | $L_{A12}$ | $L_{Q51}$ |
| 1515. | $L_{A12}$ | $L_{Q52}$ |
| 1516. | $L_{A12}$ | $L_{Q53}$ |
| 1517. | $L_{A12}$ | $L_{Q54}$ |
| 1518. | $L_{A12}$ | $L_{Q55}$ |
| 1519. | $L_{A12}$ | $L_{Q56}$ |
| 1520. | $L_{A12}$ | $L_{Q57}$ |
| 1521. | $L_{A12}$ | $L_{Q58}$ |
| 1522. | $L_{A12}$ | $L_{Q59}$ |
| 1523. | $L_{A12}$ | $L_{Q60}$ |
| 1524. | $L_{A12}$ | $L_{Q61}$ |
| 1525. | $L_{A12}$ | $L_{Q62}$ |
| 1526. | $L_{A12}$ | $L_{Q63}$ |
| 1527. | $L_{A12}$ | $L_{Q64}$ |
| 1528. | $L_{A12}$ | $L_{Q65}$ |
| 1529. | $L_{A12}$ | $L_{Q66}$ |
| 1530. | $L_{A12}$ | $L_{Q67}$ |
| 1531. | $L_{A12}$ | $L_{Q68}$ |
| 1532. | $L_{A12}$ | $L_{Q69}$ |
| 1533. | $L_{A12}$ | $L_{Q70}$ |
| 1534. | $L_{A12}$ | $L_{Q71}$ |
| 1535. | $L_{A12}$ | $L_{Q72}$ |
| 1536. | $L_{A12}$ | $L_{Q73}$ |
| 1537. | $L_{A12}$ | $L_{Q74}$ |
| 1538. | $L_{A12}$ | $L_{Q75}$ |
| 1539. | $L_{A12}$ | $L_{Q76}$ |
| 1540. | $L_{A12}$ | $L_{Q77}$ |
| 1541. | $L_{A12}$ | $L_{Q78}$ |
| 1542. | $L_{A12}$ | $L_{Q79}$ |
| 1543. | $L_{A12}$ | $L_{Q80}$ |
| 1544. | $L_{A12}$ | $L_{Q81}$ |
| 1545. | $L_{A12}$ | $L_{Q82}$ |
| 1546. | $L_{A12}$ | $L_{Q83}$ |
| 1547. | $L_{A12}$ | $L_{Q84}$ |
| 1548. | $L_{A12}$ | $L_{Q85}$ |
| 1549. | $L_{A12}$ | $L_{Q86}$ |
| 1550. | $L_{A12}$ | $L_{Q87}$ |
| 1551. | $L_{A12}$ | $L_{Q88}$ |
| 1552. | $L_{A12}$ | $L_{Q89}$ |
| 1553. | $L_{A12}$ | $L_{Q90}$ |
| 1554. | $L_{A12}$ | $L_{Q91}$ |
| 1555. | $L_{A12}$ | $L_{Q92}$ |
| 1556. | $L_{A12}$ | $L_{Q93}$ |
| 1557. | $L_{A12}$ | $L_{Q94}$ |
| 1558. | $L_{A12}$ | $L_{Q95}$ |
| 1559. | $L_{A12}$ | $L_{Q96}$ |
| 1560. | $L_{A12}$ | $L_{Q97}$ |
| 1561. | $L_{A12}$ | $L_{Q98}$ |
| 1562. | $L_{A12}$ | $L_{Q99}$ |
| 1563. | $L_{A12}$ | $L_{Q100}$ |
| 1564. | $L_{A12}$ | $L_{Q101}$ |
| 1565. | $L_{A12}$ | $L_{Q102}$ |
| 1566. | $L_{A12}$ | $L_{Q103}$ |
| 1567. | $L_{A12}$ | $L_{Q104}$ |
| 1568. | $L_{A12}$ | $L_{Q105}$ |
| 1569. | $L_{A12}$ | $L_{Q106}$ |
| 1570. | $L_{A12}$ | $L_{Q107}$ |
| 1571. | $L_{A12}$ | $L_{Q108}$ |
| 1572. | $L_{A12}$ | $L_{Q109}$ |

TABLE 1-continued

| Compound number | $L^1$ | $L^2$ |
|---|---|---|
| 1573. | $L_{A12}$ | $L_{Q110}$ |
| 1574. | $L_{A12}$ | $L_{Q111}$ |
| 1575. | $L_{A12}$ | $L_{Q112}$ |
| 1576. | $L_{A12}$ | $L_{Q113}$ |
| 1577. | $L_{A12}$ | $L_{Q114}$ |
| 1578. | $L_{A12}$ | $L_{Q115}$ |
| 1579. | $L_{A12}$ | $L_{Q116}$ |
| 1580. | $L_{A12}$ | $L_{Q117}$ |
| 1581. | $L_{A12}$ | $L_{Q118}$ |
| 1582. | $L_{A12}$ | $L_{Q119}$ |
| 1583. | $L_{A12}$ | $L_{Q120}$ |
| 1584. | $L_{A12}$ | $L_{Q121}$ |
| 1585. | $L_{A12}$ | $L_{Q122}$ |
| 1586. | $L_{A12}$ | $L_{Q123}$ |
| 1587. | $L_{A12}$ | $L_{Q124}$ |
| 1588. | $L_{A12}$ | $L_{Q125}$ |
| 1589. | $L_{A12}$ | $L_{Q126}$ |
| 1590. | $L_{A12}$ | $L_{Q127}$ |
| 1591. | $L_{A12}$ | $L_{Q128}$ |
| 1592. | $L_{A12}$ | $L_{Q129}$ |
| 1593. | $L_{A12}$ | $L_{Q130}$ |
| 1594. | $L_{A12}$ | $L_{Q131}$ |
| 1595. | $L_{A12}$ | $L_{Q132}$ |
| 1596. | $L_{A12}$ | $L_{Q133}$ |
| 1597. | $L_{A13}$ | $L_{Q1}$ |
| 1598. | $L_{A13}$ | $L_{Q2}$ |
| 1599. | $L_{A13}$ | $L_{Q3}$ |
| 1600. | $L_{A13}$ | $L_{Q4}$ |
| 1601. | $L_{A13}$ | $L_{Q5}$ |
| 1602. | $L_{A13}$ | $L_{Q6}$ |
| 1603. | $L_{A13}$ | $L_{Q7}$ |
| 1604. | $L_{A13}$ | $L_{Q8}$ |
| 1605. | $L_{A13}$ | $L_{Q9}$ |
| 1606. | $L_{A13}$ | $L_{Q10}$ |
| 1607. | $L_{A13}$ | $L_{Q11}$ |
| 1608. | $L_{A13}$ | $L_{Q12}$ |
| 1609. | $L_{A13}$ | $L_{Q13}$ |
| 1610. | $L_{A13}$ | $L_{Q14}$ |
| 1611. | $L_{A13}$ | $L_{Q15}$ |
| 1612. | $L_{A13}$ | $L_{Q16}$ |
| 1613. | $L_{A13}$ | $L_{Q17}$ |
| 1614. | $L_{A13}$ | $L_{Q18}$ |
| 1615. | $L_{A13}$ | $L_{Q19}$ |
| 1616. | $L_{A13}$ | $L_{Q20}$ |
| 1617. | $L_{A13}$ | $L_{Q21}$ |
| 1618. | $L_{A13}$ | $L_{Q22}$ |
| 1619. | $L_{A13}$ | $L_{Q23}$ |
| 1620. | $L_{A13}$ | $L_{Q24}$ |
| 1621. | $L_{A13}$ | $L_{Q25}$ |
| 1622. | $L_{A13}$ | $L_{Q26}$ |
| 1623. | $L_{A13}$ | $L_{Q27}$ |
| 1624. | $L_{A13}$ | $L_{Q28}$ |
| 1625. | $L_{A13}$ | $L_{Q29}$ |
| 1626. | $L_{A13}$ | $L_{Q30}$ |
| 1627. | $L_{A13}$ | $L_{Q31}$ |
| 1628. | $L_{A13}$ | $L_{Q32}$ |
| 1629. | $L_{A13}$ | $L_{Q33}$ |
| 1630. | $L_{A13}$ | $L_{Q34}$ |
| 1631. | $L_{A13}$ | $L_{Q35}$ |
| 1632. | $L_{A13}$ | $L_{Q36}$ |
| 1633. | $L_{A13}$ | $L_{Q37}$ |
| 1634. | $L_{A13}$ | $L_{Q38}$ |
| 1635. | $L_{A13}$ | $L_{Q39}$ |
| 1636. | $L_{A13}$ | $L_{Q40}$ |
| 1637. | $L_{A13}$ | $L_{Q41}$ |
| 1638. | $L_{A13}$ | $L_{Q42}$ |
| 1639. | $L_{A13}$ | $L_{Q43}$ |
| 1640. | $L_{A13}$ | $L_{Q44}$ |
| 1641. | $L_{A13}$ | $L_{Q45}$ |
| 1642. | $L_{A13}$ | $L_{Q46}$ |
| 1643. | $L_{A13}$ | $L_{Q47}$ |
| 1644. | $L_{A13}$ | $L_{Q48}$ |
| 1645. | $L_{A13}$ | $L_{Q49}$ |
| 1646. | $L_{A13}$ | $L_{Q50}$ |
| 1647. | $L_{A13}$ | $L_{Q51}$ |
| 1648. | $L_{A13}$ | $L_{Q52}$ |
| 1649. | $L_{A13}$ | $L_{Q53}$ |
| 1650. | $L_{A13}$ | $L_{Q54}$ |
| 1651. | $L_{A13}$ | $L_{Q55}$ |
| 1652. | $L_{A13}$ | $L_{Q56}$ |
| 1653. | $L_{A13}$ | $L_{Q57}$ |
| 1654. | $L_{A13}$ | $L_{Q58}$ |
| 1655. | $L_{A13}$ | $L_{Q59}$ |
| 1656. | $L_{A13}$ | $L_{Q60}$ |
| 1657. | $L_{A13}$ | $L_{Q61}$ |
| 1658. | $L_{A13}$ | $L_{Q62}$ |
| 1659. | $L_{A13}$ | $L_{Q63}$ |
| 1660. | $L_{A13}$ | $L_{Q64}$ |
| 1661. | $L_{A13}$ | $L_{Q65}$ |
| 1662. | $L_{A13}$ | $L_{Q66}$ |
| 1663. | $L_{A13}$ | $L_{Q67}$ |
| 1664. | $L_{A13}$ | $L_{Q68}$ |
| 1665. | $L_{A13}$ | $L_{Q69}$ |
| 1666. | $L_{A13}$ | $L_{Q70}$ |
| 1667. | $L_{A13}$ | $L_{Q71}$ |
| 1668. | $L_{A13}$ | $L_{Q72}$ |
| 1669. | $L_{A13}$ | $L_{Q73}$ |
| 1670. | $L_{A13}$ | $L_{Q74}$ |
| 1671. | $L_{A13}$ | $L_{Q75}$ |
| 1672. | $L_{A13}$ | $L_{Q76}$ |
| 1673. | $L_{A13}$ | $L_{Q77}$ |
| 1674. | $L_{A13}$ | $L_{Q78}$ |
| 1675. | $L_{A13}$ | $L_{Q79}$ |
| 1676. | $L_{A13}$ | $L_{Q80}$ |
| 1677. | $L_{A13}$ | $L_{Q81}$ |
| 1678. | $L_{A13}$ | $L_{Q82}$ |
| 1679. | $L_{A13}$ | $L_{Q83}$ |
| 1680. | $L_{A13}$ | $L_{Q84}$ |
| 1681. | $L_{A13}$ | $L_{Q85}$ |
| 1682. | $L_{A13}$ | $L_{Q86}$ |
| 1683. | $L_{A13}$ | $L_{Q87}$ |
| 1684. | $L_{A13}$ | $L_{Q88}$ |
| 1685. | $L_{A13}$ | $L_{Q89}$ |
| 1686. | $L_{A13}$ | $L_{Q90}$ |
| 1687. | $L_{A13}$ | $L_{Q91}$ |
| 1688. | $L_{A13}$ | $L_{Q92}$ |
| 1689. | $L_{A13}$ | $L_{Q93}$ |
| 1690. | $L_{A13}$ | $L_{Q94}$ |
| 1691. | $L_{A13}$ | $L_{Q95}$ |
| 1692. | $L_{A13}$ | $L_{Q96}$ |
| 1693. | $L_{A13}$ | $L_{Q97}$ |
| 1694. | $L_{A13}$ | $L_{Q98}$ |
| 1695. | $L_{A13}$ | $L_{Q99}$ |
| 1696. | $L_{A13}$ | $L_{Q100}$ |
| 1697. | $L_{A13}$ | $L_{Q101}$ |
| 1698. | $L_{A13}$ | $L_{Q102}$ |
| 1699. | $L_{A13}$ | $L_{Q103}$ |
| 1700. | $L_{A13}$ | $L_{Q104}$ |
| 1701. | $L_{A13}$ | $L_{Q105}$ |
| 1702. | $L_{A13}$ | $L_{Q106}$ |
| 1703. | $L_{A13}$ | $L_{Q107}$ |
| 1704. | $L_{A13}$ | $L_{Q108}$ |
| 1705. | $L_{A13}$ | $L_{Q109}$ |
| 1706. | $L_{A13}$ | $L_{Q110}$ |
| 1707. | $L_{A13}$ | $L_{Q111}$ |
| 1708. | $L_{A13}$ | $L_{Q112}$ |
| 1709. | $L_{A13}$ | $L_{Q113}$ |
| 1710. | $L_{A13}$ | $L_{Q114}$ |
| 1711. | $L_{A13}$ | $L_{Q115}$ |
| 1712. | $L_{A13}$ | $L_{Q116}$ |
| 1713. | $L_{A13}$ | $L_{Q117}$ |
| 1714. | $L_{A13}$ | $L_{Q118}$ |
| 1715. | $L_{A13}$ | $L_{Q119}$ |
| 1716. | $L_{A13}$ | $L_{Q120}$ |
| 1717. | $L_{A13}$ | $L_{Q121}$ |
| 1718. | $L_{A13}$ | $L_{Q122}$ |
| 1719. | $L_{A13}$ | $L_{Q123}$ |
| 1720. | $L_{A13}$ | $L_{Q124}$ |
| 1721. | $L_{A13}$ | $L_{Q125}$ |
| 1722. | $L_{A13}$ | $L_{Q126}$ |
| 1723. | $L_{A13}$ | $L_{Q127}$ |
| 1724. | $L_{A13}$ | $L_{Q128}$ |
| 1725. | $L_{A13}$ | $L_{Q129}$ |
| 1726. | $L_{A13}$ | $L_{Q130}$ |

TABLE 1-continued

| Compound number | L¹ | L² |
|---|---|---|
| 1727. | $L_{A13}$ | $L_{Q131}$ |
| 1728. | $L_{A13}$ | $L_{Q132}$ |
| 1729. | $L_{A13}$ | $L_{Q133}$ |

According to another aspect of the present disclosure, a first device comprising a first organic light emitting device is provided. The first organic light emitting device can comprise an anode, a cathode, and an organic layer, disposed between the anode and the cathode. The organic layer can include a compound comprising the first ligand $L^1$ having Formula I, as defined herein.

In one embodiment, the compound can be selected from the group consisting of Compound 8, Compound 9, Compound 12, Compound 32, Compound 43, Compound 54, Compound 55, Compound 62, Compound 83, Compound 93, Compound 118, Compound 141, Compound 142, Compound 176, Compound 278, and Compound 320.

The first device can be one or more of a consumer product, an organic light-emitting device, and/or a lighting panel.

The organic layer can be an emissive layer and the compound can be an emissive dopant in some embodiments, while the compound can be a non-emissive dopant in other embodiments.

The organic layer can also include a host. In some embodiments, the host can include a metal complex. In one embodiment, the host can be a metal 8-hydroxyquinolate. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound selected from the group consisting of carbazole, dibenzothiphene, dibenzofuran, dibenzoselenophene, azacarbazole, aza-dibenzothiophene, aza-dibenzofuran, and aza-dibenzoselenophene. The "aza" designation in the fragments described above, i.e., aza-dibenzofuran, aza-dibenzonethiophene, etc., means that one or more of the CH groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein. The host can include a metal complex. The host can be a specific compound selected from the group consisting of:

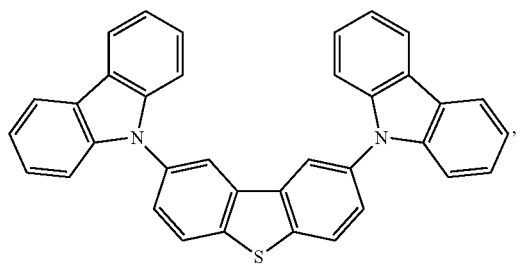

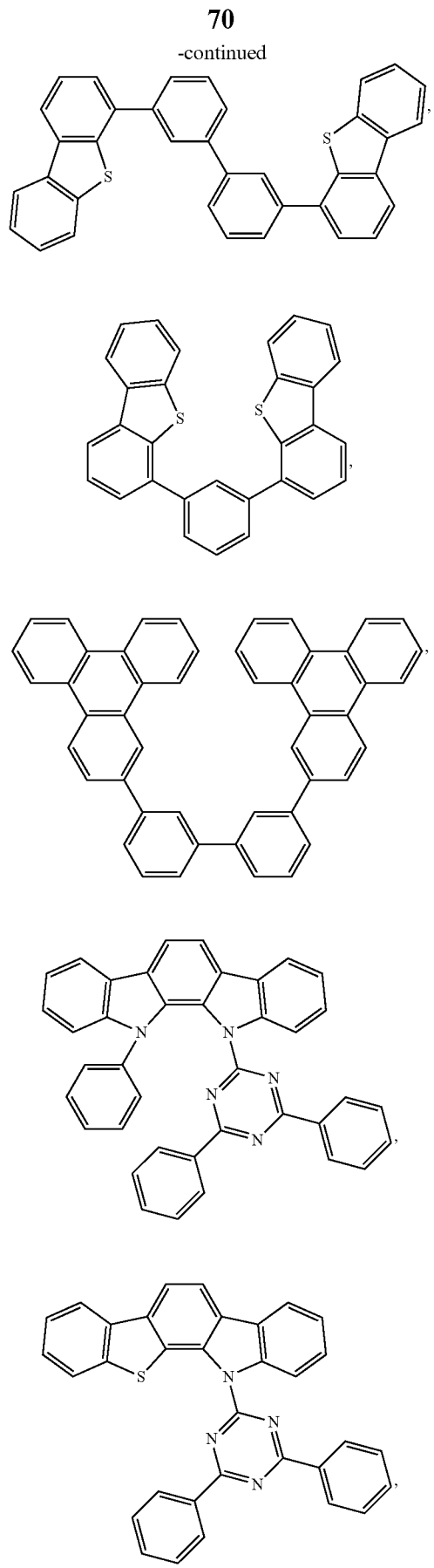

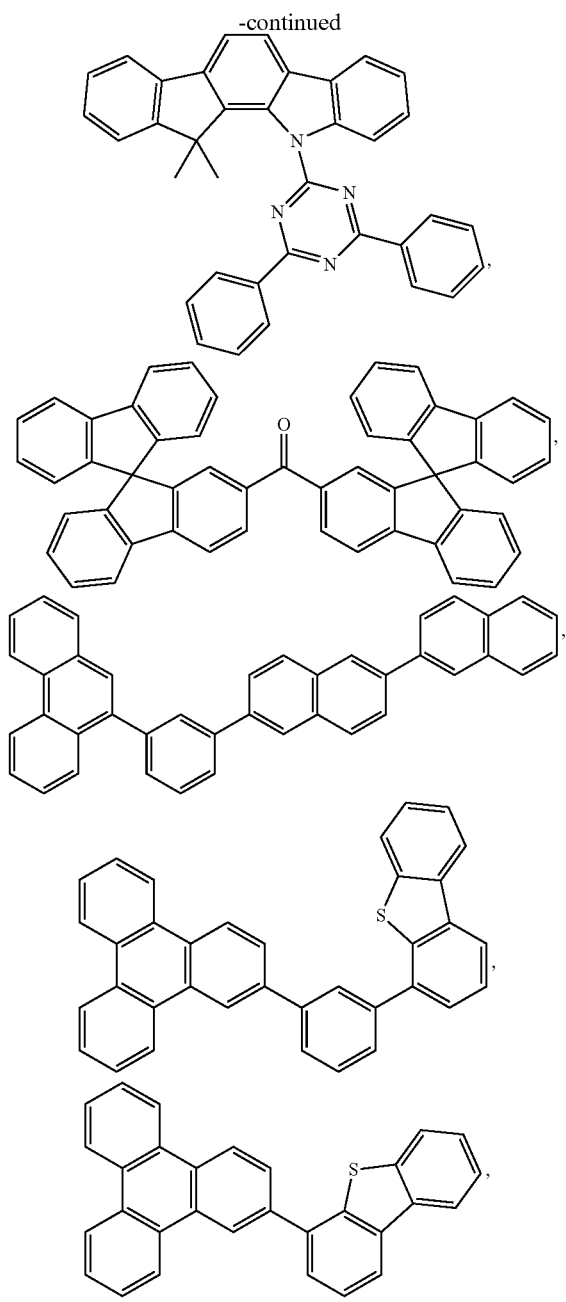

and combinations thereof.

In yet another aspect of the present disclosure, a formulation comprising the first ligand L¹ having Formula I, as defined herein, is also within the scope of the invention disclosed herein. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

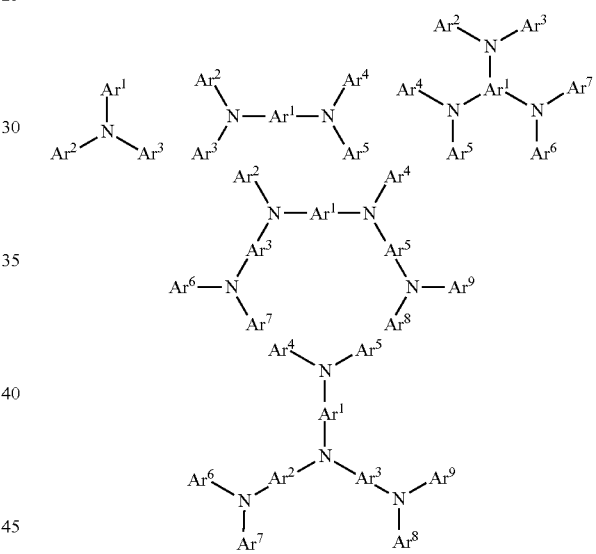

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

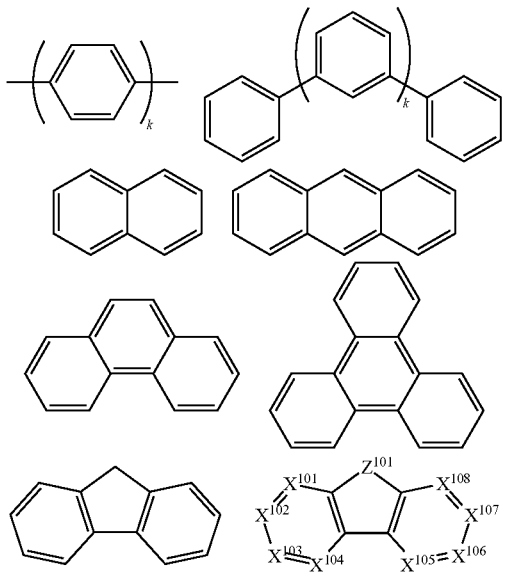

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

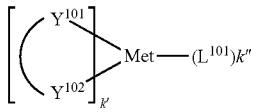

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

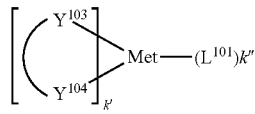

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

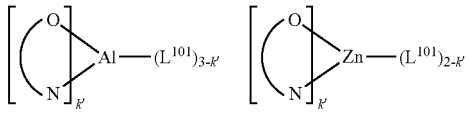

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

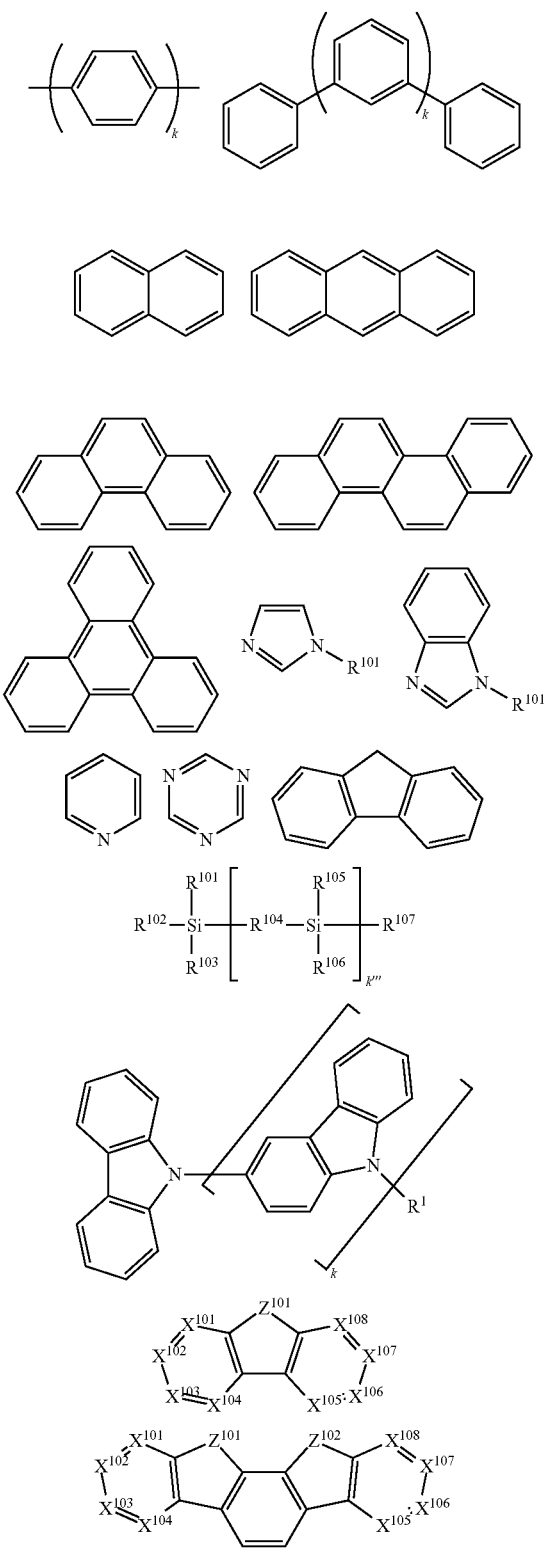

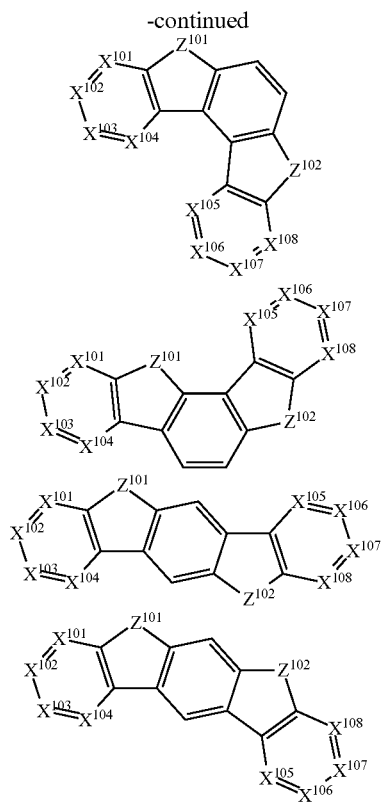

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

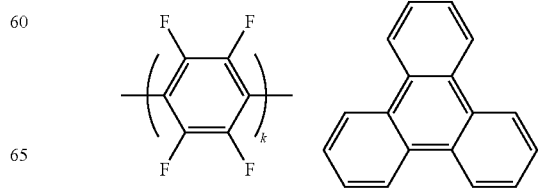

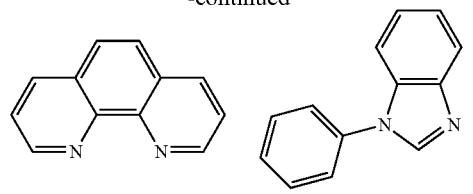

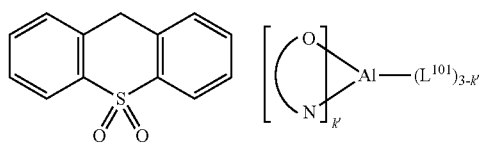

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

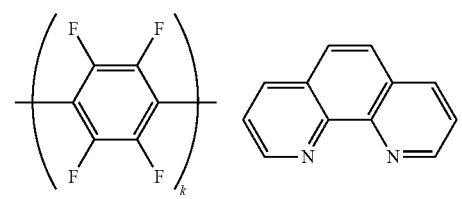

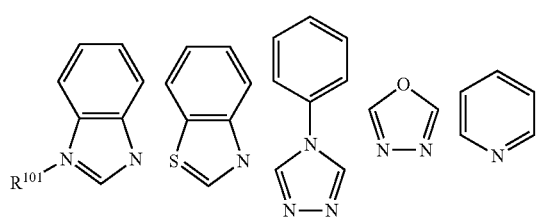

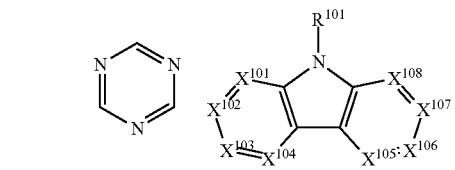

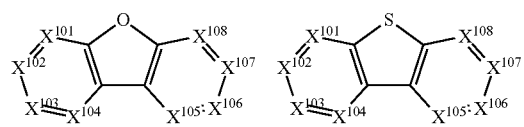

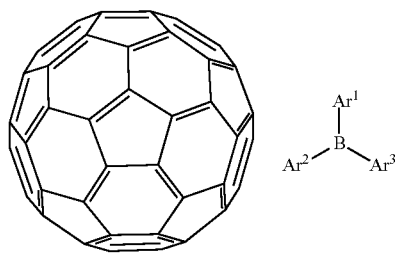

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

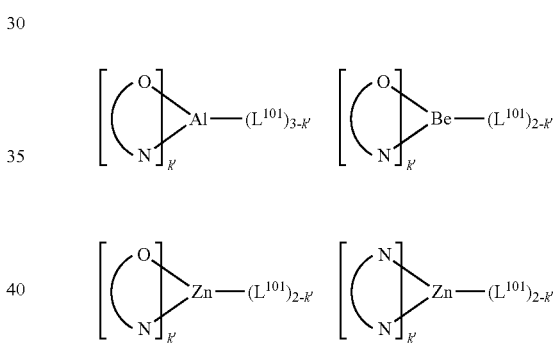

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2
| MATERIAL | EXAMPLES OF MATERIAL | PUBLICATIONS |
|---|---|---|
| Hole injection materials | | |
| Phthalocyanine and porphryin compounds | 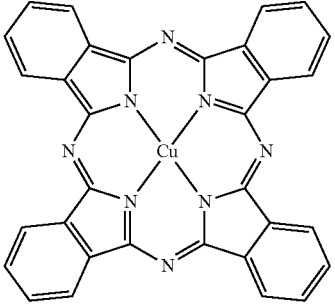 | Appl. Phys. Lett. 69, 2160 (1996) |
| Starburst triarylamines | 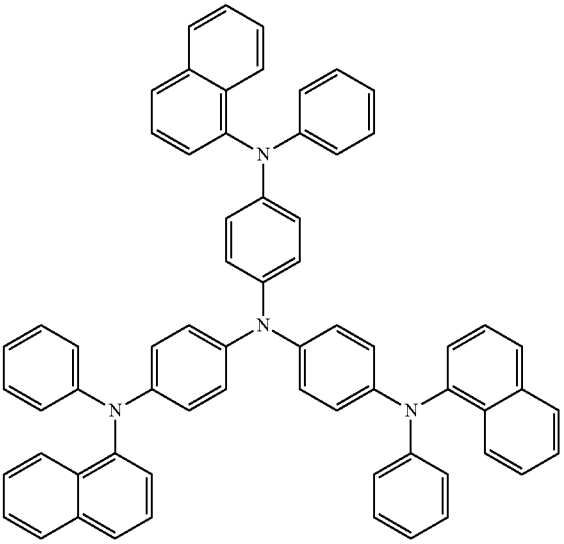 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!-\!\!(CH_xF_y)_n\!\!-\!\!-$ | Appl. Phys. Lett. 78, 673 (2001) |
| Conducting polymers (e.g., PEDOT:PSS, polyaniline, polypthiophene) | 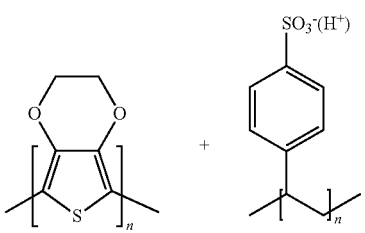 | Synth. Met. 87, 171 (1997) WO2007002683 |
| Phosphonic acid and sliane SAMs | 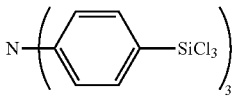 | US20030162053 |

TABLE 2-continued
| MATERIAL | EXAMPLES OF MATERIAL | PUBLICATIONS |
|---|---|---|
| Triarylamine or polythiophene polymers with conductivity dopants | 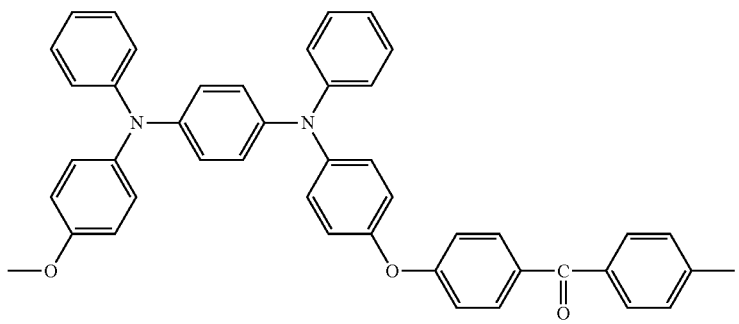 and 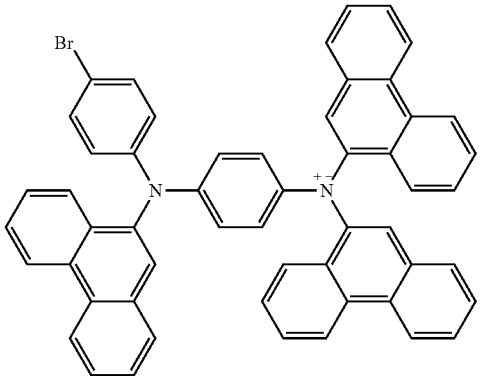 [SMILES: Brc1ccc(N(c2ccc(N(c3cc4ccccc4c4ccccc34)c3cc4ccccc4c4ccccc34)cc2)c2cc3ccccc3c3ccccc23)cc1] 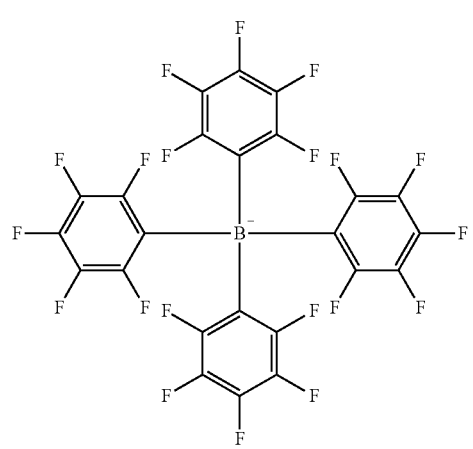 | EP1725079A1 |
| Organic compounds with conductive inorganic compounds, such as molybdenum and tungsten oxides | 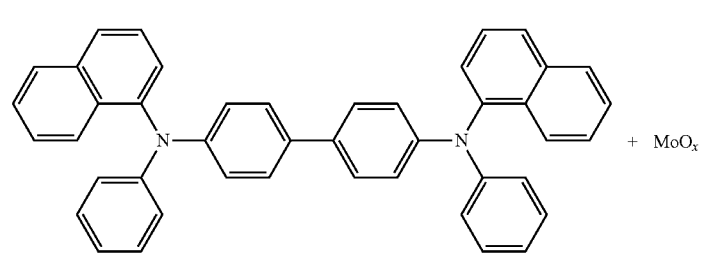 [SMILES: c1ccc(N(c2ccc(-c3ccc(N(c4ccccc4)c4cccc5ccccc45)cc3)cc2)c2cccc3ccccc23)cc1] | US20050123751 SID Symposium Digest, 37, 923 (2006) WO2009018009 |

TABLE 2-continued
| MATERIAL | EXAMPLES OF MATERIAL | PUBLICATIONS |
| --- | --- | --- |
| n-type semiconducting organic complexes | 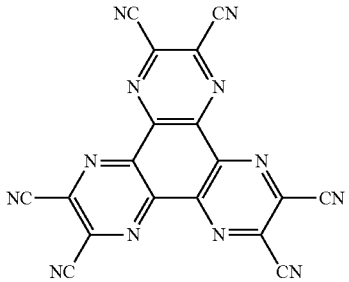 [SMILES: N#Cc1nc2c3nc(C#N)c(C#N)nc3c3nc(C#N)c(C#N)nc3c2nc1C#N] | US20020158242 |
| Metal organometallic complexes | 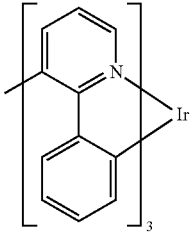 | US20060240279 |
| Cross-linkable compounds | 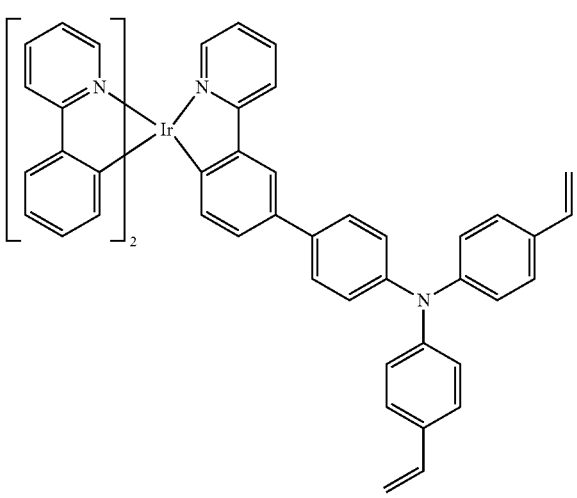 | US20080220265 |
| Polythiophene based polymers and copolymers | 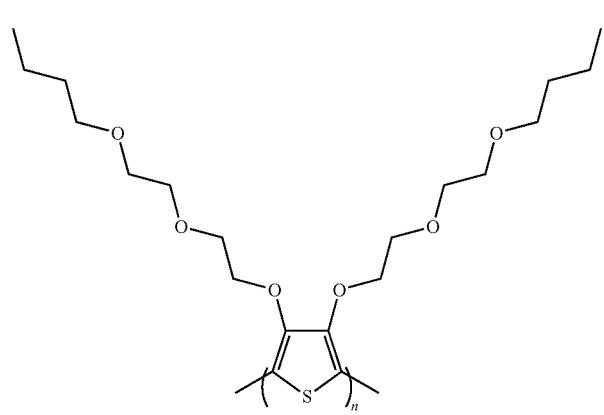 | WO 2011075644<br>EP2350216 |

TABLE 2-continued
| MATERIAL | EXAMPLES OF MATERIAL | PUBLICATIONS |
|---|---|---|
| | Hole transporting materials | |
| Triarylamines (e.g., TPD, α-NPD) | | Appl. Phys. Lett. 51, 913 (1987) US5061569 EP650955 J. Mater. Chem. 3, 319 (1993) Appl. Phys. Lett. 90, 183503 (2007) |
| | 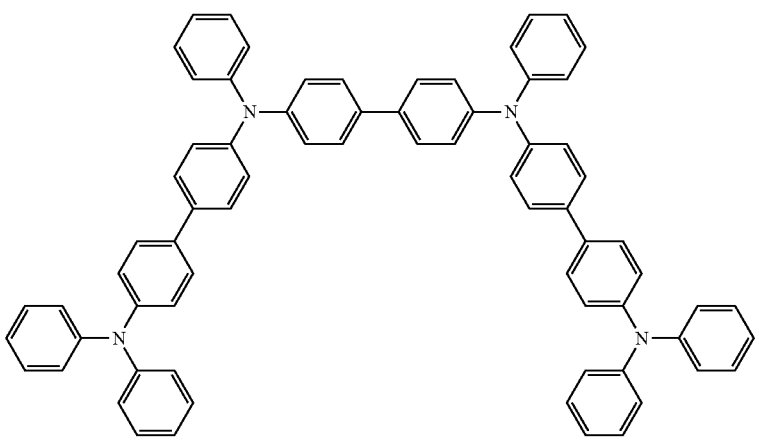 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 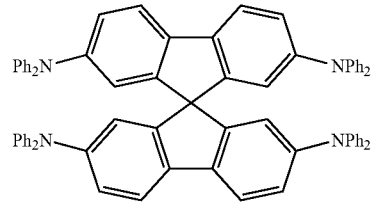 | Synth. Met. 91, 209 (1997) |
| Arylamine carbazole compounds | 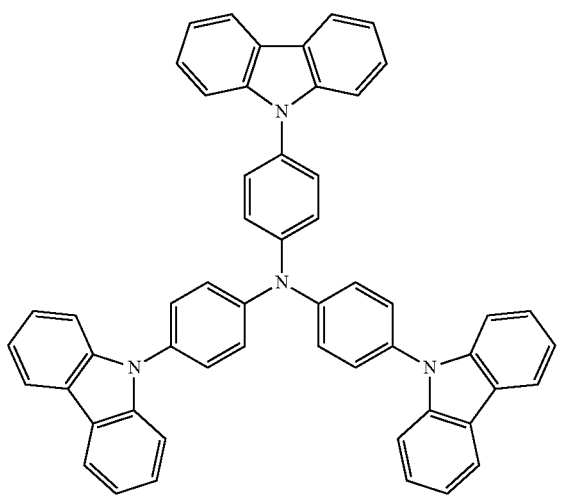 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 2-continued
| MATERIAL | EXAMPLES OF MATERIAL | PUBLICATIONS |
| --- | --- | --- |
| Triarylamine with (di)benzothiophene/ (di)benzofuran | 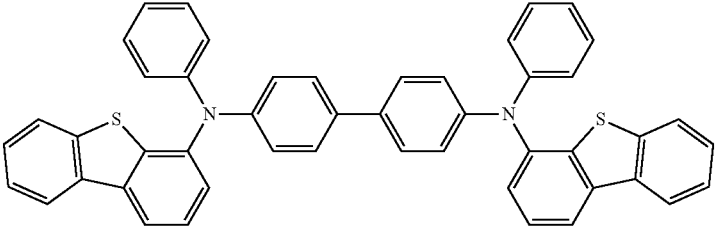 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 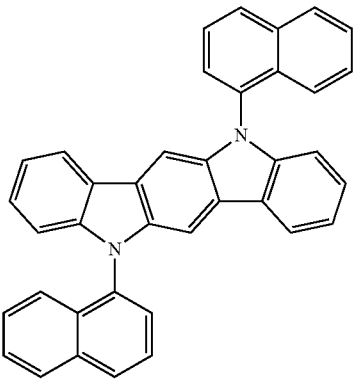 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 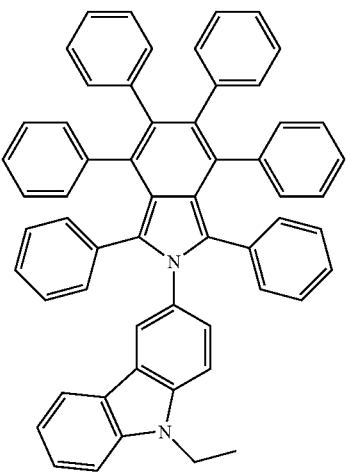 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 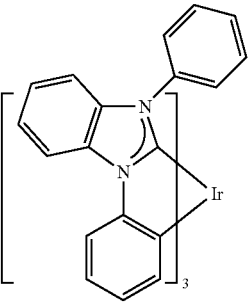 | UA20080018221 |

TABLE 2-continued

| MATERIAL | EXAMPLES OF MATERIAL | PUBLICATIONS |
|---|---|---|
| | Phosphorescent OLED host materials Red hosts | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 2-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |

TABLE 2-continued
| MATERIAL | EXAMPLES OF MATERIAL | PUBLICATIONS |
|---|---|---|
| Aryltriphenylene compounds | 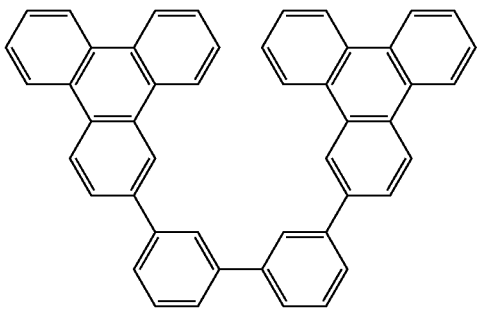 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 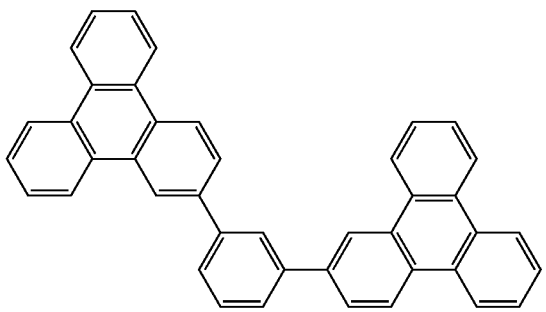 [SMILES: c1cc(-c2ccc3c4ccccc4c4ccccc4c3c2)cc(-c2ccc3c4ccccc4c4ccccc4c3c2)c1] | US20060280965 |
| | 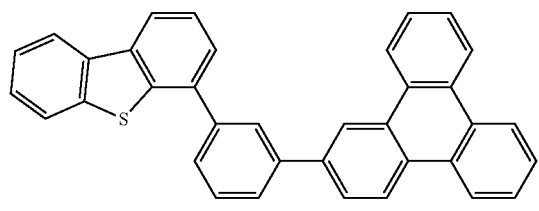 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 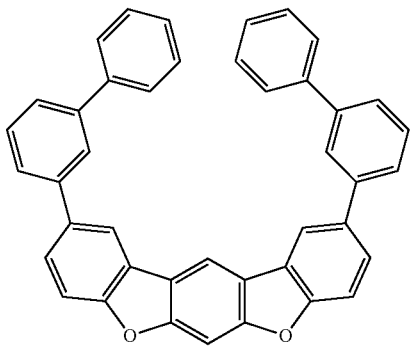 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 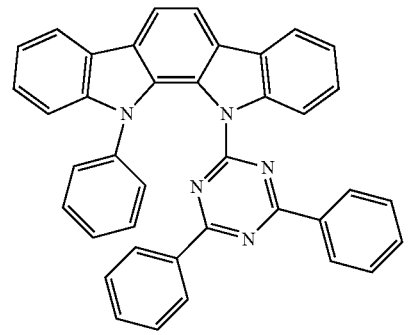 [SMILES: c1ccc(-c2nc(-c3ccccc3)nc(-n3c4ccccc4c4ccc5c6ccccc6n(-c6ccccc6)c5c43)n2)cc1] | WO2008056746 |

| MATERIAL | EXAMPLES OF MATERIAL | PUBLICATIONS |
|---|---|---|
| | 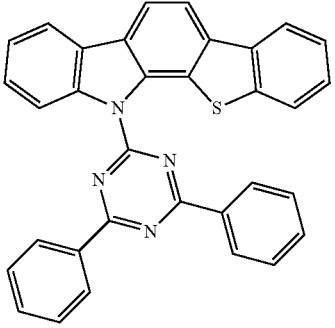 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 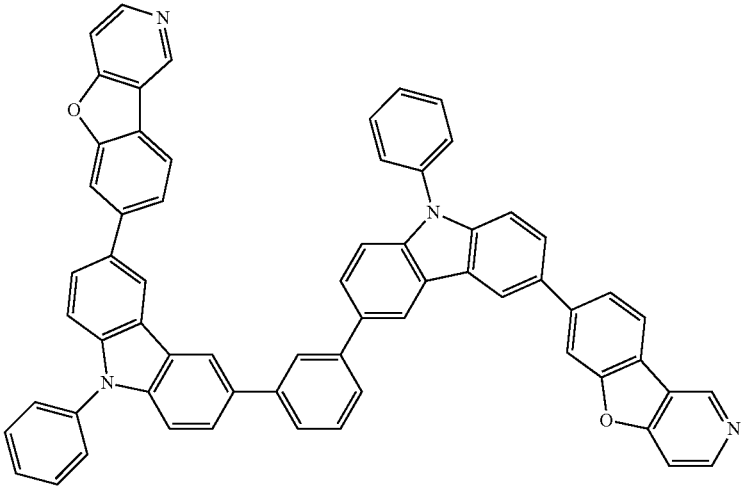 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 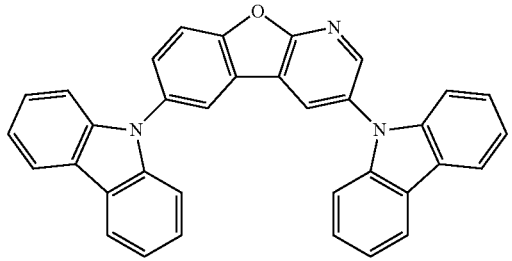 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 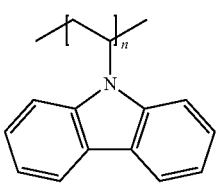 | Appl. Phys. Lett. 77, 2280 (2000) |
| Spirofluorene compounds | 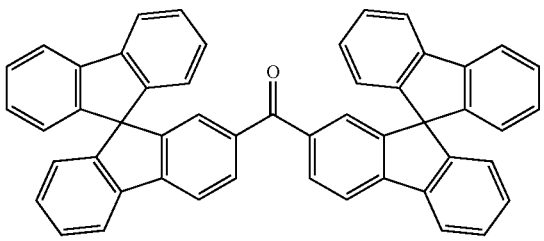 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 2-continued

| MATERIAL | EXAMPLES OF MATERIAL | PUBLICATIONS |
| --- | --- | --- |
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 2-continued

| MATERIAL | EXAMPLES OF MATERIAL | PUBLICATIONS |
| --- | --- | --- |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |谢
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 2-continued
| MATERIAL | EXAMPLES OF MATERIAL | PUBLICATIONS |
|---|---|---|
| | 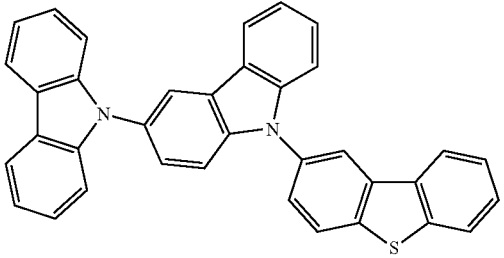 [SMILES: c1ccc2c(c1)sc1ccc(-n3c4ccccc4c4cc(-n5c6ccccc6c6ccccc65)ccc43)cc12] | WO2009086028 |
| | 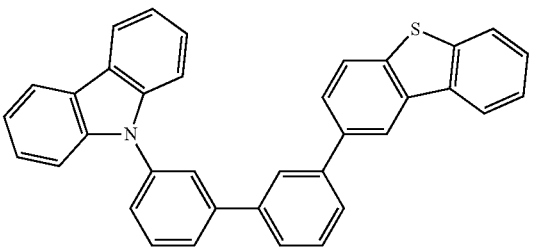 [SMILES: c1cc(-c2cccc(-n3c4ccccc4c4ccccc43)c2)cc(-c2ccc3sc4ccccc4c3c2)c1] | US20090030202, US20090017330 |
| | 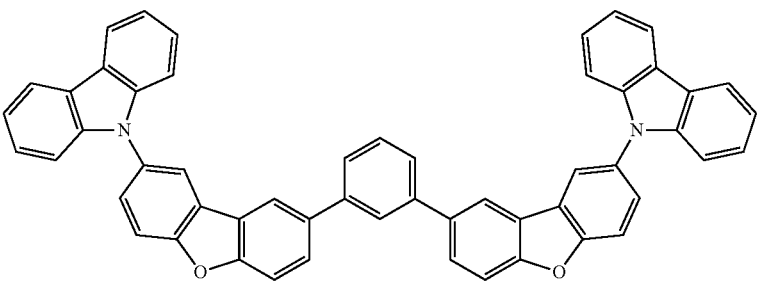 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 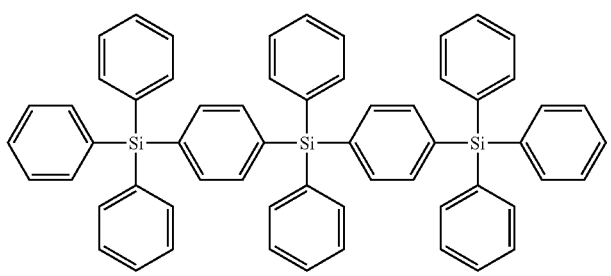 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 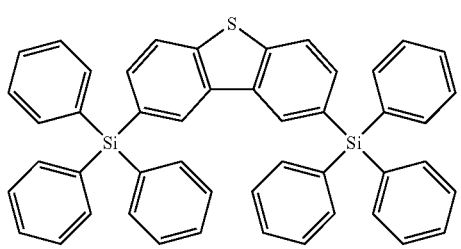 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | US7154114 |

TABLE 2-continued

| MATERIAL | EXAMPLES OF MATERIAL | PUBLICATIONS |
|---|---|---|
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 2-continued

| MATERIAL | EXAMPLES OF MATERIAL | PUBLICATIONS |
|---|---|---|
| | [structure] | US20060202194 |
| | | US20070087321 |
| | [structure] | |
| | [structure] | US20080261076<br>US20100090591 |
| | [structure] | US20070087321 |
| | [structure] | Adv. Mater. 19, 739 (2007) |

TABLE 2-continued
| MATERIAL | EXAMPLES OF MATERIAL | PUBLICATIONS |
|---|---|---|
| | 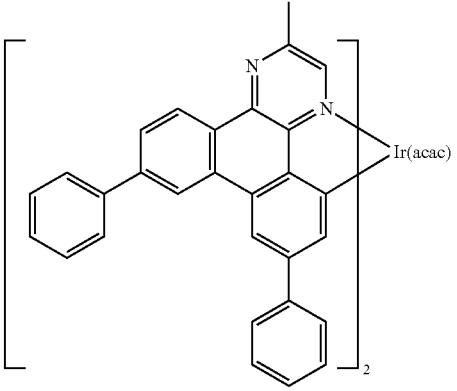 | WO2009100991 |
| | 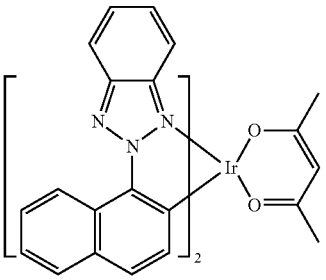 | WO2008101842 |
| | 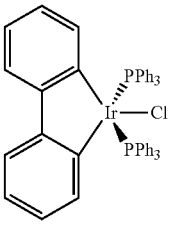 | US7232618 |
| Platinum(II) organometallic complexes | 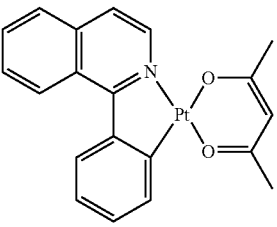 | WO2003040257 |
| | 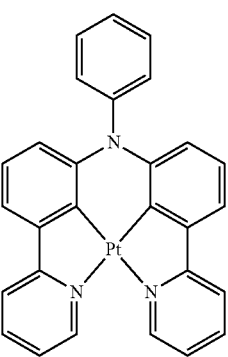 | US20070103060 |

TABLE 2-continued

| MATERIAL | EXAMPLES OF MATERIAL | PUBLICATIONS |
|---|---|---|
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

Green dopants

| | | |
|---|---|---|
| Iridium(III) organometallic complexes | | Inorg. Chem. 40, 1704 (2001) |
| | and its derivatives | |
| | | US20020034656 |

TABLE 2-continued
| MATERIAL | EXAMPLES OF MATERIAL | PUBLICATIONS |
|---|---|---|
| | 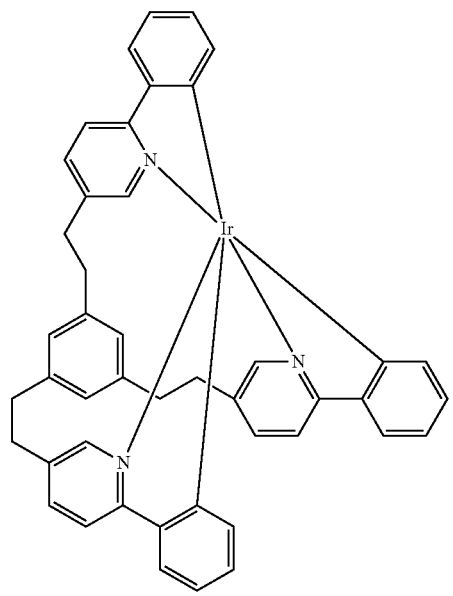 | US7332232 |
| | 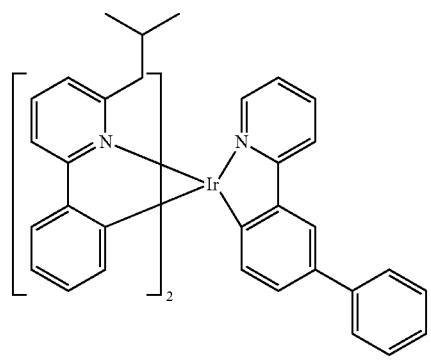 | US20090108737 |
| | 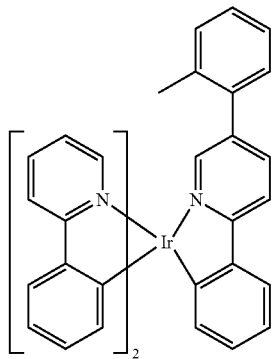 | WO2010028151 |

TABLE 2-continued

| MATERIAL | EXAMPLES OF MATERIAL | PUBLICATIONS |
|---|---|---|
| | | EP1841834B |
| | | US20060127696 |
| | | US20090039776 |
| | | US6921915 |
| | | US20100244004 |

TABLE 2-continued
| MATERIAL | EXAMPLES OF MATERIAL | PUBLICATIONS |
|---|---|---|
| | 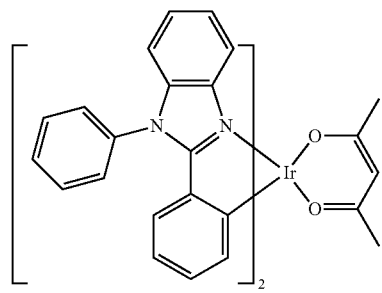 | US6687266 |
| | 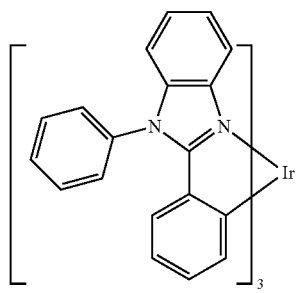 | Chem. Mater. 16, 2480 (2004) |
| | 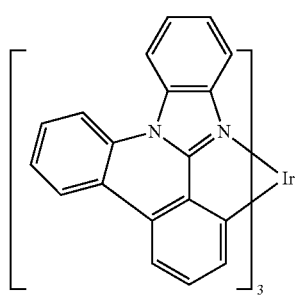 | US20070190359 |
| | 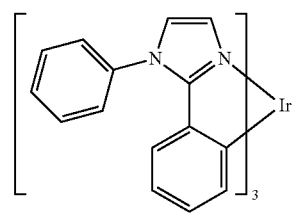 | US 20060008670<br>JP2007123392 |
| | 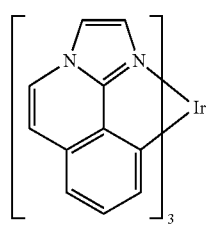 | WO2010086089,<br>WO2011044988 |
| | 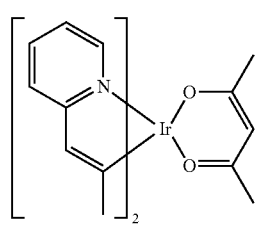 | Adv. Mater. 16, 2003 (2004) |

TABLE 2-continued
| MATERIAL | EXAMPLES OF MATERIAL | PUBLICATIONS |
|---|---|---|
| | 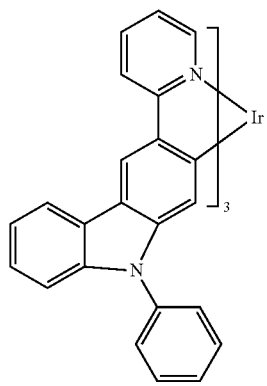 | Angew. Chem. Int. Ed. 2006, 45, 7800 |
| | 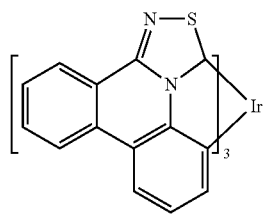 | WO2009050290 |
| | 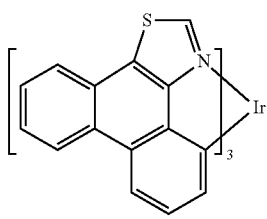 | US20090165846 |
| | 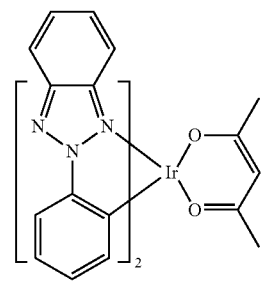 | US20080015355 |
| | 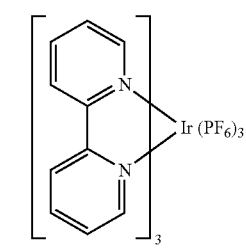 | US20010015432 |
| | 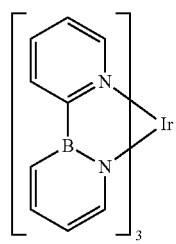 | US20100295032 |

TABLE 2-continued

| MATERIAL | EXAMPLES OF MATERIAL | PUBLICATIONS |
|---|---|---|
| Monomer for polymeric metal organometallic compounds | | US7250226, US7396598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 2-continued

| MATERIAL | EXAMPLES OF MATERIAL | PUBLICATIONS |
| --- | --- | --- |
| | | US20060263635 |
| | | US20060182992<br>US20070103060 |
| Cu complexes | | WO2009000673 |
| | | US20070111026 |

TABLE 2-continued
| MATERIAL | EXAMPLES OF MATERIAL | PUBLICATIONS |
|---|---|---|
| Gold complexes | 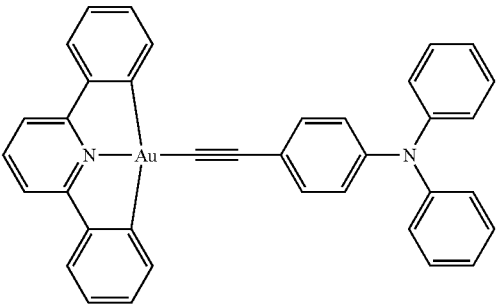 | Chem. Commun. 2906 (2005) |
| Rhenium(III) complexes | 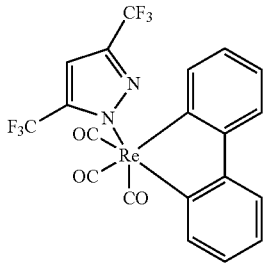 | Inorg. Chem. 42, 1248 (2003) |
| Osmium(II) complexes | 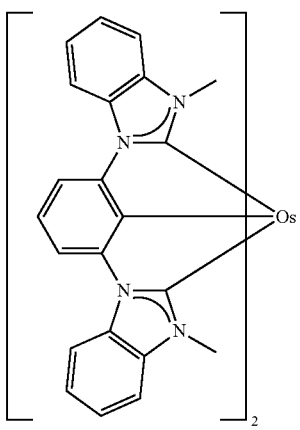 | US7279704 |
| Deuterated organometallic complexes | 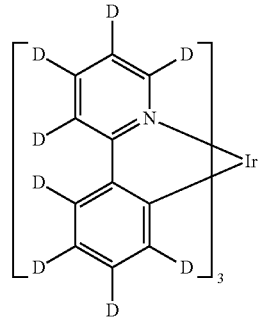 | US20030138657 |

TABLE 2-continued

| MATERIAL | EXAMPLES OF MATERIAL | PUBLICATIONS |
|---|---|---|
| Organometallic complexes with two or more metal centers | | US20030152802 |
| | | US7090928 |
| Blue dopants | | |
| Iridium(III) organometallic complexes | | WO2002002714 |
| | | WO2006009024 |
| | | US20060251923<br>US20110057559<br>US20110204333 |

TABLE 2-continued

| MATERIAL | EXAMPLES OF MATERIAL | PUBLICATIONS |
|---|---|---|
| | | US7393599, WO2006056418, US20050260441, WO2005019373 |
| | | US7534505 |
| | | WO2011051404 |
| | | US7445855 |
| | | US20070190359, US20080297033 US20100148663 |

| MATERIAL | EXAMPLES OF MATERIAL | PUBLICATIONS |
|---|---|---|
| | | US7338722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE 2-continued
| MATERIAL | EXAMPLES OF MATERIAL | PUBLICATIONS |
|---|---|---|
| | 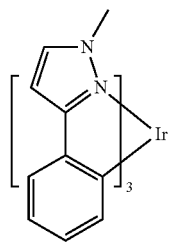 | WO2005123873 |
| | 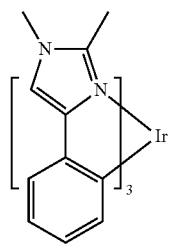 | WO2005123873 |
| | 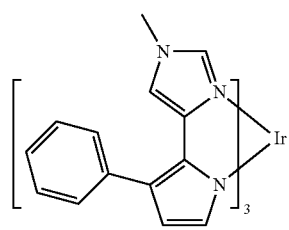 | WO2007004380 |
| | 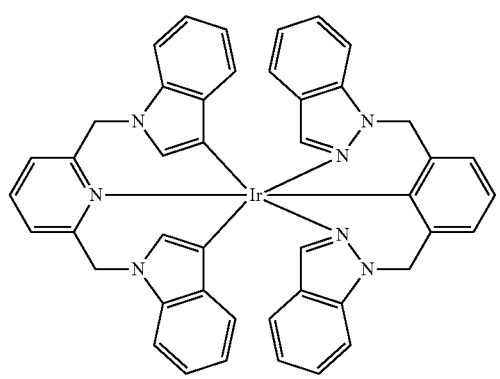 | WO2006082742 |
| Osmium(II) complexes | 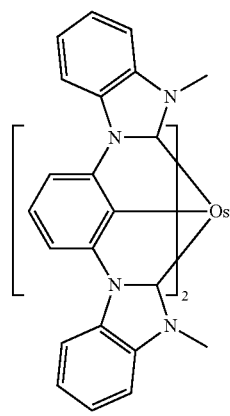 | US7279704 |

TABLE 2-continued
| MATERIAL | EXAMPLES OF MATERIAL | PUBLICATIONS |
|---|---|---|
| | 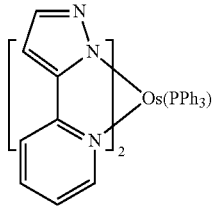 | Organometallics 23, 3745 (2004) |
| Gold complexes | 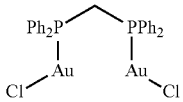 | Appl. Phys. Lett. 74, 1361 (1999) |
| Platinum(II) complexes | 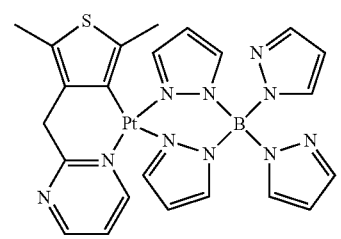 | WO2006098120, WO2006103874 |
| Pt tetradentate complexes with at least one metal-carbene bond | 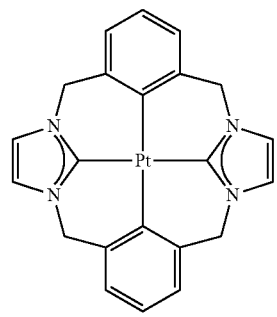 | US7655323 |
| Exciton/hole blocking layer materials | | |
| Bathocuprine compounds (e.g., BCP, BPhen) | 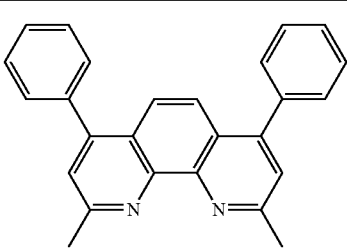 | Appl. Phys. Lett. 75, 4 (1999) |
| | 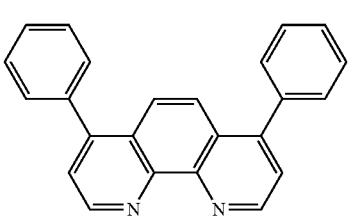 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 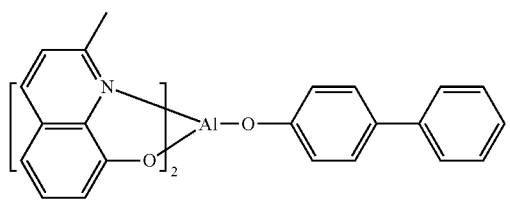 | Appl. Phys. Lett. 81, 162 (2002) |

TABLE 2-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 2-continued
| MATERIAL | EXAMPLES OF MATERIAL | PUBLICATIONS |
|---|---|---|
| Phenothiazine-S-oxide | 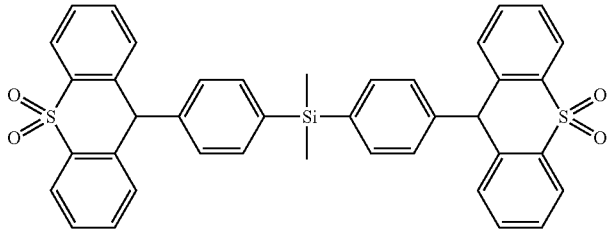 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 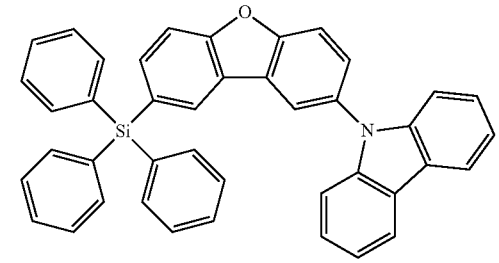 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 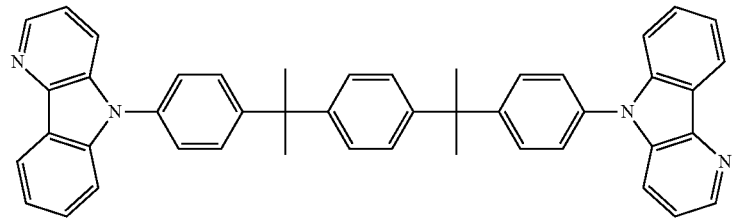 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 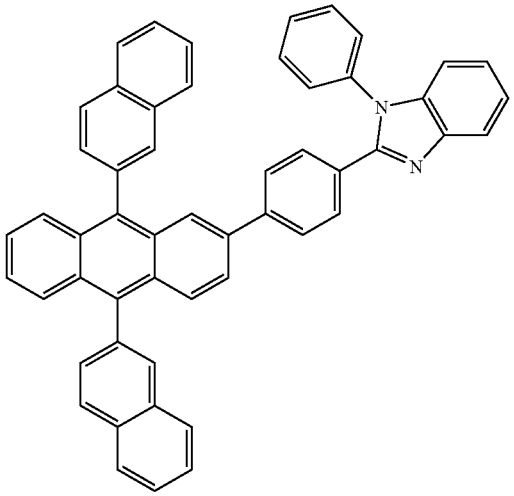 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 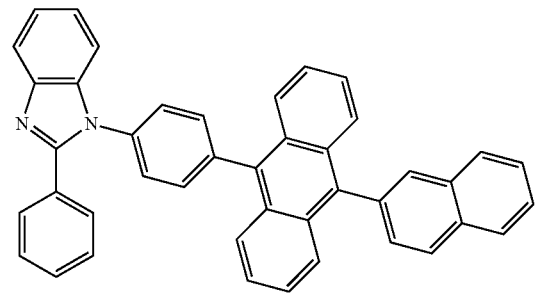 [SMILES: c1ccc(-c2nc3ccccc3n2-c2ccc(-c3c4ccccc4c(-c4ccc5ccccc5c4)c4ccccc34)cc2)cc1] | US20090179554 |

TABLE 2-continued
| MATERIAL | EXAMPLES OF MATERIAL | PUBLICATIONS |
| --- | --- | --- |
| Aza triphenylene derivatives | 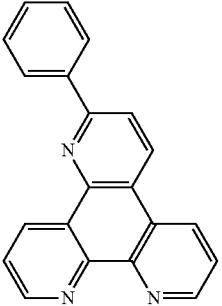 [SMILES: c1ccc(-c2ccc3c4cccnc4c4ncccc4c3n2)cc1] | US20090115316 |
| Anthracene-benzothiazole compounds | 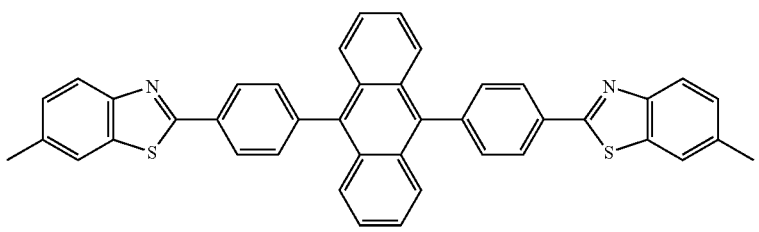 | Appl. Phys. Lett. 89, 063504 (2006) |
| Metal 8-hydroxyquinolates (e.g., Alq$_3$, Zrq$_4$) | 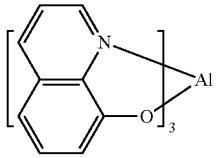 | Appl. Phys. Lett. 51, 913 (1987)<br>US7230107 |
| Metal hydroxybenoquinolates | 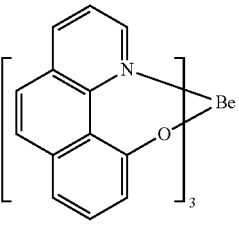 | Chem. Lett. 5, 905 (1993) |
| Bathocuprine compounds such as BCP, BPhen, etc | 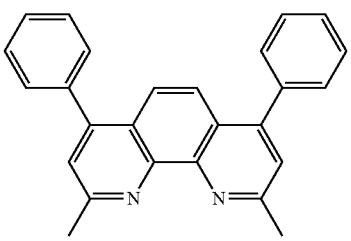 [SMILES: Cc1cc(-c2ccccc2)c2ccc3c(-c4ccccc4)cc(C)nc3c2n1] | Appl. Phys. Lett. 91, 263503 (2007) |
| | 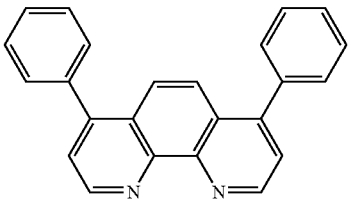 [SMILES: c1ccc(-c2ccnc3c2ccc2c(-c4ccccc4)ccnc23)cc1] | Appl. Phys. Lett. 79, 449 (2001) |

TABLE 2-continued

| MATERIAL | EXAMPLES OF MATERIAL | PUBLICATIONS |
| --- | --- | --- |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |

TABLE 2-continued
| MATERIAL | EXAMPLES OF MATERIAL | PUBLICATIONS |
|---|---|---|
| Fullerene (e.g., C60) | 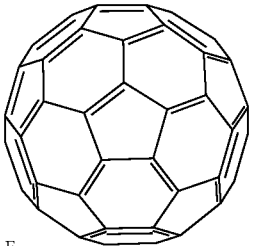 | US20090101870 |
| Triazine complexes | 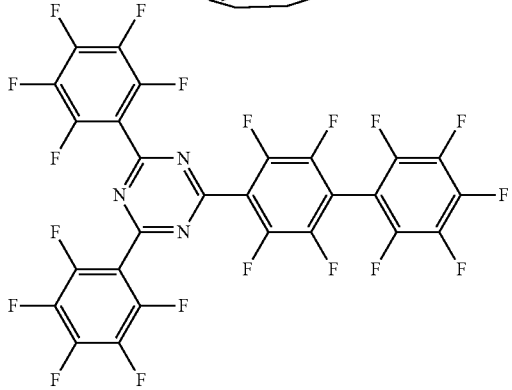 | US20040036077 |
| Zn (N^N) complexes | 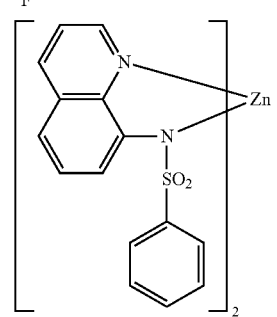 | US6528187 |
EXPERIMENTAL
Device Examples
Materials Used in the Example Devices:
Comparative compounds used are:
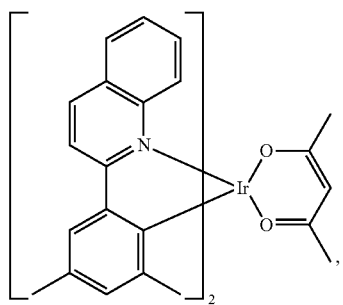
Comparative Compound 1
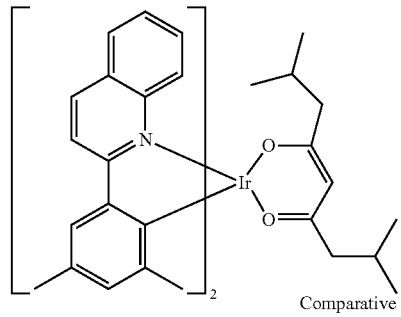
Comparative Compound 2
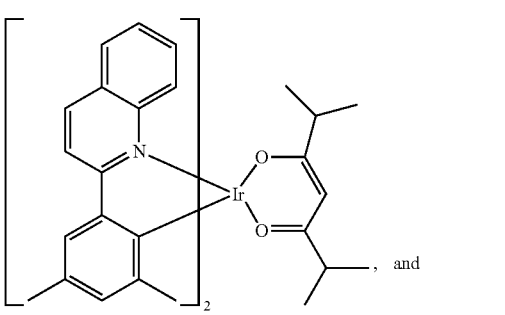
Comparative Compound 3, and Comparative Compound 4

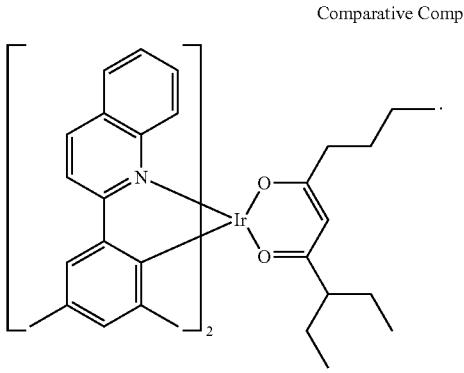

Other material used in the devices:

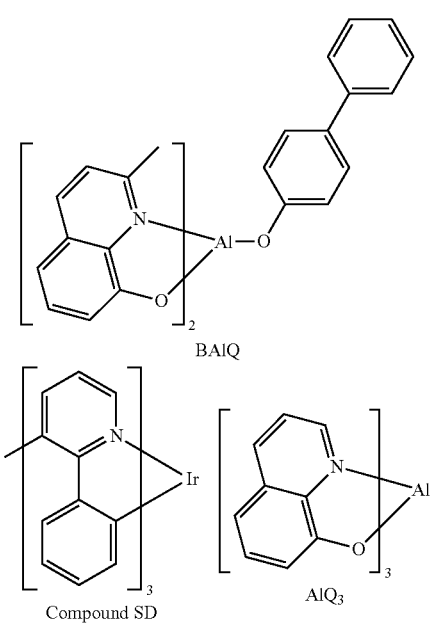

BAlQ

Compound SD

AlQ$_3$

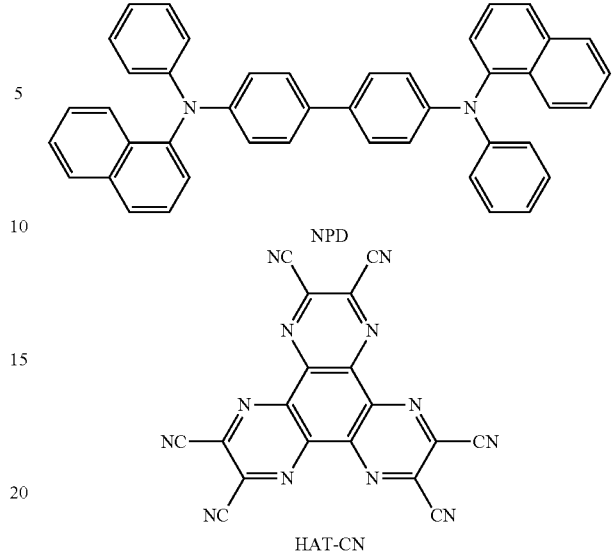

NPD

HAT-CN

All example devices were fabricated by high vacuum (<10$^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

The organic stack of the example devices consisted of sequentially from the ITO surface, 100 Å of HAT-CN as the hole injection layer (HIL), 400 Å of NPD as the hole transporting layer (HTL), 400 Å of the emissive layer (EML) which contains the compound of Formula 1, Compound SD, and Host (BAlQ), 40 Å of BAlQ as the blocking layer (BL), 450 Å of AlQ$_3$ as the electron transporting layer (ETL) and 10 Å of LiF as the electron injection layer (EIL). The comparative examples were fabricated similarly to the device examples except that the Comparative Compounds 1-4 were used as the emitter in the EML.

TABLE 3

Devices structures of inventive compounds and comparative compounds

| Example | HIL | HTL | EML (400 Å, doping %) | | | BL | ETL |
|---|---|---|---|---|---|---|---|
| Example 1 | HAT-CN 100Å | NPD 400Å | BAlQ 88% | Compound SD 9% | Compound 8 3% | BAlQ 40Å | AlQ$_3$ 450Å |
| Comparative Example 1 | HAT-CN 100Å | NPD 400Å | BAlQ 88% | Compound SD 9% | Comparative Compound 1 3% | BAlQ 40Å | AlQ$_3$ 450Å |
| Comparative Example 2 | HAT-CN 100Å | NPD 400Å | BAlQ 88% | Compound SD 9% | Comparative Compound 2 3% | BAlQ 40Å | AlQ$_3$ 450Å |
| Comparative Example 3 | HAT-CN 100Å | NPD 400Å | BAlQ 88% | Compound SD 9% | Comparative Compound 3 3% | BAlQ 40Å | AlQ$_3$ 450Å |
| Comparative Example 4 | HAT-CN 100Å | NPD 400Å | BAlQ 88% | Compound SD 9% | Comparative Compound 4 3% | BAlQ 40Å | AlQ$_3$ 450Å |

TABLE 4

Device results[1]

| Example | 1931 CIE | | | At 1,000 nits | | | |
|---|---|---|---|---|---|---|---|
| | CIE x | CIE y | FWHM [a.u.] | Voltage [a.u.] | LE [a.u.] | EQE [a.u.] | PE [a.u.] |
| Compound 8 | 0.66 | 0.34 | 1.00 | 1.00 | 1.00 | 1.00 | 1.00 |
| Comparative Compound 1 | 0.67 | 0.33 | 1.11 | 1.09 | 0.78 | 0.90 | 0.71 |
| Comparative Compound 2 | 0.66 | 0.34 | 1.07 | 1.05 | 0.84 | 0.91 | 0.82 |
| Comparative Compound 3 | 0.66 | 0.34 | 1.04 | 1.06 | 0.86 | 0.94 | 0.81 |
| Comparative Compound 4 | 0.66 | 0.34 | 1.04 | 1.03 | 0.89 | 0.93 | 0.86 |

[1]All values in Table 4 are relative numbers (arbitrary units—a.u.) except for the CIE coordinates.

Table 4 is a summary of the device data. The luminous efficiency (LE), external quantum efficiency (EQE) and power efficiency (PE) were measured at 1000 nits. The inventive Compound 8 shows similar CIE to the comparative compounds since the emission color of these compounds are dominated by the Phenylquinoline ligand. However, the emission spectrum of Compound 8 is narrower than that of the comparative compounds as can be seen from the full width at the half maximum (FWHM) values in table 2. A smaller FWHM value means narrower emission spectrum. The device measurements show that all characteristics are better when a new ancillary ligand as disclosed here is used. For example, a relative driving voltage of 1.00 was obtained for Compound 8 whereas that voltage was between 1.03 and 1.09 for the comparative examples. As for the luminous efficacy (LE), it is much better than for the comparative example where it varies from 78 to 89% of the value for Compound 8. The same trend was found for the external quantum efficiency (EQE) and the power efficacy where the data for Compound 8 is higher compared to the comparative examples.

Table 5 below shows the unexpected performance improvement exhibited by an example of the inventive compounds, Compound 12, over Comparative Compounds 5 and 6 by way of each compounds' photoluminescence quantum yield (PLQY):

TABLE 5

| Compound Structure | PLQY in 5% PMMA film |
|---|---|
| Comparative Compound 5 | 34% |
| Comparative Compound 6 | 57% |
| Compound 12 | 59% |

Inventive Compound 12 showed higher PLQY than the comparative compounds. Higher PLQY is desirable for emitters in OLEDs for high EQE.

Material Synthesis:

All reactions were carried out under nitrogen protections unless specified otherwise. All solvents for reactions are anhydrous and used as received from commercial sources.

Synthesis of Compound 8

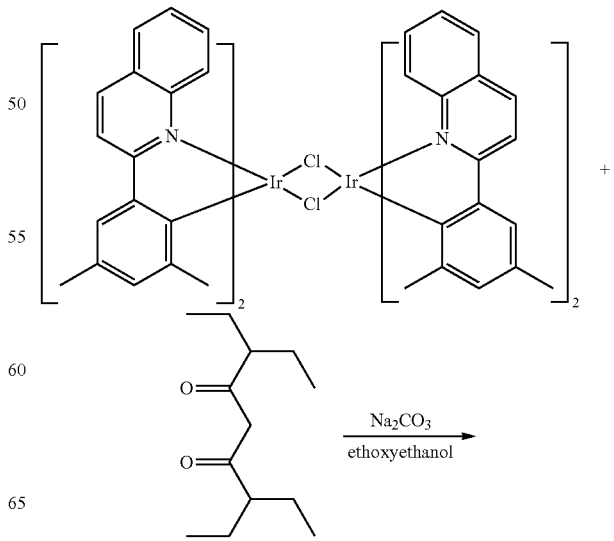

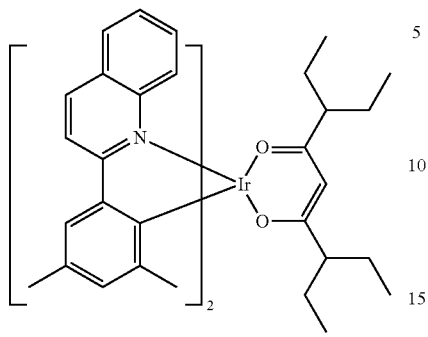

To the Iridium (III) dimer (1.50 g, 1.083 mmol) was added 3,7-diethylnonane-4,6-dione (1.725 g, 8.13 mmol) and the mixture was solubilized in 2-ethoxyethanol (40 mL). The mixture was degassed by bubbling nitrogen for 30 minutes and potassium carbonate (1.123 g, 8.13 mmol) was then added. The mixture was stirred at room temperature for 48 h followed by addition of 200 mL of isopropanol. The mixture was filtered through a Celite® plug and washed with dichloromethane. The solvent was evaporated and the crude product was purified by column chromatography using 20% dichloromethane (DCM) in heptanes in a triethylamine pre-treated silica gel column. The solid product was washed with methanol (20 mL) and filtered to obtain 0.220 g (10% yield) of pure dopant (99.5% on HPLC).

Synthesis of Compound 9

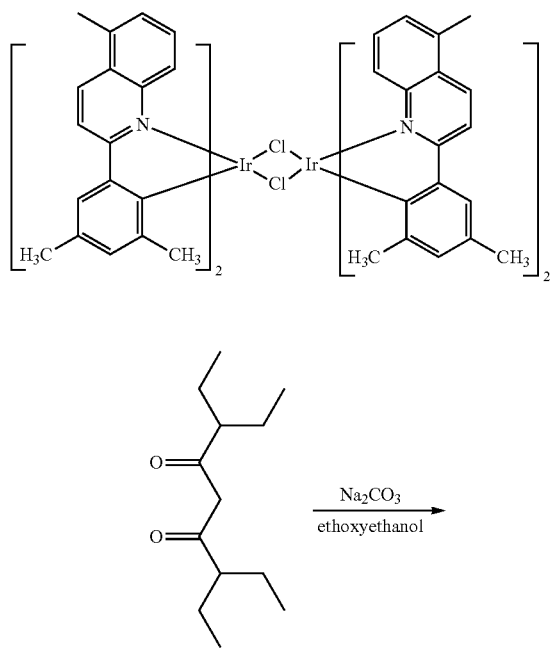

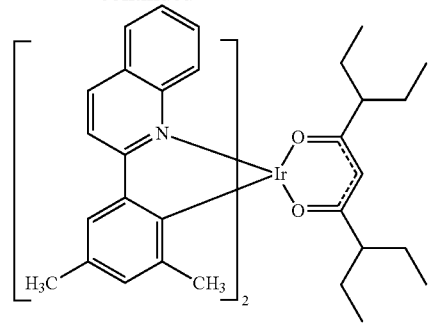

The Ir(III) Dimer (1.70 g, 1.18 mmol) and 3,7-diethylnonane-4,6-dione (2.51 g, 11.8 mmol) were dissolved in ethoxyethanol (50 mL), sodium carbonate (0.63 g, 5.90 mmol) was added followed with degassing by bubbling nitrogen through the mixture. The reaction mixture was stirred overnight at room temperature. The temperature was then increased to 45° C. for 2 hours. Upon cooling to room temperature, the precipitate was filtered through Celite®, washed with MeOH and heptanes. The filtrate with Celite® was suspended in DCM (containing 5% of Et₃N), filtered and evaporated. The red solid obtained (0.6 g) had a purity of 99.6% by HPLC.

Synthesis of Compound 12

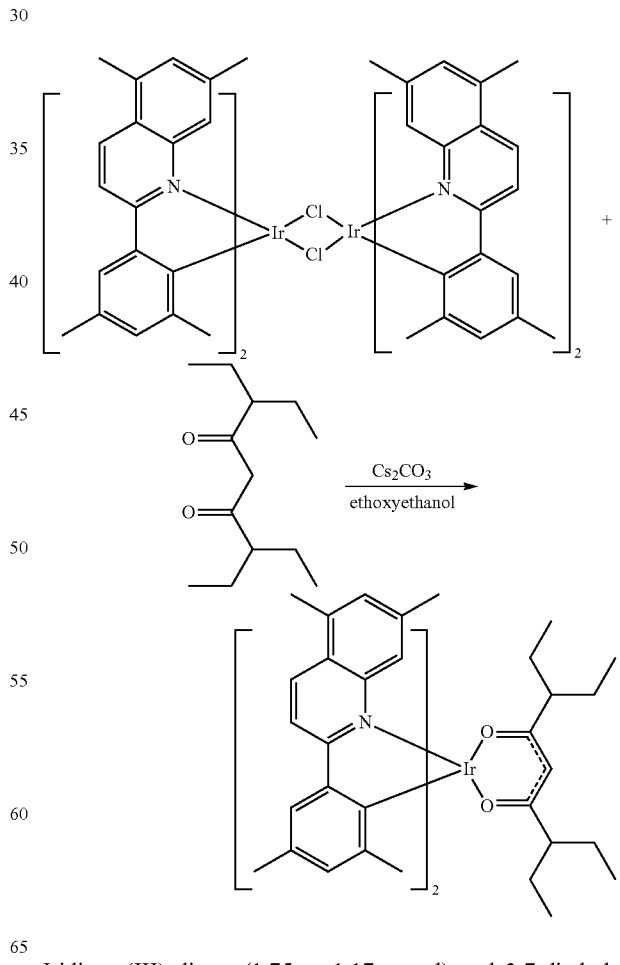

Iridium (III) dimer (1.75 g, 1.17 mmol) and 3,7-diethylnonane-4,6-dione (2.48 g, 11.7 mmol) were suspended in 2-ethoxyethanol (40 mL), degassed by bubbling nitrogen for 30 minutes and cesium carbonate (2.26 g, 11.7 mmol) was added to the solution. The mixture was then stirred at 90° C. overnight. Dichloromethane (100 mL) was added; the solution was filtered through a pad of Celite® and the pad was washed with dichloromethane. The solvents were evaporated and the red solid was coated on Celite® followed by purification by column chromatography on a triethylamine pre-treated silica gel column using 10% DCM in heptanes. Evaporation provided the red solid, which was washed with methanol to give a pure target compound (0.430 g, 40% yield) as a red solid.

Synthesis of Compound 32

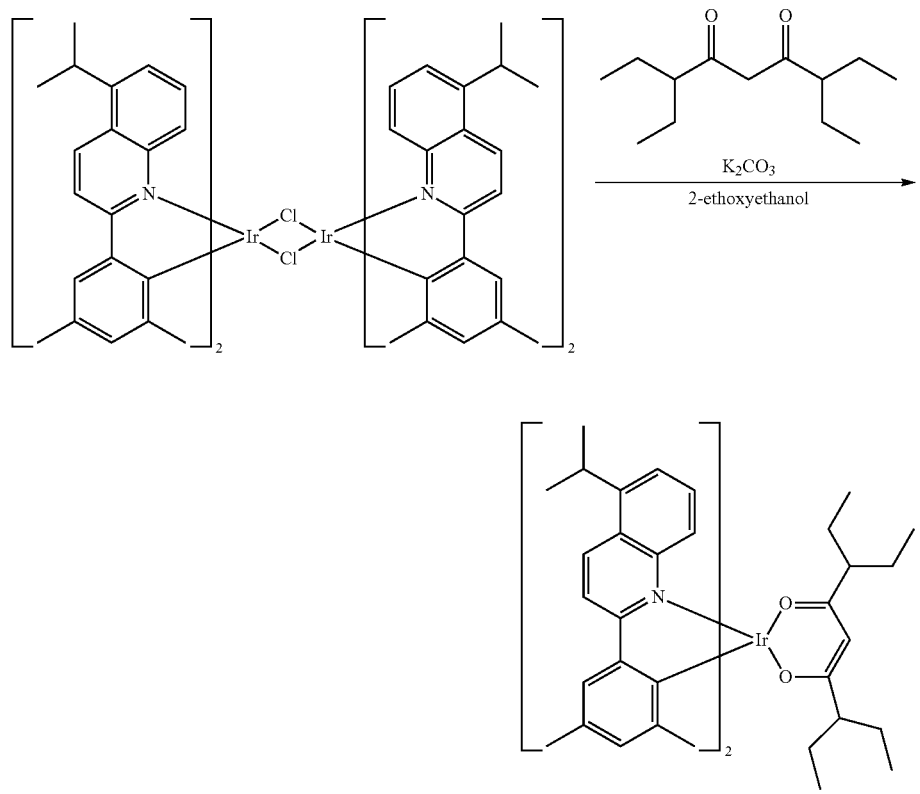

Ir(III) Dimer (1.32 g, 0.85 mmol) in 2-ethoxyethanol (40 mL) was degassed with nitrogen for 30 minutes and mixed with 3,7-diethylnonane-4,6-dione (1.81 g, 8.50 mmol) and potassium carbonate (1.18 g, 8.50 mmol). The reaction mixture was stirred at room temperature overnight. The mixture was then filtered through a plug of Celite® and washed with MeOH. The precipitate was extracted from Celite® with 5% $Et_3N/CH_2Cl_2$ affording 0.2 g of 99.9% pure material (HPLC). The filtrate was concentrated in vacuo, dissolved in DCM and crystallized by layering methanol on top. Crystals obtained are 99.6% pure and they were combined with other product for a total of 0.42 g (26% yield) of the title compound.

Synthesis of Compound 43

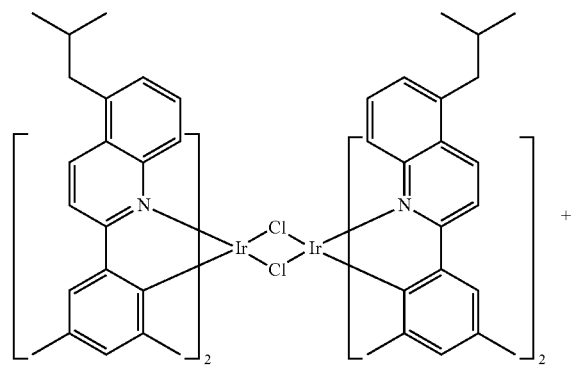

-continued

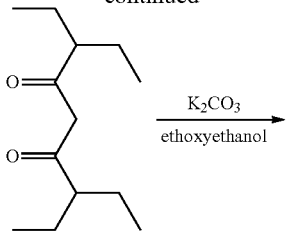

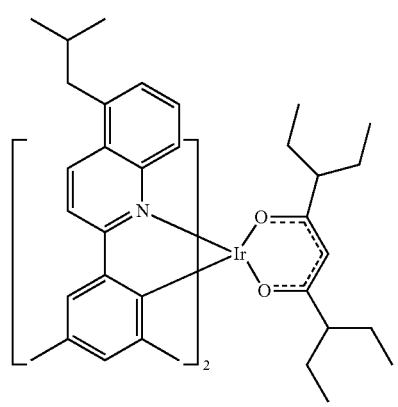

The Iridium (III) dimer (1.75 g, 1.09 mmol) and 3,7-diethylnonane-4,6-dione (2.31 g, 10.9 mmol) was diluted with 2-ethoxyethanol (40 mL), degassed by bubbling nitrogen for 30 minutes and potassium carbonate (1.50 g, 10.9 mmol) was added. The mixture was stirred at room temperature overnight. Dichloromethane (100 mL) was added; the reaction mixture was filtered through a pad of Celite® and the pad was washed with dichloromethane. The solvents were evaporated and the red solid was coated on Celite® followed by purification by column chromatography on a triethylamine pre-treated silica gel column using 10% DCM in heptanes as eluent. The red solid obtained was washed with methanol and re-purified by column chromatography by using 5% DCM in heptanes which affords the pure target compound (340 mg, 31% yield).

Synthesis of Compound 54

Synthesis of 5-cyclopentyl-2-(3,5-dimethylphenyl)quinoline

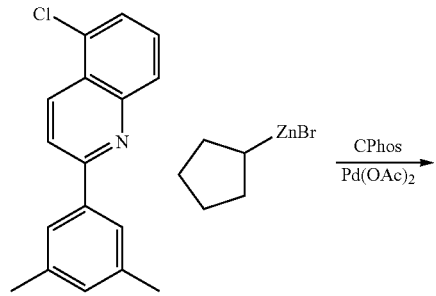

-continued

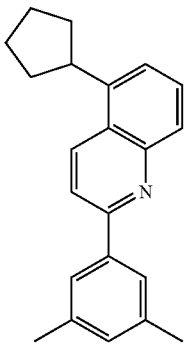

5-chloro-2-(3,5-dimethylphenyl)quinoline (4.29 g, 16.0 mmol), 2'-(dicyclohexylphosphino)-N2,N2,N6,N6-tetramethyl-[1,1'-biphenyl]-2,6-diamine (CPhos) (0.28 g, 0.64 mmol) and diacetoxypalladium (0.072 g, 0.320 mmol) were dissolved in anhydrous THF (60 mL). A solution of cyclopentylzinc(II) bromide (44.9 ml, 22.4 mmol) in THF (0.5 M) was added dropwise via syringe, and stirred at room temperature for 3 hours. The mixture was diluted in EA, washed with brine, dried with sodium sulfate, and concentrated under reduced pressure. The crude material was purified by column chromatography on silica, eluted with heptanes/EA 4/1 (v/v). The yellow powder was then recrystallized from heptanes to afford the title compound as colorless crystals (3.5 g, 72% yield).

Synthesis of Ir(III) Dimer

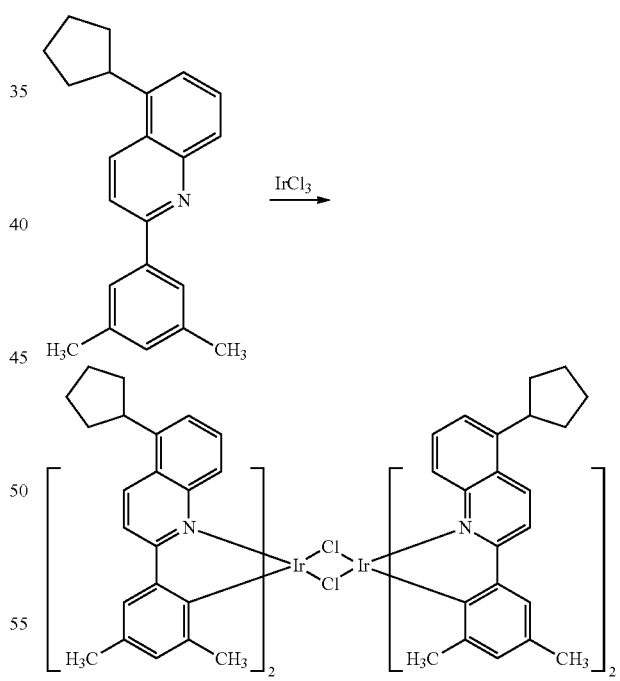

5-Cyclopentyl-2-(3,5-dimethylphenyl)quinoline (3.56 g, 11.8 mmol) and iridium(III) chloride trihydrate (1.30 g, 3.69 mmol) were dissolved in the mixture of ethoxyethanol (90 mL) and water (30 mL). Reaction mixture was degassed and heated to 105° C. for 24 h. The reaction mixture was then cooled down to room temperature and filtered through filter paper. The filtrate was washed with methanol and dried in vacuum, providing iridium complex dimer as dark solid 1.60 g (54% yield).

Synthesis of Compound 54

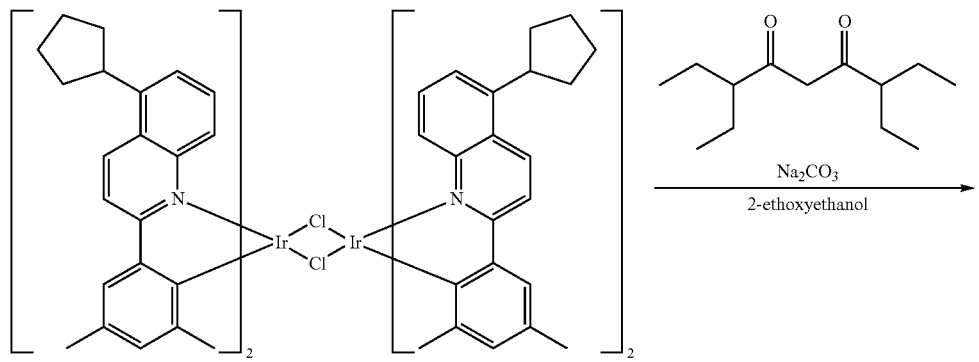

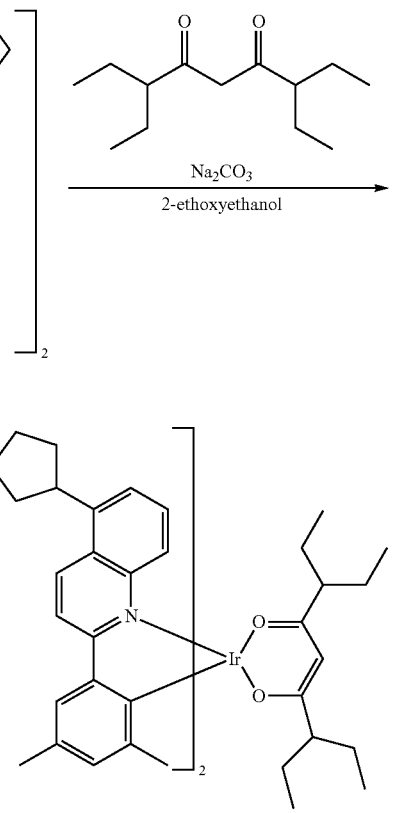

Iridium complex dimer (1.60 g, 1.00 mmol), 3,7-diethyl-nonane-4,6-dione (2.12 g, 9.98 mmol) and sodium carbonate (0.53 g, 4.99 mmol) were suspended in 50 mL of ethoxyethanol, and stirred overnight under $N_2$ at room temperature. The reaction mixture was then filtered through a pad of Celite®, washed with MeOH. Most of the red material was solubilized and passed through the Celite®. The Celite® was suspended in DCM, containing 10% of triethylamine and this suspension was combined with filtrate and evaporated. The residue was purified by column chromatography on silica gel, pre-treated with $Et_3N$, eluted with hexane/ethyl acetate 9/1 (v/v) mixture, providing a dark red solid. Additional purification with reverse-phase C18 column, eluted with acetonitrile provided after evaporation target complex as dark red solid (0.75 mg, 37% yield).

Synthesis of Compound 55

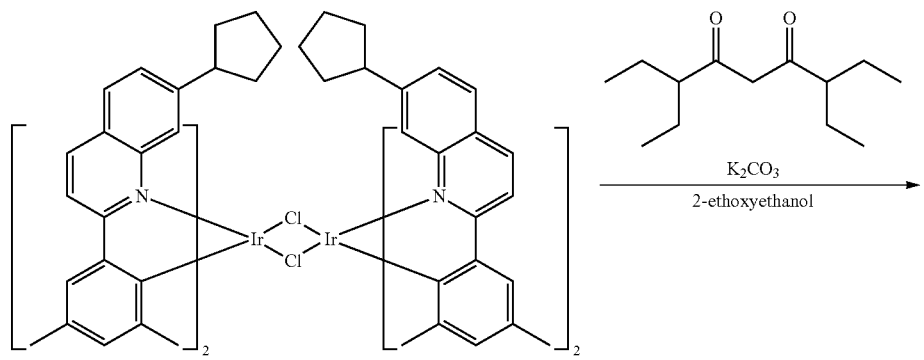

-continued

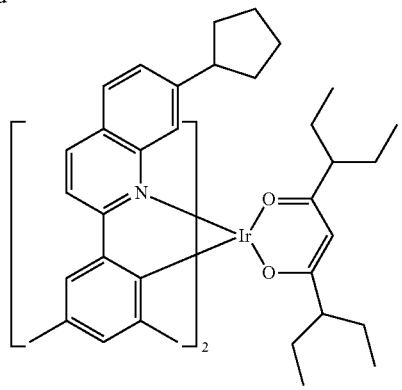

Ir(III) Dimer (2.40 g, 1.45 mmol), potassium carbonate (2.00 g, 14.5 mmol) and 3,7-diethylnonane-4,6-dione (3.08 g, 14.5 mmol) were suspended in 40 mL of ethoxyethanol, degassed and stirred overnight at 45° C. The reaction mixture was cooled down to room temperature and filtered through a pad of Celite®, the pad was washed with cold MeOH. The precipitate combined with the pad of Celite® were suspended in 50 mL of DCM with 5% of Et₃N, and filtered through silica plug. The solution was evaporated, providing red solid. Crystallization from DCM/Acetonitrile/MeOH mixture provided 1.4 g of target complex (48% yield).

Synthesis of Compound 62

To a 500 mL round bottom flask was added the chloro-bridged dimer (6.08 g, 3.54 mmol), 3,7-diethylnonane-4,6-dione (4.26 g, 20.06 mmol), sodium carbonate (3.75 g, 35.4 mmol), and 120 mL 2-ethoxyethanol. The reaction mixture was stirred overnight under nitrogen. The reaction mixture was poured onto a plug containing Celite®, basic alumina, and silica gel. The plug was pretreated with 10% triethylamine/heptane, and then washed with heptane and dichloromethane. The plug was eluted with dichloromethane. The filtrate was evaporated in the presence of isopropanol and a solid was filtered from isopropanol. The solid was dissolved in tetrahydrofuran and isopropanol was added. The tetrahydrofuran was removed under reduced pressure and the

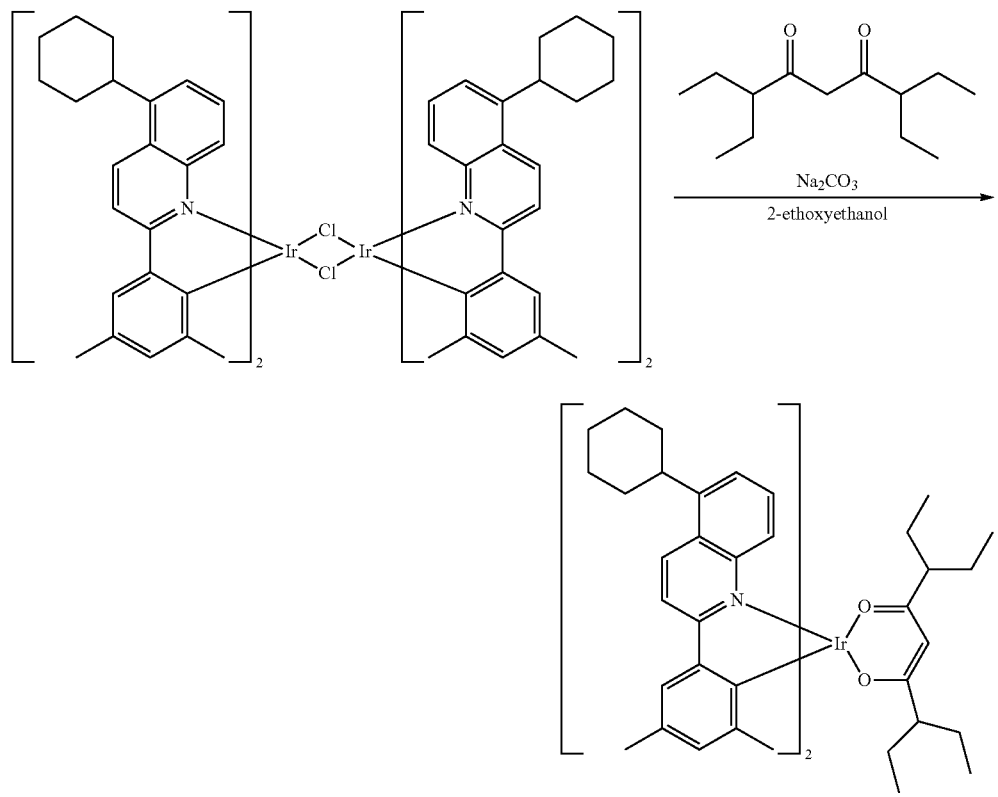

solution condensed. A red solid was filtered off, washed with isopropanol and dried (4.39 g, 60% yield).

Synthesis of Compound 83

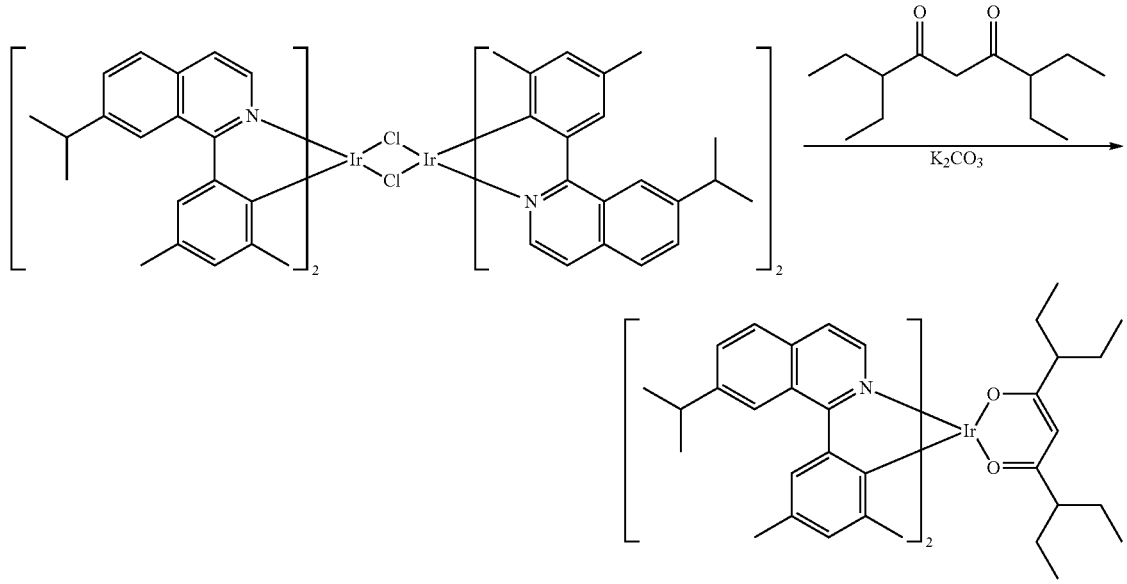

Ir(III) dimer (2.50 g, 2.49 mmol), 3,7-diethylnonane-4,6-dione (3.70 g, 17.43 mmol) and potassium carbonate (2.41 g, 17.4 mmol) were suspended in 50 mL of ethoxyethanol, the reaction mixture was degassed and stirred for 24 h at ambient temperature. Then the reaction mixture was filtered through Celite® pad and the pad was washed with MeOH. The solid filtrate with Celite® was suspended in DCM, containing 10% of Et$_3$N, filtered through silica plug and evaporated. The solid residue was crystallized from DCM/ THF/MeOH mixture, providing target complex as red solid (3.1 g, 65% yield).

Synthesis of Compound 93

Synthesis of 4-fluoro-3,5-dimethylbenzoyl chloride

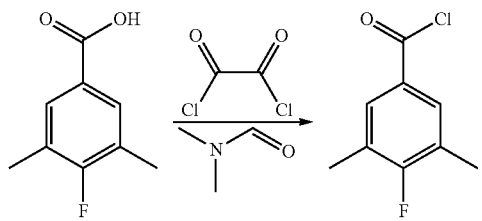

Oxalyl chloride (6.93 ml, 79 mmol) was added dropwise to a solution of 4-fluoro-3,5-dimethylbenzoic acid (12.1 g, 72.0 mmol) in dichloromethane (360 mL) and DMF (0.06 mL, 0.720 mmol) under nitrogen at room temperature. The mixture was then stirred at room temperature and monitored by TLC. Complete solubilization of the mixture occurred within 3 hours. The reaction was complete after an additional hour. Solvent was removed under reduced pressure and the crude mixture was dried in high vacuum and used without further purification.

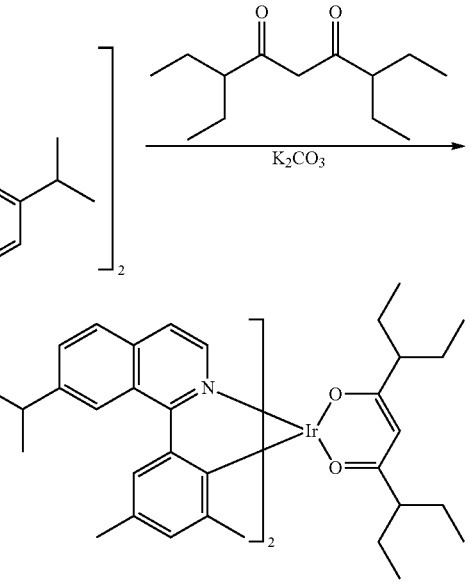

Synthesis of 4-fluoro-N-(4-isopropylphenethyl)-3,5-dimethylbenzamide

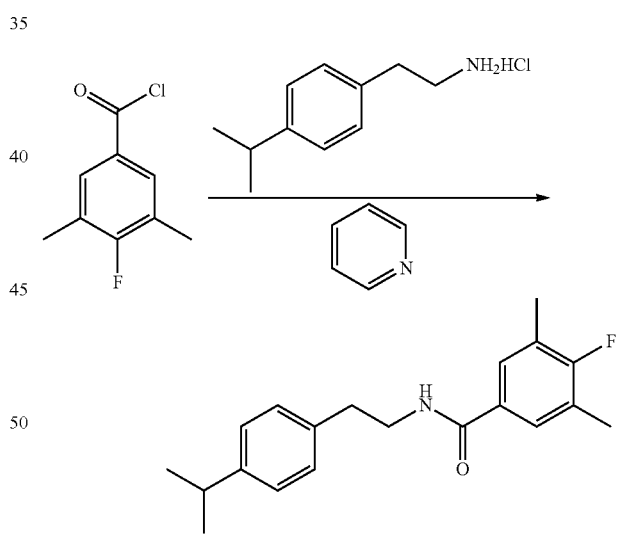

Pyridine (12.12 ml, 150 mmol) and 2-(4-isopropylphenyl) ethanamine hydrochloride (10 g, 50.1 mmol) were added into a 3-necked flask and dissolved in DCM (50 mL). The solution was cooled with an ice-bath and 4-fluoro-3,5-dimethylbenzoyl chloride (10.28 g, 55.1 mmol) was added slowly (portions) and the mixture was stirred at room temperature for 12 hours. DCM was added and the organic layer was washed with 5% HCl and then 5% NaOH solution and dried with sodium sulfate. The solvent was evaporated and the crude compound was used without further purification.

165
Synthesis of 1-(4-fluoro-3,5-dimethylphenyl)-7-isopropyl-3,4-dihydroisoquinoline

166
Synthesis of 1-(4-fluoro-3,5-dimethylphenyl)-7-isopropylisoquinoline

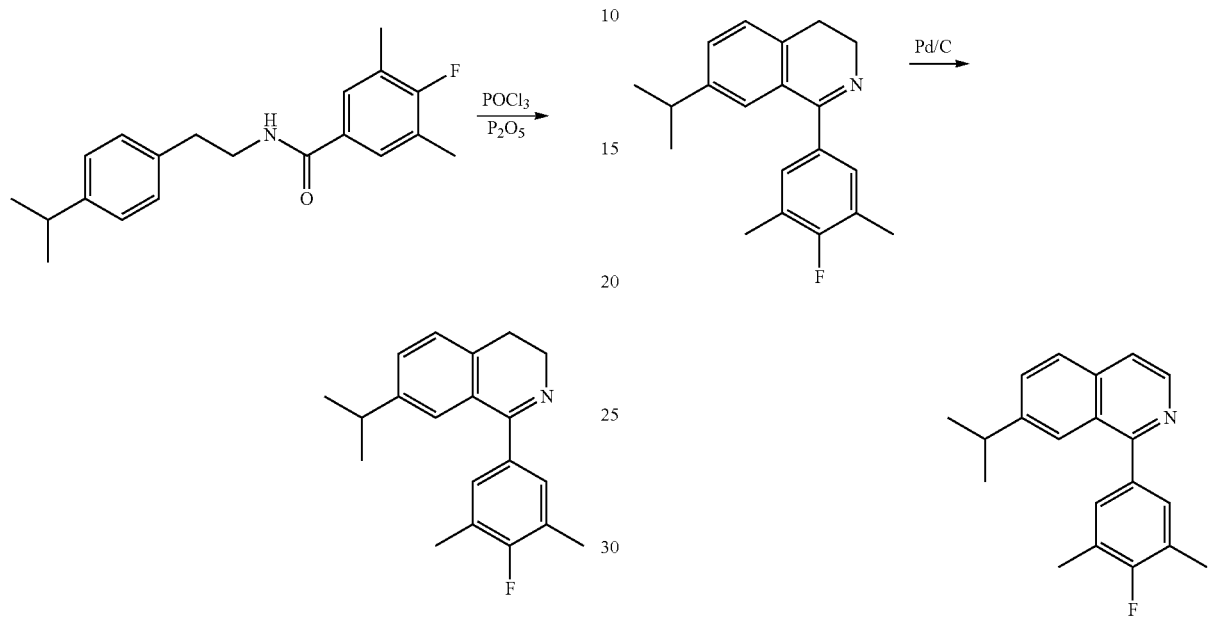

4-Fluoro-N-(4-isopropylphenethyl)-3,5-dimethylbenzamide (15 g, 47.9 mmol), phosphorus pentoxide (42.8 g, 302 mmol), and phosphoryl oxochloride (44.6 ml, 479 mmol) were diluted in xylene (100 mL) and then refluxed for 3 hours under nitrogen. By GCMS, reaction was complete after 2.5 h. The reaction mixture was cooled to RT and stir overnight, the solvent was decanted and ice was slowly added to the solid. The residue mixture in water was made weakly alkaline by adding 50% NaOH and the product was extracted with toluene. The organic layer was washed with water, dried over sodium sulfate, and the solvent was evaporated under reduced pressure. The crude product was used without further purification.

The solution of 1-(4-fluoro-3,5-dimethylphenyl)-7-isopropyl-3,4-dihydroisoquinoline (14.4 g, 47.9 mmol) in xylene (240 mL) was degassed by bubbling nitrogen for 15 minutes. In the meantime, 5% palladium (2.55 g, 2.39 mmol) on carbon was added. The mixture was heated to reflux overnight. The reaction was monitored by TLC. The mixture was filtered through a pad of Celite® and the solvents were evaporated under reduced pressure. The product was coated on Celite® and purified by column chromatography using 10% EA in heptanes to let first impurities come out the EA volume was slowly increased to 15% to let the target come out. The product contains a 2% impurity which comes 10 minutes after the target on HPLC. A reverse phase chromatography on C18 column eluted with 95/5 MeCN/water (v/v) provided 4.5 g of pure material (32% yield over 4 steps).

Synthesis of Ir(III) Dimer

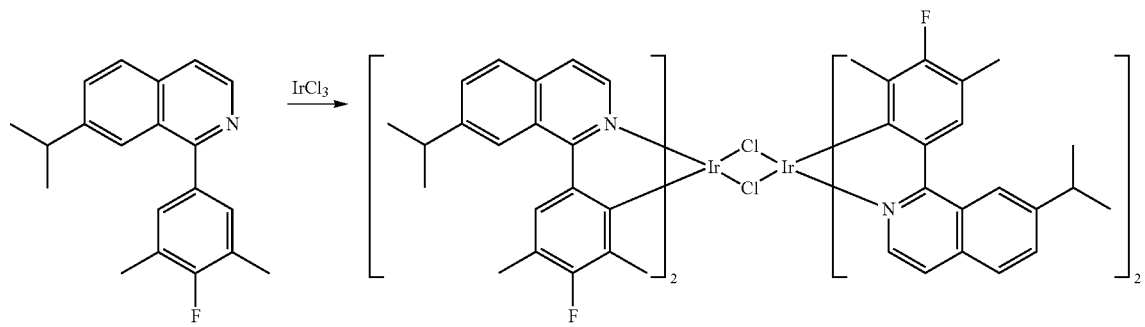

Iridium(III) chloride trihydrate (1.64 g, 4.65 mmol) and 1-(4-fluoro-3,5-dimethylphenyl)-7-isopropylisoquinoline (4.09 g, 13.95 mmol) were suspended in ethoxyethanol (50 mL) and water (12 mL), degassed by bubbling nitrogen and immersed in the oil bath at 105° C. overnight. After cooling down to room temperature, the solid was filtered, washed with MeOH and dried under vacuum to afford 1.8 g (74% yield) of red solid.

Synthesis of Compound 93

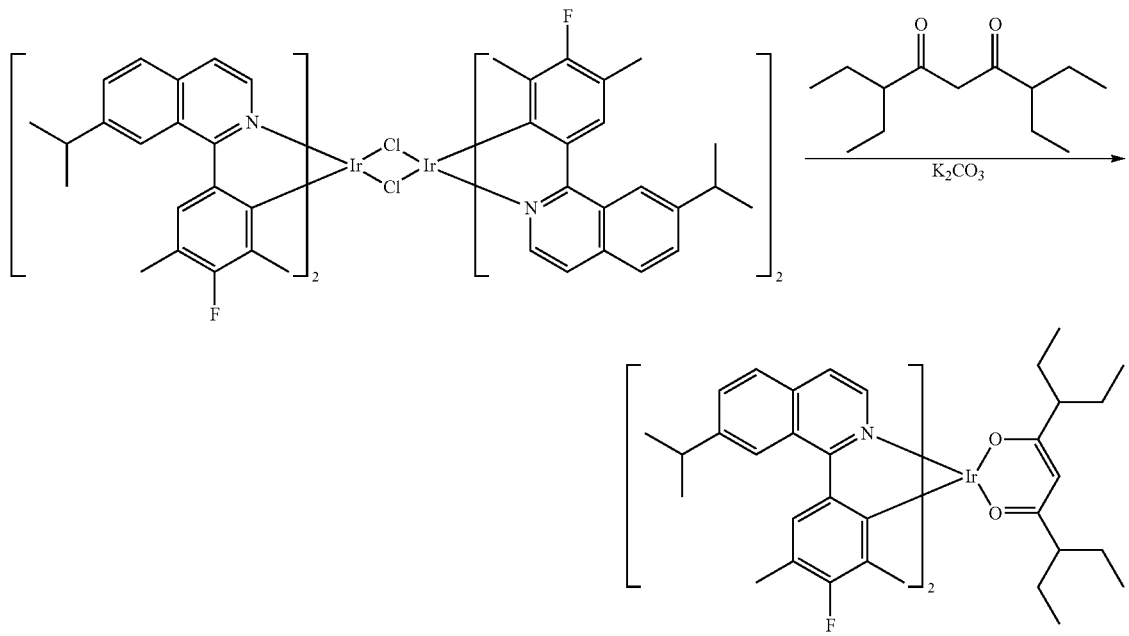

Ir(III) Dimer (1.00 g, 0.96 mmol) was combined with 3,7-diethylnonane-4,6-dione (1.53 g, 7.21 mmol) and the mixture was diluted with 2-ethoxyethanol (36 mL). The solution was degassed by bubbling nitrogen for 15 minute. Potassium carbonate (0.997 g, 7.21 mmol) was then added and the mixture was stirred at room temperature for 18 hours. Then the bright red precipitate was filtered on a Celite® pad and washed with MeOH. The filtrated was discarded and the solid on top of the Celite® was then washed with DCM. The crude product was coated on celite and purified by column chromatography using 5% DCM in heptanes on a triethylamine pre-treated silica gel column. The target compound was obtained as red solid (0.9 g).

Synthesis of Compound 118

Synthesis of 5-isobutylquinoline

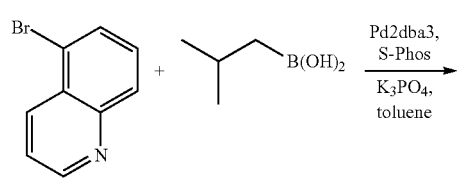

-continued

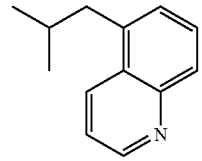

A mixture of 5-bromoquinoline (20 g, 93 mmol), isobutylboronic acid (19.4 g, 186 mmol) and potassium phosphate, H$_2$O (64.4 g, 280 mmol) in toluene (600 mL) was purged with N$_2$ for 20 minutes Pd$_2$dba$_3$ (1.71 g, 1.87 mmol) and dicyclohexyl(2',6'-dimethoxy-[1,1'-biphenyl]-2-yl)phosphine (3.06 g, 7.46 mmol) (SPhOS) were then added. The mixture was heated to reflux overnight. The reaction was worked up upon completion. The crude was purified by silica gel column chromatography using heptane/EA: 85/15 to 7/3 (v/v) gradient mixture as eluent to give an oil (11.5 g, 67% yield).

Synthesis of 5-isobutylquinoline 1-oxide

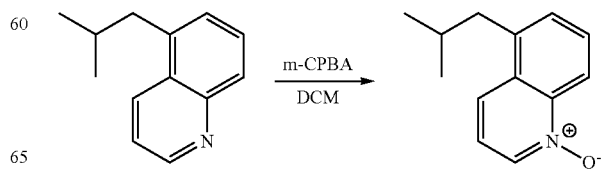

3-Chloroperoxybenzoic acid (m-CPBA) (16.6 g, 74.2 mmol) was added by portions to a solution of 5-isobutylquinoline (12.5 g, 67.5 mmol) in DCM (150 mL) cooled at 0° C. under nitrogen. The mixture was then stirred at room temperature overnight and at 50° C. for 11 hours. More m-CPBA was added to complete the reaction. Upon completion, the reaction mixture was quenched with aqueous NaHCO$_3$. Aqueous mixture was extracted with DCM, washed with water and brine, and dried over Na$_2$SO$_4$. The crude was purified by silica gel column chromatography using DCM/MeOH: 97/3 to 95/5 (v/v) gradient mixture as eluent to give an off-white solid (11.0 g, 80.0% yield).

Synthesis of 5-isobutylquinolin-2(1H)-one

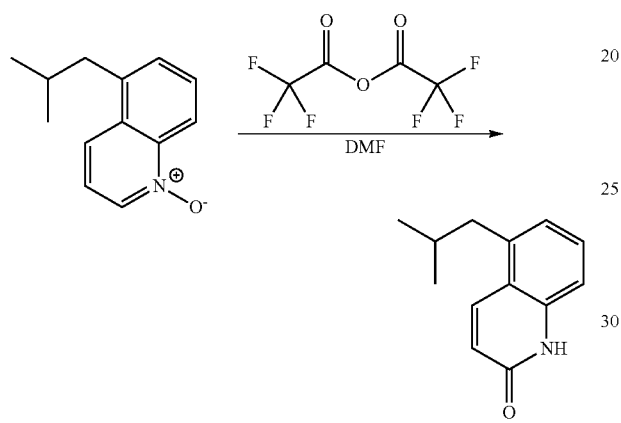

Trifluoroacetic anhydride (61.8 ml, 437 mmol) was added to a 0° C., stirred solution of 5-isobutylquinoline 1-oxide (11 g, 54.7 mmol) in DMF (70 mL) under N$_2$. The mixture was then stirred at room temperature overnight. Upon completion, the trifluoroacetic anhydride was removed under reduced pressure. The residue was quenched with aqueous NaHCO$_3$ and further diluted with water. The crude was recrystallized from aqueous DMF to give a white solid (8.2 g, 75% yield).

Synthesis of 2-chloro-5-isobutylquinoline

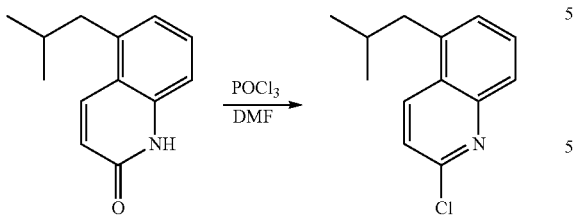

Phosphorus oxychloride (7.60 ml, 81 mmol) was added dropwise to a solution of 5-isobutylquinolin-2(1H)-one (8.2 g, 40.7 mmol) in DMF (160 mL) over 30 minutes under N$_2$. The reaction mixture was then heated at 80° C. After the reaction was complete, the remaining POCl$_3$ was evaporated under reduced pressure and aqueous Na$_2$CO$_3$ was carefully added. The solid was isolated to give an off-white solid (8.1 g, 91% yield).

Synthesis of 2-(3,5-dichlorophenyl)-5-isobutylquinoline

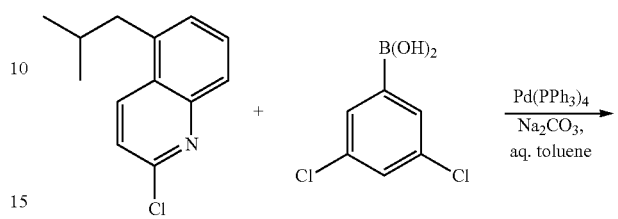

Nitrogen gas was bubbled into a mixture of (3,5-dichlorophenyl)boronic acid (10.6 g, 55.5 mmol), 2-chloro-5-isobutylquinoline (8.13 g, 37 mmol) and Na$_2$CO$_3$ (7.84 g, 74.0 mmol) in THF (250 mL) and water (50 mL) for 30 min. Tetrakis(triphenylphosphine)palladium (0) (1.71 g, 1.48 mmol) was added and the mixture was heated to reflux overnight. Upon completion (monitored by GCMS) the reaction was worked up by diluting in ethyl acetate and washing with brine and water. The organic layer was dried with sodium sulfate and solvent was evaporated under reduced pressure to give a crude material, which was purified by silica gel column chromatography using heptanes/EA: 98/2 to 96/(v/v) gradient mixture as eluent to yield a solid (8.0 g, 66% yield).

Synthesis of 2-(3,5-dimethyl(D6)phenyl)-5-isobutylquinoline

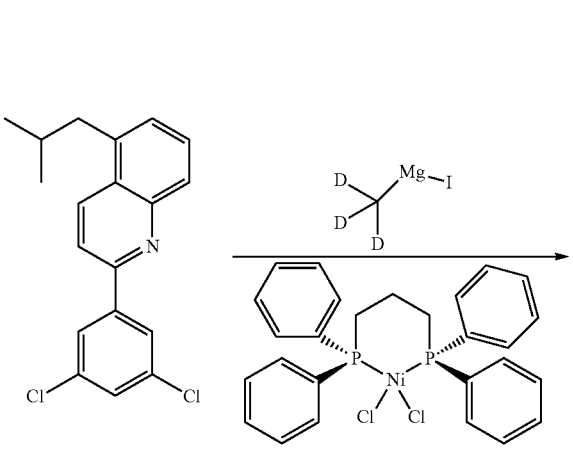

171
-continued

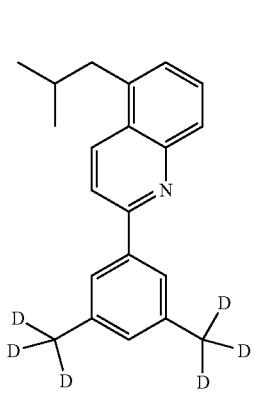

CD$_3$MgI (61 mL, 61 mmol) in diethyl ether (1.0 M) was added into a stirred mixture of 2-(3,5-dichlorophenyl)-5-isobutylquinoline (8.0 g, 24.2 mmol) and dichloro(1,3-bis(diphenylphosphino)propane)nickel (Ni(dppp)Cl$_2$) (0.39 g, 0.73 mmol) in diethyl ether (120 mL) over a period of 30 min. The mixture was stirred at room temperature overnight. Upon completion, the reaction was cooled with an ice bath and quenched carefully with water. The mixture was extracted with EA, washed with water (3 times) and brine. The crude product was purified by silica gel column chromatography using heptanes/DCM/EA 89/10/1 to 84/15/1 (v/v/v) gradient mixture as eluent to yield an oil (6.5 g, 91% yield).

172
Synthesis of Ir(III) Dimer

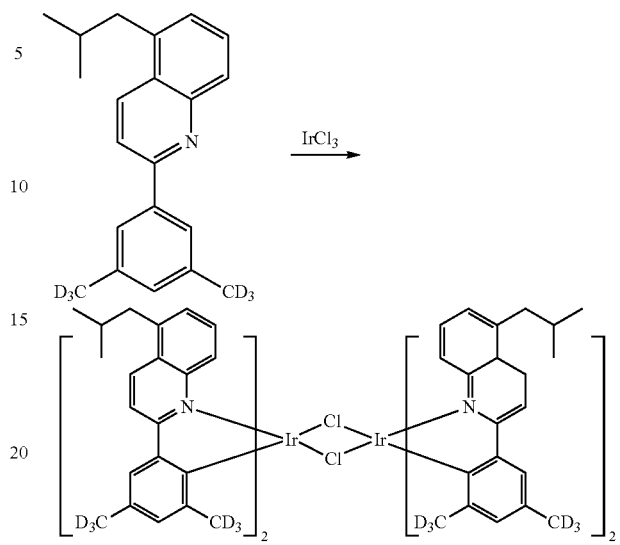

A mixture of 2-(3,5-dimethyl(D$_6$)phenyl)-5-isobutylquinoline (5.17 g, 17.5 mmol) and iridium(III) chloride (1.80 g, 4.86 mmol) in ethoxyethanol (30 mL) and water (10 mL) was degassed by bubbling N$_2$ for 30 minutes before heating at 100° C. for 19 h. The reaction mixture was cooled down and small amount of MeOH was added. The Ir(III) dimer was isolated by filtration to give a solid (2.40 g, 61% yield), which was used for next reaction without further purification.

Synthesis of Compound 118

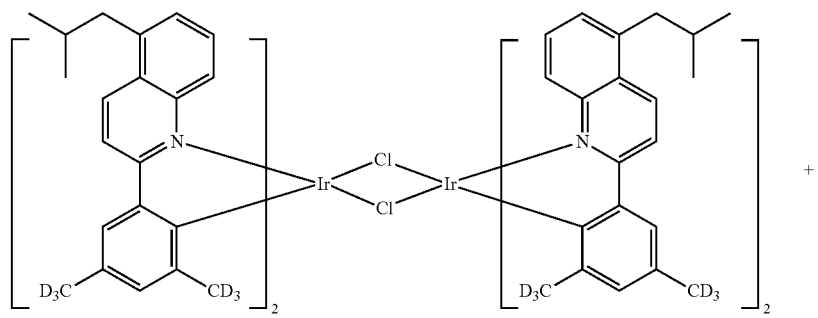

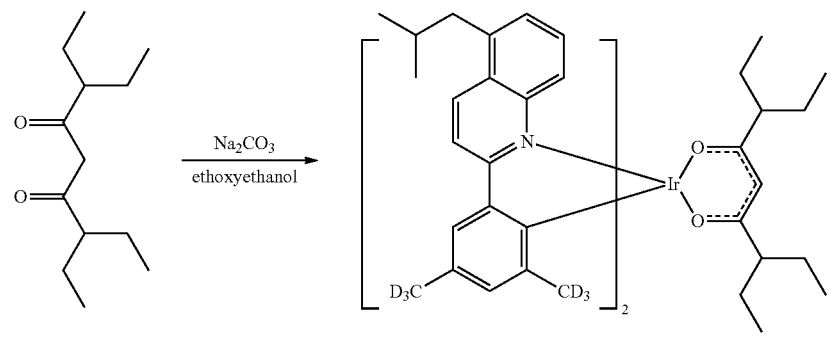

A mixture of Ir(III) dimer (1.30 g, 0.80 mmol), 3,7-diethylnonane-4,6-dione (1.69 g, 7.96 mmol), $Na_2CO_3$ (1.69 g, 15.9 mmol) in ethoxyethanol (25 mL) was degassed for 20 minutes and stirred at room temperature for 24 hours. The reaction mixture was filtered and washed with small amount of methanol and heptane. The solid was dissolved in 10% triethylamine (TEA) in DCM. The mixture was filtered and evaporated under reduced pressure. The red solid was recrystallized from DCM/IPA with 5% TEA to give a red solid (7.0 g, 44% yield).

Synthesis of Compound 141

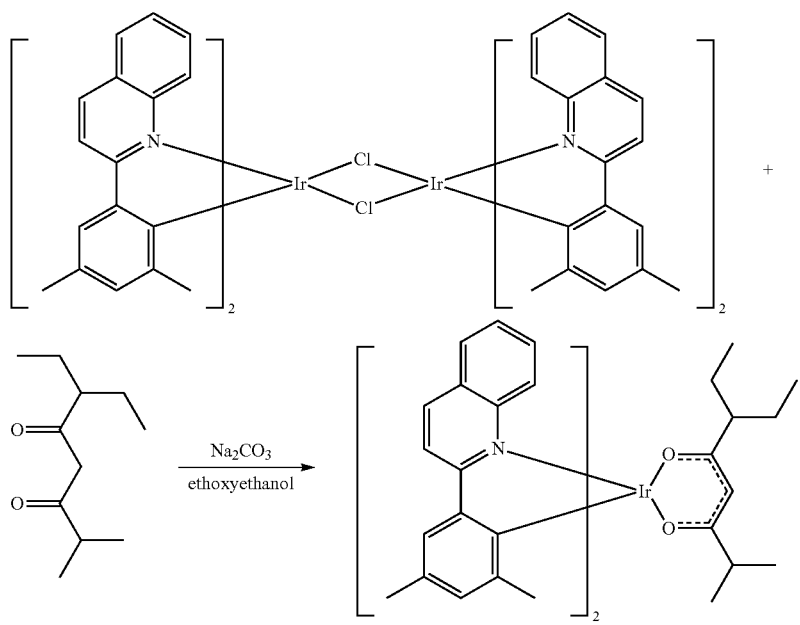

The Ir(III) dimer (0.80 g, 0.58 mmol) and 6-ethyl-2-methyloctane-3,5-dione (0.75 g, 4.06 mmol) were inserted in a round-bottom flask. The mixture was diluted in 2-ethoxyethanol (40 mL), degassed with nitrogen for 30 minutes and $K_2CO_3$ (0.60 g, 4.33 mmol) was inserted. The mixture was stirred at room temperature overnight. The precipitate was filtered through a pad of Celite®. The solvent was evaporated and the crude material was purified with column chromatography on silica gel by using a mixture of heptanes/DCM 95/5 (v/v). The pure material (0.65 g, 67% yield) was obtained.

Synthesis of Compound 142

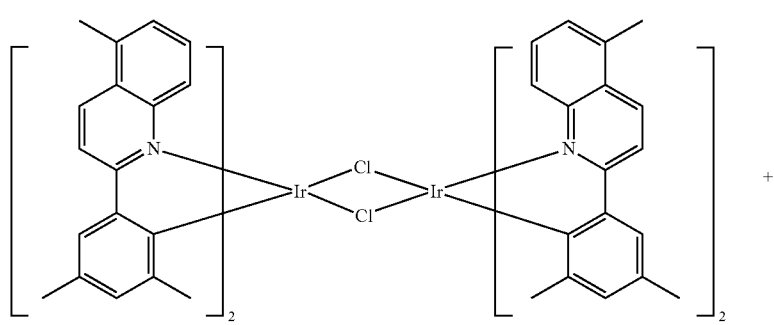

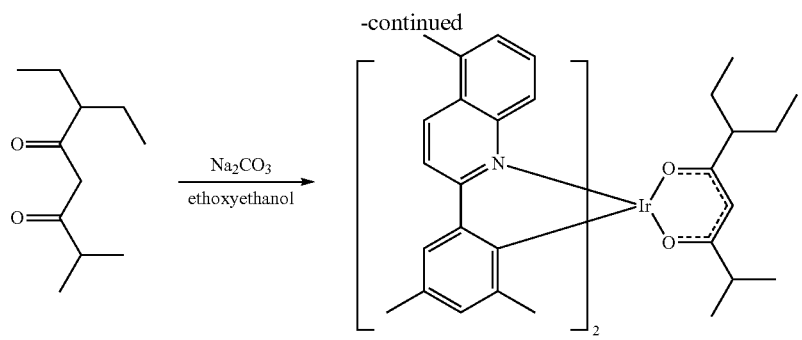

The Iridium (III) dimer (0.80 g, 0.56 mmol) and 6-ethyl-2-methyloctane-3,5-dione (0.77 g, 4.16 mmol) were diluted in ethoxyethanol (19 mL). The mixture was degassed by bubbling nitrogen for 15 minutes followed by the addition of $K_2CO_3$ (0.576 g, 4.16 mmol) and the mixture was stirred at room temperature overnight. Dichloromethane was added followed by filtration of the solution through a pad of Celite® and washed with dichloromethane until the filtrate is clear. The crude product was purified by column chromatography by using a triethylamine-treated silica gel column and eluting with a mixture of heptanes/dichloromethane 95/5 (v/v). The pure product was collected (0.35 g, 67% yield) as a red powder.

The Ir(III) Dimer (0.75 g, 0.47 mmol) and 6-ethyl-2-methyloctane-3,5-dione (0.64 g, 3.50 mmol) were diluted with ethoxyethanol (16 mL), degassed with nitrogen for 30 minutes, $K_2CO_3$ (0.48 g, 3.50 mmol) was added and the mixture was stirred at room temperature overnight. DCM was added to the mixture to solubilize the product, the reaction mixture was filtered through a pad of Celite® and evaporated. The crude material was purified with column chromatography on silica gel, eluted with the mixture of heptanes/DCM 95/5 (v/v), provided the pure material (0.59 g, 66% yield)

Synthesis of Compound 176

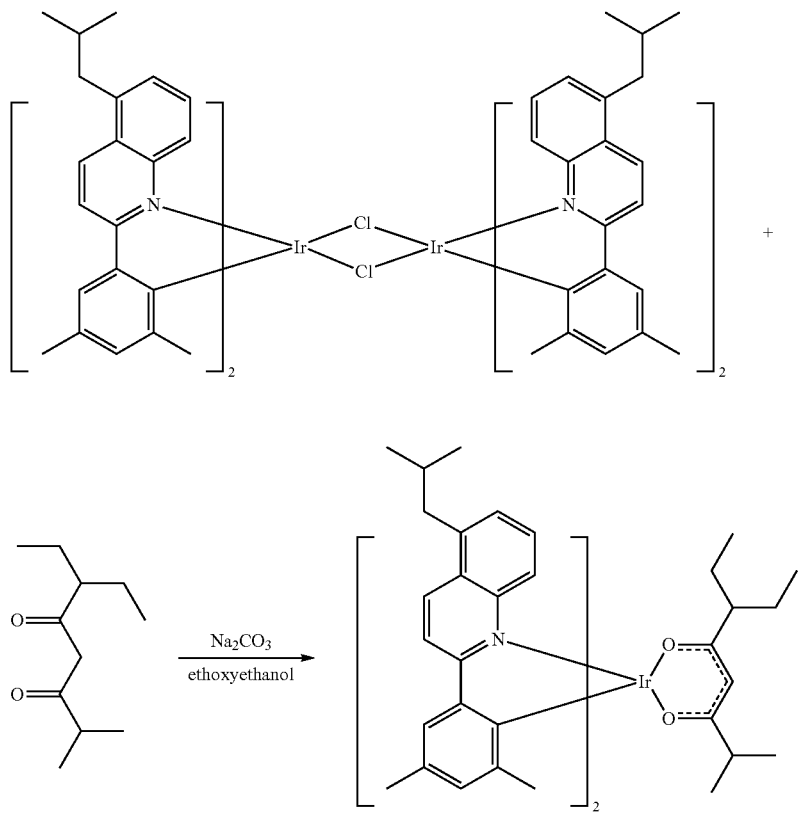

Synthesis of Compound 278

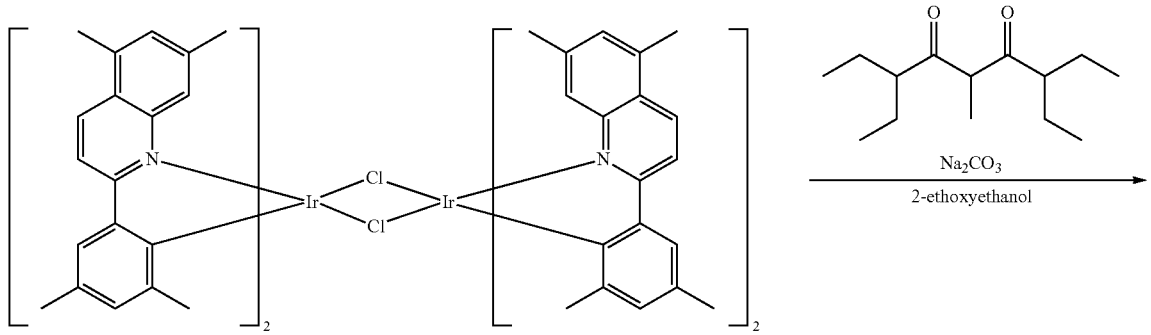

To a round bottom flask was added the chloro-bridged dimer (4.37 g, 2.91 mmol), 3,7-diethyl-5-methylnonane-4,6-dione (3.7 g, 16.4 mmol), sodium carbonate (3.08 g, 29.1 mmol), and 100 mL 2-ethoxyethanol. The reaction mixture was stirred at room temperature for 48 h under nitrogen. The reaction mixture was poured onto a plug containing Celite®, basic alumina, and silica gel. The plug was pretreated with 10% triethylamine/heptanes, and then washed with heptane and dichloromethane. The plug was eluted with dichloromethane. The filtrate was evaporated in the presence of isopropanol and a solid was filtered from isopropanol. The solid was dissolved in tetrahydrofuran and isopropanol was added. The tetrahydrofuran was removed on a rotovap and the solution condensed. A red solid was filtered off and washed with isopropanol (0.79 g, 16% yield).

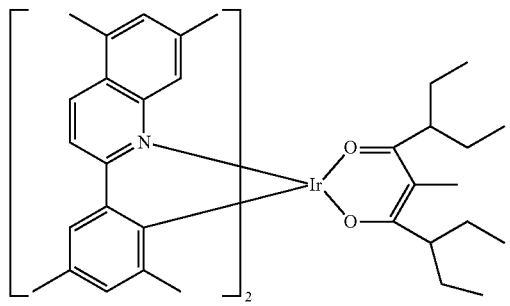

Synthesis of Compound 320

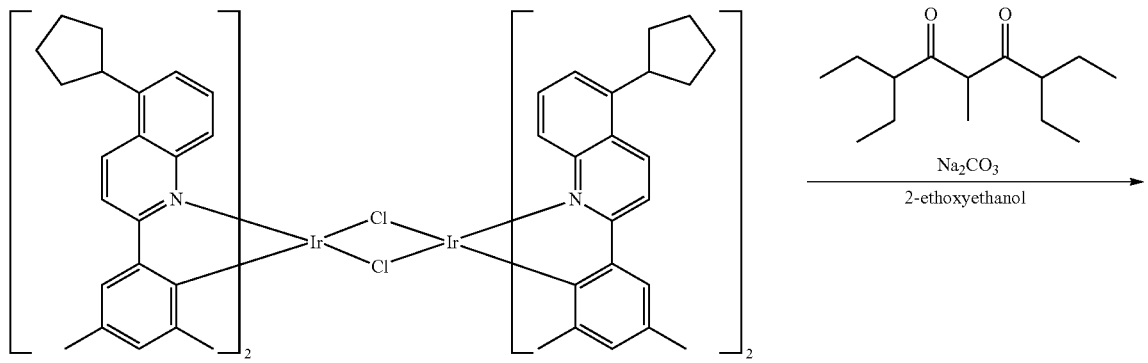

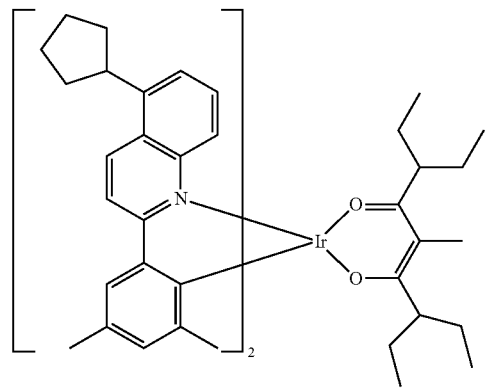

Ir(III) dimer (2.00 g, 1.25 mmol), 3,7-diethyl-5-methyl-nonane-4,6-dione (1.98 g, 8.73 mmol) and potassium carbonate (1.21 g, 8.73 mmol) were suspended in 50 mL of ethoxyethanol. The reaction mixture was degassed and stirred overnight at room temperature. It was then cooled in the ice bath, filtered through celite pad, and the pad was washed with cold MeOH. The precipitate with the Celite® was suspended in DCM, containing 5% of $Et_3N$, and filtered through silica pad. The solution was evaporated, providing red solid. The solid was purified by crystallization from DCM/MeOH, providing target complex as red solid (1.5 g, 59%).

Synthesis of Comparative Compound 4

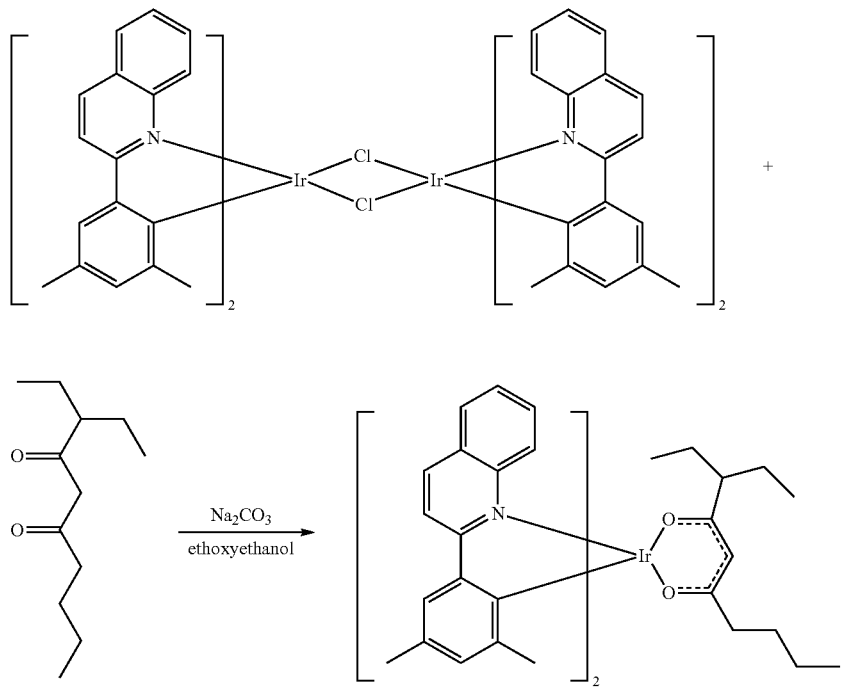

The Iridium (III) Dimer (0.70 g, 0.51 mmol) and 3-ethyl-decane-4,6-dione (0.75 g, 3.79 mmol) were suspended in ethoxyethanol (17 mL). The reaction was degassed by bubbling nitrogen for 15 minutes followed by addition of $K_2CO_3$ (0.52 g, 3.79 mmol). The mixture was stirred at room temperature overnight. Thin layer chromatography was performed on the reaction mixture in the morning showing complete consumption of the dimer. Dichloromethane was added followed by filtration of the solution through a pad of Celite® and washed with dichloromethane until the filtrate is clear. The crude product was purified by column chromatography by using a triethylamine-treated column and eluting with a mixture of heptanes/dichloromethane (95/5, v/v). The pure product was collected (0.600 g, 70% yield) as a red powder.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having the formula $Ir(L^1)_x(L^2)_y(L^3)_z$:
wherein $L^1$ is selected from the group consisting of

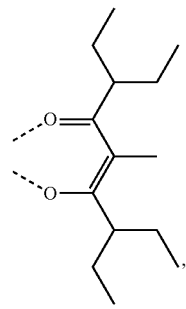
$L_{A3}$

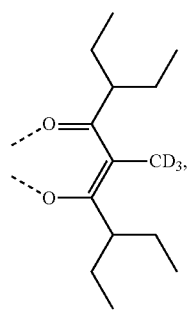
$L_{A5}$

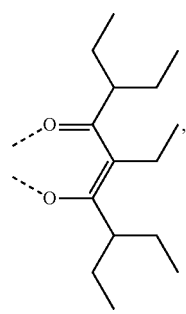
$L_{A7}$

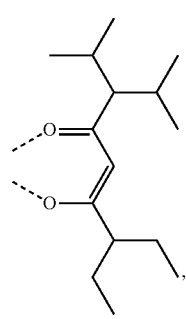
$L_{A9}$

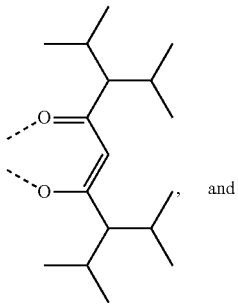
$L_{A10}$
, and

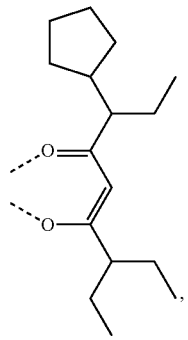
$L_{A13}$

, wherein $L^2$ is a second ligand and $L^3$ is a third ligand and $L^2$ and $L^3$ can be the same or different;

wherein the second ligand $L^2$ and the third ligand $L^3$ are structure (a) independently selected from the group consisting of:

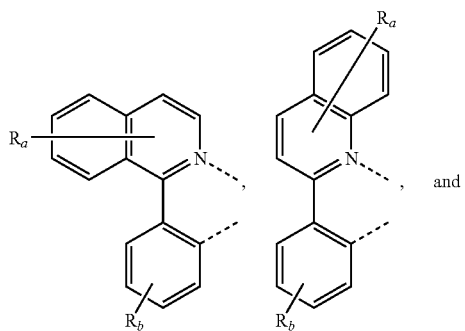
, and

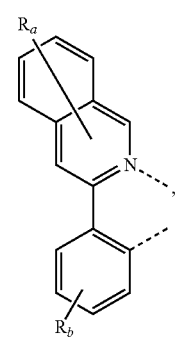
, or structure (b) independently selected from the group consisting of

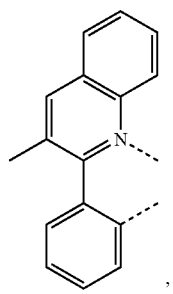 $L_{Q2}$,
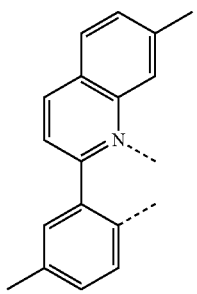 $L_{Q7}$,
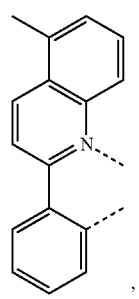 $L_{Q3}$,
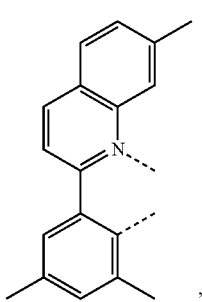 $L_{Q10}$,
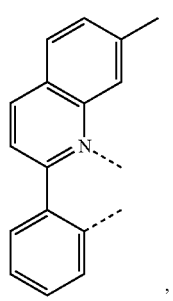 $L_{Q4}$,
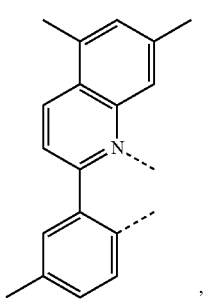 $L_{Q11}$,
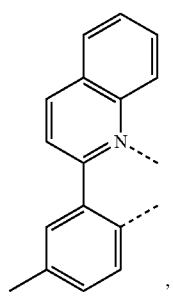 $L_{Q5}$,
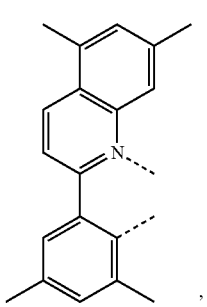 $L_{Q12}$,
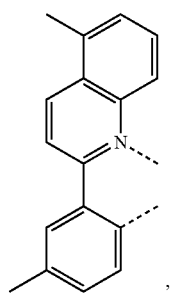 $L_{Q6}$,
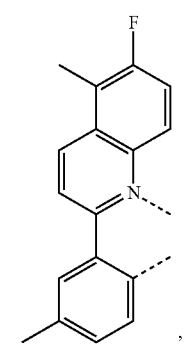 $L_{Q13}$, -continued
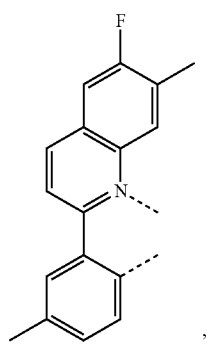 L<sub>Q14</sub>
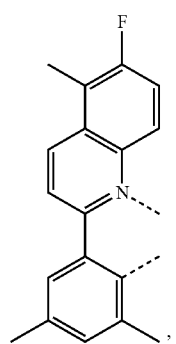 L<sub>Q15</sub>
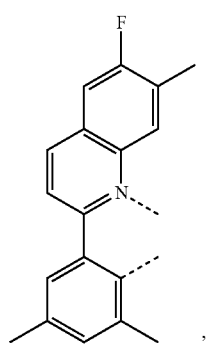 L<sub>Q16</sub>
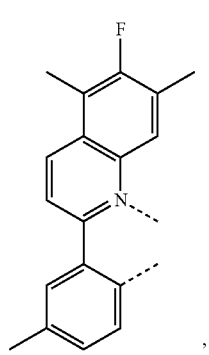 L<sub>Q17</sub>
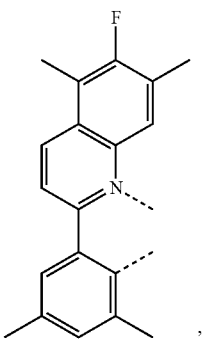 L<sub>Q18</sub>
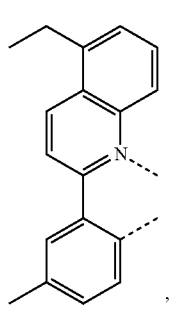 L<sub>Q19</sub>
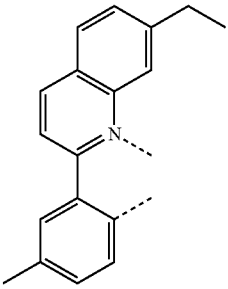 L<sub>Q20</sub>
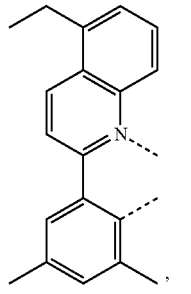 L<sub>Q21</sub>
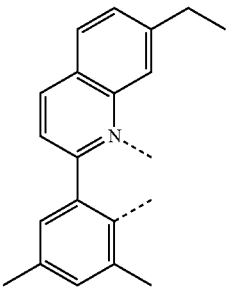 L<sub>Q22</sub>

187
-continued
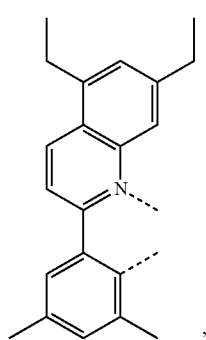
$L_{Q23}$
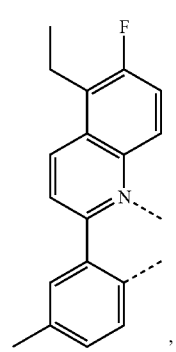
$L_{Q24}$
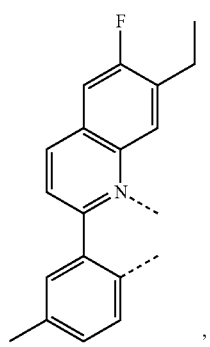
$L_{Q25}$
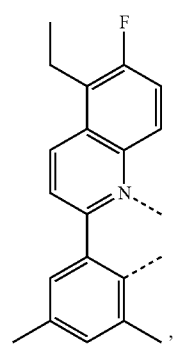
$L_{Q26}$
188
-continued
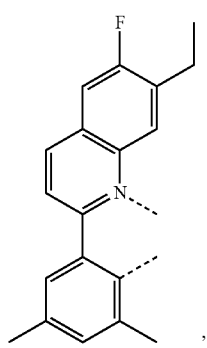
$L_{Q27}$
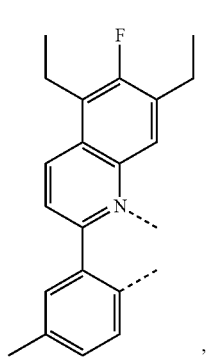
$L_{Q28}$
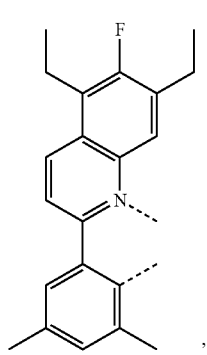
$L_{Q29}$
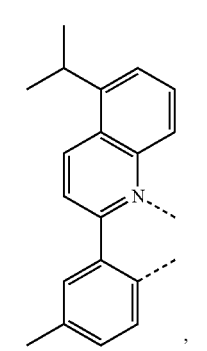
$L_{Q30}$ -continued
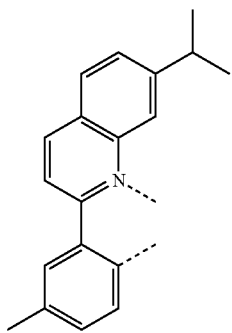 $L_{Q31}$
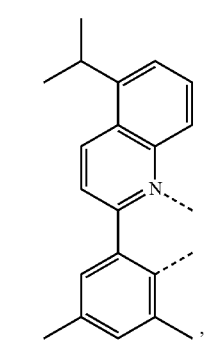 $L_{Q32}$
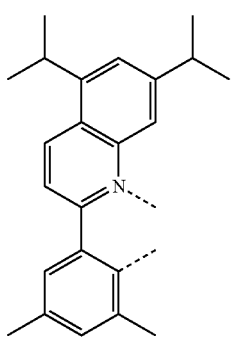 $L_{Q34}$
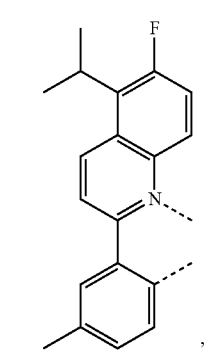 $L_{Q35}$
-continued
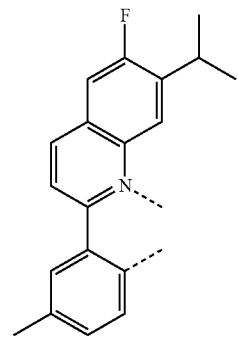 $L_{Q36}$
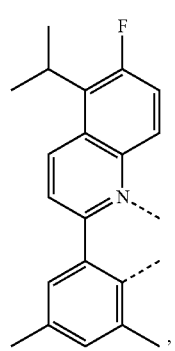 $L_{Q37}$
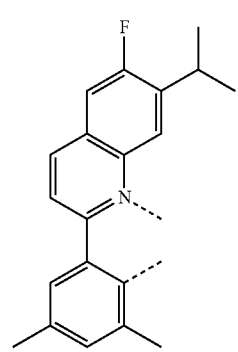 $L_{Q38}$
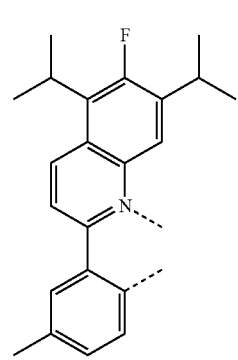 $L_{Q39}$ 191
-continued
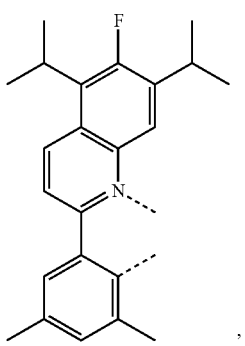
L_{Q40}
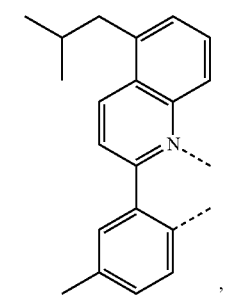
L_{Q41}
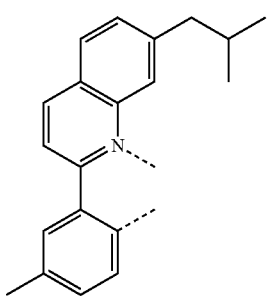
L_{Q42}
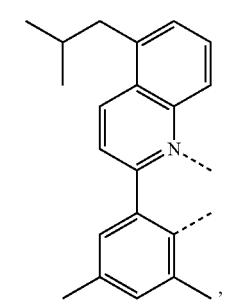
L_{Q43}
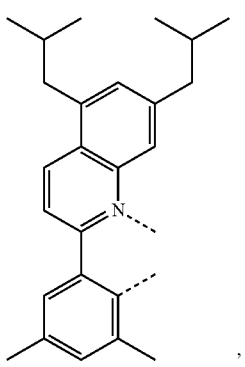
L_{Q45}
192
-continued
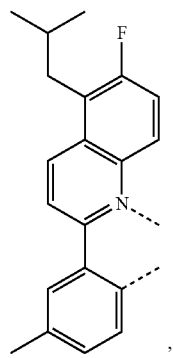
L_{Q46}
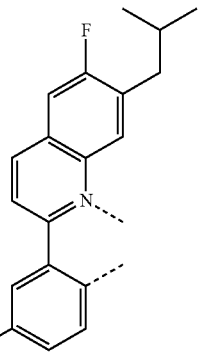
L_{Q47}
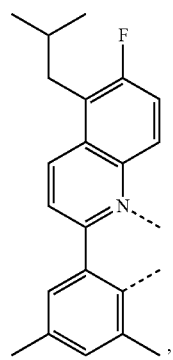
L_{Q48}
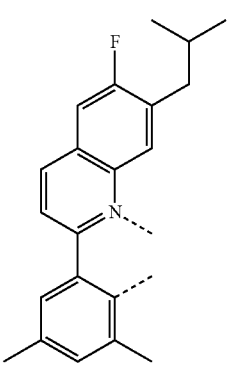
L_{Q49}

-continued $L_{Q50}$ $L_{Q51}$ $L_{Q52}$ $L_{Q53}$

-continued $L_{Q54}$ $L_{Q55}$ $L_{Q56}$ $L_{Q57}$

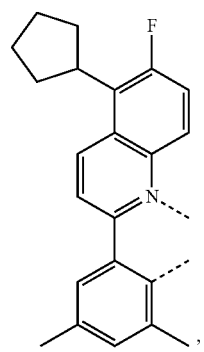 L_Q58
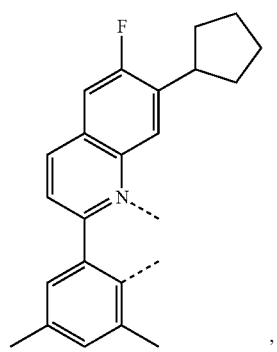 L_Q59
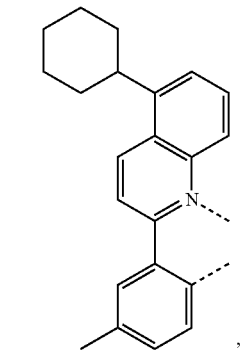 L_Q60
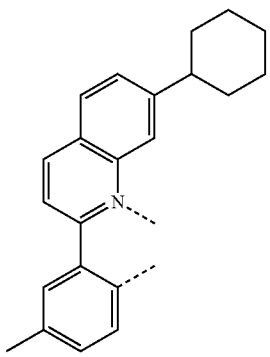 L_Q61
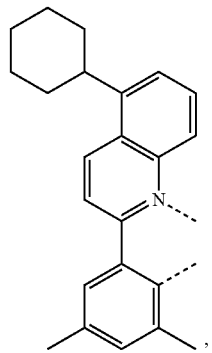 L_Q62
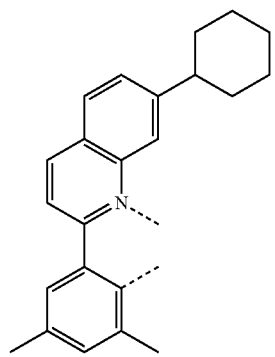 L_Q63
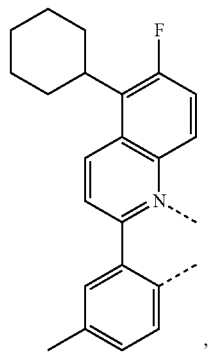 L_Q64
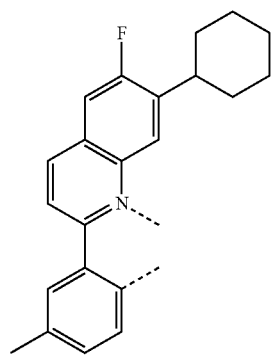 L_Q65

-continued
L_Q66 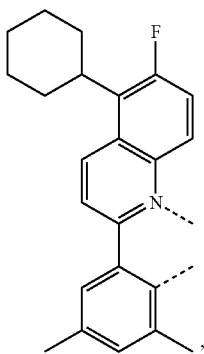,
L_Q67 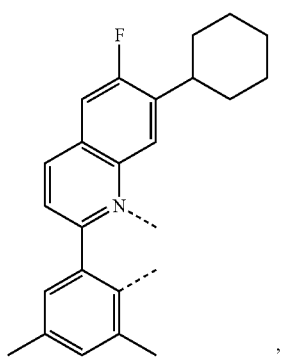,
L_Q68 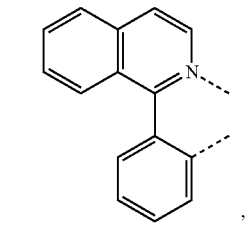,
L_Q69 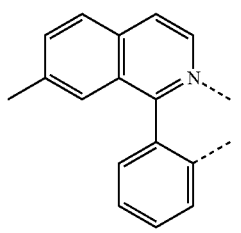,
L_Q71 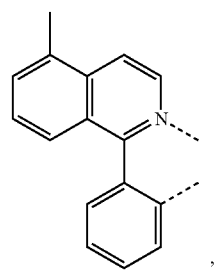,
-continued
L_Q72 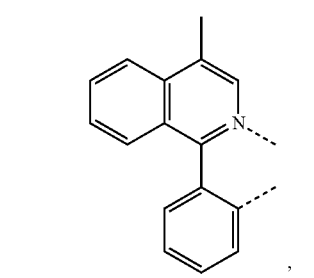,
L_Q72 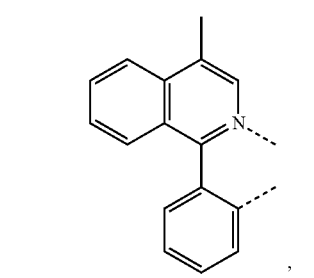,
L_Q73 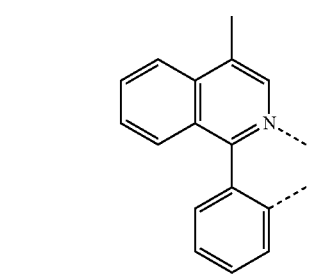,
L_Q75 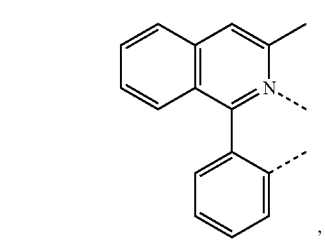,
L_Q76 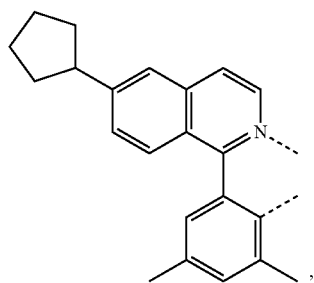,

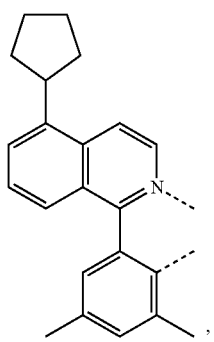
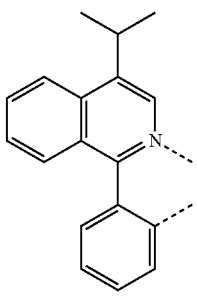
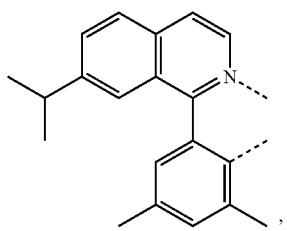
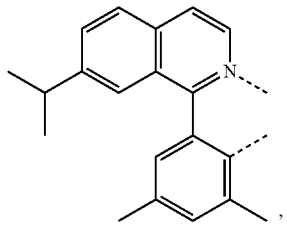
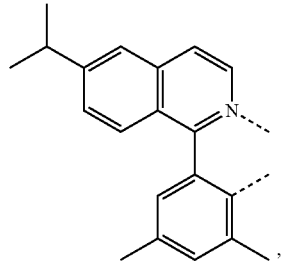
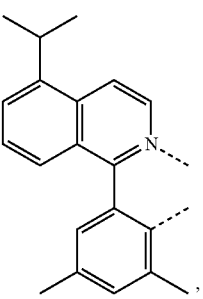
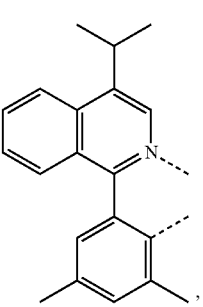

L_{Q87}
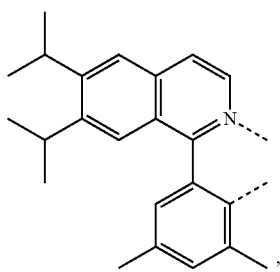
L_{Q88}
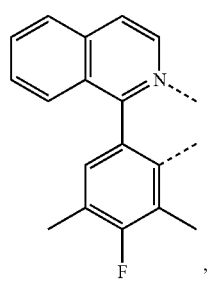
L_{Q89}
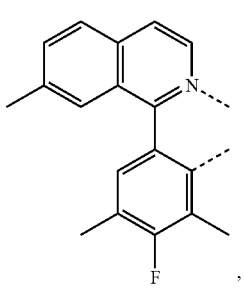
L_{Q90}
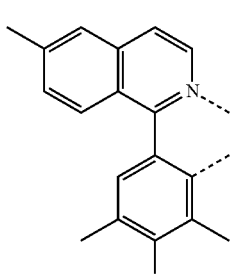
L_{Q91}
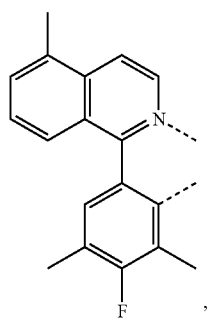
L_{Q92}
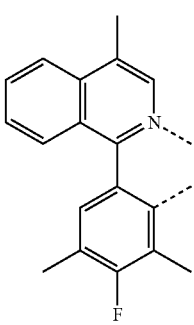
L_{Q93}
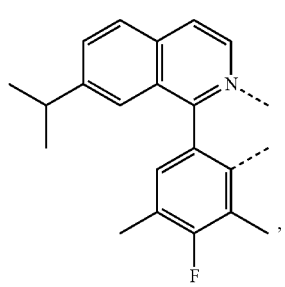
L_{Q94}
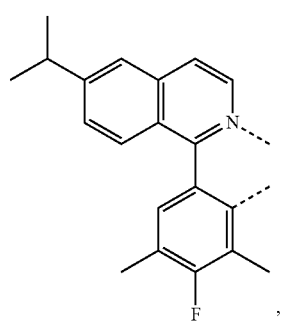
L_{Q95}
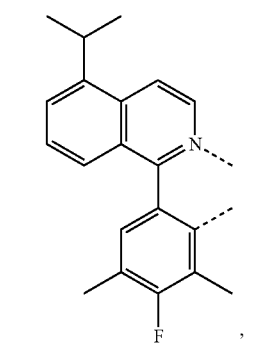
L_{Q96}
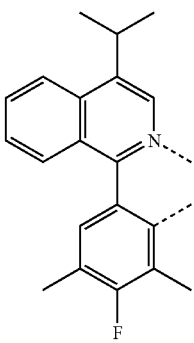

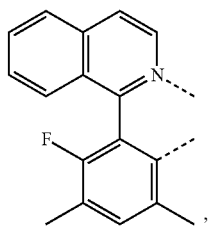 L_Q97,
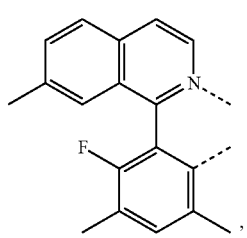 L_Q98,
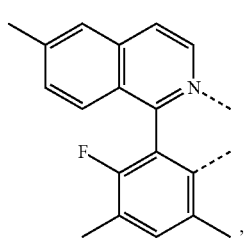 L_Q99,
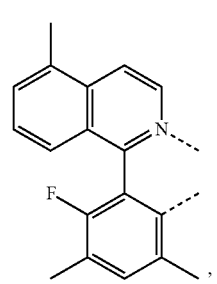 L_Q100,
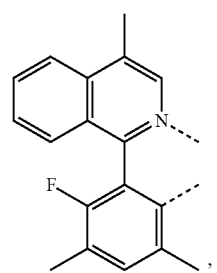 L_Q101,
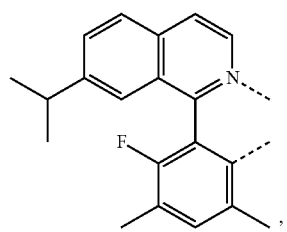 L_Q102,
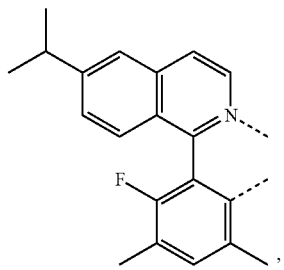 L_Q103,
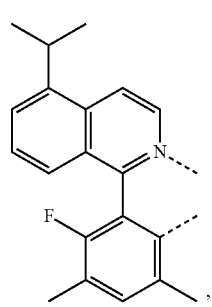 L_Q104,
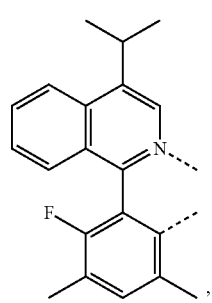 L_Q105,
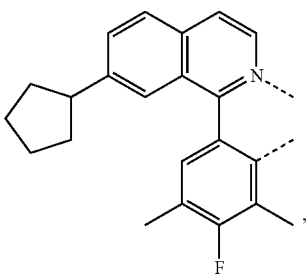 L_Q106,
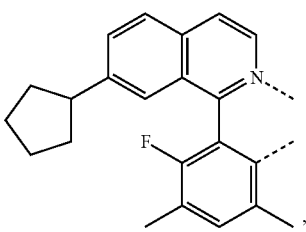 L_Q107, L_{Q109}
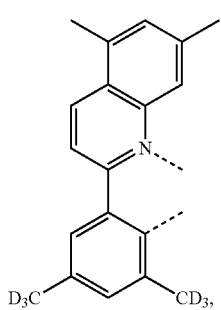
L_{Q110}
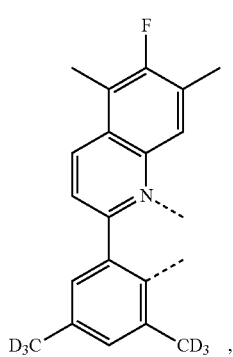
L_{Q111}
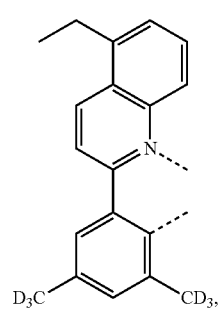
L_{Q111}
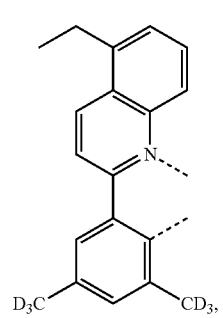
L_{Q112}
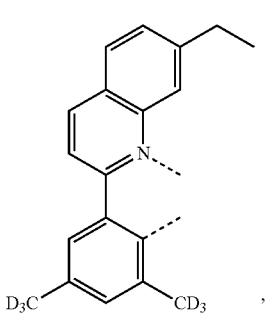
L_{Q113}
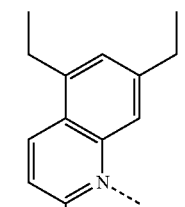
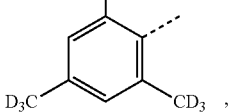
L_{Q114}
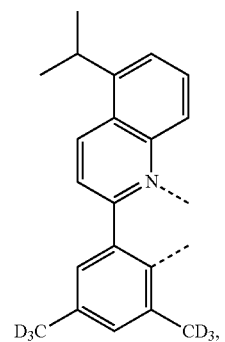
L_{Q115}
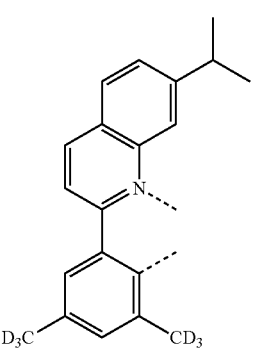
L_{Q116}
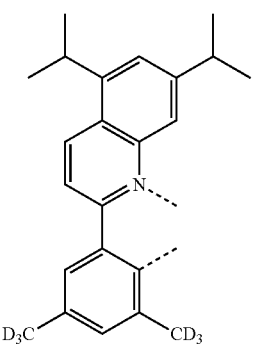

$L_{Q117}$ $L_{Q118}$ $L_{Q119}$ $L_{Q120}$ $L_{Q121}$ $L_{Q122}$ $L_{Q123}$ $L_{Q124}$

L<sub>Q125</sub>
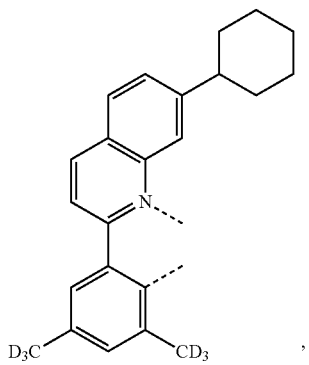

L<sub>Q127</sub>
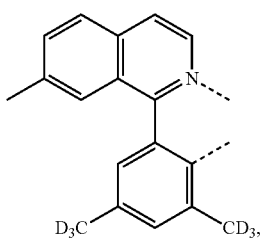

L<sub>Q128</sub>
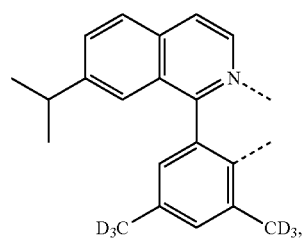

L<sub>Q129</sub>
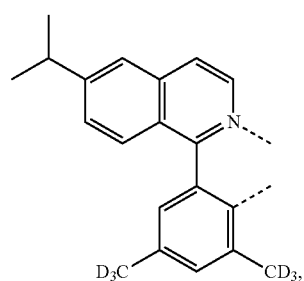

L<sub>Q130</sub>
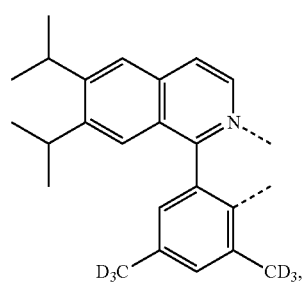

L<sub>Q131</sub>
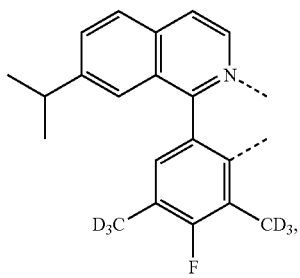

L<sub>Q132</sub>
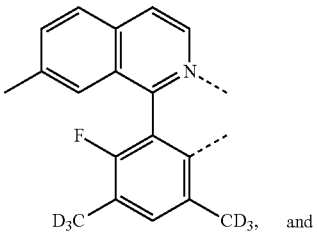

and

L<sub>Q133</sub>
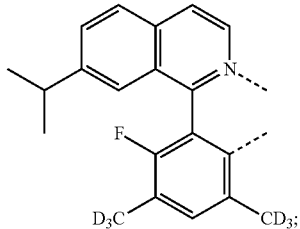

wherein x is 1 or 2;
wherein y is 1, or 2;
wherein z is 0 or 1;
wherein x+y+z is 3;
wherein each $R_a$ and $R_b$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein two adjacent substituents of $R_a$ and $R_b$ are optionally joined to form a fused ring or form a multidentate ligand.

2. The compound of claim 1, wherein the compound has the formula of $M(L^1)(L^2)_2$.

3. The compound of claim 1, wherein $L^1$ is

L<sub>A3</sub>
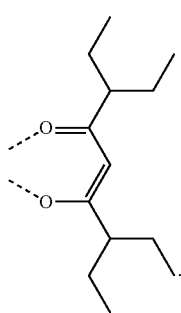

4. The compound of claim 1, wherein $L^2$ is selected from group consisting of:

211
$L_{Q2}$ 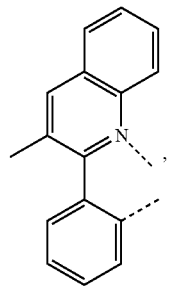
$L_{Q3}$ 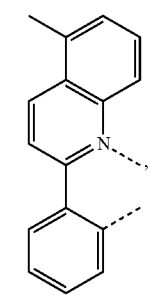
$L_{Q4}$ 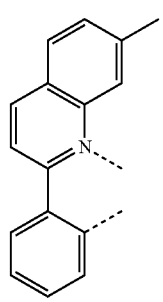
$L_{Q5}$ 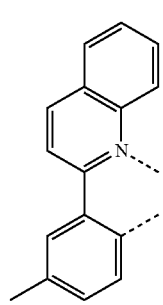
$L_{Q6}$ 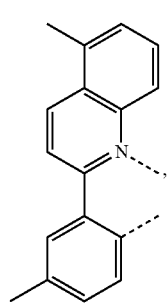
212
-continued
$L_{Q7}$ 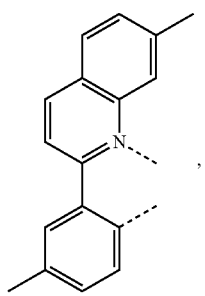
$L_{Q10}$ 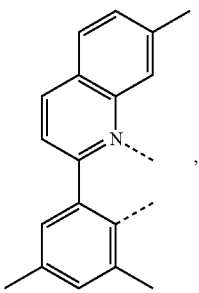
$L_{Q11}$ 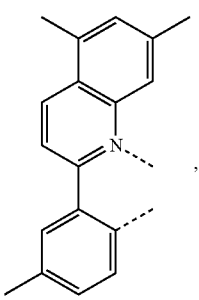
$L_{Q12}$ 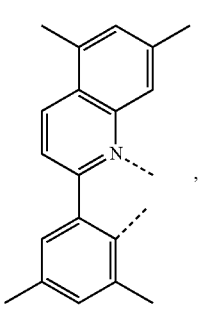
$L_{Q13}$ 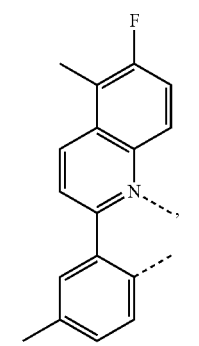

-continued
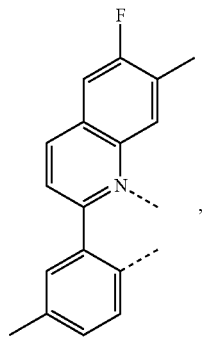 $L_{Q14}$
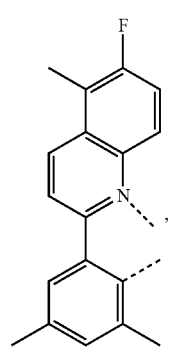 $L_{Q15}$
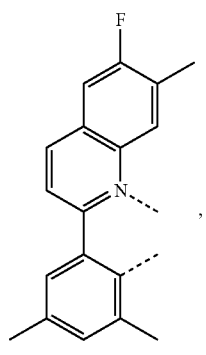 $L_{Q16}$
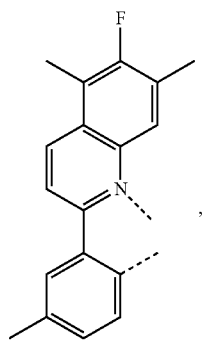 $L_{Q17}$
-continued
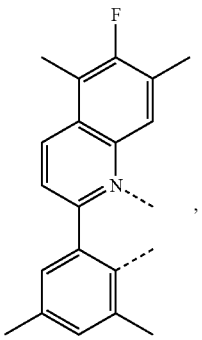 $L_{Q18}$
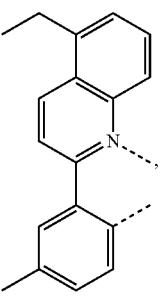 $L_{Q19}$
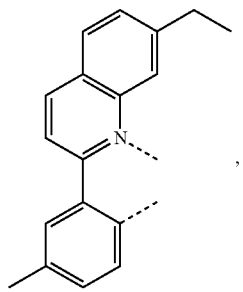 $L_{Q20}$
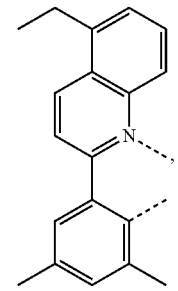 $L_{Q21}$
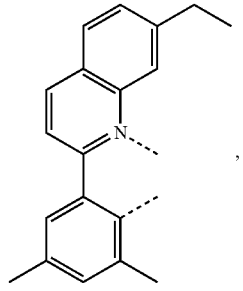 $L_{Q22}$ -continued
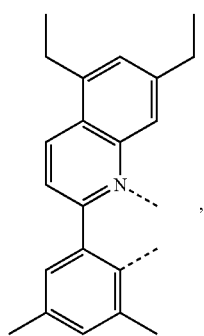
L_{Q23}
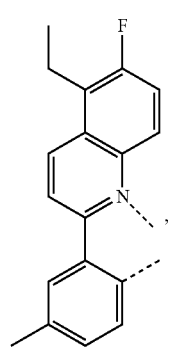
L_{Q24}
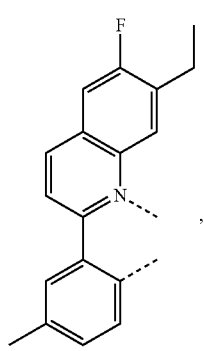
L_{Q25}
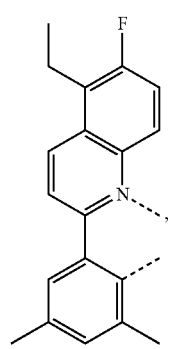
L_{Q26}
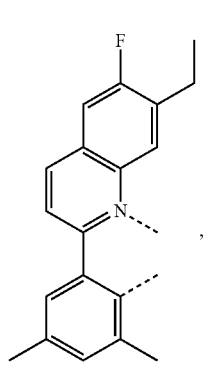
L_{Q27}
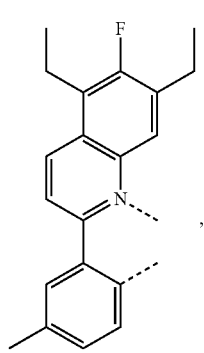
L_{Q28}
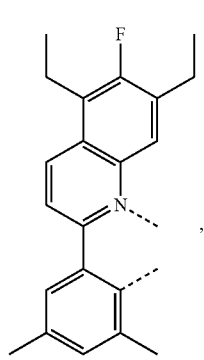
L_{Q29}
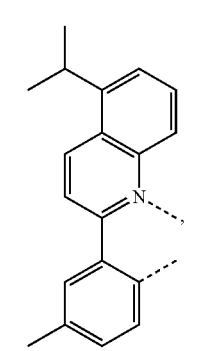
L_{Q30}

217
-continued
218
-continued
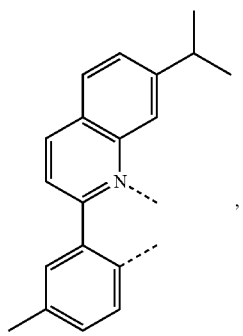
L<sub>Q31</sub>
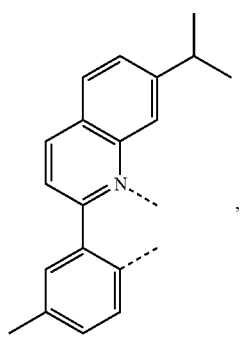
L<sub>Q36</sub>
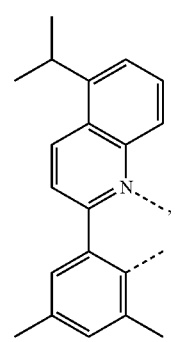
L<sub>Q32</sub>
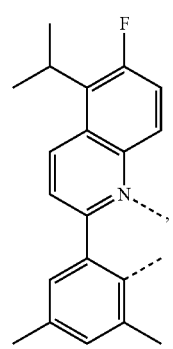
L<sub>Q37</sub>
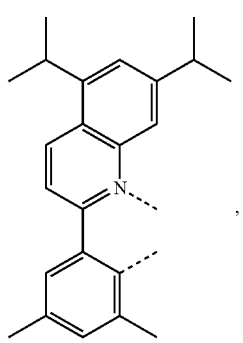
L<sub>Q34</sub>
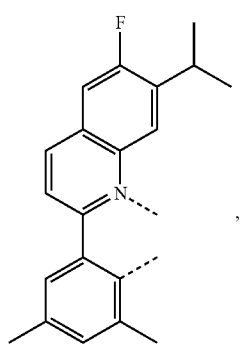
L<sub>Q38</sub>
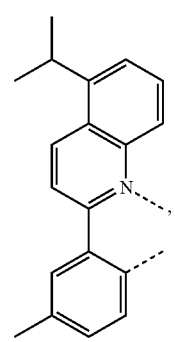
L<sub>Q35</sub>
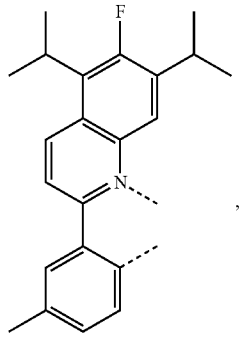
L<sub>Q39</sub>

-continued
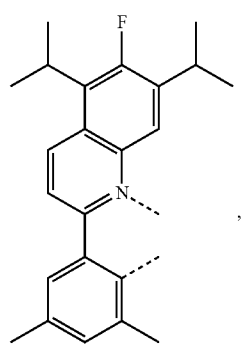 L<sub>Q40</sub>,
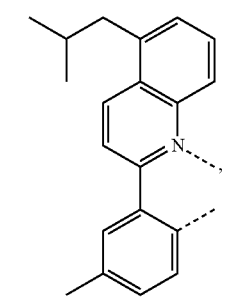 L<sub>Q41</sub>,
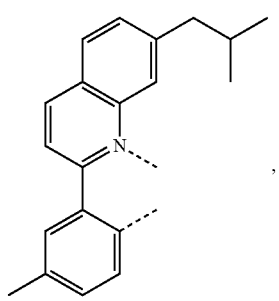 L<sub>Q42</sub>,
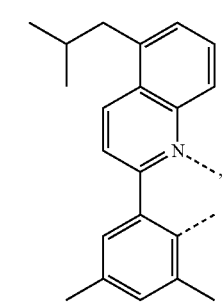 L<sub>Q43</sub>,
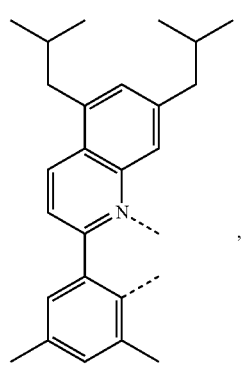 L<sub>Q45</sub>,
-continued
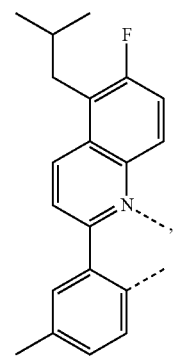 L<sub>Q46</sub>,
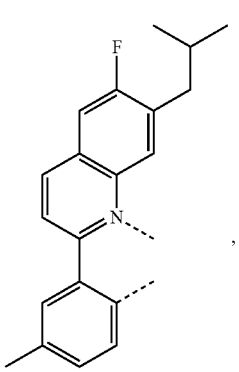 L<sub>Q47</sub>,
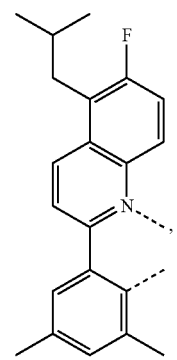 L<sub>Q48</sub>,
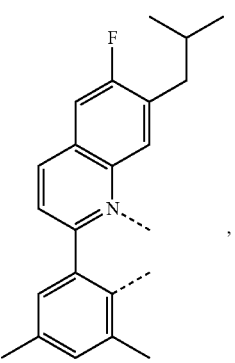 LQ49,

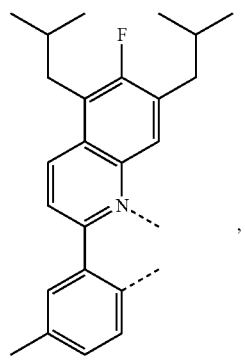 L_{Q50}
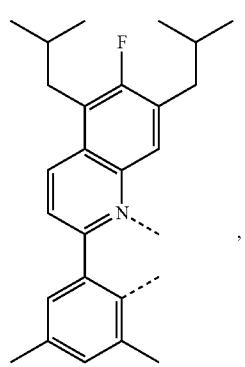 L_{Q51}
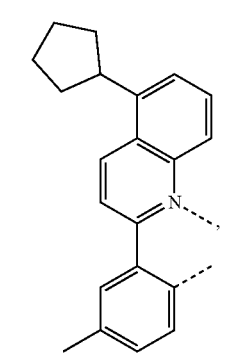 L_{Q52}
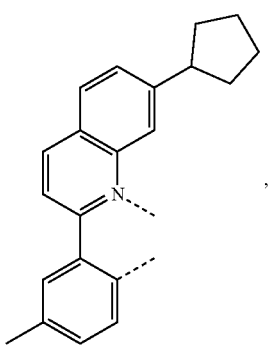 L_{Q53}
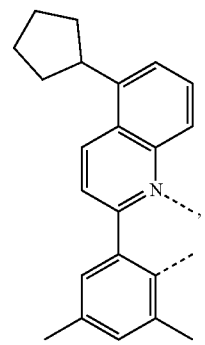 L_{Q54}
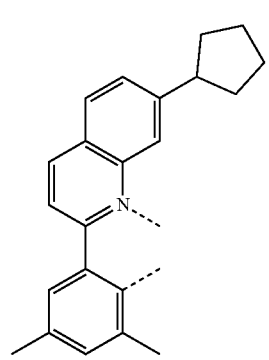 L_{Q55}
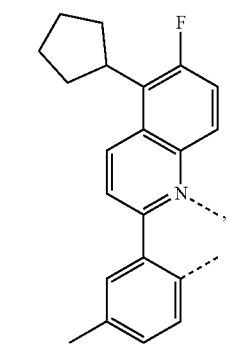 L_{Q56}
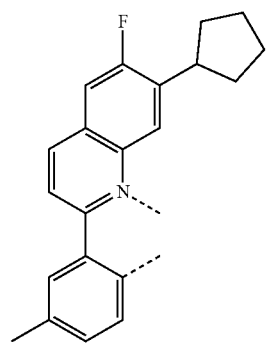 L_{Q57}

223
-continued
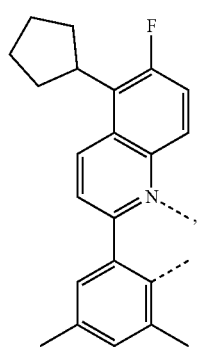 L<sub>Q58</sub>
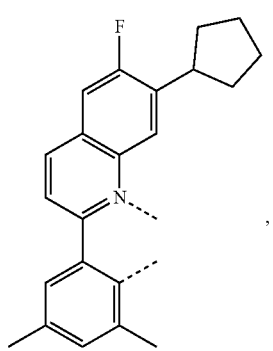 L<sub>Q59</sub>
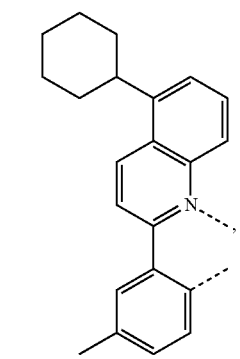 L<sub>Q60</sub>
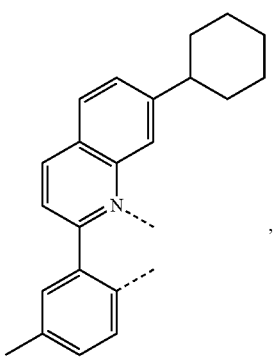 L<sub>Q61</sub>
224
-continued
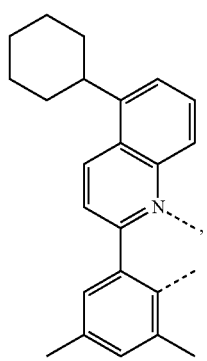 L<sub>Q62</sub>
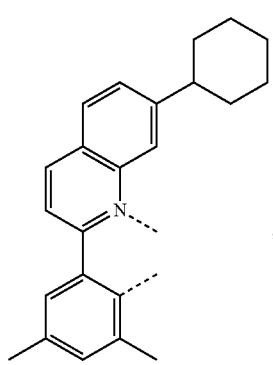 L<sub>Q63</sub>
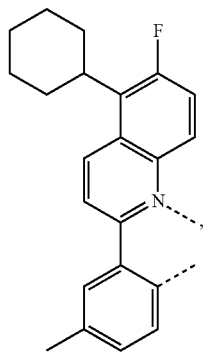 L<sub>Q64</sub>
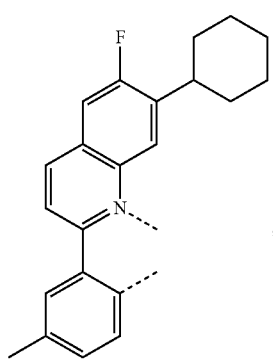 L<sub>Q65</sub>

225
-continued
L<sub>Q66</sub>
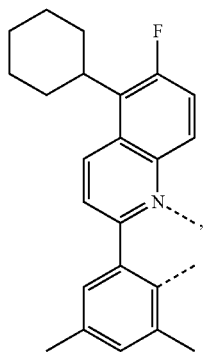
L<sub>Q67</sub>
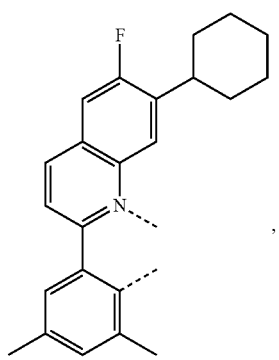
L<sub>Q68</sub>
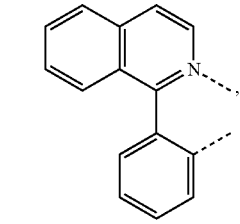
L<sub>Q69</sub>
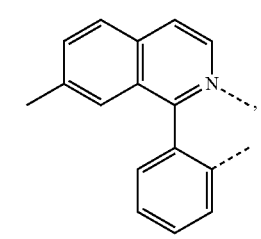
L<sub>Q71</sub>
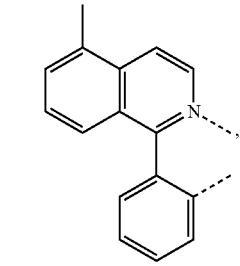
226
-continued
L<sub>Q72</sub>
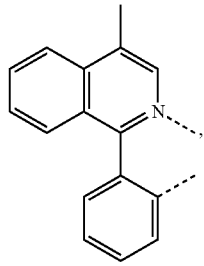
L<sub>Q73</sub>
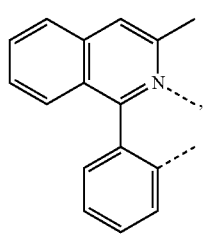
L<sub>Q75</sub>
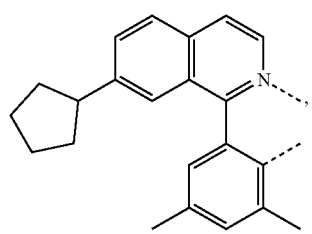
L<sub>Q76</sub>
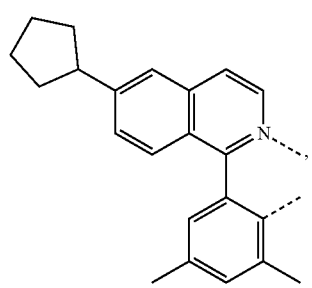
L<sub>Q77</sub>
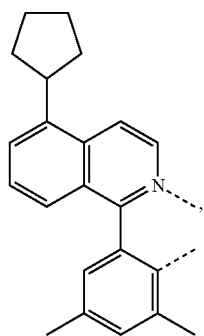

$L_{Q78}$ 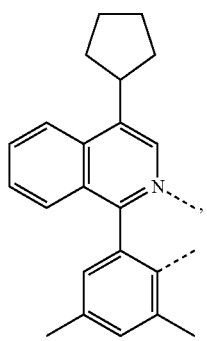
$L_{Q80}$ 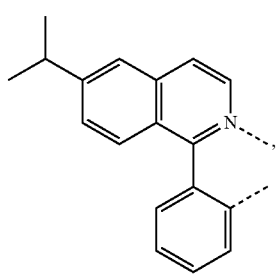
$L_{Q81}$ 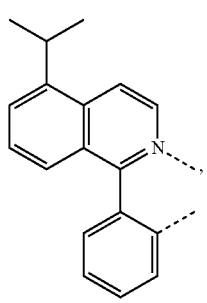
$L_{Q82}$ 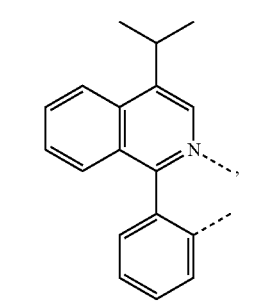
$L_{Q83}$ 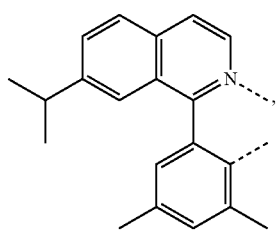
$L_{Q84}$ 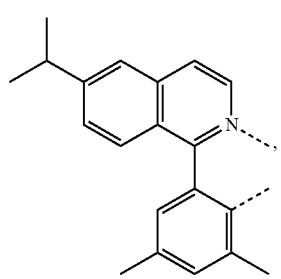
$L_{Q85}$ 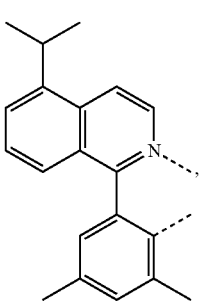
$L_{Q86}$ 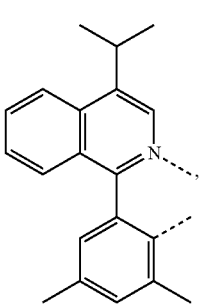
$L_{Q87}$ 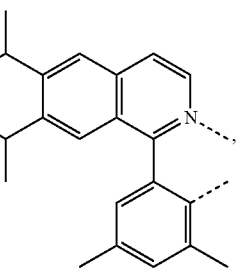
$L_{Q88}$ 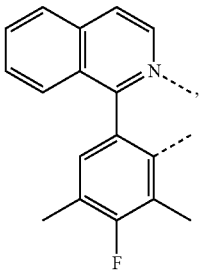

-continued
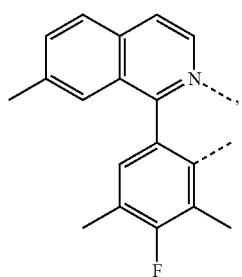
L<sub>Q89</sub>
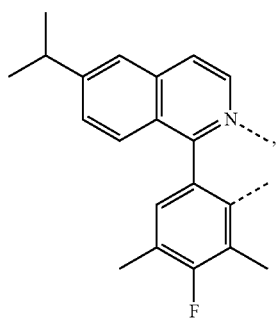
L<sub>Q94</sub>
-continued
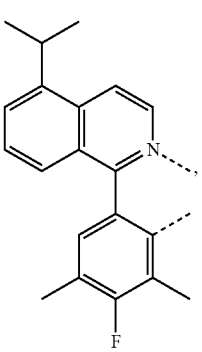
L<sub>Q90</sub>
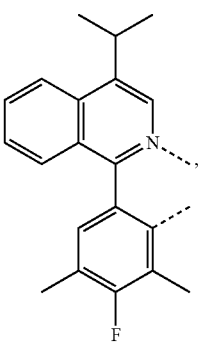
L<sub>Q95</sub>
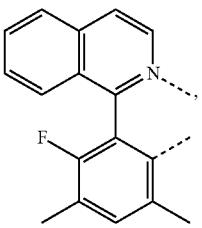
L<sub>Q91</sub>
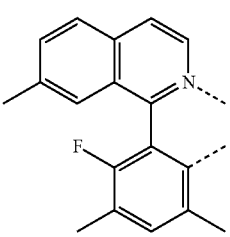
L<sub>Q96</sub>
L<sub>Q92</sub>
L<sub>Q97</sub>
L<sub>Q93</sub>
L<sub>Q98</sub>

231
-continued
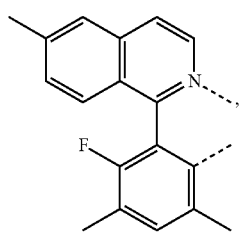  L_Q99
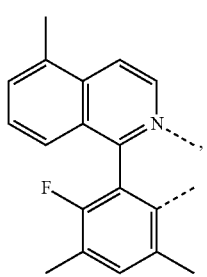  L_Q100
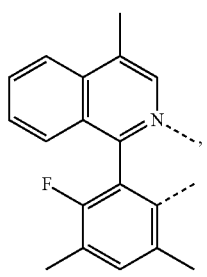  L_Q101
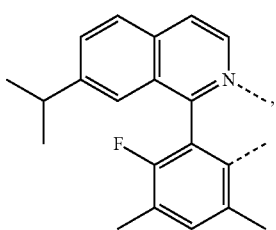  L_Q102
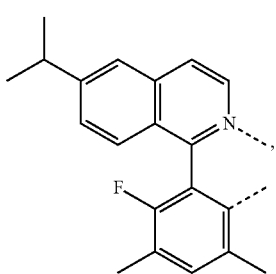  L_Q103
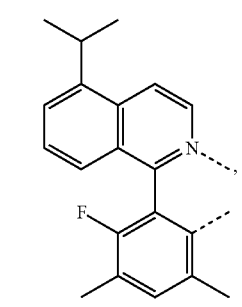  L_Q104
232
-continued
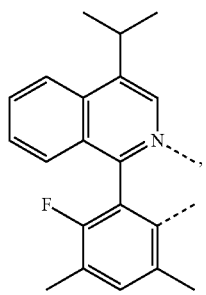  L_Q105
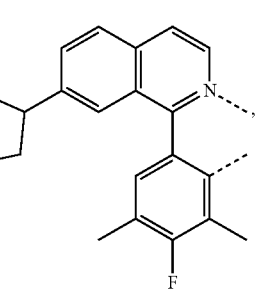  L_Q106
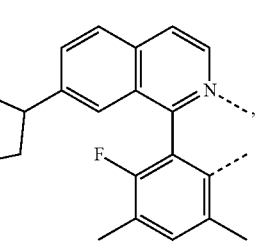  L_Q107
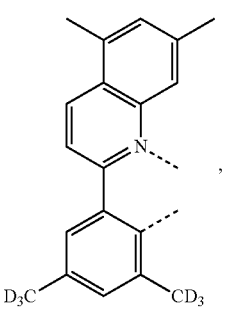  L_Q109
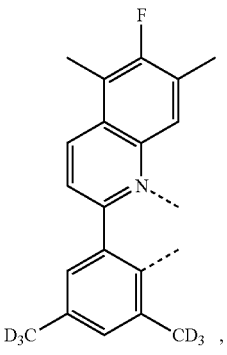  L_Q110

L_Q111 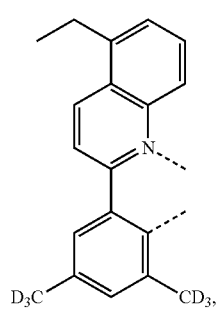
L_Q112 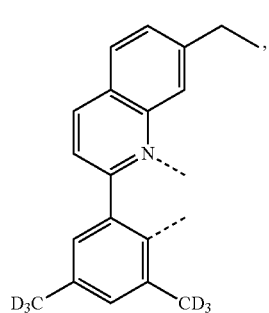
L_Q113 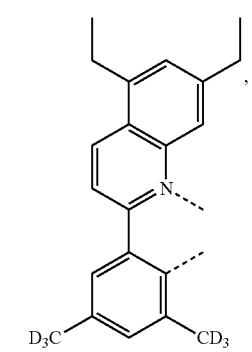
L_Q114 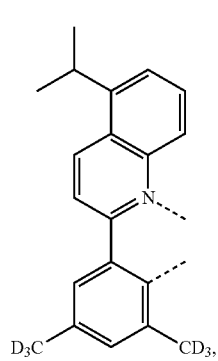
L_Q115 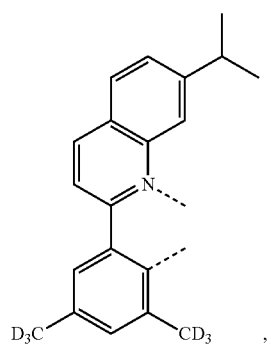
L_Q116 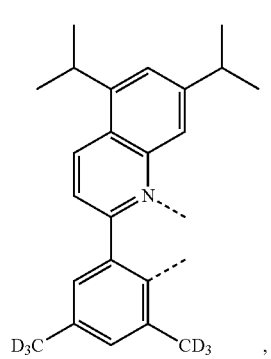
L_Q117 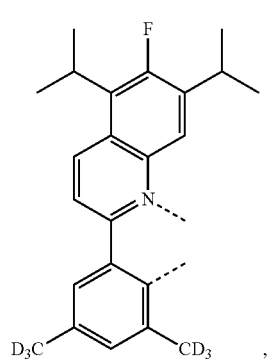
L_Q118 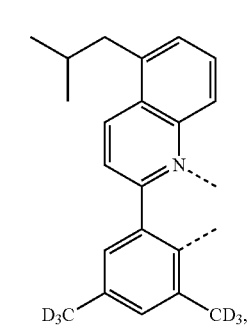

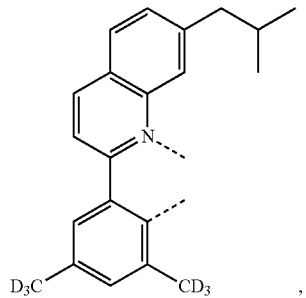 L_Q119
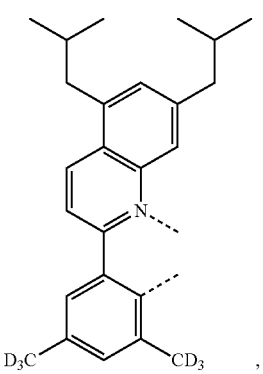 L_Q120
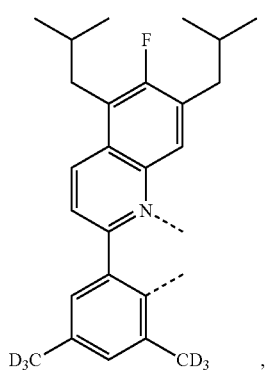 L_Q121
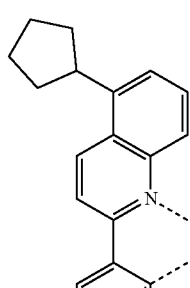 L_Q122
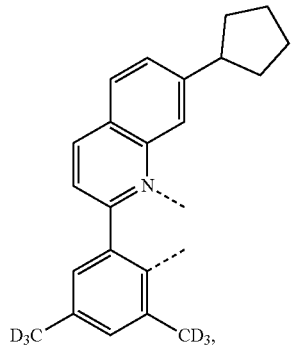 L_Q123
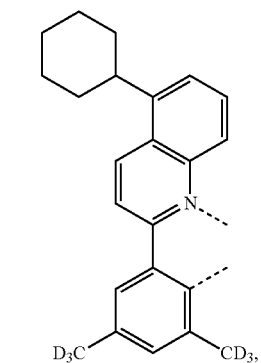 L_Q124
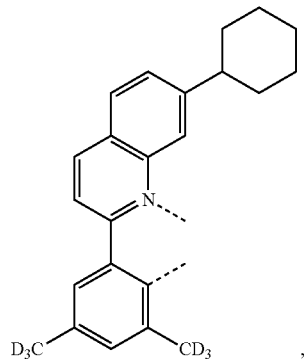 L_Q125
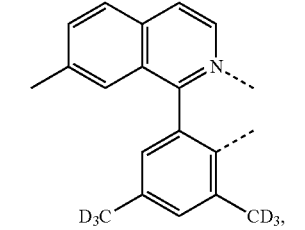 L_Q127
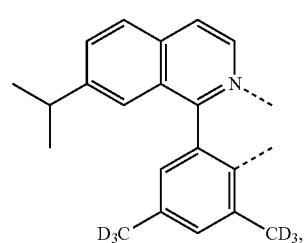 L_Q128

L_{Q129}

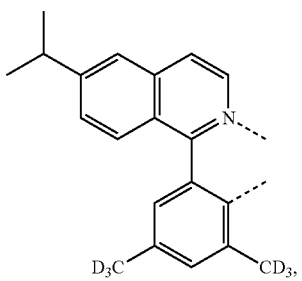

L_{Q130}

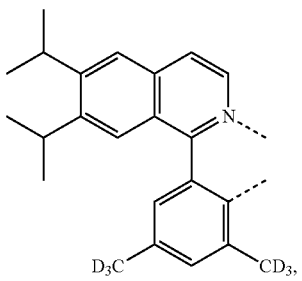

L_{Q131}

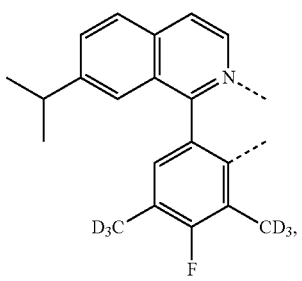

L_{Q132}

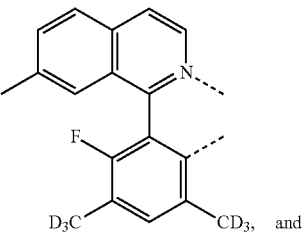, and

L_{Q133}

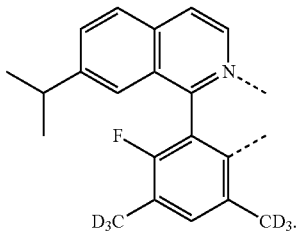.

5. The compound of claim 4, wherein the compound having the formula of $M(L^1)(L^2)_2$ is selected from the group consisting of Compounds 267-399, 533-666, 799-931, 1065-1330, and 1597-1729 defined in the table below:

| Compound number | $L^1$ | $L^2$ |
|---|---|---|
| 267. | $L_{A3}$ | $L_{Q1}$ |
| 268. | $L_{A3}$ | $L_{Q2}$ |
| 269. | $L_{A3}$ | $L_{Q3}$ |
| 270. | $L_{A3}$ | $L_{Q4}$ |
| 271. | $L_{A3}$ | $L_{Q5}$ |
| 272. | $L_{A3}$ | $L_{Q6}$ |
| 273. | $L_{A3}$ | $L_{Q7}$ |
| 274. | $L_{A3}$ | $L_{Q8}$ |
| 275. | $L_{A3}$ | $L_{Q9}$ |
| 276. | $L_{A3}$ | $L_{Q10}$ |
| 277. | $L_{A3}$ | $L_{Q11}$ |
| 278. | $L_{A3}$ | $L_{Q12}$ |
| 279. | $L_{A3}$ | $L_{Q13}$ |
| 280. | $L_{A3}$ | $L_{Q14}$ |
| 281. | $L_{A3}$ | $L_{Q15}$ |
| 282. | $L_{A3}$ | $L_{Q16}$ |
| 283. | $L_{A3}$ | $L_{Q17}$ |
| 284. | $L_{A3}$ | $L_{Q18}$ |
| 285. | $L_{A3}$ | $L_{Q19}$ |
| 286. | $L_{A3}$ | $L_{Q20}$ |
| 287. | $L_{A3}$ | $L_{Q21}$ |
| 288. | $L_{A3}$ | $L_{Q22}$ |
| 289. | $L_{A3}$ | $L_{Q23}$ |
| 290. | $L_{A3}$ | $L_{Q24}$ |
| 291. | $L_{A3}$ | $L_{Q25}$ |
| 292. | $L_{A3}$ | $L_{Q26}$ |
| 293. | $L_{A3}$ | $L_{Q27}$ |
| 294. | $L_{A3}$ | $L_{Q28}$ |
| 295. | $L_{A3}$ | $L_{Q29}$ |
| 296. | $L_{A3}$ | $L_{Q30}$ |
| 297. | $L_{A3}$ | $L_{Q31}$ |
| 298. | $L_{A3}$ | $L_{Q32}$ |
| 299. | $L_{A3}$ | $L_{Q33}$ |
| 300. | $L_{A3}$ | $L_{Q34}$ |
| 301. | $L_{A3}$ | $L_{Q35}$ |
| 302. | $L_{A3}$ | $L_{Q36}$ |
| 303. | $L_{A3}$ | $L_{Q37}$ |
| 304. | $L_{A3}$ | $L_{Q38}$ |
| 305. | $L_{A3}$ | $L_{Q39}$ |
| 306. | $L_{A3}$ | $L_{Q40}$ |
| 307. | $L_{A3}$ | $L_{Q41}$ |
| 308. | $L_{A3}$ | $L_{Q42}$ |
| 309. | $L_{A3}$ | $L_{Q43}$ |
| 310. | $L_{A3}$ | $L_{Q44}$ |
| 311. | $L_{A3}$ | $L_{Q45}$ |
| 312. | $L_{A3}$ | $L_{Q46}$ |
| 313. | $L_{A3}$ | $L_{Q47}$ |
| 314. | $L_{A3}$ | $L_{Q48}$ |
| 315. | $L_{A3}$ | $L_{Q49}$ |
| 316. | $L_{A3}$ | $L_{Q50}$ |
| 317. | $L_{A3}$ | $L_{Q51}$ |
| 318. | $L_{A3}$ | $L_{Q52}$ |
| 319. | $L_{A3}$ | $L_{Q53}$ |
| 320. | $L_{A3}$ | $L_{Q54}$ |
| 321. | $L_{A3}$ | $L_{Q55}$ |
| 322. | $L_{A3}$ | $L_{Q56}$ |
| 323. | $L_{A3}$ | $L_{Q57}$ |
| 324. | $L_{A3}$ | $L_{Q58}$ |
| 325. | $L_{A3}$ | $L_{Q59}$ |
| 326. | $L_{A3}$ | $L_{Q60}$ |
| 327. | $L_{A3}$ | $L_{Q61}$ |
| 328. | $L_{A3}$ | $L_{Q62}$ |
| 329. | $L_{A3}$ | $L_{Q63}$ |
| 330. | $L_{A3}$ | $L_{Q64}$ |
| 331. | $L_{A3}$ | $L_{Q65}$ |
| 332. | $L_{A3}$ | $L_{Q66}$ |
| 333. | $L_{A3}$ | $L_{Q67}$ |
| 334. | $L_{A3}$ | $L_{Q68}$ |
| 335. | $L_{A3}$ | $L_{Q69}$ |
| 336. | $L_{A3}$ | $L_{Q70}$ |
| 337. | $L_{A3}$ | $L_{Q71}$ |
| 338. | $L_{A3}$ | $L_{Q72}$ |
| 339. | $L_{A3}$ | $L_{Q73}$ |
| 340. | $L_{A3}$ | $L_{Q74}$ |
| 341. | $L_{A3}$ | $L_{Q75}$ |
| 342. | $L_{A3}$ | $L_{Q76}$ |
| 343. | $L_{A3}$ | $L_{Q77}$ |
| 344. | $L_{A3}$ | $L_{Q78}$ |

| Compound number | $L^1$ | $L^2$ |
| --- | --- | --- |
| 345. | $L_{43}$ | $L_{Q79}$ |
| 346. | $L_{43}$ | $L_{Q80}$ |
| 347. | $L_{43}$ | $L_{Q81}$ |
| 348. | $L_{43}$ | $L_{Q82}$ |
| 349. | $L_{43}$ | $L_{Q83}$ |
| 350. | $L_{43}$ | $L_{Q84}$ |
| 351. | $L_{43}$ | $L_{Q85}$ |
| 352. | $L_{43}$ | $L_{Q86}$ |
| 353. | $L_{43}$ | $L_{Q87}$ |
| 354. | $L_{43}$ | $L_{Q88}$ |
| 355. | $L_{43}$ | $L_{Q89}$ |
| 356. | $L_{43}$ | $L_{Q90}$ |
| 357. | $L_{43}$ | $L_{Q91}$ |
| 358. | $L_{43}$ | $L_{Q92}$ |
| 359. | $L_{43}$ | $L_{Q93}$ |
| 360. | $L_{43}$ | $L_{Q94}$ |
| 361. | $L_{43}$ | $L_{Q95}$ |
| 362. | $L_{43}$ | $L_{Q96}$ |
| 363. | $L_{43}$ | $L_{Q97}$ |
| 364. | $L_{43}$ | $L_{Q98}$ |
| 365. | $L_{43}$ | $L_{Q99}$ |
| 366. | $L_{43}$ | $L_{Q100}$ |
| 367. | $L_{43}$ | $L_{Q101}$ |
| 368. | $L_{43}$ | $L_{Q102}$ |
| 369. | $L_{43}$ | $L_{Q103}$ |
| 370. | $L_{43}$ | $L_{Q104}$ |
| 371. | $L_{43}$ | $L_{Q105}$ |
| 372. | $L_{43}$ | $L_{Q106}$ |
| 373. | $L_{43}$ | $L_{Q107}$ |
| 374. | $L_{43}$ | $L_{Q108}$ |
| 375. | $L_{43}$ | $L_{Q109}$ |
| 376. | $L_{43}$ | $L_{Q110}$ |
| 377. | $L_{43}$ | $L_{Q111}$ |
| 378. | $L_{43}$ | $L_{Q112}$ |
| 379. | $L_{43}$ | $L_{Q113}$ |
| 380. | $L_{43}$ | $L_{Q114}$ |
| 381. | $L_{43}$ | $L_{Q115}$ |
| 382. | $L_{43}$ | $L_{Q116}$ |
| 383. | $L_{43}$ | $L_{Q117}$ |
| 384. | $L_{43}$ | $L_{Q118}$ |
| 385. | $L_{43}$ | $L_{Q119}$ |
| 386. | $L_{43}$ | $L_{Q120}$ |
| 387. | $L_{43}$ | $L_{Q121}$ |
| 388. | $L_{43}$ | $L_{Q122}$ |
| 389. | $L_{43}$ | $L_{Q123}$ |
| 390. | $L_{43}$ | $L_{Q124}$ |
| 391. | $L_{43}$ | $L_{Q125}$ |
| 392. | $L_{43}$ | $L_{Q126}$ |
| 393. | $L_{43}$ | $L_{Q127}$ |
| 394. | $L_{43}$ | $L_{Q128}$ |
| 395. | $L_{43}$ | $L_{Q129}$ |
| 396. | $L_{43}$ | $L_{Q130}$ |
| 397. | $L_{43}$ | $L_{Q131}$ |
| 398. | $L_{43}$ | $L_{Q132}$ |
| 399. | $L_{43}$ | $L_{Q133}$ |
| 533. | $L_{45}$ | $L_{Q1}$ |
| 534. | $L_{45}$ | $L_{Q2}$ |
| 535. | $L_{45}$ | $L_{Q3}$ |
| 536. | $L_{45}$ | $L_{Q4}$ |
| 537. | $L_{45}$ | $L_{Q5}$ |
| 538. | $L_{45}$ | $L_{Q6}$ |
| 539. | $L_{45}$ | $L_{Q7}$ |
| 540. | $L_{45}$ | $L_{Q8}$ |
| 541. | $L_{45}$ | $L_{Q9}$ |
| 542. | $L_{45}$ | $L_{Q10}$ |
| 543. | $L_{45}$ | $L_{Q11}$ |
| 544. | $L_{45}$ | $L_{Q12}$ |
| 545. | $L_{45}$ | $L_{Q13}$ |
| 546. | $L_{45}$ | $L_{Q14}$ |
| 547. | $L_{45}$ | $L_{Q15}$ |
| 548. | $L_{45}$ | $L_{Q16}$ |
| 549. | $L_{45}$ | $L_{Q17}$ |
| 550. | $L_{45}$ | $L_{Q18}$ |
| 551. | $L_{45}$ | $L_{Q19}$ |
| 552. | $L_{45}$ | $L_{Q20}$ |
| 553. | $L_{45}$ | $L_{Q21}$ |
| 554. | $L_{45}$ | $L_{Q22}$ |
| 555. | $L_{45}$ | $L_{Q23}$ |
| 556. | $L_{45}$ | $L_{Q24}$ |
| 557. | $L_{45}$ | $L_{Q25}$ |
| 558. | $L_{45}$ | $L_{Q26}$ |
| 559. | $L_{45}$ | $L_{Q27}$ |
| 560. | $L_{45}$ | $L_{Q28}$ |
| 561. | $L_{45}$ | $L_{Q29}$ |
| 562. | $L_{45}$ | $L_{Q30}$ |
| 563. | $L_{45}$ | $L_{Q31}$ |
| 564. | $L_{45}$ | $L_{Q32}$ |
| 565. | $L_{45}$ | $L_{Q33}$ |
| 566. | $L_{45}$ | $L_{Q34}$ |
| 567. | $L_{45}$ | $L_{Q35}$ |
| 568. | $L_{45}$ | $L_{Q36}$ |
| 569. | $L_{45}$ | $L_{Q37}$ |
| 570. | $L_{45}$ | $L_{Q38}$ |
| 571. | $L_{45}$ | $L_{Q39}$ |
| 572. | $L_{45}$ | $L_{Q40}$ |
| 573. | $L_{45}$ | $L_{Q41}$ |
| 574. | $L_{45}$ | $L_{Q42}$ |
| 575. | $L_{45}$ | $L_{Q43}$ |
| 576. | $L_{45}$ | $L_{Q44}$ |
| 577. | $L_{45}$ | $L_{Q45}$ |
| 578. | $L_{45}$ | $L_{Q46}$ |
| 579. | $L_{45}$ | $L_{Q47}$ |
| 580. | $L_{45}$ | $L_{Q48}$ |
| 581. | $L_{45}$ | $L_{Q49}$ |
| 582. | $L_{45}$ | $L_{Q50}$ |
| 583. | $L_{45}$ | $L_{Q51}$ |
| 584. | $L_{45}$ | $L_{Q52}$ |
| 585. | $L_{45}$ | $L_{Q53}$ |
| 586. | $L_{45}$ | $L_{Q54}$ |
| 587. | $L_{45}$ | $L_{Q55}$ |
| 588. | $L_{45}$ | $L_{Q56}$ |
| 589. | $L_{45}$ | $L_{Q57}$ |
| 590. | $L_{45}$ | $L_{Q58}$ |
| 591. | $L_{45}$ | $L_{Q59}$ |
| 592. | $L_{45}$ | $L_{Q60}$ |
| 593. | $L_{45}$ | $L_{Q61}$ |
| 594. | $L_{45}$ | $L_{Q62}$ |
| 595. | $L_{45}$ | $L_{Q63}$ |
| 596. | $L_{45}$ | $L_{Q64}$ |
| 597. | $L_{45}$ | $L_{Q65}$ |
| 598. | $L_{45}$ | $L_{Q66}$ |
| 599. | $L_{45}$ | $L_{Q67}$ |
| 600. | $L_{45}$ | $L_{Q68}$ |
| 601. | $L_{45}$ | $L_{Q69}$ |
| 602. | $L_{45}$ | $L_{Q70}$ |
| 603. | $L_{45}$ | $L_{Q71}$ |
| 604. | $L_{45}$ | $L_{Q72}$ |
| 605. | $L_{45}$ | $L_{Q73}$ |
| 606. | $L_{45}$ | $L_{Q74}$ |
| 607. | $L_{45}$ | $L_{Q75}$ |
| 608. | $L_{45}$ | $L_{Q76}$ |
| 609. | $L_{45}$ | $L_{Q77}$ |
| 610. | $L_{45}$ | $L_{Q78}$ |
| 611. | $L_{45}$ | $L_{Q79}$ |
| 612. | $L_{45}$ | $L_{Q80}$ |
| 613. | $L_{45}$ | $L_{Q81}$ |
| 614. | $L_{45}$ | $L_{Q82}$ |
| 615. | $L_{45}$ | $L_{Q83}$ |
| 616. | $L_{45}$ | $L_{Q84}$ |
| 617. | $L_{45}$ | $L_{Q85}$ |
| 618. | $L_{45}$ | $L_{Q86}$ |
| 619. | $L_{45}$ | $L_{Q87}$ |
| 620. | $L_{45}$ | $L_{Q88}$ |
| 621. | $L_{45}$ | $L_{Q89}$ |
| 622. | $L_{45}$ | $L_{Q90}$ |
| 623. | $L_{45}$ | $L_{Q91}$ |
| 624. | $L_{45}$ | $L_{Q92}$ |
| 625. | $L_{45}$ | $L_{Q93}$ |
| 626. | $L_{45}$ | $L_{Q94}$ |
| 627. | $L_{45}$ | $L_{Q95}$ |
| 628. | $L_{45}$ | $L_{Q96}$ |
| 629. | $L_{45}$ | $L_{Q97}$ |

241
-continued

| Compound number | $L^1$ | $L^2$ |
|---|---|---|
| 630. | $L_{A5}$ | $L_{Q98}$ |
| 631. | $L_{A5}$ | $L_{Q99}$ |
| 632. | $L_{A5}$ | $L_{Q100}$ |
| 633. | $L_{A5}$ | $L_{Q101}$ |
| 634. | $L_{A5}$ | $L_{Q102}$ |
| 635. | $L_{A5}$ | $L_{Q103}$ |
| 636. | $L_{A5}$ | $L_{Q104}$ |
| 637. | $L_{A5}$ | $L_{Q105}$ |
| 638. | $L_{A5}$ | $L_{Q106}$ |
| 639. | $L_{A5}$ | $L_{Q107}$ |
| 640. | $L_{A5}$ | $L_{Q108}$ |
| 641. | $L_{A5}$ | $L_{Q109}$ |
| 642. | $L_{A5}$ | $L_{Q110}$ |
| 643. | $L_{A5}$ | $L_{Q111}$ |
| 644. | $L_{A5}$ | $L_{Q112}$ |
| 645. | $L_{A5}$ | $L_{Q113}$ |
| 646. | $L_{A5}$ | $L_{Q114}$ |
| 647. | $L_{A5}$ | $L_{Q115}$ |
| 648. | $L_{A5}$ | $L_{Q116}$ |
| 649. | $L_{A5}$ | $L_{Q117}$ |
| 650. | $L_{A5}$ | $L_{Q118}$ |
| 651. | $L_{A5}$ | $L_{Q119}$ |
| 652. | $L_{A5}$ | $L_{Q120}$ |
| 653. | $L_{A5}$ | $L_{Q121}$ |
| 654. | $L_{A5}$ | $L_{Q122}$ |
| 655. | $L_{A5}$ | $L_{Q123}$ |
| 656. | $L_{A5}$ | $L_{Q124}$ |
| 657. | $L_{A5}$ | $L_{Q125}$ |
| 658. | $L_{A5}$ | $L_{Q126}$ |
| 659. | $L_{A5}$ | $L_{Q127}$ |
| 660. | $L_{A5}$ | $L_{Q128}$ |
| 661. | $L_{A5}$ | $L_{Q129}$ |
| 662. | $L_{A5}$ | $L_{Q130}$ |
| 663. | $L_{A5}$ | $L_{Q131}$ |
| 664. | $L_{A5}$ | $L_{Q132}$ |
| 665. | $L_{A5}$ | $L_{Q133}$ |
| 799. | $L_{A7}$ | $L_{Q1}$ |
| 800. | $L_{A7}$ | $L_{Q2}$ |
| 801. | $L_{A7}$ | $L_{Q3}$ |
| 802. | $L_{A7}$ | $L_{Q4}$ |
| 803. | $L_{A7}$ | $L_{Q5}$ |
| 804. | $L_{A7}$ | $L_{Q6}$ |
| 805. | $L_{A7}$ | $L_{Q7}$ |
| 806. | $L_{A7}$ | $L_{Q8}$ |
| 807. | $L_{A7}$ | $L_{Q9}$ |
| 808. | $L_{A7}$ | $L_{Q10}$ |
| 809. | $L_{A7}$ | $L_{Q11}$ |
| 810. | $L_{A7}$ | $L_{Q12}$ |
| 811. | $L_{A7}$ | $L_{Q13}$ |
| 812. | $L_{A7}$ | $L_{Q14}$ |
| 813. | $L_{A7}$ | $L_{Q15}$ |
| 814. | $L_{A7}$ | $L_{Q16}$ |
| 815. | $L_{A7}$ | $L_{Q17}$ |
| 816. | $L_{A7}$ | $L_{Q18}$ |
| 817. | $L_{A7}$ | $L_{Q19}$ |
| 818. | $L_{A7}$ | $L_{Q20}$ |
| 819. | $L_{A7}$ | $L_{Q21}$ |
| 820. | $L_{A7}$ | $L_{Q22}$ |
| 821. | $L_{A7}$ | $L_{Q23}$ |
| 822. | $L_{A7}$ | $L_{Q24}$ |
| 823. | $L_{A7}$ | $L_{Q25}$ |
| 824. | $L_{A7}$ | $L_{Q26}$ |
| 825. | $L_{A7}$ | $L_{Q27}$ |
| 826. | $L_{A7}$ | $L_{Q28}$ |
| 827. | $L_{A7}$ | $L_{Q29}$ |
| 828. | $L_{A7}$ | $L_{Q30}$ |
| 829. | $L_{A7}$ | $L_{Q31}$ |
| 830. | $L_{A7}$ | $L_{Q32}$ |
| 831. | $L_{A7}$ | $L_{Q33}$ |
| 832. | $L_{A7}$ | $L_{Q34}$ |
| 833. | $L_{A7}$ | $L_{Q35}$ |
| 834. | $L_{A7}$ | $L_{Q36}$ |
| 835. | $L_{A7}$ | $L_{Q37}$ |
| 836. | $L_{A7}$ | $L_{Q38}$ |
| 837. | $L_{A7}$ | $L_{Q39}$ |
| 838. | $L_{A7}$ | $L_{Q40}$ |

242
-continued

| Compound number | $L^1$ | $L^2$ |
|---|---|---|
| 839. | $L_{A7}$ | $L_{Q41}$ |
| 840. | $L_{A7}$ | $L_{Q42}$ |
| 841. | $L_{A7}$ | $L_{Q43}$ |
| 842. | $L_{A7}$ | $L_{Q44}$ |
| 843. | $L_{A7}$ | $L_{Q45}$ |
| 844. | $L_{A7}$ | $L_{Q46}$ |
| 845. | $L_{A7}$ | $L_{Q47}$ |
| 846. | $L_{A7}$ | $L_{Q48}$ |
| 847. | $L_{A7}$ | $L_{Q49}$ |
| 848. | $L_{A7}$ | $L_{Q50}$ |
| 849. | $L_{A7}$ | $L_{Q51}$ |
| 850. | $L_{A7}$ | $L_{Q52}$ |
| 851. | $L_{A7}$ | $L_{Q53}$ |
| 852. | $L_{A7}$ | $L_{Q54}$ |
| 853. | $L_{A7}$ | $L_{Q55}$ |
| 854. | $L_{A7}$ | $L_{Q56}$ |
| 855. | $L_{A7}$ | $L_{Q57}$ |
| 856. | $L_{A7}$ | $L_{Q58}$ |
| 857. | $L_{A7}$ | $L_{Q59}$ |
| 858. | $L_{A7}$ | $L_{Q60}$ |
| 859. | $L_{A7}$ | $L_{Q61}$ |
| 860. | $L_{A7}$ | $L_{Q62}$ |
| 861. | $L_{A7}$ | $L_{Q63}$ |
| 862. | $L_{A7}$ | $L_{Q64}$ |
| 863. | $L_{A7}$ | $L_{Q65}$ |
| 864. | $L_{A7}$ | $L_{Q66}$ |
| 865. | $L_{A7}$ | $L_{Q67}$ |
| 866. | $L_{A7}$ | $L_{Q68}$ |
| 867. | $L_{A7}$ | $L_{Q69}$ |
| 868. | $L_{A7}$ | $L_{Q70}$ |
| 869. | $L_{A7}$ | $L_{Q71}$ |
| 870. | $L_{A7}$ | $L_{Q72}$ |
| 871. | $L_{A7}$ | $L_{Q73}$ |
| 872. | $L_{A7}$ | $L_{Q74}$ |
| 873. | $L_{A7}$ | $L_{Q75}$ |
| 874. | $L_{A7}$ | $L_{Q76}$ |
| 875. | $L_{A7}$ | $L_{Q77}$ |
| 876. | $L_{A7}$ | $L_{Q78}$ |
| 877. | $L_{A7}$ | $L_{Q79}$ |
| 878. | $L_{A7}$ | $L_{Q80}$ |
| 879. | $L_{A7}$ | $L_{Q81}$ |
| 880. | $L_{A7}$ | $L_{Q82}$ |
| 881. | $L_{A7}$ | $L_{Q83}$ |
| 882. | $L_{A7}$ | $L_{Q84}$ |
| 883. | $L_{A7}$ | $L_{Q85}$ |
| 884. | $L_{A7}$ | $L_{Q86}$ |
| 885. | $L_{A7}$ | $L_{Q87}$ |
| 886. | $L_{A7}$ | $L_{Q88}$ |
| 887. | $L_{A7}$ | $L_{Q89}$ |
| 888. | $L_{A7}$ | $L_{Q90}$ |
| 889. | $L_{A7}$ | $L_{Q91}$ |
| 890. | $L_{A7}$ | $L_{Q92}$ |
| 891. | $L_{A7}$ | $L_{Q93}$ |
| 892. | $L_{A7}$ | $L_{Q94}$ |
| 893. | $L_{A7}$ | $L_{Q95}$ |
| 894. | $L_{A7}$ | $L_{Q96}$ |
| 895. | $L_{A7}$ | $L_{Q97}$ |
| 896. | $L_{A7}$ | $L_{Q98}$ |
| 897. | $L_{A7}$ | $L_{Q99}$ |
| 898. | $L_{A7}$ | $L_{Q100}$ |
| 899. | $L_{A7}$ | $L_{Q101}$ |
| 900. | $L_{A7}$ | $L_{Q102}$ |
| 901. | $L_{A7}$ | $L_{Q103}$ |
| 902. | $L_{A7}$ | $L_{Q104}$ |
| 903. | $L_{A7}$ | $L_{Q105}$ |
| 904. | $L_{A7}$ | $L_{Q106}$ |
| 905. | $L_{A7}$ | $L_{Q107}$ |
| 906. | $L_{A7}$ | $L_{Q108}$ |
| 907. | $L_{A7}$ | $L_{Q109}$ |
| 908. | $L_{A7}$ | $L_{Q110}$ |
| 909. | $L_{A7}$ | $L_{Q111}$ |
| 910. | $L_{A7}$ | $L_{Q112}$ |
| 911. | $L_{A7}$ | $L_{Q113}$ |
| 912. | $L_{A7}$ | $L_{Q114}$ |
| 913. | $L_{A7}$ | $L_{Q115}$ |
| 914. | $L_{A7}$ | $L_{Q116}$ |

| Compound number | $L^1$ | $L^2$ |
|---|---|---|
| 915. | $L_{A7}$ | $L_{Q117}$ |
| 916. | $L_{A7}$ | $L_{Q118}$ |
| 917. | $L_{A7}$ | $L_{Q119}$ |
| 918. | $L_{A7}$ | $L_{Q120}$ |
| 919. | $L_{A7}$ | $L_{Q121}$ |
| 920. | $L_{A7}$ | $L_{Q122}$ |
| 921. | $L_{A7}$ | $L_{Q123}$ |
| 922. | $L_{A7}$ | $L_{Q124}$ |
| 923. | $L_{A7}$ | $L_{Q125}$ |
| 924. | $L_{A7}$ | $L_{Q126}$ |
| 925. | $L_{A7}$ | $L_{Q127}$ |
| 926. | $L_{A7}$ | $L_{Q128}$ |
| 927. | $L_{A7}$ | $L_{Q129}$ |
| 928. | $L_{A7}$ | $L_{Q130}$ |
| 929. | $L_{A7}$ | $L_{Q131}$ |
| 930. | $L_{A7}$ | $L_{Q132}$ |
| 931. | $L_{A7}$ | $L_{Q133}$ |
| 1065. | $L_{A9}$ | $L_{Q1}$ |
| 1066. | $L_{A9}$ | $L_{Q2}$ |
| 1067. | $L_{A9}$ | $L_{Q3}$ |
| 1068. | $L_{A9}$ | $L_{Q4}$ |
| 1069. | $L_{A9}$ | $L_{Q5}$ |
| 1070. | $L_{A9}$ | $L_{Q6}$ |
| 1071. | $L_{A9}$ | $L_{Q7}$ |
| 1072. | $L_{A9}$ | $L_{Q8}$ |
| 1073. | $L_{A9}$ | $L_{Q9}$ |
| 1074. | $L_{A9}$ | $L_{Q10}$ |
| 1075. | $L_{A9}$ | $L_{Q11}$ |
| 1076. | $L_{A9}$ | $L_{Q12}$ |
| 1077. | $L_{A9}$ | $L_{Q13}$ |
| 1078. | $L_{A9}$ | $L_{Q14}$ |
| 1079. | $L_{A9}$ | $L_{Q15}$ |
| 1080. | $L_{A9}$ | $L_{Q16}$ |
| 1081. | $L_{A9}$ | $L_{Q17}$ |
| 1082. | $L_{A9}$ | $L_{Q18}$ |
| 1083. | $L_{A9}$ | $L_{Q19}$ |
| 1084. | $L_{A9}$ | $L_{Q20}$ |
| 1085. | $L_{A9}$ | $L_{Q21}$ |
| 1086. | $L_{A9}$ | $L_{Q22}$ |
| 1087. | $L_{A9}$ | $L_{Q23}$ |
| 1088. | $L_{A9}$ | $L_{Q24}$ |
| 1089. | $L_{A9}$ | $L_{Q25}$ |
| 1090. | $L_{A9}$ | $L_{Q26}$ |
| 1091. | $L_{A9}$ | $L_{Q27}$ |
| 1092. | $L_{A9}$ | $L_{Q28}$ |
| 1093. | $L_{A9}$ | $L_{Q29}$ |
| 1094. | $L_{A9}$ | $L_{Q30}$ |
| 1095. | $L_{A9}$ | $L_{Q31}$ |
| 1096. | $L_{A9}$ | $L_{Q32}$ |
| 1097. | $L_{A9}$ | $L_{Q33}$ |
| 1098. | $L_{A9}$ | $L_{Q34}$ |
| 1099. | $L_{A9}$ | $L_{Q35}$ |
| 1100. | $L_{A9}$ | $L_{Q36}$ |
| 1101. | $L_{A9}$ | $L_{Q37}$ |
| 1102. | $L_{A9}$ | $L_{Q38}$ |
| 1103. | $L_{A9}$ | $L_{Q39}$ |
| 1104. | $L_{A9}$ | $L_{Q40}$ |
| 1105. | $L_{A9}$ | $L_{Q41}$ |
| 1106. | $L_{A9}$ | $L_{Q42}$ |
| 1107. | $L_{A9}$ | $L_{Q43}$ |
| 1108. | $L_{A9}$ | $L_{Q44}$ |
| 1109. | $L_{A9}$ | $L_{Q45}$ |
| 1110. | $L_{A9}$ | $L_{Q46}$ |
| 1111. | $L_{A9}$ | $L_{Q47}$ |
| 1112. | $L_{A9}$ | $L_{Q48}$ |
| 1113. | $L_{A9}$ | $L_{Q49}$ |
| 1114. | $L_{A9}$ | $L_{Q50}$ |
| 1115. | $L_{A9}$ | $L_{Q51}$ |
| 1116. | $L_{A9}$ | $L_{Q52}$ |
| 1117. | $L_{A9}$ | $L_{Q53}$ |
| 1118. | $L_{A9}$ | $L_{Q54}$ |
| 1119. | $L_{A9}$ | $L_{Q55}$ |
| 1120. | $L_{A9}$ | $L_{Q56}$ |
| 1121. | $L_{A9}$ | $L_{Q57}$ |
| 1122. | $L_{A9}$ | $L_{Q58}$ |
| 1123. | $L_{A9}$ | $L_{Q59}$ |
| 1124. | $L_{A9}$ | $L_{Q60}$ |
| 1125. | $L_{A9}$ | $L_{Q61}$ |
| 1126. | $L_{A9}$ | $L_{Q62}$ |
| 1127. | $L_{A9}$ | $L_{Q63}$ |
| 1128. | $L_{A9}$ | $L_{Q64}$ |
| 1129. | $L_{A9}$ | $L_{Q65}$ |
| 1130. | $L_{A9}$ | $L_{Q66}$ |
| 1131. | $L_{A9}$ | $L_{Q67}$ |
| 1132. | $L_{A9}$ | $L_{Q68}$ |
| 1133. | $L_{A9}$ | $L_{Q69}$ |
| 1134. | $L_{A9}$ | $L_{Q70}$ |
| 1135. | $L_{A9}$ | $L_{Q71}$ |
| 1136. | $L_{A9}$ | $L_{Q72}$ |
| 1137. | $L_{A9}$ | $L_{Q73}$ |
| 1138. | $L_{A9}$ | $L_{Q74}$ |
| 1139. | $L_{A9}$ | $L_{Q75}$ |
| 1140. | $L_{A9}$ | $L_{Q76}$ |
| 1141. | $L_{A9}$ | $L_{Q77}$ |
| 1142. | $L_{A9}$ | $L_{Q78}$ |
| 1143. | $L_{A9}$ | $L_{Q79}$ |
| 1144. | $L_{A9}$ | $L_{Q80}$ |
| 1145. | $L_{A9}$ | $L_{Q81}$ |
| 1146. | $L_{A9}$ | $L_{Q82}$ |
| 1147. | $L_{A9}$ | $L_{Q83}$ |
| 1148. | $L_{A9}$ | $L_{Q84}$ |
| 1149. | $L_{A9}$ | $L_{Q85}$ |
| 1150. | $L_{A9}$ | $L_{Q86}$ |
| 1151. | $L_{A9}$ | $L_{Q87}$ |
| 1152. | $L_{A9}$ | $L_{Q88}$ |
| 1153. | $L_{A9}$ | $L_{Q89}$ |
| 1154. | $L_{A9}$ | $L_{Q90}$ |
| 1155. | $L_{A9}$ | $L_{Q91}$ |
| 1156. | $L_{A9}$ | $L_{Q92}$ |
| 1157. | $L_{A9}$ | $L_{Q93}$ |
| 1158. | $L_{A9}$ | $L_{Q94}$ |
| 1159. | $L_{A9}$ | $L_{Q95}$ |
| 1160. | $L_{A9}$ | $L_{Q96}$ |
| 1161. | $L_{A9}$ | $L_{Q97}$ |
| 1162. | $L_{A9}$ | $L_{Q98}$ |
| 1163. | $L_{A9}$ | $L_{Q99}$ |
| 1164. | $L_{A9}$ | $L_{Q100}$ |
| 1165. | $L_{A9}$ | $L_{Q101}$ |
| 1166. | $L_{A9}$ | $L_{Q102}$ |
| 1167. | $L_{A9}$ | $L_{Q103}$ |
| 1168. | $L_{A9}$ | $L_{Q104}$ |
| 1169. | $L_{A9}$ | $L_{Q105}$ |
| 1170. | $L_{A9}$ | $L_{Q106}$ |
| 1171. | $L_{A9}$ | $L_{Q107}$ |
| 1172. | $L_{A9}$ | $L_{Q108}$ |
| 1173. | $L_{A9}$ | $L_{Q109}$ |
| 1174. | $L_{A9}$ | $L_{Q110}$ |
| 1175. | $L_{A9}$ | $L_{Q111}$ |
| 1176. | $L_{A9}$ | $L_{Q112}$ |
| 1177. | $L_{A9}$ | $L_{Q113}$ |
| 1178. | $L_{A9}$ | $L_{Q114}$ |
| 1179. | $L_{A9}$ | $L_{Q115}$ |
| 1180. | $L_{A9}$ | $L_{Q116}$ |
| 1181. | $L_{A9}$ | $L_{Q117}$ |
| 1182. | $L_{A9}$ | $L_{Q118}$ |
| 1183. | $L_{A9}$ | $L_{Q119}$ |
| 1184. | $L_{A9}$ | $L_{Q120}$ |
| 1185. | $L_{A9}$ | $L_{Q121}$ |
| 1186. | $L_{A9}$ | $L_{Q122}$ |
| 1187. | $L_{A9}$ | $L_{Q123}$ |
| 1188. | $L_{A9}$ | $L_{Q124}$ |
| 1189. | $L_{A9}$ | $L_{Q125}$ |
| 1190. | $L_{A9}$ | $L_{Q126}$ |
| 1191. | $L_{A9}$ | $L_{Q127}$ |
| 1192. | $L_{A9}$ | $L_{Q128}$ |
| 1193. | $L_{A9}$ | $L_{Q129}$ |
| 1194. | $L_{A9}$ | $L_{Q130}$ |
| 1195. | $L_{A9}$ | $L_{Q131}$ |
| 1196. | $L_{A9}$ | $L_{Q132}$ |
| 1197. | $L_{A9}$ | $L_{Q133}$ |
| 1198. | $L_{A10}$ | $L_{Q1}$ |
| 1199. | $L_{A10}$ | $L_{Q2}$ |

| Compound number | $L^1$ | $L^2$ |
| --- | --- | --- |
| 1200. | $L_{A10}$ | $L_{Q3}$ |
| 1201. | $L_{A10}$ | $L_{Q4}$ |
| 1202. | $L_{A10}$ | $L_{Q5}$ |
| 1203. | $L_{A10}$ | $L_{Q6}$ |
| 1204. | $L_{A10}$ | $L_{Q7}$ |
| 1205. | $L_{A10}$ | $L_{Q8}$ |
| 1206. | $L_{A10}$ | $L_{Q9}$ |
| 1207. | $L_{A10}$ | $L_{Q10}$ |
| 1208. | $L_{A10}$ | $L_{Q11}$ |
| 1209. | $L_{A10}$ | $L_{Q12}$ |
| 1210. | $L_{A10}$ | $L_{Q13}$ |
| 1211. | $L_{A10}$ | $L_{Q14}$ |
| 1212. | $L_{A10}$ | $L_{Q15}$ |
| 1213. | $L_{A10}$ | $L_{Q16}$ |
| 1214. | $L_{A10}$ | $L_{Q17}$ |
| 1215. | $L_{A10}$ | $L_{Q18}$ |
| 1216. | $L_{A10}$ | $L_{Q19}$ |
| 1217. | $L_{A10}$ | $L_{Q20}$ |
| 1218. | $L_{A10}$ | $L_{Q21}$ |
| 1219. | $L_{A10}$ | $L_{Q22}$ |
| 1220. | $L_{A10}$ | $L_{Q23}$ |
| 1221. | $L_{A10}$ | $L_{Q24}$ |
| 1222. | $L_{A10}$ | $L_{Q25}$ |
| 1223. | $L_{A10}$ | $L_{Q26}$ |
| 1224. | $L_{A10}$ | $L_{Q27}$ |
| 1225. | $L_{A10}$ | $L_{Q28}$ |
| 1226. | $L_{A10}$ | $L_{Q29}$ |
| 1227. | $L_{A10}$ | $L_{Q30}$ |
| 1228. | $L_{A10}$ | $L_{Q31}$ |
| 1229. | $L_{A10}$ | $L_{Q32}$ |
| 1230. | $L_{A10}$ | $L_{Q33}$ |
| 1231. | $L_{A10}$ | $L_{Q34}$ |
| 1232. | $L_{A10}$ | $L_{Q35}$ |
| 1233. | $L_{A10}$ | $L_{Q36}$ |
| 1234. | $L_{A10}$ | $L_{Q37}$ |
| 1235. | $L_{A10}$ | $L_{Q38}$ |
| 1236. | $L_{A10}$ | $L_{Q39}$ |
| 1237. | $L_{A10}$ | $L_{Q40}$ |
| 1238. | $L_{A10}$ | $L_{Q41}$ |
| 1239. | $L_{A10}$ | $L_{Q42}$ |
| 1240. | $L_{A10}$ | $L_{Q43}$ |
| 1241. | $L_{A10}$ | $L_{Q44}$ |
| 1242. | $L_{A10}$ | $L_{Q45}$ |
| 1243. | $L_{A10}$ | $L_{Q46}$ |
| 1244. | $L_{A10}$ | $L_{Q47}$ |
| 1245. | $L_{A10}$ | $L_{Q48}$ |
| 1246. | $L_{A10}$ | $L_{Q49}$ |
| 1247. | $L_{A10}$ | $L_{Q50}$ |
| 1248. | $L_{A10}$ | $L_{Q51}$ |
| 1249. | $L_{A10}$ | $L_{Q52}$ |
| 1250. | $L_{A10}$ | $L_{Q53}$ |
| 1251. | $L_{A10}$ | $L_{Q54}$ |
| 1252. | $L_{A10}$ | $L_{Q55}$ |
| 1253. | $L_{A10}$ | $L_{Q56}$ |
| 1254. | $L_{A10}$ | $L_{Q57}$ |
| 1255. | $L_{A10}$ | $L_{Q58}$ |
| 1256. | $L_{A10}$ | $L_{Q59}$ |
| 1257. | $L_{A10}$ | $L_{Q60}$ |
| 1258. | $L_{A10}$ | $L_{Q61}$ |
| 1259. | $L_{A10}$ | $L_{Q62}$ |
| 1260. | $L_{A10}$ | $L_{Q63}$ |
| 1261. | $L_{A10}$ | $L_{Q64}$ |
| 1262. | $L_{A10}$ | $L_{Q65}$ |
| 1263. | $L_{A10}$ | $L_{Q66}$ |
| 1264. | $L_{A10}$ | $L_{Q67}$ |
| 1265. | $L_{A10}$ | $L_{Q68}$ |
| 1266. | $L_{A10}$ | $L_{Q69}$ |
| 1267. | $L_{A10}$ | $L_{Q70}$ |
| 1268. | $L_{A10}$ | $L_{Q71}$ |
| 1269. | $L_{A10}$ | $L_{Q72}$ |
| 1270. | $L_{A10}$ | $L_{Q73}$ |
| 1271. | $L_{A10}$ | $L_{Q74}$ |
| 1272. | $L_{A10}$ | $L_{Q75}$ |
| 1273. | $L_{A10}$ | $L_{Q76}$ |
| 1274. | $L_{A10}$ | $L_{Q77}$ |
| 1275. | $L_{A10}$ | $L_{Q78}$ |
| 1276. | $L_{A10}$ | $L_{Q79}$ |
| 1277. | $L_{A10}$ | $L_{Q80}$ |
| 1278. | $L_{A10}$ | $L_{Q81}$ |
| 1279. | $L_{A10}$ | $L_{Q82}$ |
| 1280. | $L_{A10}$ | $L_{Q83}$ |
| 1281. | $L_{A10}$ | $L_{Q84}$ |
| 1282. | $L_{A10}$ | $L_{Q85}$ |
| 1283. | $L_{A10}$ | $L_{Q86}$ |
| 1284. | $L_{A10}$ | $L_{Q87}$ |
| 1285. | $L_{A10}$ | $L_{Q88}$ |
| 1286. | $L_{A10}$ | $L_{Q89}$ |
| 1287. | $L_{A10}$ | $L_{Q90}$ |
| 1288. | $L_{A10}$ | $L_{Q91}$ |
| 1289. | $L_{A10}$ | $L_{Q92}$ |
| 1290. | $L_{A10}$ | $L_{Q93}$ |
| 1291. | $L_{A10}$ | $L_{Q94}$ |
| 1292. | $L_{A10}$ | $L_{Q95}$ |
| 1293. | $L_{A10}$ | $L_{Q96}$ |
| 1294. | $L_{A10}$ | $L_{Q97}$ |
| 1295. | $L_{A10}$ | $L_{Q98}$ |
| 1296. | $L_{A10}$ | $L_{Q99}$ |
| 1297. | $L_{A10}$ | $L_{Q100}$ |
| 1298. | $L_{A10}$ | $L_{Q101}$ |
| 1299. | $L_{A10}$ | $L_{Q102}$ |
| 1300. | $L_{A10}$ | $L_{Q103}$ |
| 1301. | $L_{A10}$ | $L_{Q104}$ |
| 1302. | $L_{A10}$ | $L_{Q105}$ |
| 1303. | $L_{A10}$ | $L_{Q106}$ |
| 1304. | $L_{A10}$ | $L_{Q107}$ |
| 1305. | $L_{A10}$ | $L_{Q108}$ |
| 1306. | $L_{A10}$ | $L_{Q109}$ |
| 1307. | $L_{A10}$ | $L_{Q110}$ |
| 1308. | $L_{A10}$ | $L_{Q111}$ |
| 1309. | $L_{A10}$ | $L_{Q112}$ |
| 1310. | $L_{A10}$ | $L_{Q113}$ |
| 1311. | $L_{A10}$ | $L_{Q114}$ |
| 1312. | $L_{A10}$ | $L_{Q115}$ |
| 1313. | $L_{A10}$ | $L_{Q116}$ |
| 1314. | $L_{A10}$ | $L_{Q117}$ |
| 1315. | $L_{A10}$ | $L_{Q118}$ |
| 1316. | $L_{A10}$ | $L_{Q119}$ |
| 1317. | $L_{A10}$ | $L_{Q120}$ |
| 1318. | $L_{A10}$ | $L_{Q121}$ |
| 1319. | $L_{A10}$ | $L_{Q122}$ |
| 1320. | $L_{A10}$ | $L_{Q123}$ |
| 1321. | $L_{A10}$ | $L_{Q124}$ |
| 1322. | $L_{A10}$ | $L_{Q125}$ |
| 1323. | $L_{A10}$ | $L_{Q126}$ |
| 1324. | $L_{A10}$ | $L_{Q127}$ |
| 1325. | $L_{A10}$ | $L_{Q128}$ |
| 1326. | $L_{A10}$ | $L_{Q129}$ |
| 1327. | $L_{A10}$ | $L_{Q130}$ |
| 1328. | $L_{A10}$ | $L_{Q131}$ |
| 1329. | $L_{A10}$ | $L_{Q132}$ |
| 1330. | $L_{A10}$ | $L_{Q133}$ |
| 1597. | $L_{A13}$ | $L_{Q1}$ |
| 1598. | $L_{A13}$ | $L_{Q2}$ |
| 1599. | $L_{A13}$ | $L_{Q3}$ |
| 1600. | $L_{A13}$ | $L_{Q4}$ |
| 1601. | $L_{A13}$ | $L_{Q5}$ |
| 1602. | $L_{A13}$ | $L_{Q6}$ |
| 1603. | $L_{A13}$ | $L_{Q7}$ |
| 1604. | $L_{A13}$ | $L_{Q8}$ |
| 1605. | $L_{A13}$ | $L_{Q9}$ |
| 1606. | $L_{A13}$ | $L_{Q10}$ |
| 1607. | $L_{A13}$ | $L_{Q11}$ |
| 1608. | $L_{A13}$ | $L_{Q12}$ |
| 1609. | $L_{A13}$ | $L_{Q13}$ |
| 1610. | $L_{A13}$ | $L_{Q14}$ |
| 1611. | $L_{A13}$ | $L_{Q15}$ |
| 1612. | $L_{A13}$ | $L_{Q16}$ |
| 1613. | $L_{A13}$ | $L_{Q17}$ |
| 1614. | $L_{A13}$ | $L_{Q18}$ |
| 1615. | $L_{A13}$ | $L_{Q19}$ |
| 1616. | $L_{A13}$ | $L_{Q20}$ |
| 1617. | $L_{A13}$ | $L_{Q21}$ |

| Compound number | L¹ | L² |
|---|---|---|
| 1618. | $L_{A13}$ | $L_{Q22}$ |
| 1619. | $L_{A13}$ | $L_{Q23}$ |
| 1620. | $L_{A13}$ | $L_{Q24}$ |
| 1621. | $L_{A13}$ | $L_{Q25}$ |
| 1622. | $L_{A13}$ | $L_{Q26}$ |
| 1623. | $L_{A13}$ | $L_{Q27}$ |
| 1624. | $L_{A13}$ | $L_{Q28}$ |
| 1625. | $L_{A13}$ | $L_{Q29}$ |
| 1626. | $L_{A13}$ | $L_{Q30}$ |
| 1627. | $L_{A13}$ | $L_{Q31}$ |
| 1628. | $L_{A13}$ | $L_{Q32}$ |
| 1629. | $L_{A13}$ | $L_{Q33}$ |
| 1630. | $L_{A13}$ | $L_{Q34}$ |
| 1631. | $L_{A13}$ | $L_{Q35}$ |
| 1632. | $L_{A13}$ | $L_{Q36}$ |
| 1633. | $L_{A13}$ | $L_{Q37}$ |
| 1634. | $L_{A13}$ | $L_{Q38}$ |
| 1635. | $L_{A13}$ | $L_{Q39}$ |
| 1636. | $L_{A13}$ | $L_{Q40}$ |
| 1637. | $L_{A13}$ | $L_{Q41}$ |
| 1638. | $L_{A13}$ | $L_{Q42}$ |
| 1639. | $L_{A13}$ | $L_{Q43}$ |
| 1640. | $L_{A13}$ | $L_{Q44}$ |
| 1641. | $L_{A13}$ | $L_{Q45}$ |
| 1642. | $L_{A13}$ | $L_{Q46}$ |
| 1643. | $L_{A13}$ | $L_{Q47}$ |
| 1644. | $L_{A13}$ | $L_{Q48}$ |
| 1645. | $L_{A13}$ | $L_{Q49}$ |
| 1646. | $L_{A13}$ | $L_{Q50}$ |
| 1647. | $L_{A13}$ | $L_{Q51}$ |
| 1648. | $L_{A13}$ | $L_{Q52}$ |
| 1649. | $L_{A13}$ | $L_{Q53}$ |
| 1650. | $L_{A13}$ | $L_{Q54}$ |
| 1651. | $L_{A13}$ | $L_{Q55}$ |
| 1652. | $L_{A13}$ | $L_{Q56}$ |
| 1653. | $L_{A13}$ | $L_{Q57}$ |
| 1654. | $L_{A13}$ | $L_{Q58}$ |
| 1655. | $L_{A13}$ | $L_{Q59}$ |
| 1656. | $L_{A13}$ | $L_{Q60}$ |
| 1657. | $L_{A13}$ | $L_{Q61}$ |
| 1658. | $L_{A13}$ | $L_{Q62}$ |
| 1659. | $L_{A13}$ | $L_{Q63}$ |
| 1660. | $L_{A13}$ | $L_{Q64}$ |
| 1661. | $L_{A13}$ | $L_{Q65}$ |
| 1662. | $L_{A13}$ | $L_{Q66}$ |
| 1663. | $L_{A13}$ | $L_{Q67}$ |
| 1664. | $L_{A13}$ | $L_{Q68}$ |
| 1665. | $L_{A13}$ | $L_{Q69}$ |
| 1666. | $L_{A13}$ | $L_{Q70}$ |
| 1667. | $L_{A13}$ | $L_{Q71}$ |
| 1668. | $L_{A13}$ | $L_{Q72}$ |
| 1669. | $L_{A13}$ | $L_{Q73}$ |
| 1670. | $L_{A13}$ | $L_{Q74}$ |
| 1671. | $L_{A13}$ | $L_{Q75}$ |
| 1672. | $L_{A13}$ | $L_{Q76}$ |
| 1673. | $L_{A13}$ | $L_{Q77}$ |
| 1674. | $L_{A13}$ | $L_{Q78}$ |
| 1675. | $L_{A13}$ | $L_{Q79}$ |
| 1676. | $L_{A13}$ | $L_{Q80}$ |
| 1677. | $L_{A13}$ | $L_{Q81}$ |
| 1678. | $L_{A13}$ | $L_{Q82}$ |
| 1679. | $L_{A13}$ | $L_{Q83}$ |
| 1680. | $L_{A13}$ | $L_{Q84}$ |
| 1681. | $L_{A13}$ | $L_{Q85}$ |
| 1682. | $L_{A13}$ | $L_{Q86}$ |
| 1683. | $L_{A13}$ | $L_{Q87}$ |
| 1684. | $L_{A13}$ | $L_{Q88}$ |
| 1685. | $L_{A13}$ | $L_{Q89}$ |
| 1686. | $L_{A13}$ | $L_{Q90}$ |
| 1687. | $L_{A13}$ | $L_{Q91}$ |
| 1688. | $L_{A13}$ | $L_{Q92}$ |
| 1689. | $L_{A13}$ | $L_{Q93}$ |
| 1690. | $L_{A13}$ | $L_{Q94}$ |
| 1691. | $L_{A13}$ | $L_{Q95}$ |
| 1692. | $L_{A13}$ | $L_{Q96}$ |
| 1693. | $L_{A13}$ | $L_{Q97}$ |
| 1694. | $L_{A13}$ | $L_{Q98}$ |
| 1695. | $L_{A13}$ | $L_{Q99}$ |
| 1696. | $L_{A13}$ | $L_{Q100}$ |
| 1697. | $L_{A13}$ | $L_{Q101}$ |
| 1698. | $L_{A13}$ | $L_{Q102}$ |
| 1699. | $L_{A13}$ | $L_{Q103}$ |
| 1700. | $L_{A13}$ | $L_{Q104}$ |
| 1701. | $L_{A13}$ | $L_{Q105}$ |
| 1702. | $L_{A13}$ | $L_{Q106}$ |
| 1703. | $L_{A13}$ | $L_{Q107}$ |
| 1704. | $L_{A13}$ | $L_{Q108}$ |
| 1705. | $L_{A13}$ | $L_{Q109}$ |
| 1706. | $L_{A13}$ | $L_{Q110}$ |
| 1707. | $L_{A13}$ | $L_{Q111}$ |
| 1708. | $L_{A13}$ | $L_{Q112}$ |
| 1709. | $L_{A13}$ | $L_{Q113}$ |
| 1710. | $L_{A13}$ | $L_{Q114}$ |
| 1711. | $L_{A13}$ | $L_{Q115}$ |
| 1712. | $L_{A13}$ | $L_{Q116}$ |
| 1713. | $L_{A13}$ | $L_{Q117}$ |
| 1714. | $L_{A13}$ | $L_{Q118}$ |
| 1715. | $L_{A13}$ | $L_{Q119}$ |
| 1716. | $L_{A13}$ | $L_{Q120}$ |
| 1717. | $L_{A13}$ | $L_{Q121}$ |
| 1718. | $L_{A13}$ | $L_{Q122}$ |
| 1719. | $L_{A13}$ | $L_{Q123}$ |
| 1720. | $L_{A13}$ | $L_{Q124}$ |
| 1721. | $L_{A13}$ | $L_{Q125}$ |
| 1722. | $L_{A13}$ | $L_{Q126}$ |
| 1723. | $L_{A13}$ | $L_{Q127}$ |
| 1724. | $L_{A13}$ | $L_{Q128}$ |
| 1725. | $L_{A13}$ | $L_{Q129}$ |
| 1726. | $L_{A13}$ | $L_{Q130}$ |
| 1727. | $L_{A13}$ | $L_{Q131}$ |
| 1728. | $L_{A13}$ | $L_{Q132}$ |
| 1729. | $L_{A13}$ | $L_{Q133}$. |

6. The compound of claim 1, wherein the compound is selected from the group consisting of:

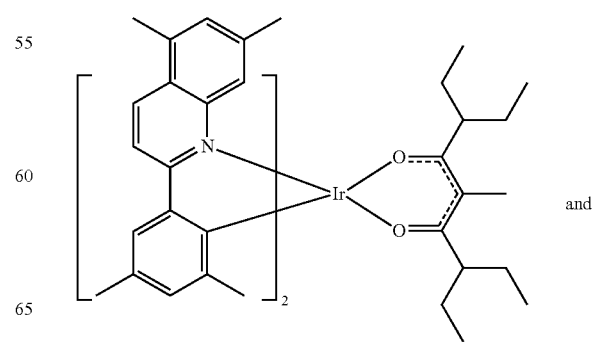

Compound 278 and

-continued

Compound 320

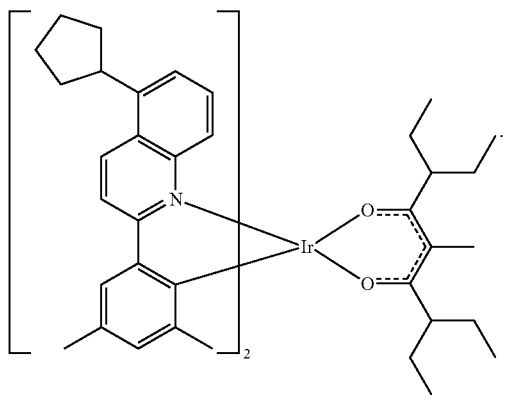

7. The compound of claim 1, wherein $L^1$ is

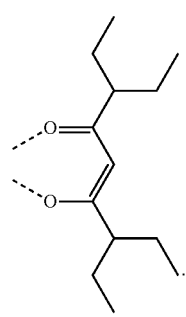

$L_{A3}$

8. The compound of claim 1, wherein $L^1$ is

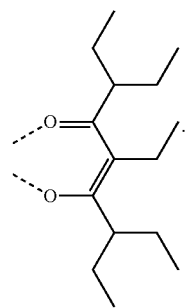

$L_{A7}$

9. The compound of claim 1, wherein $L^1$ is,

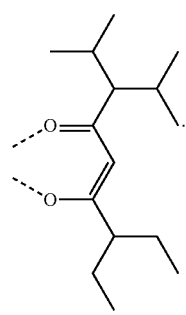

$L_{A9}$

10. The compound of claim 1, wherein $L^1$ is

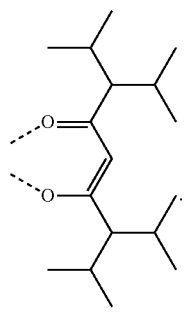

$L_{A10}$

11. The compound of claim 1, wherein $L^1$ is

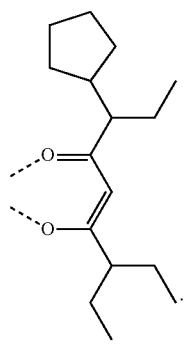

$L_{A13}$

12. A first device comprising a first organic light emitting device, the first organic light emitting device comprising:
  an anode;
  a cathode; and
  an organic layer, disposed between the anode and the cathode, comprising a compound having the formula $Ir(L^1)_x(L^2)_y(L^3)_z$:
  wherein $L^1$ is selected from the group consisting of

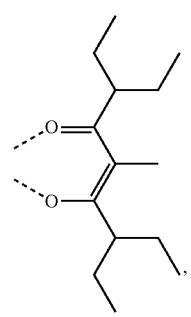

$L_{A3}$

-continued
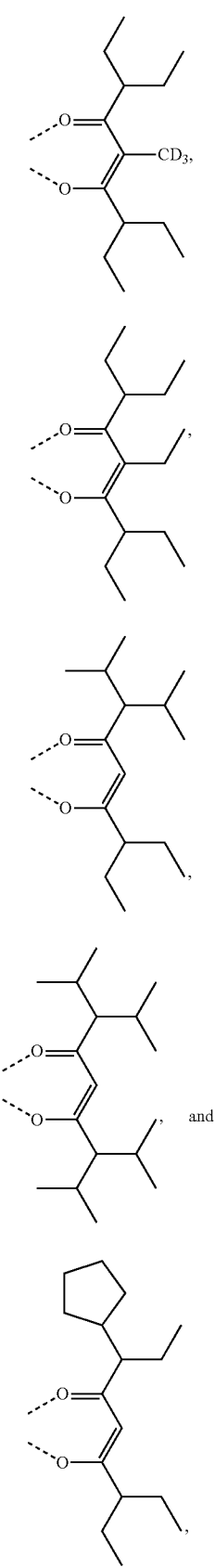
L$_{A5}$,
L$_{A7}$,
L$_{A9}$,
L$_{A10}$ and
L$_{A13}$
wherein L$^2$ is a second ligand and L$^3$ is a third ligand and L$^2$ and L$^3$ can be the same or different;
wherein the second ligand L$^2$ and the third ligand L$^3$ are structure (a) independently selected from the group consisting of:
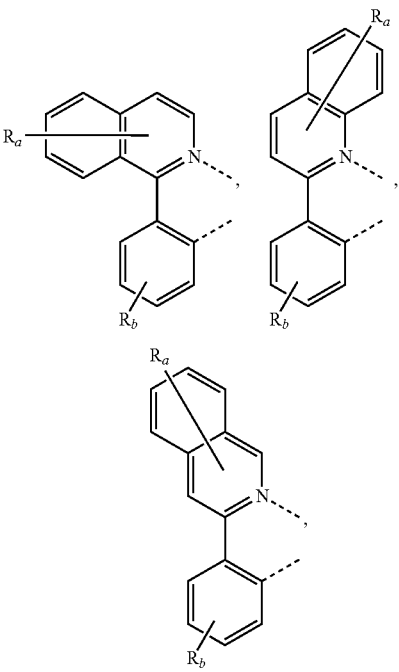
or structure (b) independently selected from the group consisting of
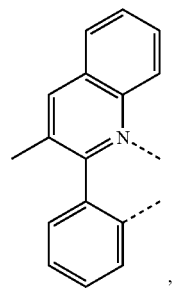
L$_{Q2}$,
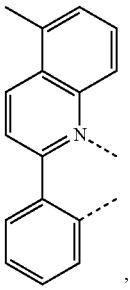
L$_{Q3}$, L_{Q4}
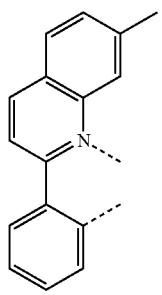,
L_{Q5}
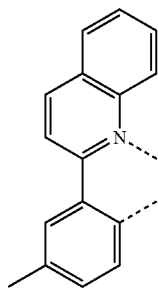,
L_{Q6}
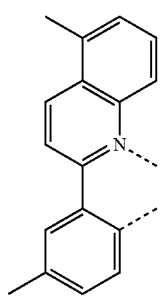,
L_{Q7}
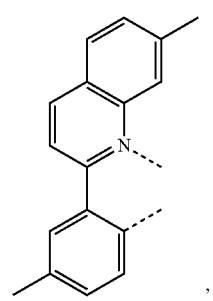,
L_{Q10}
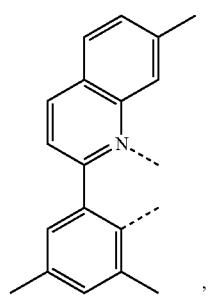,
L_{Q11}
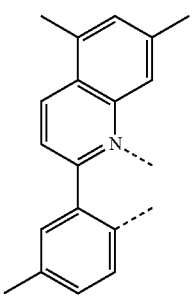,
L_{Q12}
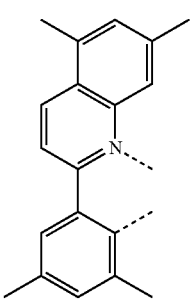,
L_{Q13}
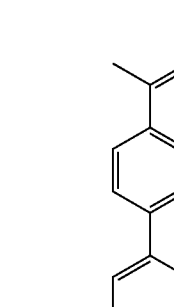,
L_{Q14}
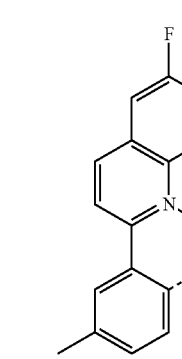,
L_{Q15}
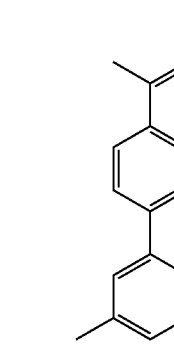, L<sub>Q16</sub> 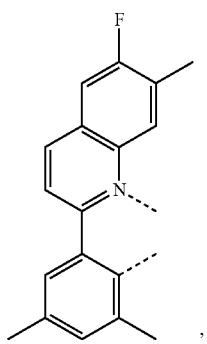
L<sub>Q17</sub> 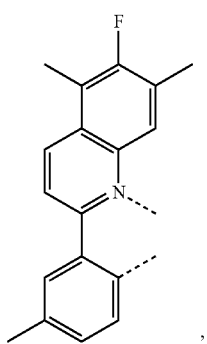
L<sub>Q18</sub> 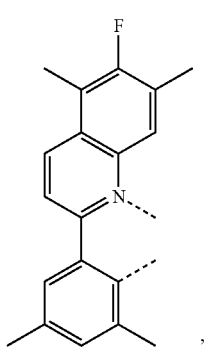
L<sub>Q19</sub> 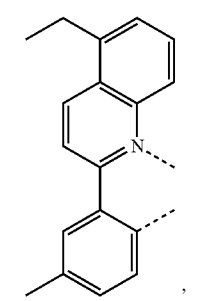
L<sub>Q20</sub> 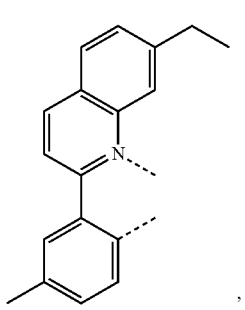
L<sub>Q21</sub> 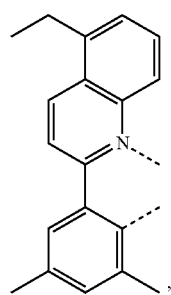
L<sub>Q22</sub> 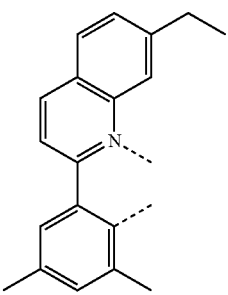
L<sub>Q23</sub> 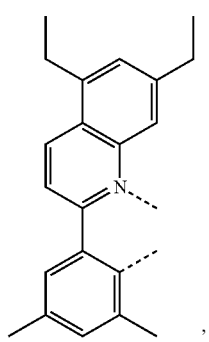
L<sub>Q24</sub> 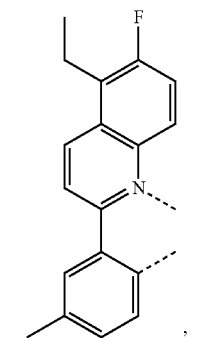
L<sub>Q25</sub> 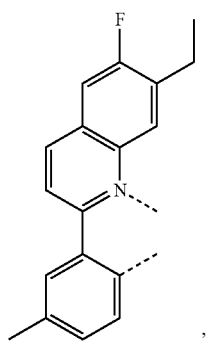

-continued
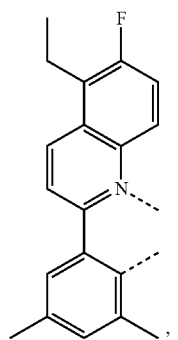  L_{Q26}
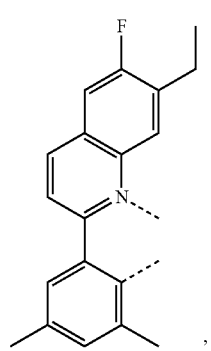  L_{Q27}
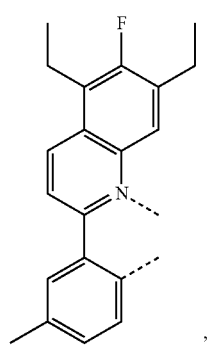  L_{Q28}
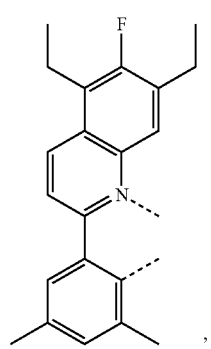  L_{Q29}
-continued
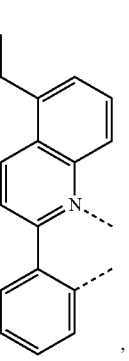  L_{Q30}
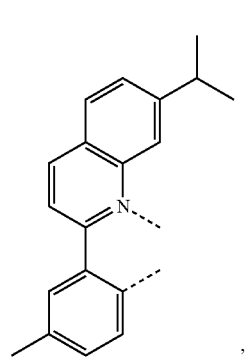  L_{Q31}
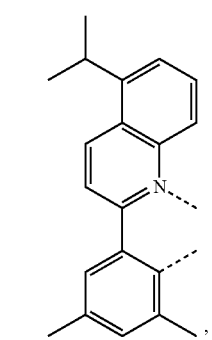  L_{Q32}
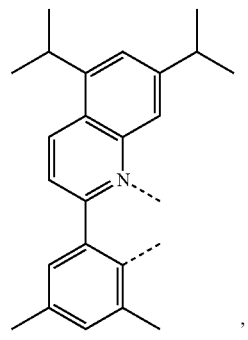  L_{Q34}

-continued
L$_{Q35}$
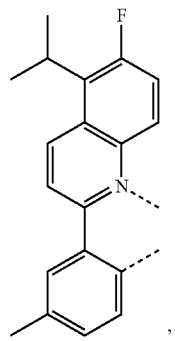
L$_{Q36}$
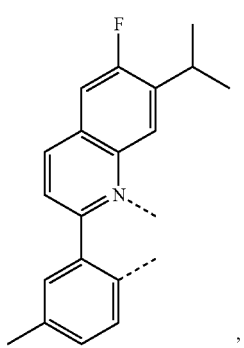
L$_{Q37}$
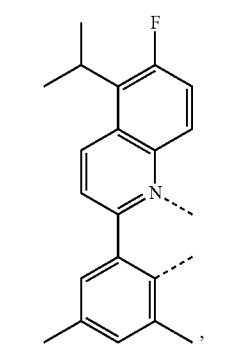
L$_{Q38}$
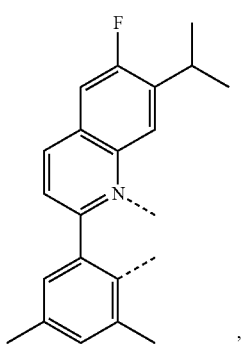
-continued
L$_{Q39}$
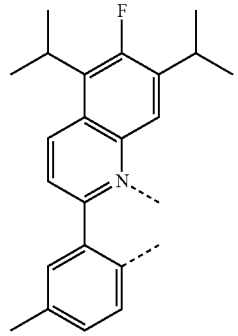
L$_{Q40}$
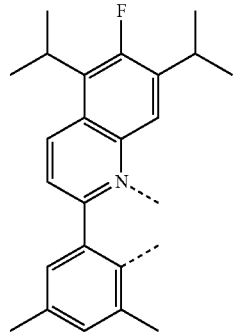
L$_{Q41}$
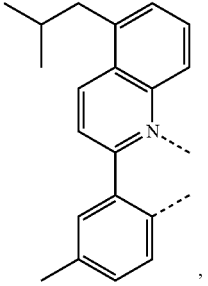
L$_{Q42}$
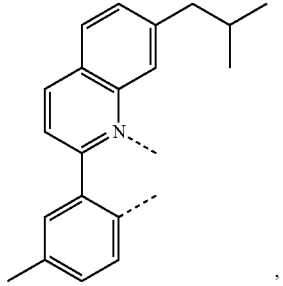
L$_{Q43}$
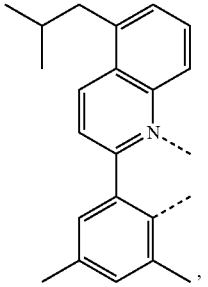

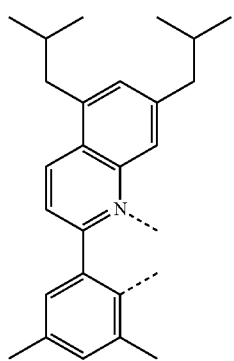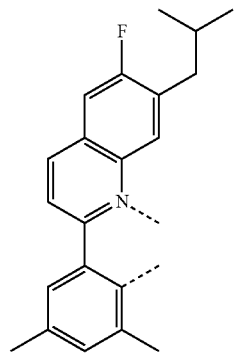

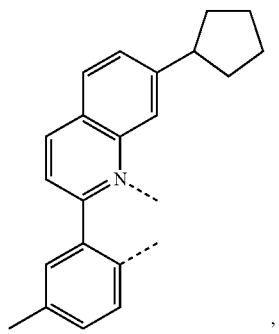 L_{Q53}
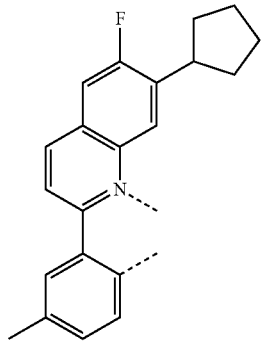 L_{Q57}
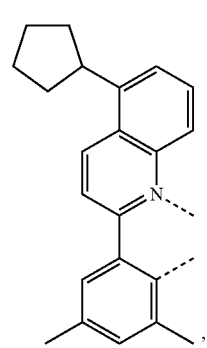 L_{Q54}
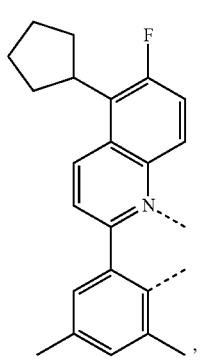 L_{Q58}
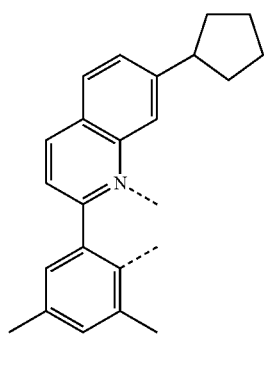 L_{Q55}
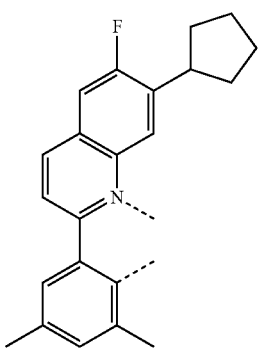 L_{Q59}
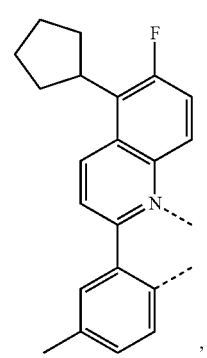 L_{Q56}
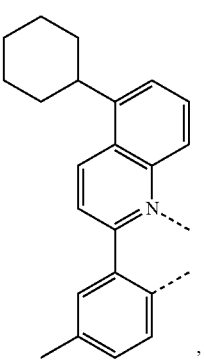 L_{Q60}

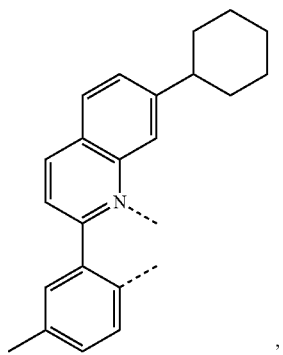 $L_{Q61}$
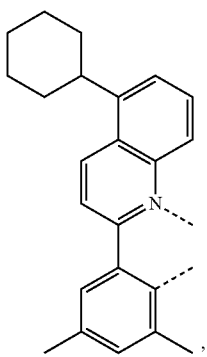 $L_{Q62}$
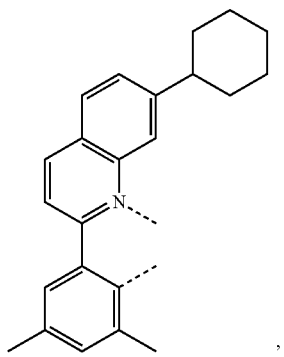 $L_{Q63}$
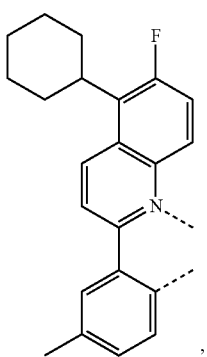 $L_{Q64}$
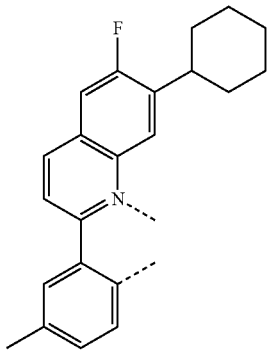 $L_{Q65}$
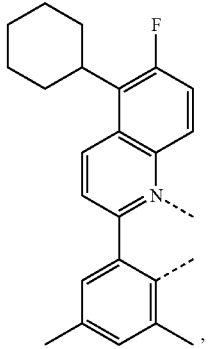 $L_{Q66}$
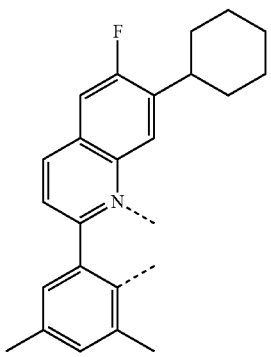 $L_{Q67}$
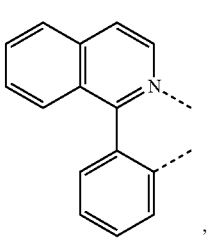 $L_{Q68}$
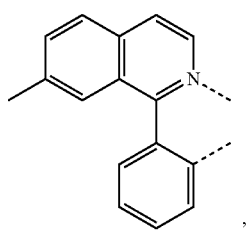 $L_{Q69}$

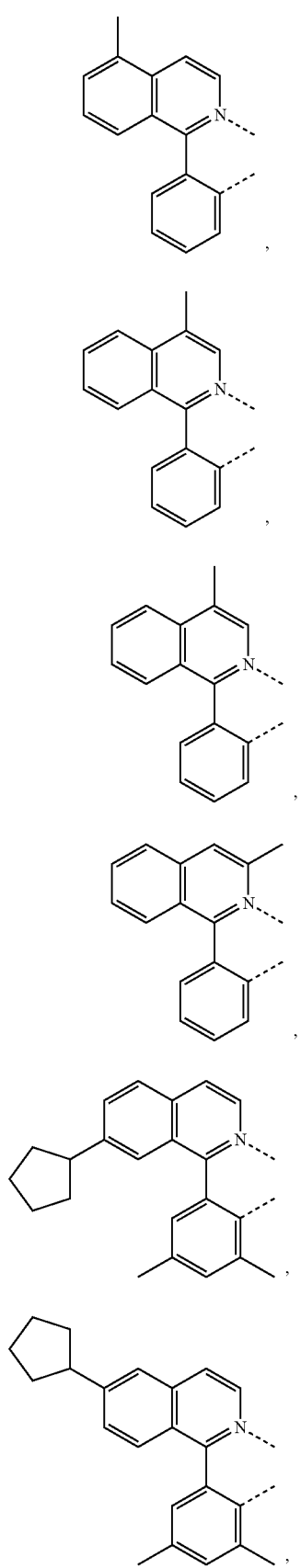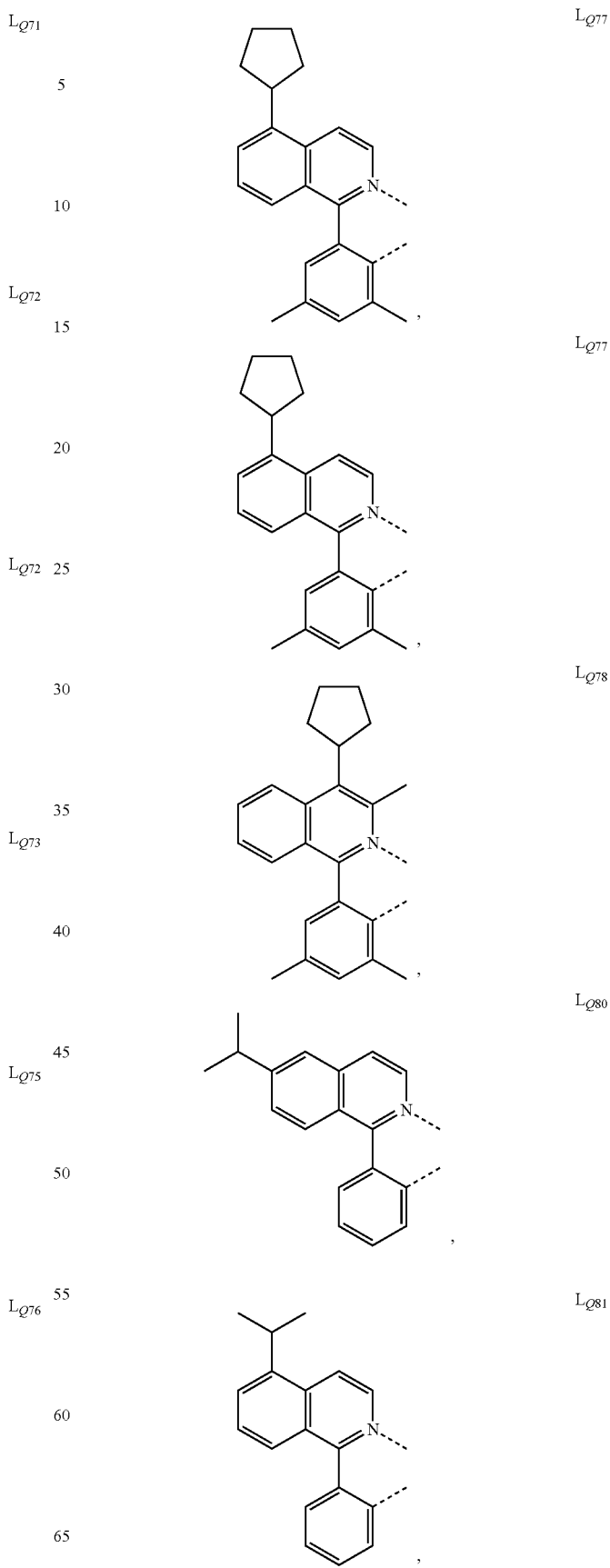

269
-continued
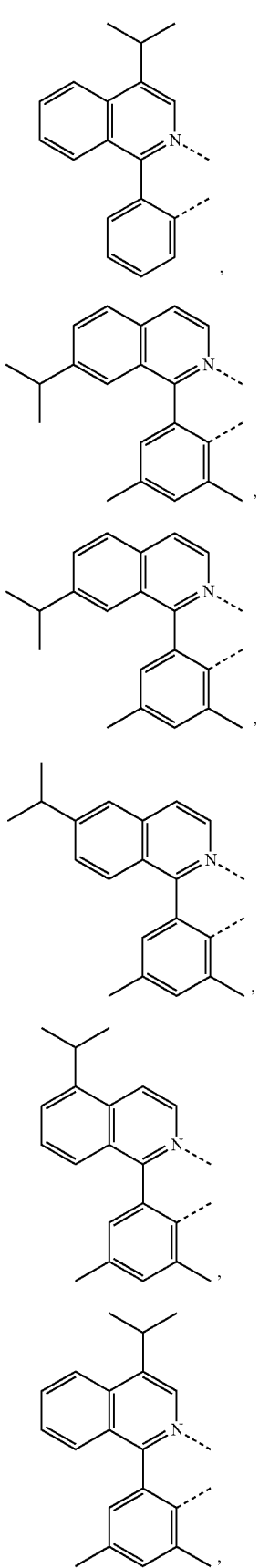
270
-continued
$L_{Q82}$
$L_{Q83}$
$L_{Q83}$
$L_{Q84}$
$L_{Q85}$
$L_{Q86}$
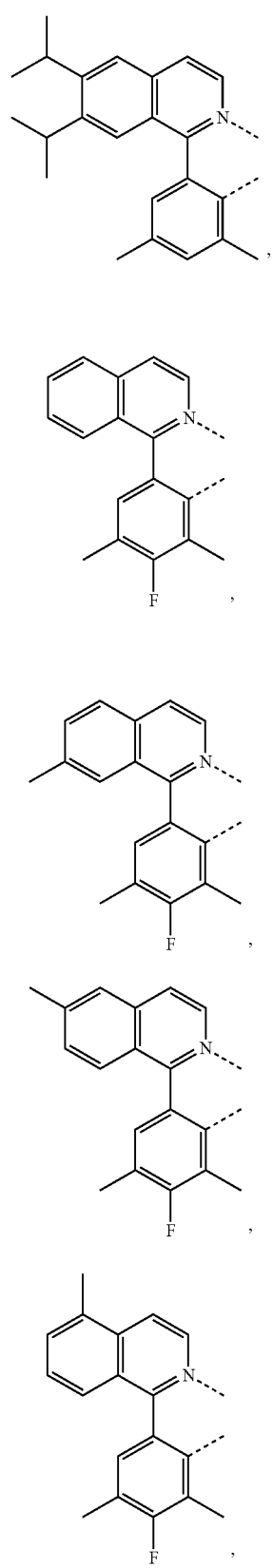
$L_{Q87}$
$L_{Q88}$
$L_{Q89}$
$L_{Q90}$
$L_{Q91}$ -continued
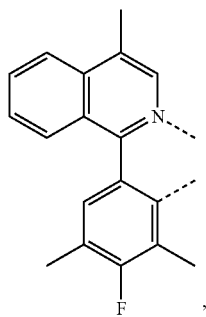  L_{Q92}
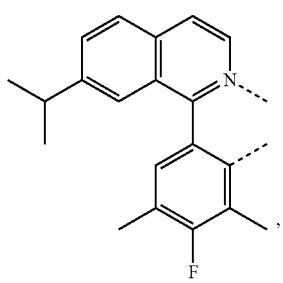  L_{Q93}
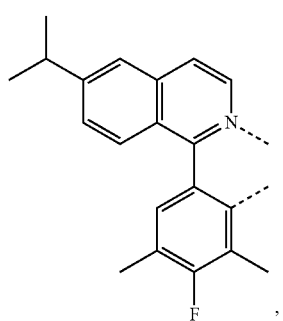  L_{Q94}
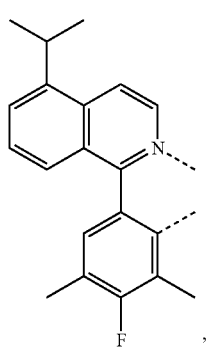  L_{Q95}
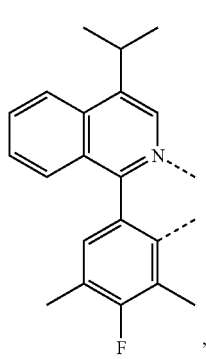  L_{Q96}
-continued
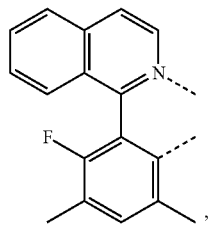  L_{Q97}
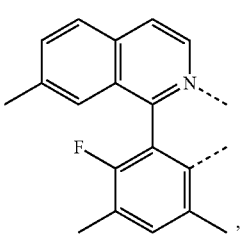  L_{Q98}
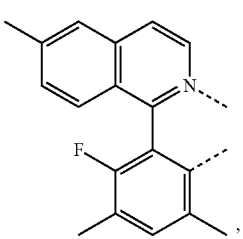  L_{Q99}
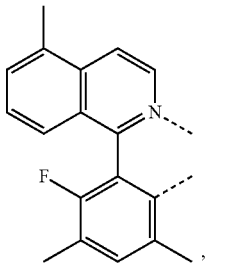  L_{Q100}
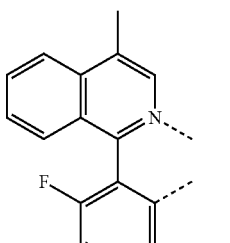  L_{Q101}
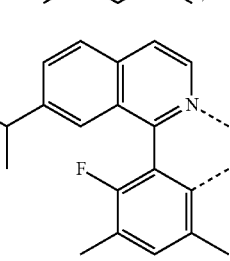  L_{Q102}

L_Q103 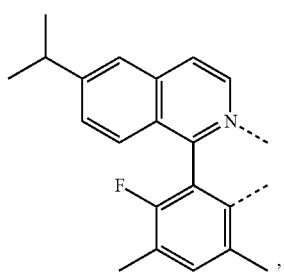
L_Q104 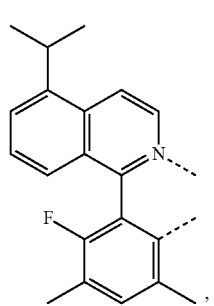
L_Q105 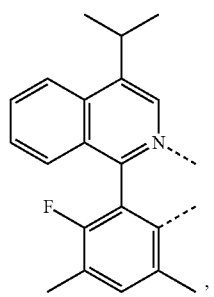
L_Q106 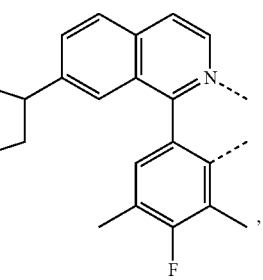
L_Q107 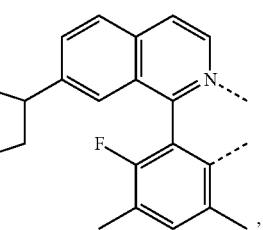
L_Q109 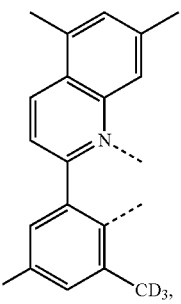
L_Q110 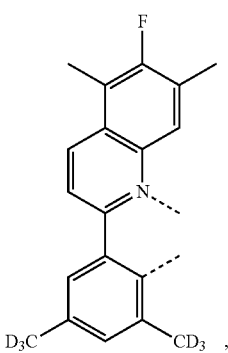
L_Q111 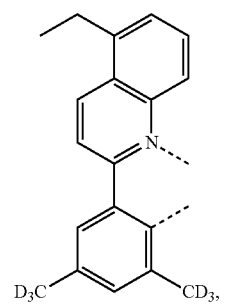
L_Q111 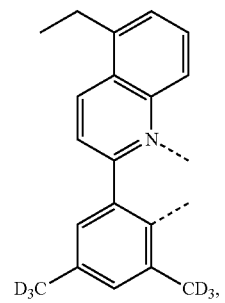
L_Q112 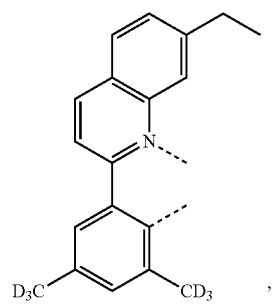

L_Q113
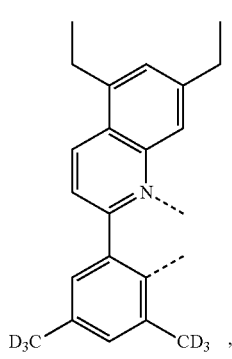
L_Q114
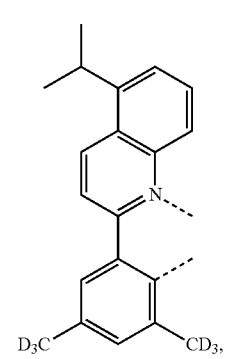
L_Q115
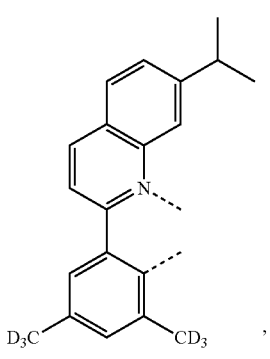
L_Q116
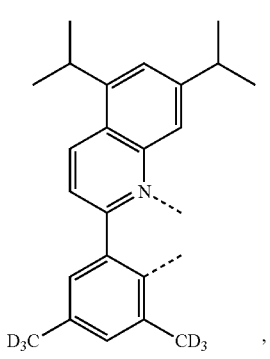
L_Q117
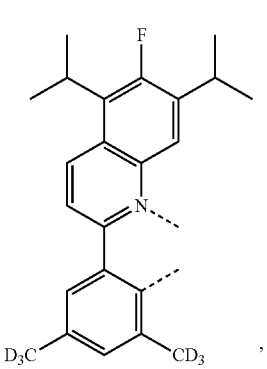
L_Q118
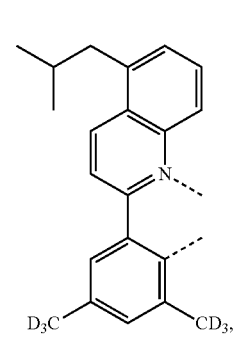
L_Q119
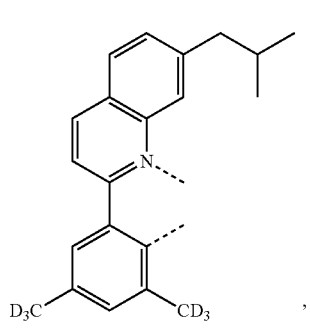
L_Q120
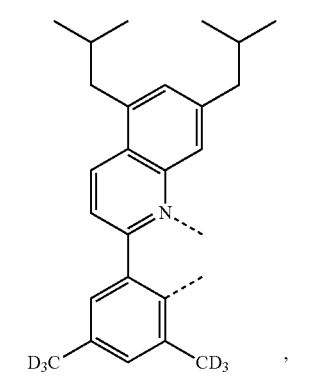

277
-continued
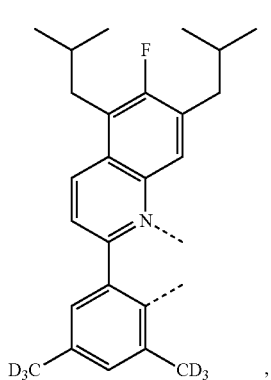
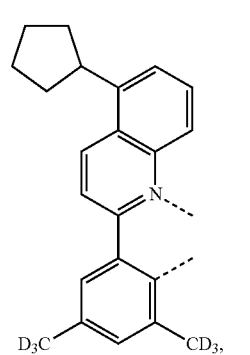
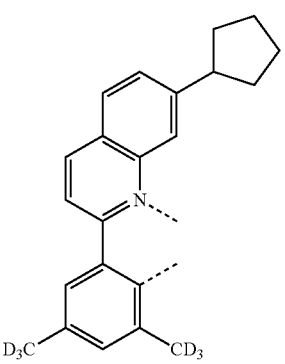
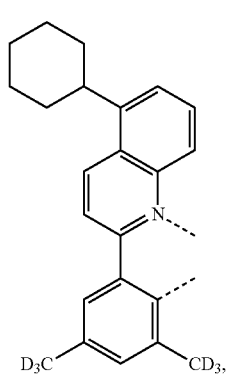
278
-continued
$L_{Q121}$
$L_{Q122}$
$L_{Q123}$
$L_{Q124}$
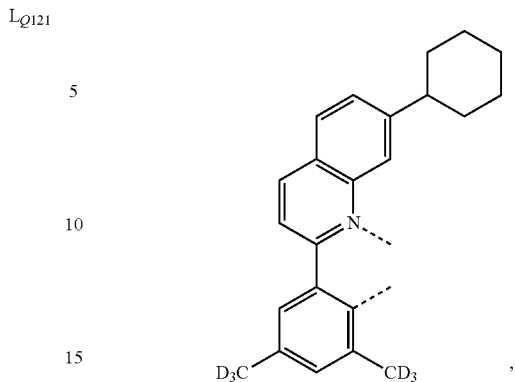
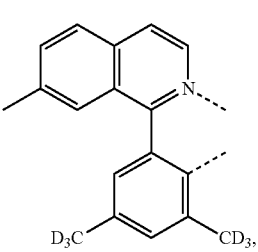
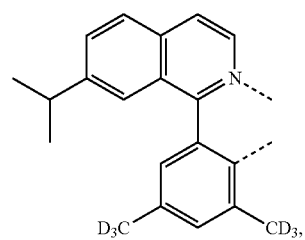
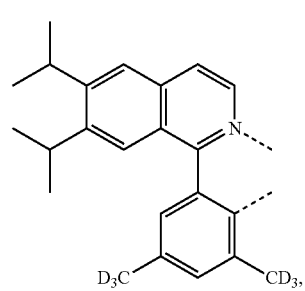
$L_{Q125}$
$L_{Q127}$
$L_{Q128}$
$L_{Q129}$
$L_{Q130}$ -continued

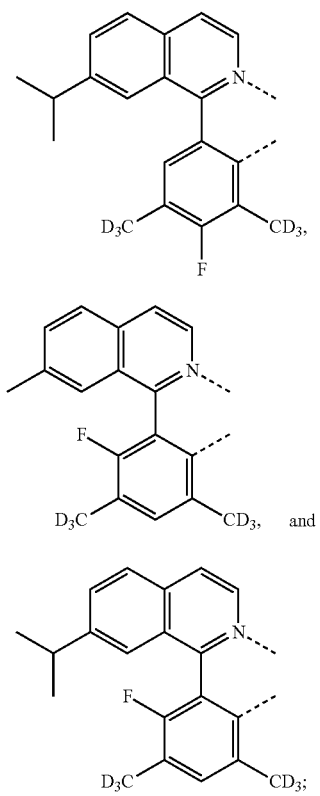

wherein x is 1 or 2;
wherein y is 1, or 2;
wherein z is 0 or 1;
wherein x+y+z is 3;
wherein each $R_a$ and $R_b$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein two adjacent substituents of $R_a$ and $R_b$ are optionally joined to form a fused ring or form a multidentate ligand.

13. The first device of claim 12, wherein the compound is selected from the group consisting of Compound 278

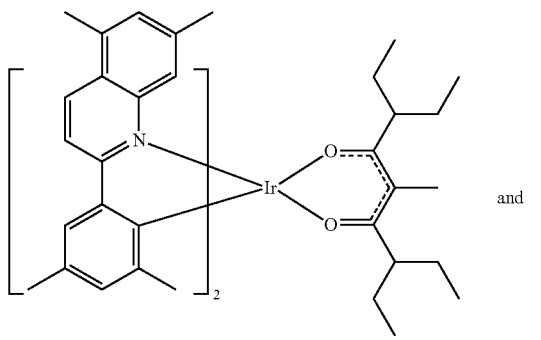

and

-continued

Compound 320

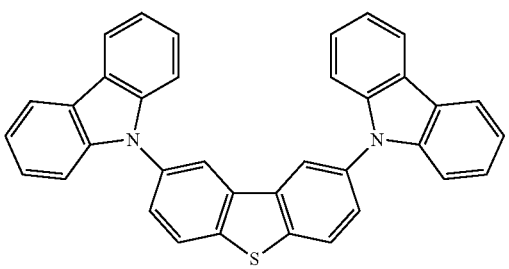

14. The first device of claim 12, wherein the first device is a consumer product selected from the group consisting of a flat panel display, a computer monitor, a medical monitor, a television, a billboard, lights for interior or exterior illumination and/or signaling, a heads up display, a fully transparent display, a flexible display, a laser printer, a telephone, a cell phone, a personal digital assistant (PDA), a laptop computer, a digital camera, a camcorder, a viewfinder, a micro-display, a 3-D display, a vehicle, a wall, theater or stadium screen, and a sign.

15. The first device of claim 12, wherein the organic layer is an emissive layer and the compound is an emissive dopant, or the organic layer is an emissive layer and the compound is a non-emissive dopant.

16. The first device of claim 12, wherein the organic layer further comprises a host material.

17. The first device of claim 16, wherein the host material comprises a triphenylene containing benzo-fused thiophene or benzo-fused furan;
wherein any substituent in the host material is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH\!=\!CH\!-\!C_nH_{2n+1}$, $C\!\equiv\!C\!-\!C_nH_{2n+1}$, $Ar_1$, $Ar_1$-$Ar_2$, and $C_nH_{2n}\!-\!Ar_1$;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.

18. The first device of claim 16, wherein the host material comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

19. The first device of claim 16, wherein the host material is selected from the group consisting of:

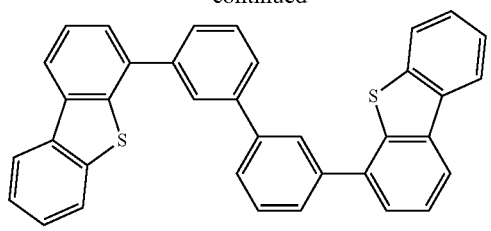
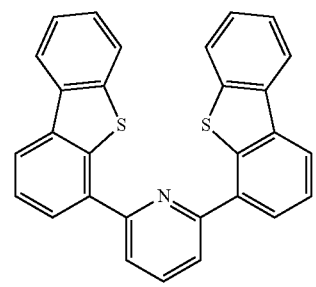
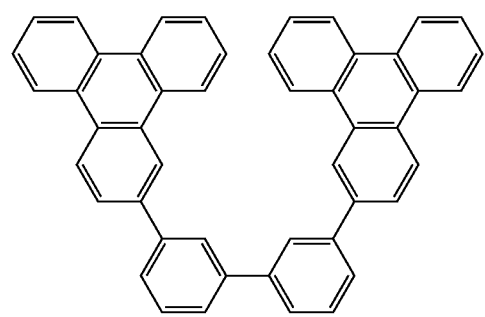
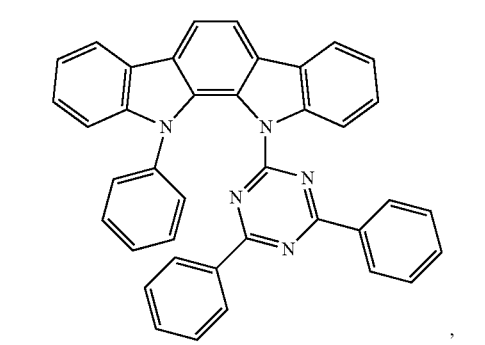
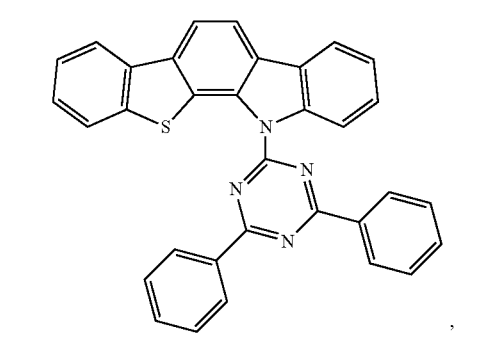
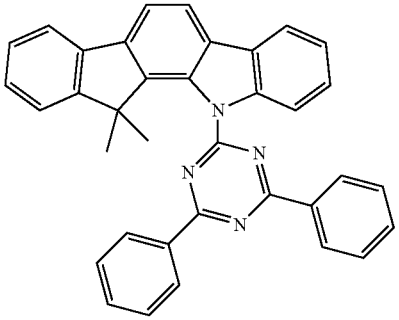
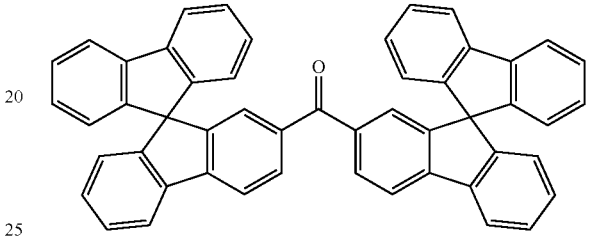
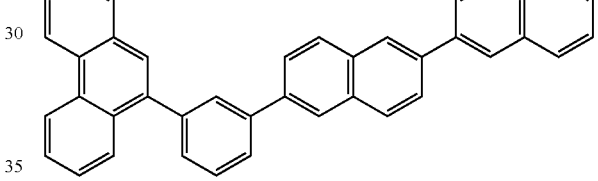
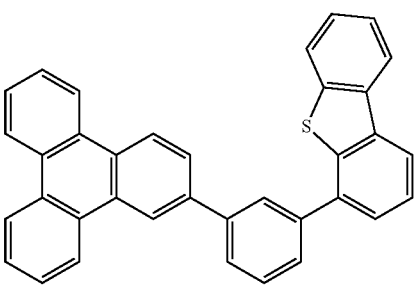
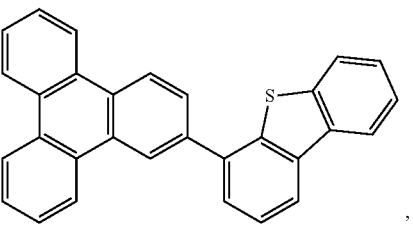
and combinations thereof.
20. The first device of claim 16, wherein the host material comprises a metal complex.
21. The first device of claim 20, wherein the host material is a metal 8-hydroxyquinolate.
22. A formulation comprising a compound having the formula $Ir(L^1)_x(L^2)_y(L^3)_z$:

wherein L¹ is selected from the group consisting of
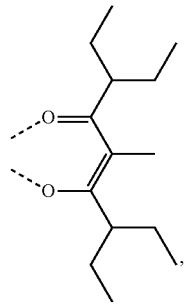
L_{A3}
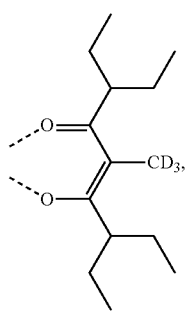
L_{A5}
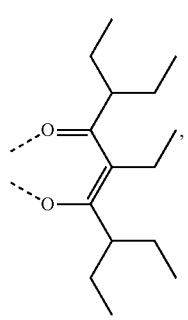
L_{A7}
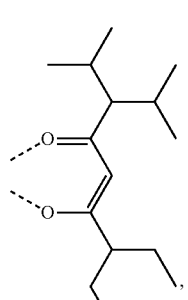
L_{A9}
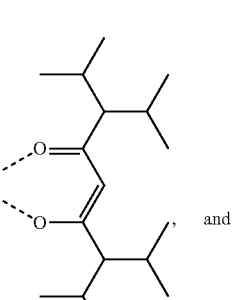
L_{A10}, and
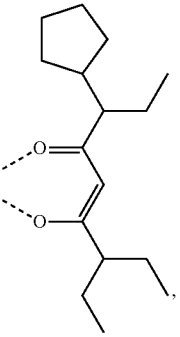
L_{A13}
wherein L² is a second ligand and L³ is a third ligand and L² and L³ can be the same or different;
wherein the second ligand L² and the third ligand L³ are structure (a) independently selected from the group consisting of:
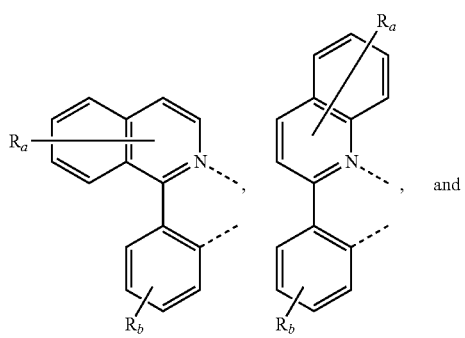
and
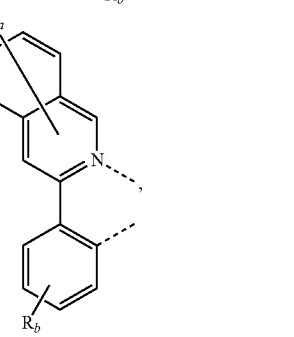
or structure (b) independently selected from the group consisting of
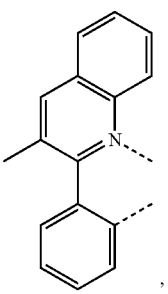
L_{Q2}

-continued
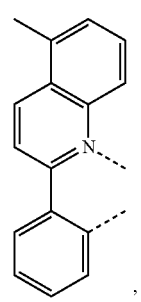 $L_{Q3}$,
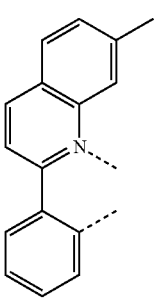 $L_{Q4}$,
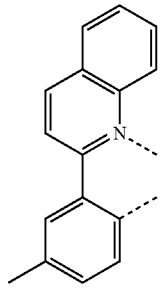 $L_{Q5}$,
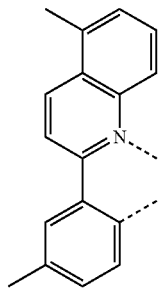 $L_{Q6}$,
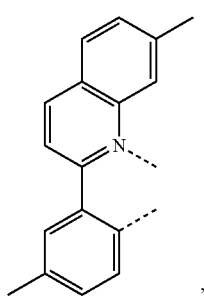 $L_{Q7}$,
-continued
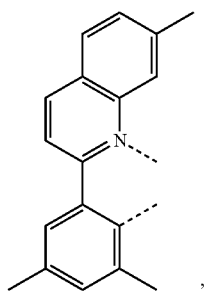 $L_{Q10}$,
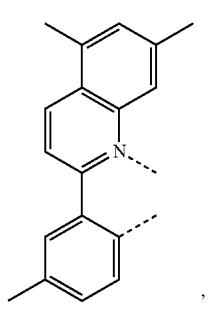 $L_{Q11}$,
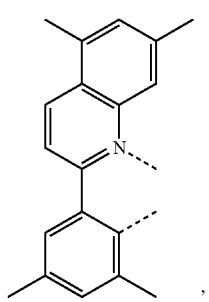 $L_{Q12}$,
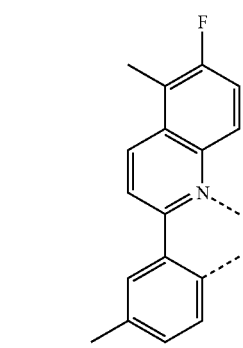 $L_{Q13}$,
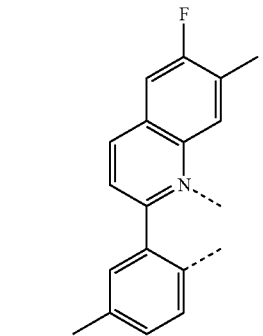 $L_{Q14}$,

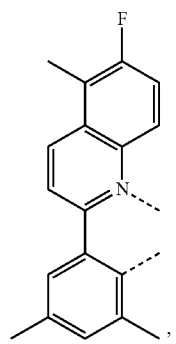 $L_{Q15}$
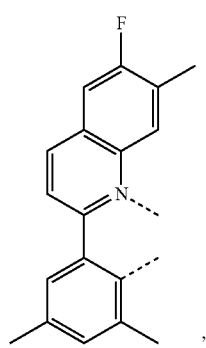 $L_{Q16}$
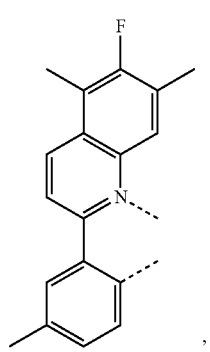 $L_{Q17}$
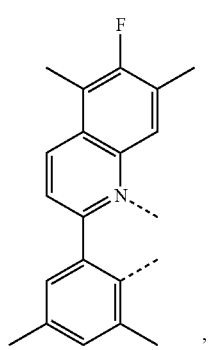 $L_{Q18}$
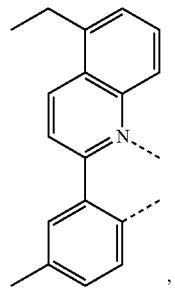 $L_{Q19}$
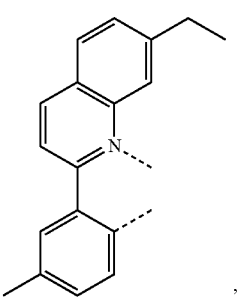 $L_{Q20}$
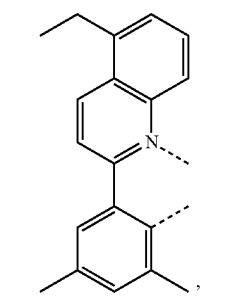 $L_{Q21}$
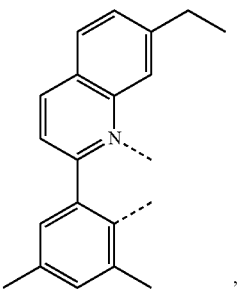 $L_{Q22}$
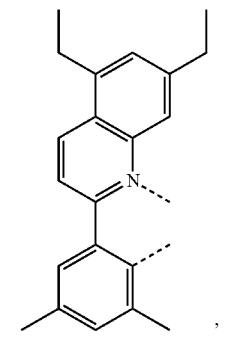 $L_{Q23}$

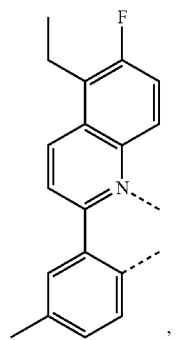 L_Q24
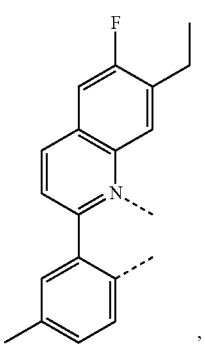 L_Q25
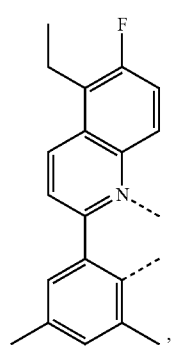 L_Q26
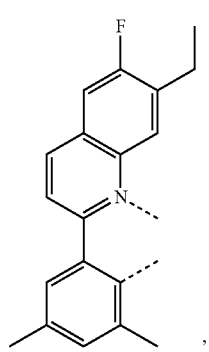 L_Q27
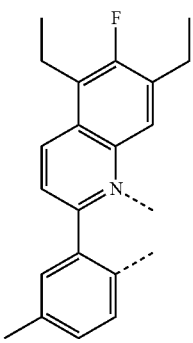 L_Q28
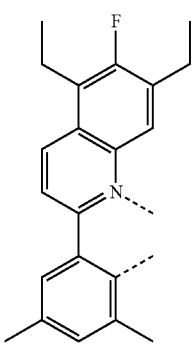 L_Q29
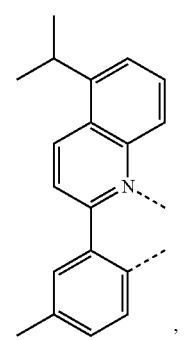 L_Q30
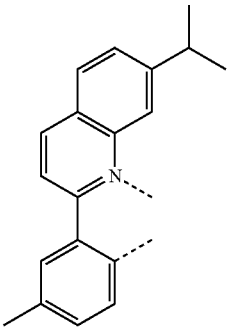 L_Q31

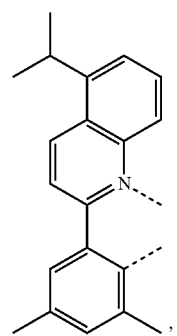 $L_{Q32}$
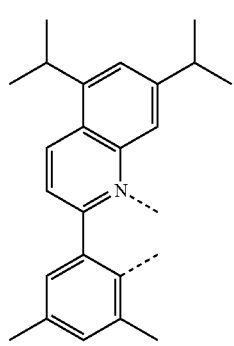 $L_{Q34}$
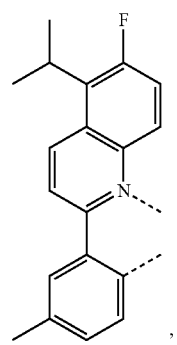 $L_{Q35}$
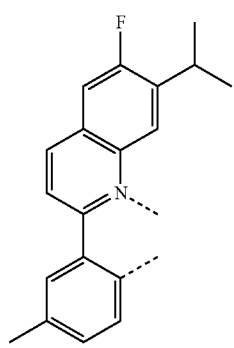 $L_{Q36}$
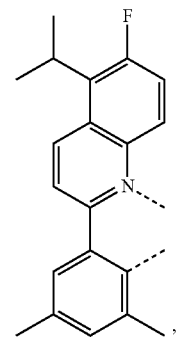 $L_{Q37}$
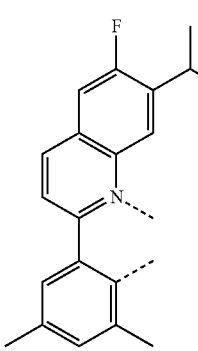 $L_{Q38}$
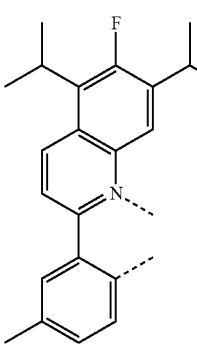 $L_{Q39}$
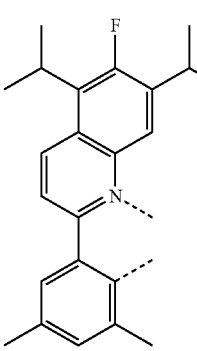 $L_{Q40}$

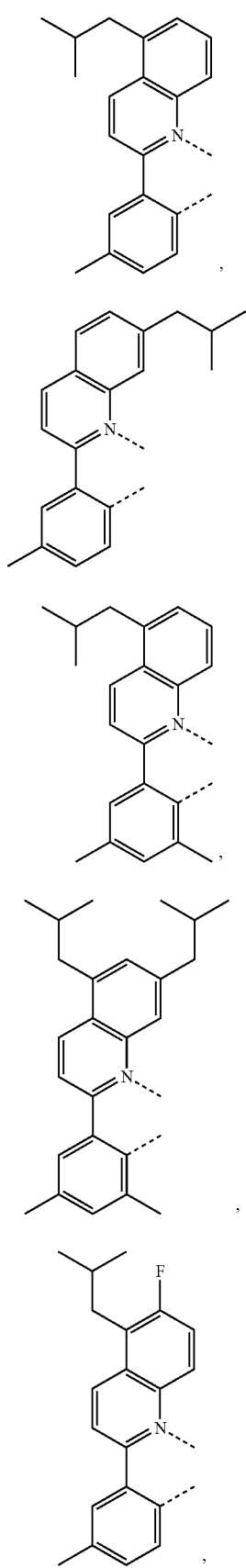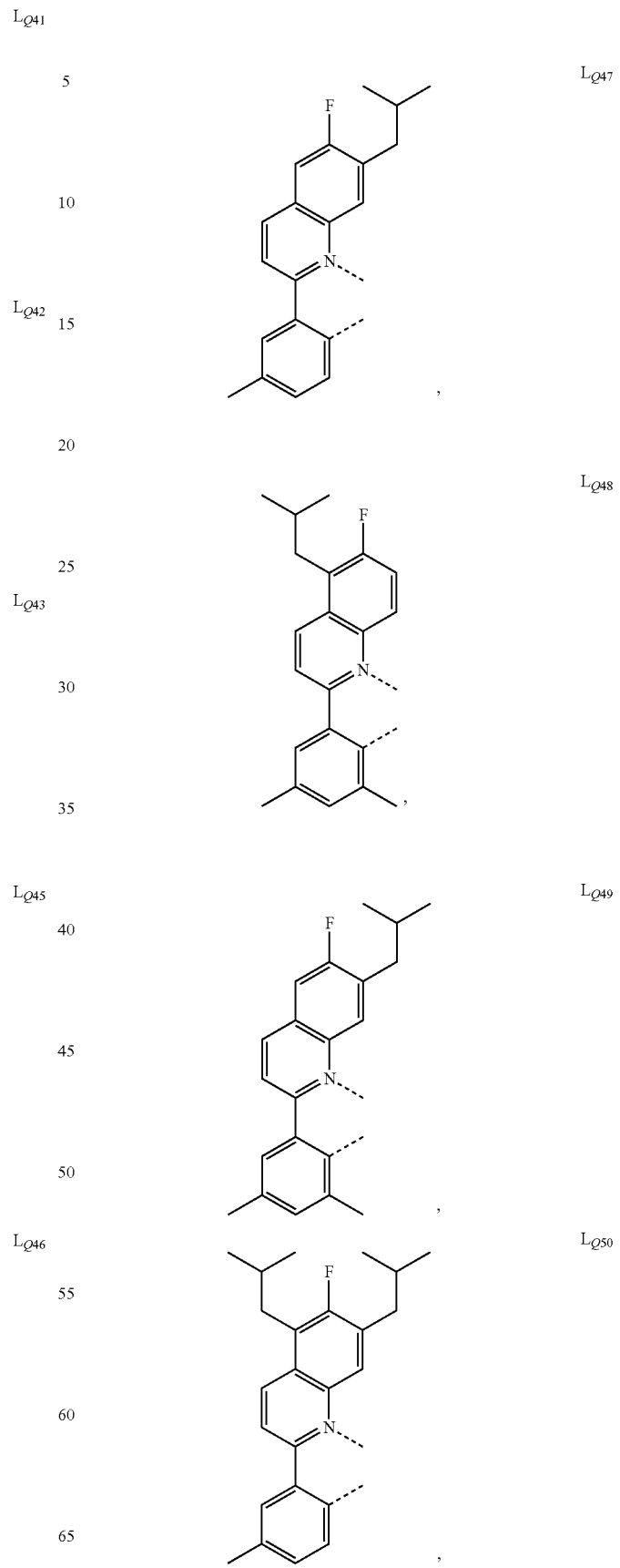

-continued $L_{Q51}$ $L_{Q52}$ $L_{Q53}$ $L_{Q54}$

-continued $L_{Q55}$ $L_{Q56}$ $L_{Q57}$ $L_{Q58}$

L<sub>Q59</sub> 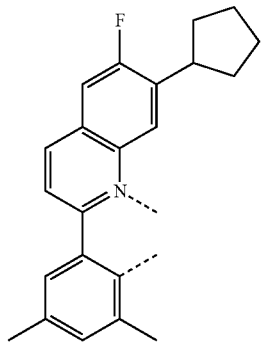
L<sub>Q60</sub> 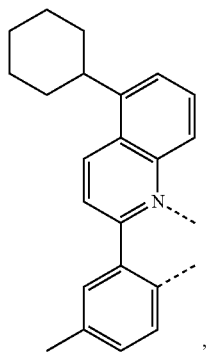
L<sub>Q61</sub> 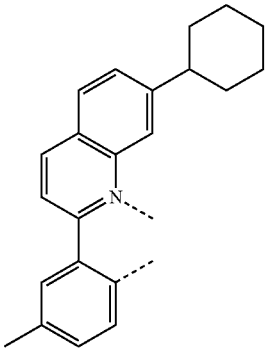
L<sub>Q62</sub> 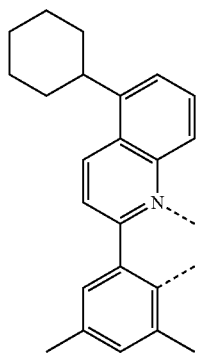
L<sub>Q63</sub> 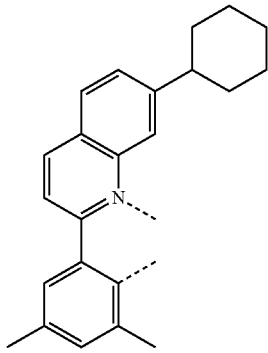
L<sub>Q64</sub> 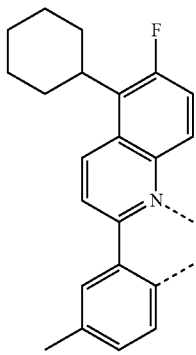
L<sub>Q65</sub> 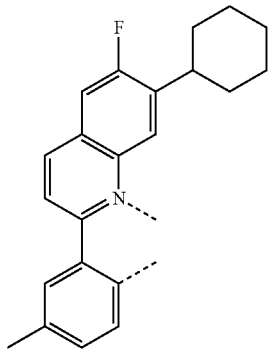
L<sub>Q66</sub> 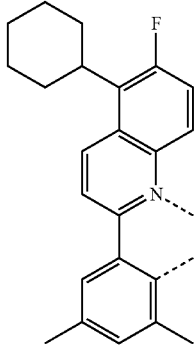

-continued $L_{Q67}$ $L_{Q68}$ $L_{Q69}$ $L_{Q71}$ $L_{Q72}$

-continued $L_{Q72}$ $L_{Q73}$ $L_{Q75}$ $L_{Q76}$ $L_{Q77}$

301
-continued
L_{Q77}
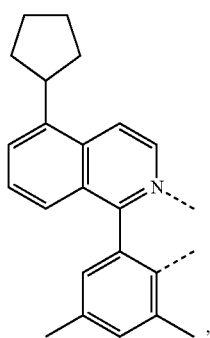
L_{Q78}
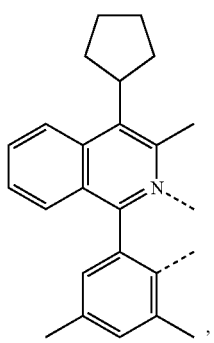
L_{Q80}
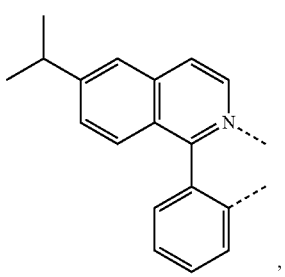
L_{Q81}
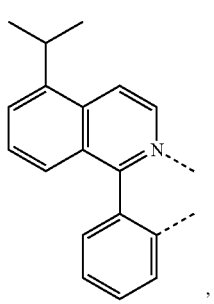
L_{Q82}
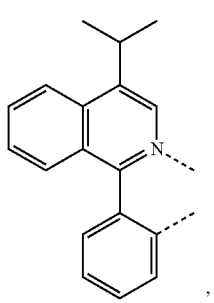
302
-continued
L_{Q83}
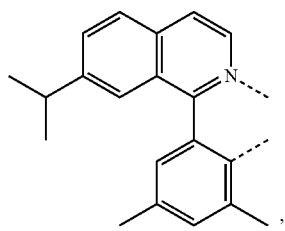
L_{Q83}
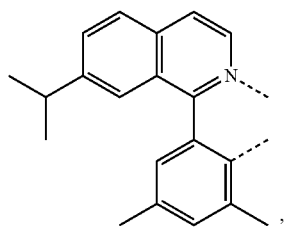
L_{Q84}
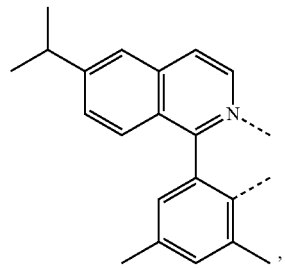
L_{Q85}
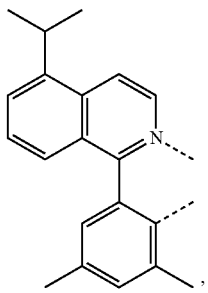
L_{Q86}
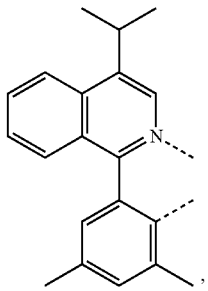
L_{Q87}
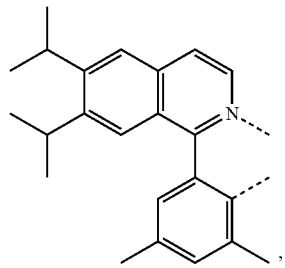

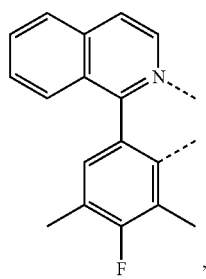 L<sub>Q88</sub>
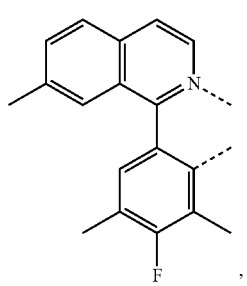 L<sub>Q89</sub>
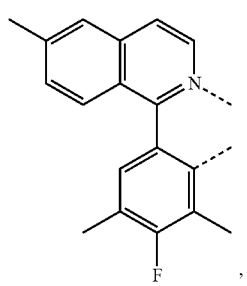 L<sub>Q90</sub>
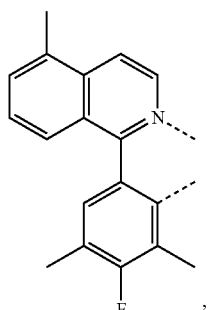 L<sub>Q91</sub>
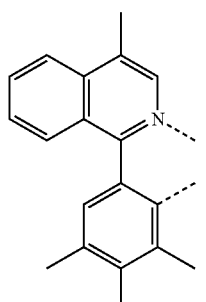 L<sub>Q92</sub>
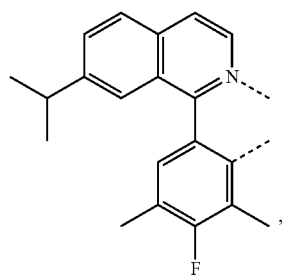 L<sub>Q93</sub>
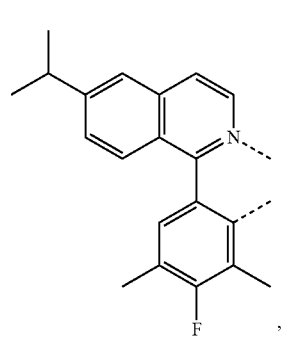 L<sub>Q94</sub>
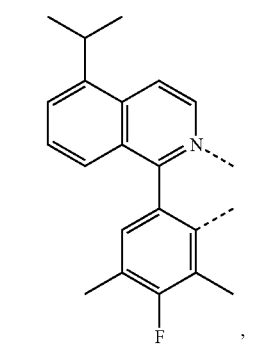 L<sub>Q95</sub>
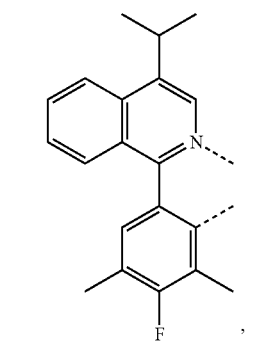 L<sub>Q96</sub>
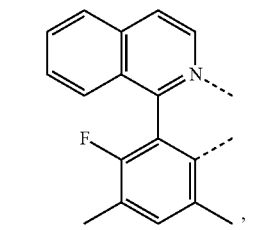 L<sub>Q97</sub>

L<sub>Q98</sub> 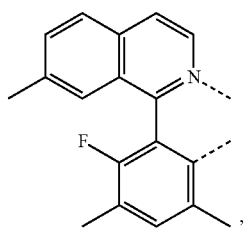
L<sub>Q99</sub> 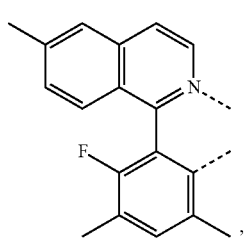
L<sub>Q100</sub> 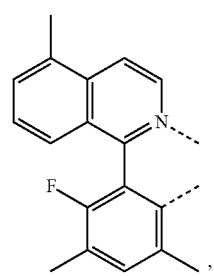
L<sub>Q101</sub> 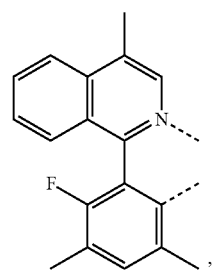
L<sub>Q102</sub> 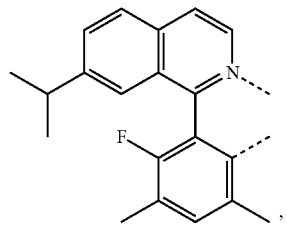
L<sub>Q103</sub> 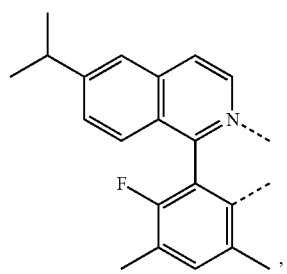
L<sub>Q104</sub> 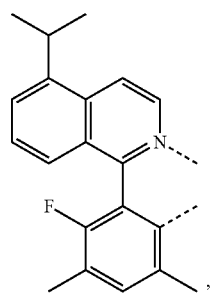
L<sub>Q105</sub> 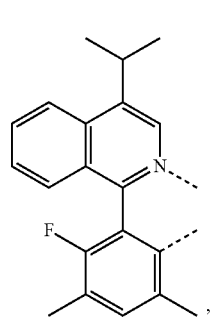
L<sub>Q106</sub> 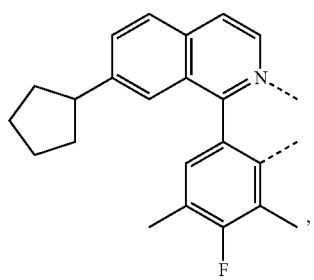
L<sub>Q107</sub> 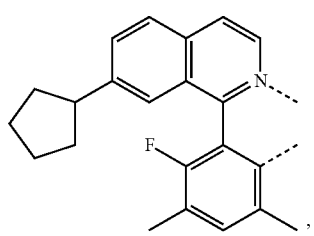
L<sub>Q109</sub> 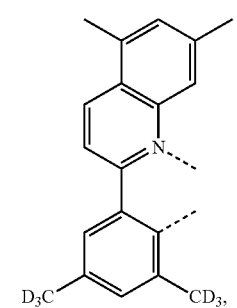

307
-continued
$L_{Q110}$
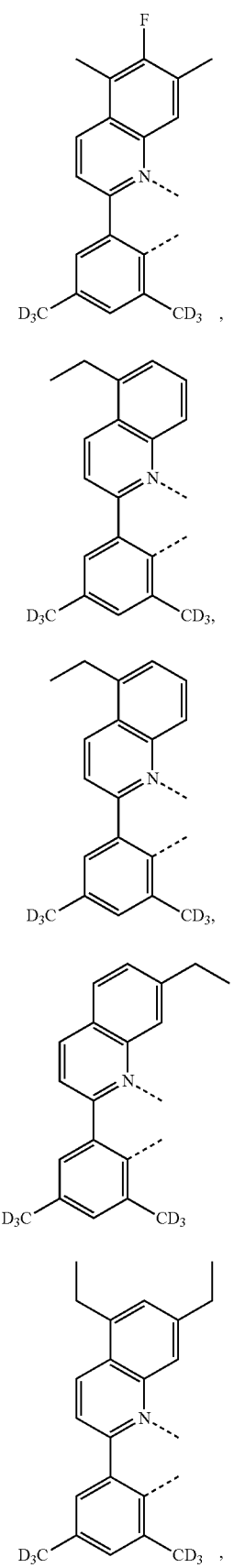
$L_{Q111}$
$L_{Q111}$
$L_{Q112}$
$L_{Q113}$
308
-continued
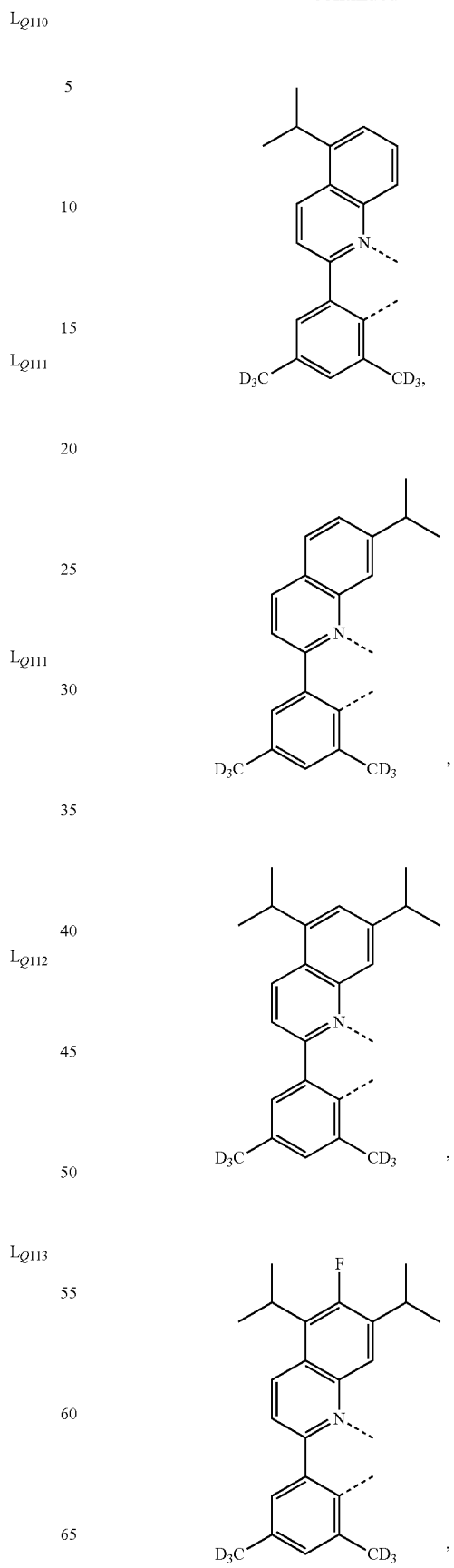
$L_{Q114}$
$L_{Q115}$
$L_{Q116}$
$L_{Q117}$ 309
-continued
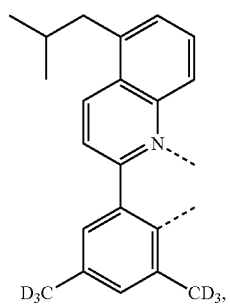  L_{Q118}
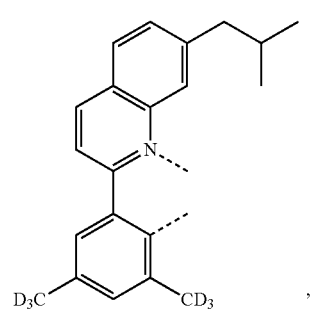  L_{Q119}
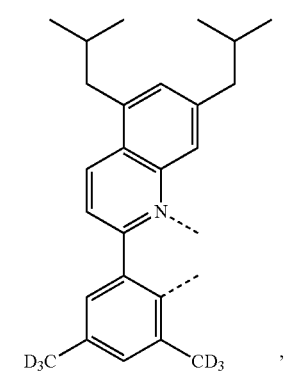  L_{Q120}
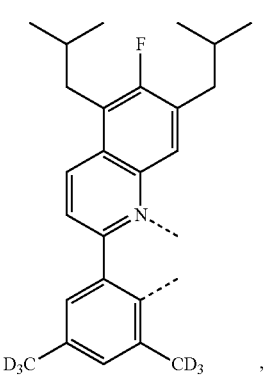  L_{Q121}
310
-continued
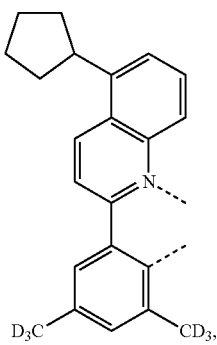  L_{Q122}
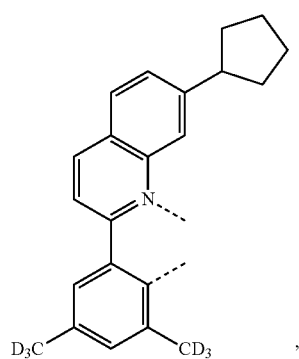  L_{Q123}
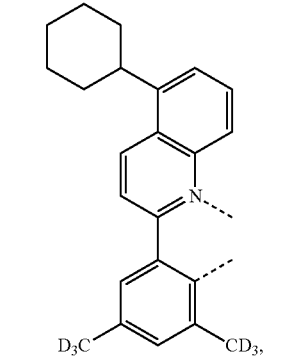  L_{Q124}
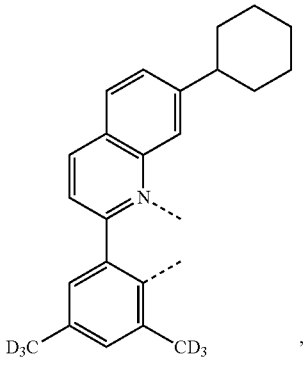  L_{Q125}
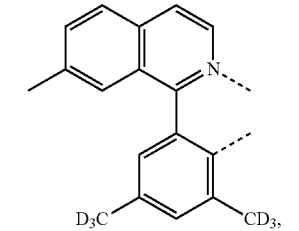  L_{Q127}

311
-continued

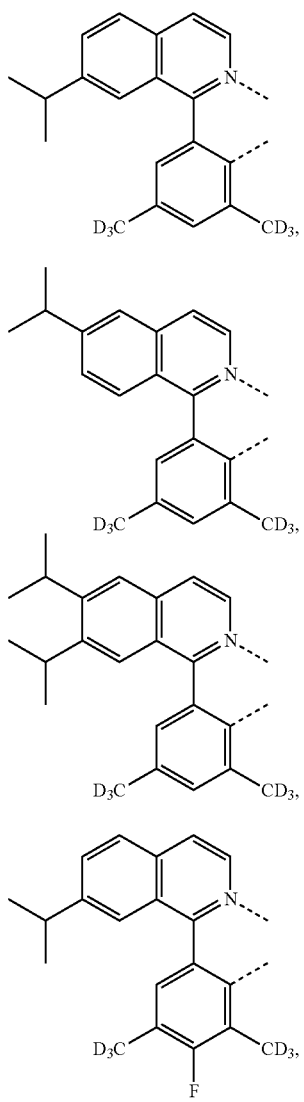

L_{Q128}

L_{Q129}

L_{Q130}

L_{Q131}

312
-continued

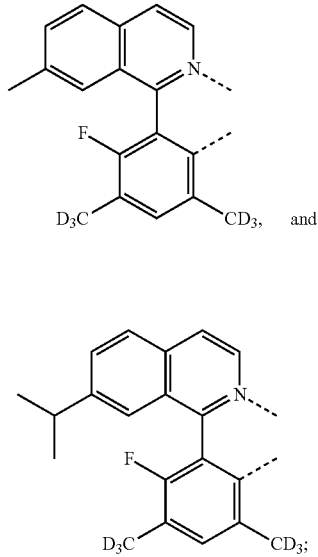

L_{Q132}

L_{Q133} wherein x is 1 or 2;

wherein y is 1, or 2;

wherein z is 0 or 1;

wherein x+y+z is 3;

wherein each $R_a$ and $R_b$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$ and $R_b$ are optionally joined to form a fused ring or form a multidentate ligand.

\* \* \* \* \*

UNITED STATES PATENT AND TRADEMARK OFFICE
CERTIFICATE OF CORRECTION

PATENT NO. : 10,199,581 B2
APPLICATION NO. : 13/932508
DATED : February 5, 2019
INVENTOR(S) : Pierre-Luc T. Boudreault et al.

It is certified that error appears in the above-identified patent and that said Letters Patent is hereby corrected as shown below:

In the Claims

In Claim 3, Column 210, Lines 53-65, please delete the compound

" 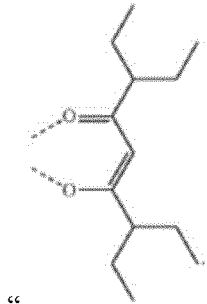 " and insert -- 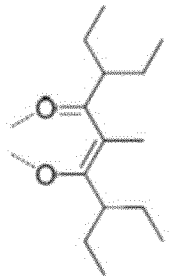 --

In Claim 4, Column 217, Lines 53-67, please delete the compound

" 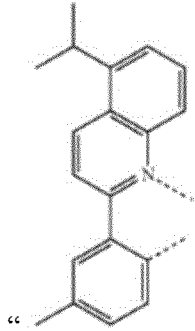 " and insert -- 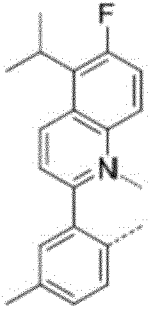 --

Signed and Sealed this
Seventh Day of May, 2019

Andrei Iancu
*Director of the United States Patent and Trademark Office*

CERTIFICATE OF CORRECTION (continued)
U.S. Pat. No. 10,199,581 B2

In Claim 4, Column 218, Lines 1-20, please delete the compound

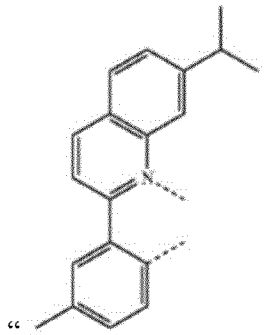

" 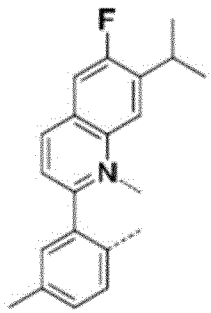 " and insert --  --

In Claim 7, Column 249, Lines 23-36, please delete the compound

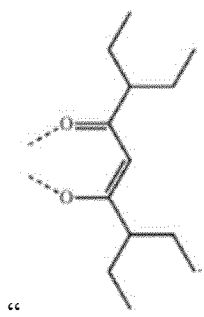

" 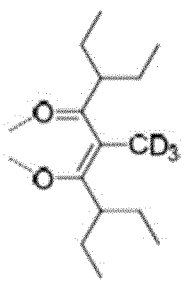 " and insert --  --